(12) United States Patent
Jones

(10) Patent No.: US 12,330,138 B2
(45) Date of Patent: Jun. 17, 2025

(54) SURFACE FUNCTIONALISED MATERIALS FOR SAMPLING BIOLOGICAL MOLECULES

(71) Applicant: Paul Antonio Jones, London (GB)

(72) Inventor: Paul Antonio Jones, London (GB)

(73) Assignee: Paul Antonio Jones, London (GB)

( * ) Notice: Subject to any disclaimer, the term of this patent is extended or adjusted under 35 U.S.C. 154(b) by 1050 days.

(21) Appl. No.: 16/981,197

(22) PCT Filed: Mar. 15, 2019

(86) PCT No.: PCT/GB2019/050736
§ 371 (c)(1),
(2) Date: Sep. 15, 2020

(87) PCT Pub. No.: WO2019/175599
PCT Pub. Date: Sep. 19, 2019

(65) Prior Publication Data
US 2021/0023534 A1 Jan. 28, 2021

(30) Foreign Application Priority Data
Mar. 16, 2018 (GB) .................... 1804217

(51) Int. Cl.
| A61B 10/00 | (2006.01) |
| B01J 20/10 | (2006.01) |
| B01J 20/28 | (2006.01) |
| B01J 20/30 | (2006.01) |
| B01J 20/32 | (2006.01) |
| G01N 33/50 | (2006.01) |
| G01N 33/68 | (2006.01) |

(52) U.S. Cl.
CPC ..... *B01J 20/28047* (2013.01); *A61B 10/0051* (2013.01); *A61B 10/007* (2013.01); *B01J 20/103* (2013.01); *B01J 20/3085* (2013.01); *B01J 20/3255* (2013.01); *B01J 20/3257* (2013.01); *B01J 20/3268* (2013.01); *G01N 33/5005* (2013.01); *G01N 33/6866* (2013.01); *A61B 2010/0054* (2013.01); *A61B 2010/0061* (2013.01); *A61B 2010/0074* (2013.01); *G01N 2333/555* (2013.01); *G01N 2800/26* (2013.01)

(58) Field of Classification Search
None
See application file for complete search history.

(56) References Cited

U.S. PATENT DOCUMENTS

| 6,013,187 A | 1/2000 | Burns et al. |
| 6,057,377 A | 5/2000 | Sasaki et al. |
| 2007/0122333 A1 | 5/2007 | Yang |
| 2008/0276804 A1 | 11/2008 | Sayari et al. |
| 2014/0076070 A1 | 3/2014 | Nakanishi et al. |
| 2014/0154257 A1* | 6/2014 | DeChristopher .. G01N 33/6893 435/69.6 |

FOREIGN PATENT DOCUMENTS

| DE | 10144251 | 3/2003 |
| DE | 10144251 A1 | 3/2003 |
| WO | 2016/142691 | 3/2016 |

OTHER PUBLICATIONS

Bhatia et al., Analytical Biochemistry, 1989, 178:408-413 (Year: 1989).*
Hartmann et al., Clin. Vaccine Immunol., Nov. 2006, 13(11):1278-1286 (Year: 2006).*
Boxx and Cheng, Cell Host & Microbe, 2016, 19(6):760-769 (Year: 2016).*
Search Report received for GB1804217.6, dated Oct. 19, 2018, 4 pages.
Abbasi, et al., 'Modification of polysiloxane polymers for biomedical applications: a review', Polym Int, 50, 2001, pp. 1279-1287.
Kataoka, et al., 'Applications of solid-phase microextraction in food analysis', Journal of Chromatography A, 880 (2000) pp. 35-62.
Hayase, et al., 'Facile Synthesis of Marshmallow-like Macroporous Gels Usable under Harsh Conditions for the Separation of Oil and Water', Angew. Chem. Int., 2013, 52, pp. 1986-1989.
Hayase, et al., 'New flexible aerogels and xerogels derived from methyltrimethoxysilane/dimethyldimethoxysilane co-precursors', J. Mater. Chem, 2011, 21, pp. 17077-17079.
Hayase, et al., 'A Superamphiphobic Macroporous Silicone Monolith with Marshmallow-like Flexibility', Angew Chem. Int., 2013, 52, pp. 10788-10791.
Greszta, et al., '"Living" Radical Polymerization. 1. Possibilities and Limitations', Macromolecules, 1994, 27, pp. 638-644.
De la Fuente, Solvent Effects on the Synthesis of Poly(methylmethacrylate) by Atom-Transfer Radical Polymerization (ATRP), Macromol. Chem. Phys., 2001, 202, pp. 2565-2571.
Bhatia, 'Use of thiol-terminal silanes and heterobifunctional crosslinkers for immobilation of antibodies on silica surfaces', Analytical Biochemistry, 1989, 178, 2, pp. 408-413.
Paris, 'Bulk Atom Transfer Radical Polymerization of Allyl Methacrylate', Wiley InterScience, 2004, pp. 2395-2406.
Powell, 'Rapid extraction of oxygenated metabolites of arachidonic acid from biological samples using octadecylsilyl silica', Prostaglandins, 1980, 20, 5, pp. 947-957.
Pruski, et al., 'Medical Swab Analysis Using Desorption Electrospray Ionization Mass Spectrometry: A Noninvasive Approach for Mucosal Diagnostics', Anal Chem., 2017, 89, pp. 1540-1550.

(Continued)

*Primary Examiner* — Stacy B Chen
(74) *Attorney, Agent, or Firm* — Kilpatrick Townsend & Stockton LLP

(57) ABSTRACT

The invention relates to materials, methods and devices useful for sampling biological molecules, including biomarkers and/or metabolites. In particular, the invention relates to surface functionalised xerogels and surface functionalised poly(dimethyl) siloxane (PDMS), devices comprising those materials, and methods of using the materials and devices for sampling, analysing or detecting biological molecules.

20 Claims, 95 Drawing Sheets

(56) References Cited

OTHER PUBLICATIONS

Kanamori, et al., 'New Transparent Methylsilsesquioxane Aerogels and Xerogels with Improved Mechanical Properties', Adv. Mater, 2007, 19, pp. 1589-1593.
Shriver-Lake, 'Antibody immobilization using heterobifunctional crosslinkers', Biosensors & Bioelectronics, 1997, 12, 11, pp. 1101-1106.
Yu, et al., 'A controlled thiol-initiated surface polymerization strategy for the preparation of hydrophilic polymer stationary phases', Chem Commun, 2015, 51, pp. 14778-14780.
PCT/GB2019/050736; International Search Report and Written Opinion; Jul. 22, 2019; 24 pages.
Hohenesche Cdfv et al: "Development of standard operation procedures for the manufacture of n-octadecyl bonded silicas as packing material in certified reference columns for reversed-phase liquid chromatography", Journal of Chromatography, Elsevier, Amsterdam, NL, vol. 1025, No. 2, Feb. 6, 2004 (Feb. 6, 2004), pp. 177-187.

\* cited by examiner a b

C

| Composition | N | MD |
|---|---|---|
| Strain at 5 N (%) | 80.45 ± 1.34 | 80.63 ± 2.19 |
| Stress at 5 N (MPa) | 0.19 ± 0.04 | 0.18 ± 0.03 |

| | Ratio | Fatty acids | | [M+H]+ |
|---|---|---|---|---|
| Glycerophosphatidylcholines | PC 34:2 | 16:0 | 18:2 | 758.5694 |
| | PC 34:1 | 16:0 | 18:1 | 760.5851 |
| | PC 36:4 | 18:2 | 18:2 | 782.5694 |
| | PC 36:3 | 18:1 | 18:2 | 784.5851 |
| | PC 36:2 | 18:0 | 18:2 | 786.6007 |
| | PC 36:1 | 18:0 | 18:1 | 788.6164 |
| | PC 38:6 | 16:0 | 22:6 | 806.5694 |
| | PC 38:5 | 16:0 | 22:5 | 808.5851 |
| | PC 38:4 | 18:0 | 20:4 | 810.6007 |
| | PC 38:3 | 18:0 | 20:3 | 812.6164 | b c

1. Functional Group Macroinitiator Synthesis

2. Block Copolymerisation with AMA Surface Coupling agent

SURFACE FUNCTIONALISED MATERIALS FOR SAMPLING BIOLOGICAL MOLECULES

FIELD OF THE INVENTION

This invention relates to materials, methods and devices useful for sampling biological molecules, including biomarkers and/or metabolites. In particular, the invention relates to surface functionalised xerogels and surface functionalised poly(dimethyl) siloxane (PDMS), devices comprising those materials, and methods of using the materials and devices for sampling, analysing or detecting biological molecules, including biomarkers and/or metabolites.

BACKGROUND TO THE INVENTION

The mis-use and over-prescription of broad-spectrum antibiotics has resulted in the evolution of treatment-resistant bacterial strains. Few antibiotics are effective against such strains, resulting in increased treatment costs and mortality rates, in both humans and animals.

The treatment of respiratory infections is a particular concern for Antimicrobial Resistance (AMR). A key example of this is the common cold—one of the most complex diseases to diagnose. Patients with symptoms such as 'runny nose' or 'sore throat' will commonly self-diagnose this to be a 'cold'. From a medical perspective, many different infections, predominantly viral but also bacterial, are known to cause these symptoms. A lack of adequate differential bacterial versus viral diagnostic methods combined with the availability and convenience of broad spectrum antibiotics, often results that any patient presenting with even a mild form of such a condition will either be prescribed—or buy—broad spectrum antibiotics.

A feature common to all existing diagnostic methods is the undesirable length of time taken to generate a result. The longer a patient is left undiagnosed, the longer the disease has to cause harm, thus the more complex and often ineffective the delivered treatment is, and the cost burden on healthcare systems also increases with time. Patient diagnosis of infection still largely relies on 19$^{th}$-century methods combining patient history and physical examination.

In the particular context of lung condition diagnosis, the non-invasive process of audio investigation (made possible and improved by increasingly sensitive stethoscope technology) uses a combination of inspection, palpation, percussion and auscultation as defined by clinical method handbooks. More precise investigations have typically relied on either direct visualisation by means of bronchoscopy or open-chest surgery (both invasive and high-risk procedures given the necessary use of anaesthetic) or slow laboratory-based testing of biological fluids and biopsied tissue during the procedures. For instance, etiologic diagnosis of lung infection requires bacterial culture. This involves extracting or biopsying a small sample of representative fluid or tissue and culturing extracted bacteria in predetermined media known to promote specific known bacterial species, thus allowing the identification of the disease. However, this process is time-consuming and often requires samples to be purified prior to testing as other microorganisms in the sample may inhibit bacterial growth. This was made clear in the case of the conventional bacterial pneumonia diagnosis process, where the traditionally used sputum samples were deemed to lead to inaccurate diagnosis due to foreign contaminants within the sputum samples leading to significant inter-patient variability and testing method corruption.

A turning point in terms of lung-related pathology-focused research was the shift from the 1990s onwards to the 'one airway, one disease' concept whereby the presence of key markers of the pathophysiological state of inflammation could be identified in both the lower airway (bronchi) and nasal secretions. This was later also termed 'United Airway Disease' or UAD with increasing pathophysiological evidence pointing towards the common traits between both lower and upper airway epithelial fluid biomarker compositions identified in the nasal passage, either in the nasal fluid or the epithelial lining. However, different means of extracting said markers, from nasal lavage and vacuum collection to biopsies and micro-sampling, are known not only to cause patient discomfort but critically to affect the thus obtained results by contaminating samples with blood post-irritation.

Alam et al (Journal of Immunological Methods, 1992. 155(1): p. 25-29) notes the need for a more suitable means of collecting nasal fluid than the standard nasal lavage process. A standardised method of collecting nasal fluid regardless of mucosal secretion was proposed, for which Alam et al propose the term Synthetic Absorptive Matrix (SAM), consisting of strips of Whatman filter paper. Assessing for cytokine extraction and recovery, the authors reported detection of IL-1β and GM-CSF cytokines post-nasal challenge when using filter paper to extract the markers, whilst no markers were detected when using the nasal lavage process. Cytokine recovery from filter strips was reported to be between 67% and 89% by leaving strips to air-dry post extraction and eluted using Hepes buffer with 0.3% human serum albumin, a known lipoprotein. Filter paper's absorbance capacity is however inherently limited. This limits the amount of analyte such swabs can effectively extract. Further work has therefore since focused on developing an improved 'gold standard' extraction material that allows the standardisation of the nasal fluid collecting procedure. However, comparative studies have yet to promote a viable candidate, current research being subject to much debate.

The use of polyurethane-based materials has also been proposed, forming a similar foam-like swab device introduced into the nasal cavity to extract biological markers. Such methods report higher sensitivity detection (approximately 10 fold increase) than nasal lavage.

In a different area of endeavour, U.S. Pat. No. 6,013,187 describes a method for removing metal contaminants (e.g. Mg, Ca, Cu, Ag) from solution (be that organic (polar or non-polar) or aqueous) using a mercapto-functional silica xerogel. The physical format of the final decontamination product is a powder. This method essentially provides a filter to remove metal contaminants and does not make any further use of the elements removed from solution. No consideration is given to a possible biological or medical application, nor to the possible analysis of the extracted elements.

US Patent Application No. 2007/0122333 A1 describes a silica gel, formed into a Chemically Surface Modified Gel (CSMG) to produce what is effectively a "sieve" for heavy metals. This sieve is used in the purification of contaminated fluids such as water, i.e. applications such as oil spills or heavy metal leakage. No consideration is given to a possible biological or medical application, nor to the possible analysis of the extracted elements. Furthermore, the described material appears to be used in wet state to be effective and is used in a powder format.

US Patent Application No. 2008/0276804 A1 describes a surface-functionalised mesoporous solid silica support for the adsorption of acid gases when passed through or over the material. The physical format of the material is understood to be particulate, and is not described by authors as a xerogel.

U.S. Pat. No. 6,057,377 describes molecular receptors in metal oxide sol-gel materials prepared via molecular imprinting. Here, sol-gel based materials are synthesized to allow the surface to react with specific molecules. Once the imprinting molecule is removed, the site is a specific recognition site to that molecule, allowing the overall material to behave as a detection, or capturing, device for the desired molecule. The material is crushed into particles, and the utility relies on this physical format of powder (as it is placed into a HPLC column as discussed in Example 3). Medical and diagnostic applications are not suggested.

US Patent Application No. 2014/0076070 A1 describes monolithic silicone and its use in methods of separation, purification and concentration in the fields of analytical chemistry and industrial separation/recovery. There is no mention of functionalisation of the material, which is therefore not designed to extract anything in particular. There is no selectivity and the material extracts all components of the solution into which it is introduced.

Turning back to the field of biological molecule detection and sampling, a recent comparative study of various materials for SAM-based application was conducted by Panpradist et al (PLOS ONE, 2014. 9(9): p. e105786), comparing rayon fibres, cotton, nylon, PE, PU and calcium alginate and their respective volume and organism recovery capacities, as well as their relative performance during manual handling procedures (such as stirring or agitation time and vigour). PU substrates performed best in the outlined tests, with their apparently suitable performance being due to optimal consistency despite user-induced handling variability. In simple terms, however handled, the material allowed the same diagnostic output. This is key in designing such materials as the device should allow for straightforward clinical integration; this implies that the device can yield an identical result regardless of user.

Although there has been progress in the methods used to collect diagnostically relevant nasal fluid (be it for lipidomics, proteomics or cell-based analysis methods), even the push for a 'gold standard' can be identified as incomplete for the simple reason that they only allow for fluid extraction and do not take into account downstream processing. Analysis methods such as HPLC-MS or ELISA tests require high-purity and 'single species' samples for optimal analysis. This is typically achieved using Folch or Blight and Dyer liquid lipid extraction methods to separate out lipid constituents from their aqueous sample phase. They can then be reconstituted in known amounts for precise quantification to be performed relative to known lipid standards.

There is therefore a need for a means of both extracting and separating previously identified relevant biomarkers in a less time-consuming and labour-intensive and a more efficient and precise manner. This would assist the aim of significantly reducing the time elapsed between a patient presenting symptoms and their precise diagnosis. This would allow precise treatment to be delivered to the patient as opposed to less effective broad-spectrum alternatives currently used. Such a tool would be a significant step towards solving issues such as AMR and the associated strain put on healthcare systems.

SUMMARY OF THE INVENTION

The present invention relates to new materials, methods and devices for sampling biological molecules, including biomarkers and/or metabolites. The biological molecules are typically sampled from a mucous membrane, but may alternatively be sampled from a bodily fluid such as sputum, saliva, urine, or ascitic fluid. The methods and devices make use of a surface functionalised xerogel or surface functionalised poly(dimethyl) siloxane (PDMS), comprising a functional group capable of selectively binding to a biological molecule of interest, such as from a bodily fluid or from a mucous membrane of a subject.

Xerogels of the invention and PDMS of the invention can be functionalised with one or more of a variety of different moieties to selectively bind different biomarkers, biological molecules and/or metabolites. The specific functionalisation can be chosen based on the surface chemistry of the xerogel or PDMS, the nature of the functional moiety, the properties of the biomarker, biological molecule and/or metabolite being bound and the intended purpose. For example, thiol-xerogels can be functionalised with octadecylsilyl (ODS) to selectively bind lipid biomarkers. Alternatively, thiol-xerogels can be functionalised with antigen-binding proteins to selectively bind protein biomarkers.

The present invention therefore provides in one aspect a surface-functionalised xerogel comprising a functional group capable of selectively binding to a biomarker and/or a biological molecule from a subject. The xerogel may be any suitable xerogel including silica xerogels.

Xerogels of the invention combine physical properties that are particularly suitable for sampling biological fluid from mucous membranes, including compressibility, elasticity, durability, wicking and/or absorbance. They can be formed into a suitable size and shape for insertion into a body orifice and therefore simplify sampling from that orifice. The xerogels of the invention are surface-functionalised with a functional group capable of selectively binding to a biomarker, biological molecule and/or metabolite from a biological fluid, and in particular a biological fluid from a mucous membrane.

The xerogels and PDMS of the invention can be formed into a suitable size and shape for insertion into the body, for example using a catheter or cannula (or other appropriate tube or insertion technique), or for placement into the lumen of the cannula, catheter or other tube for sampling fluid that is removed or drained from the body and passes through that lumen. A notable additional benefit is provided in these embodiments, because the xerogel/PDMS does not expand when exposed to fluid, and therefore does not lose any relevant fluid when being pulled back through the tube (e.g. catheter or cannula) upon being removed from the body. The lack of dimension change after fluid sampling is demonstrated and discussed in Example 9 and FIG. 28A, below.

Accordingly, the xerogel and PDMS of the invention is useful in both non-invasive and minimally-invasive testing, sampling or diagnosis procedures.

Minimally-invasive procedures typically involve no more than a small incision to the subject's body. Minimally-invasive procedures include catheterisation, cannulisation, endoscopy, arthroscopy and laparoscopy. A lumbar puncture is one example of a well-known minimally-invasive diagnostic procedure.

One embodiment that is provided, is introducing the xerogel or PDMS into an internal body cavity. Body cavities include the dorsal and ventral cavities. The dorsal cavity comprises the cranial cavity and the vertebral (spinal) cavity. The ventral cavity comprises the thoracic cavity, the abdominal cavity and the pelvic cavity. The cavity may be a flexible cavity or a rigid cavity. Flexible cavities include the thoracic cavity, the abdominal cavity and the pelvic cavity. The rigid cavity is typically the cranial cavity. When the xerogel or PDMS is inserted into a bodily cavity, it can sample the content, typically the bodily fluids, of that cavity. In the cranial cavity or the spinal cavity, this may be cerebrospinal fluid. In the abdominal cavity, this may be ascitic fluid (as present in the condition ascites). In one embodiment, the xerogel or PDMS of the invention is used to sample ascitic fluid, which may be achieved by inserting the xerogel or PDMS into the abdominal cavity using a catheter or similar device. When the central nervous system is to be sampled, the xerogel or PDMS of the invention may be used to collect cerebrospinal fluid from a lumbar puncture, or to collect brain ventricular fluid.

Another embodiment is the probing of any suitable area of the body using the xerogel or PDMS. Typically the area of the body will comprise a space, void, cavity or lumen into which the xerogel or PDMS can be inserted. For example, the xerogel or PDMS can be formed into a suitable size and shape for probing a tube, e.g. a fallopian tube (also known as an oviduct or uterine tube), or the uterus. In this embodiment, the xerogel or PDMS may be introduced (for example using a catheter or other minimally-invasive insertion technique) into the fallopian tube to sample that region of the body. A xerogel or PDMS that is of a shape and size suitable for introduction into the fallopian tube can be inserted into the fallopian tube using a catheter and can be used, for example, in the diagnosis or detection of ovarian cancer. The ovarian cancer may be early stage ovarian cancer. As will be explained below, when cancer is to be detected, the xerogel or PDMS will typically be functionalised to detect a cancer cell or a cancer cell marker.

In some embodiments, the functional group of the xerogel or PDMS is capable of selectively binding to a cell, a biological molecule such as a protein, a lipid, a nucleic acid or a carbohydrate, a biomarker or a metabolite. In certain embodiments, the functional group is selected from an antigen-binding protein, a nucleic acid, a lipid-binding moiety, a sugar or glycoprotein, or a block group-presenting co-polymer.

In certain specific embodiments, the functional group may bind hydrophobic biomarkers, biological molecules and/or metabolites such as lipids, fatty acids and/or hydrophobic peptides. A specific example of a functional group that binds to hydrophobic metabolites is a $C_4$-$C_{20}$ alkyl silicate, for example an octadecylsilyl (ODS) group, or a divinyl benzene (DVB). In other embodiments, the functional group comprises a mannose moiety, for example mannose methacrylate. In other embodiments, the functional group comprises an antigen-binding protein such as an antibody or a fragment thereof.

The biomarker, biological molecule and/or metabolite may be from a mucous membrane or biological fluid. In particular embodiments, the biological fluid is a biological fluid from a mucous membrane. This may typically be a nasal fluid.

The invention also provides a method of sampling one or more biological molecules of a subject comprising contacting the one or more biological molecules with a surface-functionalised xerogel of the invention. Typically, the biological molecule is sampled from a mucous membrane of the subject, such as the nasal membrane.

The invention further provides the use of a surface-functionalised xerogel of the invention for sampling a biological fluid from a subject. The invention also provides a surface-functionalised xerogel of the invention for use in sampling a biological fluid from a subject. In particular, the biological fluid may be from a mucous membrane of a subject.

In another aspect, the invention further provides a method for the preparation of a surface functionalised xerogel of the invention, comprising surface functionalising the xerogel with a functional group capable of selectively binding to a biological molecule from a subject.

The invention also provides a sampling device for sampling a biological fluid, typically from a mucous membrane, comprising a surface-functionalised xerogel of the invention or surface-functionalised PDMS of the invention.

The invention also provides a method of sampling one or more biological molecules of a subject comprising contacting the one or more biological molecules with a surface-functionalised PDMS of the invention. Typically, the biological molecule is sampled from a mucous membrane of the subject, such as the nasal membrane.

In a further embodiment, the invention provides a method of sampling and analysing a biological molecule comprising contacting the biological molecule with a surface-functionalised PDMS comprising a functional group capable of selectively binding to a biological molecule from a subject and optionally analysing the collected sample while it is on the PDMS. The biological molecule is typically from a mucous membrane of a subject. The PDMS may be in the form of a rod.

In a further embodiment, the invention provides a method of sampling and analysing a biological molecule comprising contacting the biological molecule with a surface-functionalised xerogel comprising a functional group capable of selectively binding to a biological molecule from a subject and optionally analysing the collected sample while it is on the xerogel. The biological molecule is typically from a mucous membrane of a subject.

The invention further provides a kit for detecting biomarkers in a sample of biological fluid from a patient, said kit comprising one or more sampling devices comprising a surface functionalised xerogel and/or surface functionalised poly(dimethyl) siloxane (PDMS) of the invention, and optionally reagents for the elution and/or analysis of the sampled biological molecules.

The invention also provides a biosensor comprising a surface-functionalised xerogel or and/or surface functionalised PDMS comprising a functional group capable of selectively binding to a biological molecule from a subject.

BRIEF DESCRIPTION OF THE FIGURES

The invention is described with reference to the following Figures.

DETAILED DESCRIPTION OF THE INVENTION

Figure 1:
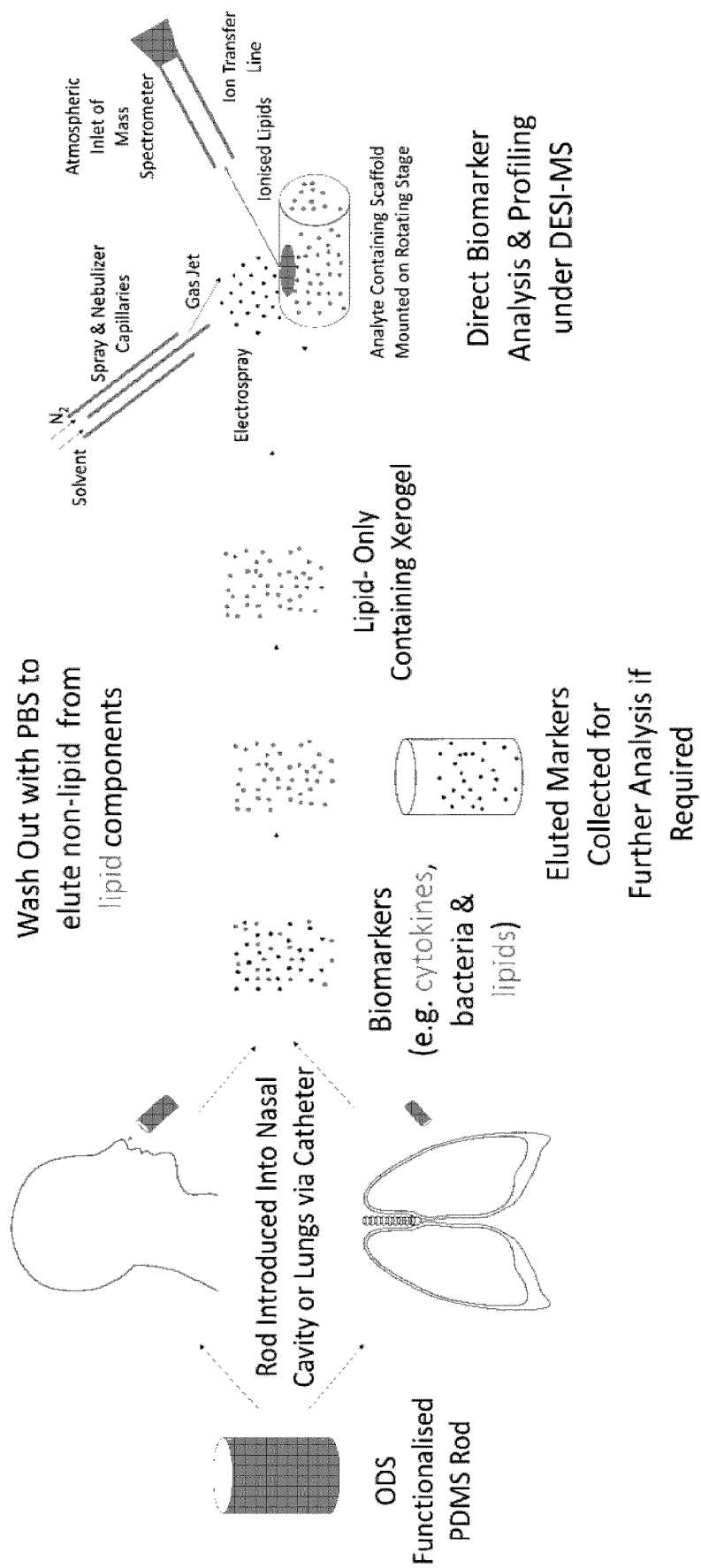
FIG. 1: Schematic of clinical lipid extraction process using proposed ODS surface functionalised lipid extracting swabs, specifically designed for DESI-MS enabled rapid analysis.

The invention is based on the surprising identification of materials that simplify and improve the sampling and analysis of biological molecules, metabolites and/or biomarkers. In one aspect, the invention relates to surface-functionalised poly(dimethyl) siloxane (PDMS). In another aspect, the invention relates to a surface-functionalised xerogel. These materials can be used to obtain biologically-relevant samples from the body, in particular from mucosal membranes, or from bodily fluids. In particular, it has been observed through extensive testing that xerogels or PDMS comprising a functional group capable of selectively binding to one or more biomarkers, metabolites and/or biological molecules have advantageous properties for taking samples of biomarkers, metabolites and/or biological molecules.

The mucosal linings and biological fluids of the mucous membranes are highly revealing of the underlying biological conditions in a subject. However, sampling biological fluids from the mucous membranes has proven difficult and has generally required the lavage of the mucous membrane to sample the biological fluids associated with the mucosa, and consequently the dilution of the biological fluids. This in turn makes it difficult to analyse the biomarkers in the biological fluids, leading to a loss of relevant diagnostic information. The present invention addresses at least this problem by providing materials particularly suited for such in situ sampling of mucosal membranes.

Furthermore, the materials allow for analysis of a sampled biological molecule while in situ on the material, without interfering with the analytical procedures. This removes the need to purify or otherwise process the sampled biological molecules before analysis.

The material may optionally contain two different surface functionalisations to detect two or more biological molecules. One way of achieving this would be to combine two materials of the invention, each of which has been differently functionalised, into a single moiety. For example, one side of a sampling device could be for detecting a first protein and the other side a second protein, or one side could be used to detect lipid and the other side to detect a protein (or more than one protein). Alternatively, a single xerogel or PDMS of the invention could be functionalised with two, three or more different moieties to selectively bind different biomarkers, biological molecules and/or metabolites. The presence of multiple binding moieties would be useful for detecting more than one biomarker, biological molecule and/or metabolite and thereby improving the accuracy of diagnosis.

Poly(Dimethyl) Siloxane

Polydimethylsiloxane (PDMS) is a widely used silicon-based organic polymer which belongs to a group of polymeric organosilicon compounds referred to as silicones. It is particularly known for its tuneable physical properties. PDMS is optically clear, and, in general, inert, non-toxic, and non-flammable. It is also called dimethicone and is one of several types of silicone oil (polymerised siloxane). Its applications range from contact lenses and medical devices to elastomers; it is also present in shampoos (as dimethicone makes hair shiny and slippery), food (antifoaming agent), caulking, lubricating oils, and heat-resistant tiles.

The chemical formula for PDMS is $CH_3[SiO(CH_3)_2]_nSi(CH_3)_3$, where n is the number of repeating monomer $[SiO(CH_3)_2]$ units. Industrial synthesis can begin from dimethyldichlorosilane and water by the following net reaction:
$$n\ Si(CH_3)_2Cl_2 + n+1\ H_2O \rightarrow HO[-SiO(CH_3)_2-]_nH + 2n\ HCl$$

The polymerisation reaction produces hydrogen chloride. For medical and domestic applications, a process was developed in which the chlorine atoms in the silane precursor were replaced with acetate groups. In this case, the polymerisation produces acetic acid, which is less chemically aggressive than HCl. Hydrolysis of $Si(CH_3)_2Cl_2$ generates a polymer that is terminated with two silanol groups ($-Si(CH_3)_2OH$). These reactive centers are typically "capped" by reaction with trimethylsilyl chloride. Silane precursors with more acid-forming groups and fewer methyl groups, such as methyltrichlorosilane, can be used to introduce branches or cross-links in the polymer chain. Under ideal conditions, each molecule of such a compound becomes a branch point. This can be used to produce hard silicone resins. In a similar manner, precursors with three methyl groups can be used to limit molecular weight, since each such molecule has only one reactive site and so forms the end of a siloxane chain. Manipulation of these by altering the conditions of the polymerisation allow for the production of a variety of polydimethylsiloxanes with tuneable physical properties.

Xerogels

Xerogels are known in the art. A xerogel is a porous, sponge-like matrix obtained from a gel by drying. Xerogels are typically produced by liquid phase processes or sol-gel processes, and then subsequent drying (e.g. freeze-drying or conventional drying methods). Such processes are generally known in the art, see for example Haysase G et al Angewandte Chemie International Edition, 2013. 52(7): p. 1986-1989; US 2014/0076070; and Japanese Patent Nos. 2893104 and 3394255). The xerogels are typically silica xerogels, but it will be apparent to one skilled in the art of xerogels that other xerogels can be used.

Xerogels can be prepared with very tunable physical properties simply by modifying experimental parameters, such as solvent, catalytic agent, pH, reagents and reaction time etc., during xerogel synthesis, see for example, Chapter 13 of Sol-Gel Science—The Physics and Chemistry of Sol-Gel processing, Brinker et al., Academic press, 1990.

Xerogels typically have a pore size within the range of 1-1000 nm. The xerogels of the present invention may typically have a pore size of 1-500 nm, a pore size of 1-250 nm, or a pore size of 1-150 nm.

Xerogels also have large surface areas within the range of 150-1000 $m^2/g$ as determined by the BET method as described by Brunauer, Emmett, and Teller, Jour. Am. Chem. Soc., 60, 309, 1938.

Xerogels can be prepared with a variety of chemical compositions, such as inorganic oxides (e.g. silica, alumina, and titania), inorganic alkoxides and their corresponding hydroxides (e.g. silicon alkoxides, aluminium alkoxide, zirconium alkoxide, vanadium alkoxide and titanium alkoxide), organic crosslinked polymers (e.g. resorcinol-formaldehyde), and biopolymers (e.g. cellulose and chitosan).

Typically the xerogel of the invention is a silica xerogel. Again, these can be prepared according to known methods, such as those disclosed in Haysase G et al Angewandte Chemie International Edition, 2013. 52(7): p. 1986-1989.

The silica based xerogel may be prepared by dissolving a silica source precursor into an aqueous solution, adjusting the pH of the solution to the range of 2-8 using a suitable pH modifier and stirring to form a gel, and then subsequently drying. Such a reaction is depicted below:

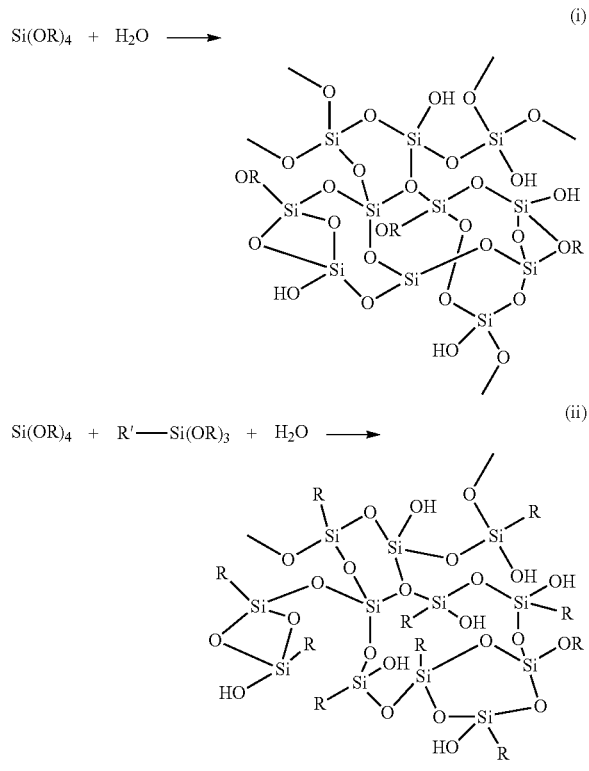

It will be readily apparent to one skilled in the art which R substituents are suitable. Each R may be individually selected from methyl, ethyl, propyl, butyl, pentyl, and hexyl and their branched forms such as i-propyl etc. In reaction (ii), a trifunctional alkoxysilane is used (i.e. an alkoxysilane having three alkoxyl groups involved in the polymerisation). R' may be selected from $C_1$-$C_8$ alkyls, $C_1$-$C_8$ haloalkyl, $C_1$-$C_8$ alkyl amines, $C_1$-$C_8$ alkyl thiols, $C_1$-$C_8$ alkylvinyls, phenyl groups. Again, it would be readily apparent to one skilled in the art which R' substituents are suitable. It would also be readily apparent that bifunctional alkoxylsilanes (i.e. an alkoxysilane having two alkoxyl groups involved in the polymerisation and two R' groups).

One advantage of using trifunctional and bifunctional alkoxysilanes is that they allow for modification of the surface groups of the xerogel. When a metal oxide or alkoxide is used, the metal oxide gel will be terminated with either hydroxyl (OH) or alkoxyl (OR) groups. In contrast, when a trifunctional or bifunctional alkoxysilane is used the R' groups are present on the surface of the silica xerogel. One skilled in the art would recognise that this allows for modification of silica xerogel's properties, such as the hydrophobicity/hydrophilicity, by selecting the appropriate R' group. In a specific embodiment, at least one of the bifunctional or trifunctional siloxane precursors is a mercaptosilane. In this embodiment, the R' groups are present on the surface of the silica xerogel are thiol (SH) groups.

Typical silica sources suitable for preparing a xerogel include tetramethoxysilane (TMOS), tetraethoxysilane (TEOS), tetrapropylsilane (TPOS), tetrabutoxysilane (TBOS), sodium silicate, potassium silicate, lithium silicate, dimethyldimethoxysilane (DMDMS, methyltrimethoxysilane (MTMS), 3,3,3-triflyoropropylmethydimethoxysilane, methylphenyldimethoxysilane, vinyltrimethoxysilane (VTMS), vinylmethyldimethoxysilane (VMDMS) methylvinyldimethoxysilane, 3-mercaptopropyltrimethoxysilane, mercaptomethylmethyldiethoxysilane, 3-mercaptopropylmethyldimethoxysilane, 3-mercaptopropyltriethoxysilane, and 3-mercaptopropyltrimethoxysilane. However, it will be apparent to one skilled in the art that other silica sources can be used.

In a specific embodiment, the xerogel of the invention is a silica xerogel that is a reaction product of tri-functional and di-functional siloxane precursors, wherein at least one of the tri-functional and/or di-functional siloxane precursors is a mercaptosilane. In a further embodiment, tri-functional and di-functional siloxane precursors are: (3-Mercaptopropyl)trimethoxysilane and Dimethoxydimethylsilane, optionally combined in a 3:2 molar ratio; Trimethoxymethylsilane and (3-Mercaptopropyl)methyldimethoxysilane, optionally combined in a 3:2 molar ratio.

An exemplary method for producing silica xerogels for the present invention involves:
(i) copolymerising a bifunctional alkoxylsilane with a trifunctional or higher functional alkoxysilane in a sol-gel reaction forming an Si—O—Si network;
(ii) drying to form a xerogel.

Polymerisation is conducted under conditions where silanol groups are produced through hydrolysis, with subsequent condensation polymerisation (also known as "gelation") occurring to form the Si—O—Si network. Such conditions are generally known by one skilled in the art.

Suitable polymerisation conditions include both acidic and basic conditions with a suitable pH modifier. Suitable acids include mineral acids (such as hydrochloric, sulfuric, nitric and phosphoric), carboxylic acids (such as acetic acid, citric acid, formic acid, gluconic acid, lactic, oxalic acid and tartaric acid), sulfonic acids (such as methanesulfonic acid, ethanesulfonic acid). In a specific embodiment, the acid is acetic acid.

Suitable bases include metal hydroxides, urea, and cyclic amine bases such as include piperazine, N-methyl piperazine, piperidine, N-methyl piperidine, morpholine, N-methyl morpholine, pyrrolidine, collidine, 1,8-Diazabicyclo[5.4.0]undec-7-ene (DBU), 1,4-Diazabicyclo[2.2.2]octane (DABCO), imidazole, N-methyl imidazole and benzimidazole. In a specific embodiment, the base is urea.

Polymerisation may be conducted in the presence of a surfactant, including cationinc surfactants, anionic surfactants and non-ionic surfactants. Suitable surfactants include CTAC, trimethyloctadecylammonium chloride (STAC), and dodecyltrimethylammonium chloride (DTAC), Behentrimonium Chloride (BTAC).

In a specific embodiment, the invention provides a method making a xerogel of the invention, wherein tri-functional and di-functional siloxane precursors are contacted under conditions that promote hydrolysis, optionally in the presence of an acidic and a basic pH modifier, optionally wherein the base is urea and the acid is acetic acid. In a further embodiment, CTAC is also present.

Suitable solvents include water, alcohols, nitriles (such as acetonitrile and propionitrile), acid amides (such as N,N-dimethylformamide and dimethylacetamide), and cyclic ethers (such as tetrohydrofuran and 1,4-dioxane), and combinations thereof (such as aqueous alcohols). Again, one of skill in the art will recognize other solvents that may be suitable for use in this reaction.

The reaction is typically done at room temperature (25° C.), but heating above room temperature may be used if necessary. The reaction may be completed at multiple temperatures, for example an initial temperature of 25° C. for the hydrolysis step with subsequent heating for the condensation polymerisation. Preferably, the condensation reaction occurs at a temperature between 25-100° C., most preferably about 80° C.

Reaction times are typically between 30 minutes to 3 hours, preferably about 1 hour for the initial hydrolysis reaction, and then up to 24 hours for the subsequent condensation reaction/gelation step. Again, one skilled in the art may recognise a variety of other suitable conditions for formation of the xerogel.

Suitable drying methods include conventional evaporative drying at room temperature or at an elevated temperature such as up to 100° C., or supercritical drying. In a specific embodiment, the gel is dried at 10-50° C., for example 20-35° C.

Xerogels of the present invention exhibit a high degree of wicking and/or absorbance, permitting the xerogel of the invention to absorb a biological fluid upon contact. The surface functionalisation of the xerogel allows for selective binding of a desired biomarker, biological molecule and/or metabolite present in the biological fluid.

The xerogels of the invention typically exhibit a wicking capacity of at least 0.25 g/g, 0.5 g/g, 0.75 g/g, 1 g/g, 2 g/g or 5 g/g within 120 s. In some embodiments, the wicking capacity is 0.25 g/g to 5 g/g in 120 s. In another embodiment, the wicking capacity is 0.5 g/g to 2 g/g in 120 s. In a further embodiment, the wicking capacity is 0.5 g/g to 1 g/g in 120 s.

The high degree of wicking is particularly advantageous when sampling a biological fluid from a mucous membrane. When the xerogel of the invention is brought into contact with the mucous membrane, the biological fluids associated with that membrane are wicked into the xerogel, thereby collecting a sample of undiluted biological fluid from the mucous membrane in the xerogel. It is also particularly advantageous to collect the sample in as short a timeframe as possible, in order to minimise discomfort to the subject and to minimise the contact time required to obtain an adequate sample of the biological fluid for subsequent analysis. The xerogels of the invention can wick sufficient biological fluid in less than 5 minutes. In a particular embodiment, the xerogels of the invention can wick sufficient biological fluid in 60 s to 5 minutes, 120 s to 5 minutes or 120 s to 180 s.

The xerogels of the invention also have a high absorbance capacity. The absorbance of the xerogels of the invention is typically at least 0.25 g/g, 0.5 g/g, 0.75 g/g, 1 g/g, 2 g/g or 5 g/g. In some embodiments, the absorbance is 0.25 g/g to 5 g/g. In another embodiment, the absorbance is 0.5 g/g to 2 g/g. In a further embodiment, the absorbance is 0.5 g/g to 1 g/g.

The favourable durability, absorbance and wicking characteristics of the xerogels of the invention can also be used advantageously to sample biological molecules in a bodily fluid. These fluids have typically been excreted or extracted from the body, such as sputum, mucus, saliva, blood, sweat or urine. Other fluids include phlegm, bile, cerebrospinal fluid and amniotic fluid. Ascitic fluid is another typical bodily fluid. In certain embodiments, the fluid is nasal fluid. In one embodiment, a xerogel of the invention can be used to extract one or more biological molecules of interest from a nasal lavage. This would simplify the processing steps required to analyse the content of the nasal lavage.

The xerogels of the present invention may have a spongy feel. The xerogels may be compressible and elastic. In a particular embodiment, the xerogels of the invention exhibit a strain of at least 60% at 5N, for example at least 70%, at least 75% or at least 80%, or 60-90%, 70-85%, 75%-83% at 5N. In a further embodiment, the xerogels of the invention exhibit a stress of at least 0.1 at 5N, for example at least 0.1, at least 0.15 or at least 0.2, or 0.1-0.3%, 0.15-0.3, 0.2-0.3% at 5N. In certain embodiments, the stress is at least 60% at 5N and the strain is at least 0.1 at 5N. In another embodiment, the stress is 60-90% at 5N and the strain is 0.1-0.3 at 5N.

Surface Functionalisation

The xerogels and PDMS materials of the invention can be surface functionalised with a variety of different moieties as required to selectively bind different biomarkers, biological molecules and/or metabolites. Each xerogel or PDMS material will typically be functionalised to selectively bind a single class of biological molecule, for example lipids or proteins, and may be functionalised to bind a specific single target molecule. The specific functionalisation can be chosen based on the surface chemistry of the xerogel or PDMS, the nature of the functional moiety, the properties of the biomarker, biological molecule and/or metabolite being bound and the intended purpose of the xerogel.

"Surface functionalisation" relates to the modification of the surface chemistry of the xerogel or PDMS substrate with a functional moiety that specifically binds to a biological molecule and/or biomarker.

In one embodiment, the xerogel of the invention or PDMS disclosed herein is surface modified to covalently bind a functional moiety which is capable of selectively binding to a biomarker, biological molecule and/or metabolite. The covalent bond between the xerogel or PDMS and the functional group may include at least one selected from a silyl group, ester group, an ether group, a carbonyl group, an amide group, and a thiol group. However, one skilled in the art would recognise that a variety of other covalent bonds are suitable.

As disclosed herein, xerogels have the advantage that they can be prepared to have a variety of surface moieties based on the precise selection of starting materials. This allows for a variety of surface functionalisation to modify the surface of the xerogel using a variety of well-known techniques in the art.

In some embodiments, to introduce surface modification, a pretreatment process may be necessary to introduce a nucleophilic group to the surface of the xerogel or PDMS. This may be performed by a variety of methods known in the art such as through a wet process using a strong acid, ultrasound (or ultrasonic treatment), or heat in a liquid phase or a dry process using plasma or vacuum UV irradiation. However, one skilled in the art would recognise that a variety of other pretreatments are suitable.

In some embodiments, the pretreatment is plasma treatment with oxygen plasma. This is used to provide labile hydroxyl groups on the surface of the PDMS or xerogel as depicted below:

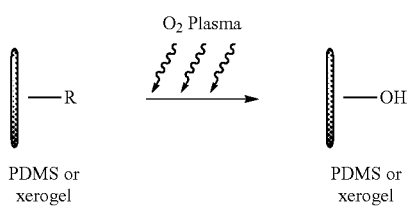

By introducing this nucleophilic functional group onto the surface of the PDMS or xerogel, conventional chemistry techniques can then be utilised to add groups which are capable of selectively binding to a biological molecule.

In one embodiment, a $C_4$-$C_{20}$ alkyl silicate is grafted to the surface of the PDMS or xerogel by reaction of a nucleophilic surface group (intrinsically present because of the choice of the starting materials or introduced by a pretreatment process as described above) with a $C_4$-$C_{20}$ alkyl silicate that contains at least one suitable leaving group (such as a tosylate group, mesylate group, alkoxide or halogen) in a suitable solvent (such as hexane, chloroform, DMSO etc.). The alkyl silicate may contain up to three suitable leaving groups, and therefore be bound to the xerogel or PDMS by multiple covalent bonds. An example is depicted below with octadecyl-trichlorosilane (OTS) as the $C_4$-$C_{20}$ alkyl silicate. However, one skilled in the art would readily recognise that other solvents and leaving groups may be suitable.

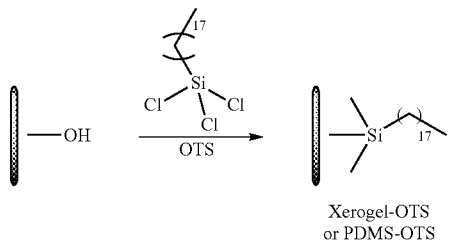

This type of "click" chemistry is suitable to attach a range of functional groups to the surface of the xerogel or PDMS substrate by simply using a precursor which contains the functional group and suitable leaving group. The nucleophilic surface group reacts with this precursor to leave the surface modified xerogel or PDMS with the relevant functional group attached to the surface.

Suitable functional groups which can be attached to the surface of the xerogel or PDMS include sugars (such as mannose), modified sugars (such as mannose methacrylate), and a variety of block copolymers (such as methacrylate-methylmethacrylate copolymers). In one embodiment, the copolymer to be grafted to the xerogel or PDMS is a methacrylate-methylmethacrylate polymer, in the method depicted below. The values of n and m can be readily controlled by varying the polymerisation conditions used to prepare the block copolymer. This is well known to one skilled in the art.

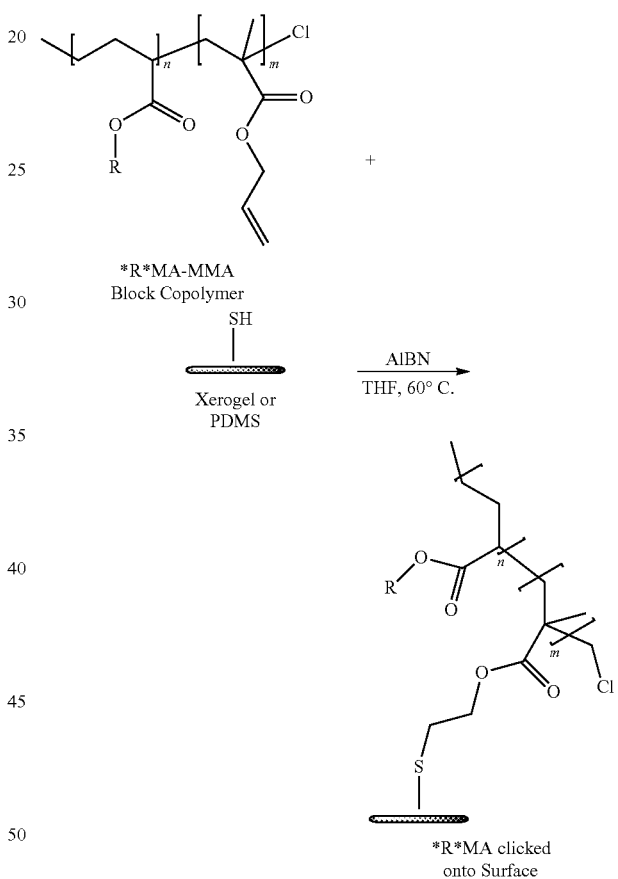

Although this depicts the use of a xerogel or PDMS with a thiol group as the nucleophilic functional group, it would be immediately apparent that other nucleophilic functional groups such a hydroxy or amine would be suitable using conventional chemistry techniques. Again, it would be readily apparent to one skilled in the art what reaction conditions are appropriate.

In some embodiments, the surface of the xerogel or PDMS may be modified to include a polymer using conventional methods in the art such as Atom transfer radical polymerisation (ATRP) or Reversible addition-fragmentation chain transfer (RAFT) polymerisation.

Again this is achieved using conventional chemistry techniques. A suitable initiator is attached to the surface of the xerogel or PDMS using nucleophilic substitution of an initiator which contains a suitable leaving group (as described above in relation to alkyl silicates) by a nucleophilic group on the surface of the PDMS or xerogel (intrinsically present because of the choice of the starting materials or introduced by a pretreatment process as described above). This prepares a xerogel or PDMS with an initiator terminated surface. An example of this is provided below.

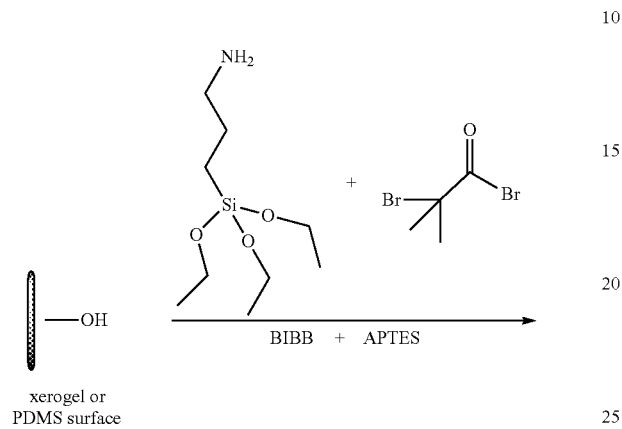

xerogel or PDMS surface

BIBB + APTES

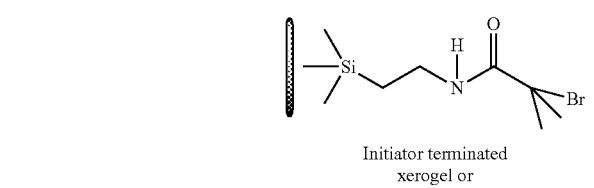

Initiator terminated xerogel or PDMS surface

Although this example contains a hydroxyl group as the relevant nucleophilic group on the surface of the xerogel or PDMS substrate, one skilled in the art would recognise that other nucleophilic groups such as amine and thiol groups would also be suitable.

A suitable monomer is then added and conventional polymerisation ensues, resulting in a polymer grafted to the surface of the xerogel or PDMS by the initiator. The properties and composition of the polymer can be controlled using standard techniques in the art known to the skilled person, e.g. controlling the amount of monomer and catalyst etc. An example of this is provided below using an octyldecylmethacrylate monomer.

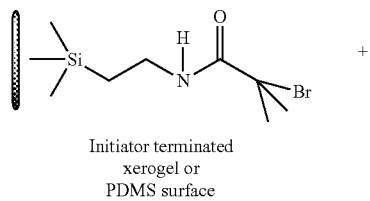

Initiator terminated xerogel or PDMS surface

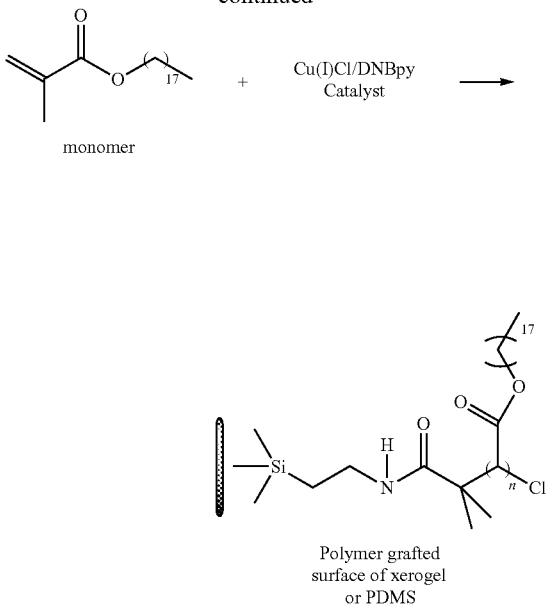

monomer

Polymer grafted surface of xerogel or PDMS

As one skilled in the art would recognise, the degree of polymerisation may be altered by suitably adjusting the reaction time, ratio of xerogel/PDS:monomer and solvent.

In some embodiments, the xerogel or PDMS already contains a nucleophilic functional group on the surface. These are therefore suitable for surface-initiated polymerisation (SIP) with suitable monomers.

Preferably the xerogel or PDMS will contain thiol groups, amine groups or hydroxide groups on the surface. In one embodiment, a xerogel which contains surface thiol groups is suitable for SIP polymerisation (i.e. thiol-ene surface-initiated polymerisation (TSIP)) with a variety of monomers, such a methacrylates (in particular, octadecylmethacrylate or mannose methacrylate), using conventional polymerisation techniques.

The xerogel or PDMS of the present invention can also be surface modified to include a variety of antigen-binding proteins such as antibodies or antibody receptors. Again, the covalent binding of these antigen-binding proteins, such as antibodies, onto the surface of the xerogel can be achieved through the "click" chemistry methodology described above. These are prepared by reacting the xerogel or PDMS which contains a surface nucleophilic functional group (such as thiol, amine or hydroxy) with the relevant antibody which contains a suitable leaving group. This is achieved using convention techniques known in the art for the preparation of ELISA assays on glass plates.

In one embodiment, the xerogel or PDMS will have surface thiol groups and a heterobifunctional crosslinking compound will be used (such as N-maleimidoburyryl-oxysuccinimide ester, known as GMBS or m-maleimidobenzoyl-N-hydroxysuccinimide ester (MBS), N-ε-malemidocaproyl-oxysuccinimide ester (EMCS), succinimidyl 3-(2-pyridyldithio)propionate (SPDP), Succinimidyl 6-[3-(2-pyridyldithio)propionamido] hexanoate (LC-SPDP), succinimidyl 4-(p-maleimidophenyl)butyrate (SMPB), 4-(4-N-maleimidophenyl)butyric acid hydrazide (MPBH), or 3-(2-pyridyldithio)propionyl hydrazide (PDPH)). This is depicted below.

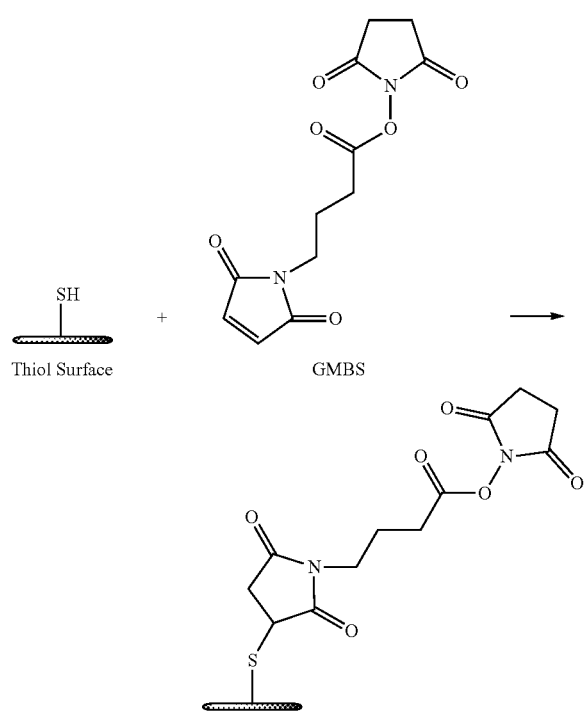

One skilled in the art is aware of suitable reaction conditions for this reaction, such as those described in Shriver-Lake et al. The skilled person would readily appreciate that the above chemistry applies equally for a xerogel or PDMS group which contains an amine or hydroxyl group on the surface.

In a specific embodiment, the invention provides a method for the preparation of a surface functionalised xerogel of the invention comprising surface functionalising the xerogel with: poly N-octadecyl methacrylate (ODMA) by thiol-ene surface-initiated polymerisation (TSIP); mannose by thiol-ene surface-initiated polymerisation (TSIP); or an antibody by reacting a thiol xerogel with a heterobifunctional crosslinking compound and an antibody.

Uses of the Surface-Functionalised Xerogels

The xerogels of the present invention can be used to sample biomarkers, biological molecules and/or biological fluids. In particular, the invention provides the use of a xerogel of the invention for sampling a biological fluid from a mucous membrane of a subject.

In some embodiments, a xerogel of the invention can be formed into a size and shape for easy sampling of a biological fluid from a mucus membrane. In a particular embodiment, a xerogel of the invention is suitable for insertion into a bodily orifice, for example a nostril, for direct contact with the mucosa. Compressibility, elasticity and durability are important characteristics for sampling from bodily orifices. The xerogels of the invention are therefore particularly suited to sampling in this way. Orifices include the nostrils, ear canals, mouth, anus/rectum, vagina, or urethra. The xerogels of the invention are particularly suited to sampling from the mucosa, such as the oral mucosa, the nasal mucosa, the rectal mucosa, the aural mucosa, the vaginal mucosa, and/or the urethral mucosa. The fallopian tube mucosa is another example of a mucosa that can be sampled using a xerogel of the invention, as described herein, and the xerogel can be provided in a suitable size and shape.

In a particular embodiment, the xerogel is dimensioned for insertion into the nostril for sampling a biological fluid from the nasal mucosa. In another embodiment, the xerogel is dimensioned for insertion into the ear canal for sampling a biological fluid from the aural mucosa. In another embodiment, the xerogel is dimensioned for insertion into the mouth for sampling a biological fluid from the oral mucosa. In another embodiment, the xerogel is dimensioned for insertion into the throat for sampling a biological fluid from the tracheal mucosa. In another embodiment, the xerogel is dimensioned for insertion into the vagina for sampling a biological fluid from the vaginal mucosa. In another embodiment, the xerogel is dimensioned for insertion into the anus for sampling a biological fluid from the anal and/or rectal mucosa. In another embodiment, the xerogel is dimensioned for insertion into the urethra for sampling a biological fluid from the urethral mucosa. Typically the nostrils will be the site of sampling, and the xerogel shaped to enter one or both nostrils and contact the nasal mucosa without undue discomfort to the subject.

In some embodiments, the biological fluid is a bodily fluid. This may be sputum, mucus, saliva, blood, sweat or urine. Other fluids include phlegm, bile, cerebrospinal fluid and amniotic fluid. Another bodily fluid is ascitic fluid. In the condition known as ascites, ascitic fluid accumulates in the abdomen, typically the peritoneal cavity. Ascites can be caused by a number of disorders, including liver disease (e.g. cirrhosis), cancer, heart failure, tuberculosis, pancreatitis and blockage of the hepatic vein. Sampling ascitic fluid is therefore often diagnostically useful. In one embodiment, a xerogel of the invention is dimensioned to sample ascitic fluid, for example for insertion into the peritoneal cavity. Sampling ascitic fluid using the xerogel of the invention can be used, for example, to assist in the diagnosis of cancer. This sampling may be carried out using a catheter to introduce the xerogel to the ascitic fluid in the abdomen.

As noted elsewhere herein, in some embodiments the xerogel is dimensioned for insertion in the body in a minimally-invasive procedure, for example catheter insertion. In these embodiments, the xerogel can be used to sample body cavities and, in particular, internal fluids. An example of an internal fluid is ascites. Another example is insertion into the fallopian tube. The lack of expansion of the xerogel of the invention is particularly beneficial in these embodiments, because the xerogel will not expand and become stuck in the catheter (or other tube or sampling device) after contact with the body fluid.

In these embodiments, the xerogels of the present invention may have a spongy feel and may be compressible and elastic. In a particular embodiment, the xerogels of the invention exhibit a strain of at least 60% at 5N, for example at least 70%, at least 75% or at least 80%, or 60-90%, 70-85%, 75%-83% at 5N. In a further embodiment, the xerogels of the invention exhibit a stress of at least 0.1 at 5N, for example at least 0.1, at least 0.15 or at least 0.2, or 0.1-0.3%, 0.15-0.3, 0.2-0.3% at 5N. In certain embodiments, the stress is at least 60% at 5N and the strain is at least 0.1 at 5N. In another embodiment, the stress is 60-90% at 5N and the strain is 0.1-0.3 at 5N.

In certain embodiments, the xerogels of the invention may be described as monolithic. Monolithic silica, for example, is known in the art.

The invention also provides method of sampling a biological molecule from a mucous membrane of a subject comprising contacting the mucous membrane with a xerogel or sampling device of the invention. When the xerogel or sampling device of the invention is brought into contact with the mucous membrane, the biological fluids associated with that membrane are wicked into the xerogel, thereby collecting a sample of undiluted biological fluid from the mucous membrane in the xerogel. The surface modification of the xerogel or sampling device of the invention may also preferentially take up a particular biological molecule and/or biomarker of interest. In the sampling methods of the invention, it is advantageous to collect the sample in as short a timeframe as possible, in order to minimise discomfort to the subject and to minimise the contact time required to obtain an adequate sample of the biological fluid for subsequent analysis. The xerogels of the invention can wick sufficient biological fluid in less than 5 minutes. In a particular embodiment, the xerogels of the invention can wick sufficient biological fluid in 60 seconds to 5 minutes, 120 seconds to 5 minutes or 120 seconds to 180 seconds. The methods of the invention may therefore involve a contacting step that is of in 60 seconds to 5 minutes, 120 seconds to 5 minutes or 120 seconds to 180 seconds.

The methods of the invention may further comprise an elution step and/or and analysis step. The analysis may be carried out on the eluate from the xerogel or sampling device, or may be carried out directly on the xerogel or sampling device.

The invention therefore provides a method of sampling a biological molecule and/or biomarker from a mucous membrane of a subject comprising contacting the mucous membrane with a xerogel of the invention or a sampling device of the invention; optionally eluting the biological molecule and/or biomarker; and analysing the eluate and/or the xerogel for the presence or absence of the biological molecule and/or biomarker.

Examples of direct analysis include analysis of colour changes, including visual inspection, and fluorometry; Mass Spectrometry, including LC-MS, HPLC-MS, DESI-MS and use of tandem mass spectrometry (MS/MS) on such MS systems; microscopy including fluorescent microscopy, with or without prior staining; sandwich ELISA; and nucleic acid analysis and/or amplification including PCR, qPCR, RT-PCR, LCR, sequencing including Sanger sequencing and next generation sequencing.

As shown in the Examples, a preferred embodiment of the invention relates to ODS-functionalised silica xerogels and their analysis by mass spectrometry, such as LC-MS (Liquid Chromatography Mass Spectrometry).

The present invention provides a further advantage over known methods of sampling biological fluids in that viable cells can be eluted from the xerogels and sampling devices of the present invention. The present invention therefore provides a method of sampling a cell from a mucous membrane of a subject comprising contacting the mucous membrane with a xerogel of the invention or a sampling device of the invention; optionally eluting the cell from the xerogel of the invention or sampling device of the invention; and analysing the cells in the eluate and/or the xerogel.

Uses of the Surface-Functionalised PDMS

The PDMS of the invention can be used for the same applications as the xerogels.

For the avoidance of doubt, the PDMS of the present invention can thus be used to sample biomarkers, biological molecules and/or biological fluids. In particular, the invention provides the use of a PDMS of the invention for sampling a biological fluid from the mucous membrane of a subject.

The PDMS of the invention can be used advantageously to sample biological molecules from a bodily fluid. These fluids have typically been excreted or extracted from the body, such as sputum, mucus, saliva, blood, sweat or urine. Other fluids include phlegm, bile, cerebrospinal fluid and amniotic fluid. Ascitic fluid is another typical bodily fluid. In certain embodiments, the fluid is nasal fluid. In one embodiment, a PDMS of the invention can be used to extract one or more biological molecules of interest from a nasal lavage. This would simplify the processing steps required to analyse the content of the nasal lavage.

In some embodiments, a PDMS of the invention can be formed into a size and shape for easy sampling of a biological fluid from a mucus membrane. In a particular embodiment, a PDMS of the invention is suitable for insertion into a bodily orifice, for example a nostril, for direct contact with the mucosa. The fallopian tube mucosa is another example of a mucosa that can be sampled using a PDMS of the invention, as described herein, and the PDMS can be provided in a suitable size and shape.

In a particular embodiment, the PDMS is dimensioned for insertion into the nostril for sampling a biological fluid from the nasal mucosa. In another embodiment, the PDMS is dimensioned for insertion into the ear canal for sampling a biological fluid from the aural mucosa. In another embodiment, the PDMS is dimensioned for insertion into the mouth for sampling a biological fluid from the oral mucosa. In another embodiment, the xerogel is dimensioned for insertion into the throat for sampling a biological fluid from the tracheal mucosa. In another embodiment, the PDMS is dimensioned for insertion into the vagina for sampling a biological fluid from the vaginal mucosa. In another embodiment, the PDMS is dimensioned for insertion into the anus for sampling a biological fluid from the anal mucosa. In another embodiment, the PDMS is dimensioned for insertion into the urethra for sampling a biological fluid from the urethral mucosa. Typically the nostrils will be the site of sampling, and the PDMS is shaped to enter one or both nostrils and contact the nasal mucosa without undue discomfort to the subject.

In some embodiments, the biological fluid is a bodily fluid. This may be sputum, mucus, saliva, blood, sweat or urine. Other fluids include phlegm, bile, cerebrospinal fluid and amniotic fluid. Another bodily fluid is ascitic fluid. In the condition known as ascites, ascitic fluid accumulates in the abdomen, typically the peritoneal cavity. Ascites can be caused by liver disease (e.g. cirrhosis), cancer, heart failure, tuberculosis, pancreatitis and blockage of the hepatic vein.

Sampling ascitic fluid is therefore often diagnostically useful. In one embodiment, a PDMS of the invention is dimensioned to sample ascitic fluid, for example for insertion into the peritoneal cavity. Sampling ascitic fluid using the PDMS of the invention can be used, for example, to assist in the diagnosis of cancer. This sampling may be carried out using a catheter to introduce the PDMS to the ascitic fluid in the abdomen.

As noted elsewhere herein, in some embodiments the PDMS is dimensioned for insertion in the body in a minimally-invasive procedure, for example catheter insertion. In these embodiments, the PDMS can be used to sample body cavities and, in particular, internal fluids. An example of an internal fluid is ascites. Another example is insertion into the fallopian tube. The lack of expansion of the PDMS of the invention is particularly beneficial in these embodiments, because the PDMS will not expand and become stuck in the catheter (or other tube or sampling device) after contact with the body fluid.

In certain embodiments, the PDMS of the invention may be described as monolithic.

As shown in the Examples, a preferred embodiment of the invention relates to ODS surface functionalisation of PDMS. This ODS-functionalised PDMS is particularly suitable for mass spectrometry, in particular DESI-MS (Desorption electrospray ionisation mass spectrometry) analysis. This can be used to sample and analyse lipids, for example. DESI-MS provides rapid (almost instant) analysis capabilities, so the use of ODS-PDMS in DESI-MS provides a streamlined system.

Sampling Devices

Sampling as used herein is the gathering of matter from a subject. In particular, the matter gathered may be a biological fluid, typically sputum, mucus, saliva, blood, sweat or urine. Ascitic fluid is another typical bodily fluid. In a specific embodiment, the biological fluid is a biological fluid from a mucous membrane, for example nasal fluid. The site of sampling will typically dictate the dimensions and properties of the sampling device of the invention. The sampling device must be proportioned and have properties suitable for sampling from the desired site.

Sampling devices of the invention comprise a xerogel of the invention and/or surface modified PDMS as described herein.

Sampling devices of the invention include dip sticks, saliva collection devices, urine collection devices, sponges, swabs, gauzes, pads and rods. In a particular embodiment, the sampling device of the present invention comprises a surface-modified PDMS rod as described herein. In one embodiment, the surface-modified PDMS rod is proportioned for insertion into a bodily orifice. In particular, the surface-modified PDMS is typically proportioned for insertion into a nasal passage for sampling a biological fluid, biological molecule and/or biomarker from the nasal mucosa. In a specific embodiment, the PDMS is an ODS surface-modified PDMS rod. Sampling devices of this aspect of the invention are particularly suited to the sampling of lipid biomarkers and also to direct analysis by DESI-MS. Although a rod is envisioned as a convenient sampling configuration, other suitable configurations may be used such as, for example, a disk, sphere, cone or frustocone.

In certain embodiments, the PDMS or xerogel of the invention is attached to a supporting or surrounding device for ease of introduction, sampling and removal. For example, the PDMS or xerogel can be comprised within a cannula or catheter apparatus, which can aid the introduction and/or removal of the PDMS or xerogel into the body, such as into a fallopian tube as described above. A device of the invention for sampling a fallopian tube may have particular utility in diagnosing ovarian cancer, such as early-stage ovarian cancer.

In a further embodiment, the sampling device of the present invention comprises a xerogel of the present invention proportioned for insertion into a bodily orifice. In particular, the surface-modified xerogel is typically proportioned for insertion into a nasal passage for sampling a biological fluid, biological molecule and/or biomarker from the nasal mucosa. In this embodiment, the xerogels of the present invention may have a spongy feel and may be compressible and elastic. In a particular embodiment, the xerogels of the invention exhibit a strain of at least 60% at 5N, for example at least 70%, at least 75% or at least 80%, or 60-90%, 70-85%, 75%-83% at 5N. In a further embodiment, the xerogels of the invention exhibit a stress of at least 0.1 at 5N, for example at least 0.1, at least 0.15 or at least 0.2, or 0.1-0.3%, 0.15-0.3, 0.2-0.3% at 5N. In certain embodiments, the stress is at least 60% at 5N and the strain is at least 0.1 at 5N. In another embodiment, the stress is 60-90% at 5N and the strain is 0.1-0.3 at 5N.

In a specific embodiment, one or more sampling devices of the invention is provided in a kit, said kit optionally comprising further reagents for the elution and/or analysis of the biomarkers. The kit may comprise a wash buffer or eluant, and a separate analytical buffer. The kit may include instructions for using the device and carrying out the subsequent analysis. Suitable analytical techniques are described elsewhere herein, and include mass spectrometry and microscopy.

Methods of Diagnosis

The present invention also provides a method of diagnosing a condition, disease, disorder or irregularity in a subject, said method comprising obtaining a sample of a biological fluid, optionally from a membrane, using a surface functionalised xerogel or PDMS according to the invention or a sampling device according to the invention; detecting the presence or absence of a biomarker, biological molecule or metabolite in the sample of biological fluid; and diagnosing the subject based on the presence or absence of the biomarker, biological molecule or metabolite in the biological fluid.

This may be used to detect a biomarker of a disease or disorder, or to detect the presence of a metabolite that is indicative of good or poor health. Alternatively, this method could be used to detect the presence of a narcotic, illicit drug or performance-enhancing drug in the subject.

In some disclosed embodiments, a further step of treating the patient for a diagnosed disease or disorder may be carried out.

In one embodiment, a method is provided of diagnosing a disease or disorder in a subject, said method comprising obtaining a sample of a biological fluid, optionally from a membrane, with a surface functionalised xerogel or PDMS according to the invention or a sampling device according to the invention; detecting the presence or absence of a biomarker in the sample of biological fluid; and diagnosing the subject with a disease or disorder based on the presence or absence of the biomarker in the biological fluid.

In some embodiments, the biological fluid is ascitic fluid.

In one embodiment, a method is provided of diagnosing an infection in a subject, said method comprising obtaining a sample of a biological fluid from a membrane with a surface functionalised xerogel or PDMS according the invention or a sampling device according to the invention; detecting the presence or absence of a biomarker in the sample of biological fluid; and diagnosing the subject with an infection based on the presence or absence of the biomarker in the biological fluid.

The infection may typically be a respiratory infection wherein the sample is collected by contacting the xerogel or PDMS of the invention with nasal mucosa.

Typically, the xerogel will be an antibody functionalised xerogel and the biomarker will be a protein biomarker. However, the invention also encompasses other functionalisations, including the detection of cells using mannose surface functionalised xerogels of the invention.

When the intention is to determine whether a subject has a bacterial or viral infection, the protein (or other) biomarker is associated with a bacterial or viral infection. Such biomarkers will be apparent to the skilled person, and include cytokines such as the interleukin family of proteins.

In one embodiment, the invention provides method of diagnosing a bacterial infection or a viral infection, wherein the xerogel or PDMS is an antibody functionalised xerogel or PDMS comprising an anti-interferon α, the biological fluid is from a subject with an infection and wherein the protein biomarker is interferon α, and wherein the presence of interferon α is indicative of a bacterial infection and the absence of interferon α is indicative of a viral infection. In a specific embodiment, the biological fluid is mucosal fluid from the nasal mucosa.

Further biomarkers that are indicative of bacterial infections include cytokines and interleukins. Particular biomarkers include: TNF-related apoptosis-inducing ligand (TRAIL), Granulocyte-macrophage colony-stimulating factor (GM-CSF), Interleukin 1-beta (IL-1β), C-reactive protein (CRP), soluble triggering receptor expressed on myeloid cells 1 (sTREM1), proadrenomedullin, serum procalcitonin (PCT), soluble urokinase-type plasminogen activator receptor (suPAR), atrial natriuretic peptide (ANP), IL-6, IL-8, IL-27, and CD64.

Further specific biomarkers that are indicative of viral infections include: Interferon-stimulated gene 15 (ISG15), IL-16, oligoadenylate synthetases-like protein (OASL), Adhesion G protein-coupled receptor E5 (ADGRE5).

The invention also provides a method of sampling cells of interest from a subject, said method comprising: obtaining a sample of biological fluid, optionally from a mucous membrane, with xerogel or PDMS of the invention or a sampling device of the invention; and detecting the presence or absence of the cells of interest in the sample of biological fluid.

Specific cells that are indicative of a disease, disorder or infection to be diagnosed include bacterial cells, including gram-negative bacterial cells, gram positive bacterial cells; host cells such as immune cells, such as dendritic cells, lymphocytes including B cells and T cells, macrophages, NK cells, innate lymphoid cells, eosinophils, basophils, mast cells, neutrophils and/or monocytes; host cells such as cancerous or pre-cancerous cells including, but not limited to, cancer of the respiratory tract such as mouth cancer, tongue cancer, nasal and paranasal sinus cancer, pharyngeal cancer, laryngeal cancer, tracheal cancer, oesophageal cancer, lung cancer, bronchial adenoma; cervical cancer; prostate cancer; colon cancer; rectal cancer; ovarian cancer.

In this embodiment of the invention, the surface functionalisation of the xerogel, PDMS or device of the invention is specific for the cell of interest. In one embodiment, the xerogel, PDMS or device is functionalised with a protein or sugar molecule to which the cell of interest will bind. For example, different cells possess different cell surface markers. In a specific embodiment, dendritic cells display DC-SIGN (Dendritic Cell-Specific Intercellular adhesion molecule-3-Grabbing Non-integrin, also known as CD209) and mannose receptor (CD206), which bind to mannose-functionalised materials of the invention.

In a specific embodiment, the invention provides a method of sampling dendritic cells from a subject, said method comprising: obtaining a sample of biological fluid, optionally from a mucous membrane with a mannose surface-functionalised xerogel of the invention or a sampling device of the invention comprising a mannose surface-functionalised xerogel; and detecting the presence or absence of dendritic cells in the sample of biological fluid.

In a further embodiment, the xerogel is functionalised with an antibody that is specific for a particular cell type. For example, B lymphocytes can be sampled using a xerogel of the invention functionalised with an anti-CD20 antibody. The xerogel may be functionalised with an antibody that is specific for a particular tumour antigen or tumour cell type, for the detection and/or diagnosis of cancer. The xerogel may be functionalised with an antibody that is specific for a particular viral antigen or virus type, for the detection and/or diagnosis of a viral disease. Specific viruses of interest include influenza viruses, parainfluenza viruses, adenoviruses, rotaviruses, respiratory syncytial virus (RSV), coronaviruses, including the SARS coronavirus, Ebola virus, HIV, and enteroviruses. Suitable antibodies for the detection of these viruses are known in the art. In some embodiments, the virus may be a bacterial virus, or bacteriophage.

In some embodiments, the surface functionalisation of the xerogel, PDMS or device of the invention provides for binding to a bacteriophage. This xerogel, PDMS or device can then be used for detection or diagnosis of the presence of the bacteriophage. In one embodiment, the xerogel, PDMS or device is functionalised with a protein or sugar molecule to which the bacteriophage of interest will bind. The protein may typically be an antibody, e.g. an antibody that is specific for a bacteriophage coat protein. The antibody may bind to the bacteriophage of interest and not to other bacteriophages.

The site of sampling will typically dictate the infection to be determined. For example, sampling the nasal mucosa will typically be to diagnose a respiratory tract infection. Sampling the ear canal will typically be to diagnose an ear infection. Sampling the mouth or throat will typically be of assistance in diagnosing a throat infection. Sampling the vagina or urethra may be useful in detecting a sexually transmitted infection or a urinary tract infection, as appropriate. Sampling the fallopian tube may be useful in detecting ovarian cancer.

Typical respiratory tract infections include upper respiratory tract infections and lower respiratory tract infections. Upper respiratory tract infections can include the common cold, tonsillitis, sinusitis, laryngitis and influenza. Lower respiratory tract infections can include influenza, bronchitis, pneumonia, bronchiolitis and tuberculosis.

In certain animals, such as cattle, tuberculosis is a particular concern and its early detection particularly important. Indeed, "Bovine TB" (caused by the bacterium *Mycobacterium bovis*) can infect and cause disease in mammals other than cattle, including humans, deer, goats, pigs, cats, dogs and badgers. In this instance, the xerogel can be functionalised with an anti-tuberculosis antibody.

Definitions

As used herein, the term "subject" includes human and animal subjects. In certain aspects, the subject is a mammal, for example a rodent, for example a rat, mouse or Guinea pig, a cat, a dog, a goat, a pig, a cow, a horse, or a primate, for example a human. In certain embodiments, the subject is a human. The animal may be a bird. In other embodiments, the subject is a farm animal, for example an ovine animal, a bovine animal, a caprine animal, an equine animal or a bird such as a chicken, turkey, goose or duck.

The term "antigen-binding protein" refers to a protein that is capable of specifically binding an antigen, e.g. a target or its signaling partner, or that is capable of binding an antigen with a measurable binding affinity. Examples of antigen-binding proteins include antibodies or antigen-binding fragments thereof, peptibodies, polypeptides and peptides, optionally conjugated to other peptide moieties or non-peptidic moieties. Antigens to which an antigen-binding protein may bind include any proteinaceous or non-proteinaceous molecule that is capable of eliciting an antibody response, or that is capable of binding to a polypeptide binding agent with detectable binding affinity greater than non-specific binding. The antigen to which a modulating antigen-binding protein binds may include a target, a signaling partner of a target, and/or a complex comprising the target and its signaling partner.

The term "antibody" is used in the broadest sense and includes fully assembled antibodies, tetrameric antibodies, monoclonal antibodies, polyclonal antibodies, multispecific antibodies (e.g., bispecific antibodies), antibody fragments that can bind an antigen (e.g., Fab', F'(ab)2, Fv, single chain antibodies, diabodies), and recombinant peptides comprising the forgoing as long as they exhibit the desired biological activity. An "immunoglobulin" or "tetrameric antibody" is a tetrameric glycoprotein that consists of two heavy chains and two light chains, each comprising a variable region and a constant region. Antigen-binding portions may be produced by recombinant DNA techniques or by enzymatic or chemical cleavage of intact antibodies. Antibody fragments or antigen-binding portions include, inter alia, Fab, Fab', F(ab')2, Fv, domain antibody (dAb), complementarity determining region (CDR) fragments, CDR-grafted antibodies, single-chain antibodies (scFv), single chain antibody fragments, chimeric antibodies, diabodies, triabodies, tetrabodies, minibody, linear antibody, chelating recombinant antibody, a tribody or bibody, an intrabody, a nanobody, a small modular immunopharmaceutical (SMIP), an antigen-binding-domain immunoglobulin fusion protein, a camelized antibody, a VHH containing antibody, or a variant or a derivative thereof, and polypeptides that contain at least a portion of an immunoglobulin that is sufficient to confer specific antigen binding to the polypeptide, such as one, two, three, four, five or six CDR sequences, as long as the antibody retains the desired biological activity.

The term "antibody fragment" herein refers to an antigen-binding fragment of an antibody which retains at least 50% (e.g. at least 60%, 70%, 80% or 90%) of the binding affinity of the entire antibody.

Specific antibodies that may be used in the present invention include: anti-interferon α, anti-interferon 13, anti-interferon γ, anti-CRP, anti-TRAIL, anti-sTREM-1, anti-procalcitonin, anti-ANP, anti-proadrenomedullin, anti-suPAR, anti-lactoferrin, anti-ISG15, anti-OASL, anti-ADGRE5, anti-galectin-9, anti-CD14, anti-CD32, anti-CD35, anti-CD46, anti-CD55, anti-CD59, anti-CD64, anti-CD88, anti-IL-1, anti-IL-4, anti-IL-6, anti-IL-8, anti-IL-10, anti-IL-12, anti-IL-17, anti-IL-27, anti-p40, anti-p53, anti-p63, anti-p73, anti-survivin, anti-Hsp60, anti-Ras, anti-RPLP60, anti-HPV16, anti-HPV18, anti-E6, anti-E7, anti-TTF-1, anti-cytokeratin, anti-napsin A, anti-p504 s, anti-MLH-1, anti-PMS2, anti-MSH2, anti-MSH6, anti-BRAF$_{V600E}$, anti-CDX-2.

As used herein, a "functional group" that is capable of selectively binding to a biomarker is a functional group with greater affinity for the specific biomarker than other biomarkers present in the same biological fluid. The term "selective" encompasses groups that have an affinity for their target biomarker that is more than 2 times greater than for other biomarkers present in the same biological fluid. For example, the affinity for the target biomarker may be 2-10$^9$ times greater than for other biomarkers. In some aspects, the affinity for the target biomarker is more than 10 times, 100 time, 1000 times, 10$^4$ times, 10$^5$ times, 10$^6$ times, 10$^9$ times greater for the target biomarker than for other biomarkers in the same biological fluid.

As used herein, a "biomarker" is a characteristic that can be objectively measured and evaluated as an indicator of normal biological processes, pathogenic processes, or pharmacologic responses to a therapeutic intervention. Biomarkers may be cells, biological molecules such as proteins, lipids, hormones and/or nucleic acids. The term "biomarker" as used herein include biological molecules and metabolites. The biomarker may be a class of biomarkers, such as proteins, lipids, cells, hormones and/or nucleic acids. The functional group may bind selectively to the entire class of biomarker or may bind to a subset of the class of biomarker. For example, when the biomarker is a peptide, the functional group may bind to all peptide, to specific classes of peptides such as interferons, immunoglobulins, or cytokines; or to individual peptides such as interferon α, interferon β, interferon γ, CRP, TRAIL, sTREM-1, procalcitonin, ANP, provasopressin, proadrenomedullin, suPAR, lactoferrin, galectin-9, CD14, CD32, CD35, CD46, CD55, CD59, CD64, CD88, interleukins including IL-1, IL-4, IL-6, IL-8, IL-10, IL-12, IL-17, IL-27. In a further example, when the biomarker is a cell, the functional group may bind to all cells, or to a specific class of cells such as: bacterial cells, including gram-negative bacterial cells, gram positive bacterial cells; host cells such as immune cells, such as dendritic cells, lymphocytes including B cells and T cells, macrophages, NK cells, eosinophils, basophils, neutrophils and/or monocytes; host cells such as cancerous or pre-cancerous cells including, but not limited to, cancer of the respiratory tract such as mouth cancer, tongue cancer, oesophageal cancer, lung cancer; cervical cancer; prostate cancer; colon cancer; rectal cancer, ovarian cancer.

OVERVIEW OF THE EXAMPLES

The invention is further described below with reference to a number of non-limiting examples.

In the first series of experiments, the lipid extraction and DESI-MS analysis capacity of surface-functionalised ODS groups on glass is assessed. Focus then shifts to transferring and expanding the concept of ODS surface functionalisation to PDMS in the interest of ensuring the clinical feasibility of the substrate. A more rigorous assessment process for surface functionalised PDMS is used. It involves the following steps: (i) fully characterising the surface chemistry of the material; (ii) assessing its lipid extraction and elution ability by means of fluorescence intensity studies; and (iii) subjecting it to both single and multiple component solutions analysed under DESI-MS. Surface Functionalisation of PDMS for DESI-MS Enabled Lipidomics is demonstrated as summarised in FIG. 1. Briefly, an OTS-surface coated rod would be inserted into the nose or lungs of the patient, upon which the specific surface interactions would allow for in-situ lipid extraction and retention. Upon removal, the sample would be washed with an aqueous solution such as PBS to remove non-lipid compounds (e.g. cells or proteins) from the surface that may hinder or obstruct the lipid signal under DESI-MS. The thus lipid-only containing device would then be placed onto the DESI-MS holder for analysis.

The next series of experiments, starting at Example 9, transfer the techniques that allowed preferential lipid extraction, retention and re-elution. Xerogels synthesised via sol-gel method prepared from various organosilane precursors as reported by Hayase et al are explored as substitute substrates for PDMS rods. Their high surface area and flexible mechanical properties promise to satisfy the clinical requirements of patient comfort; various compositions of xerogels synthesised using selected precursors will be investigated and characterised in the search for a suitable based material.

Figure 23:
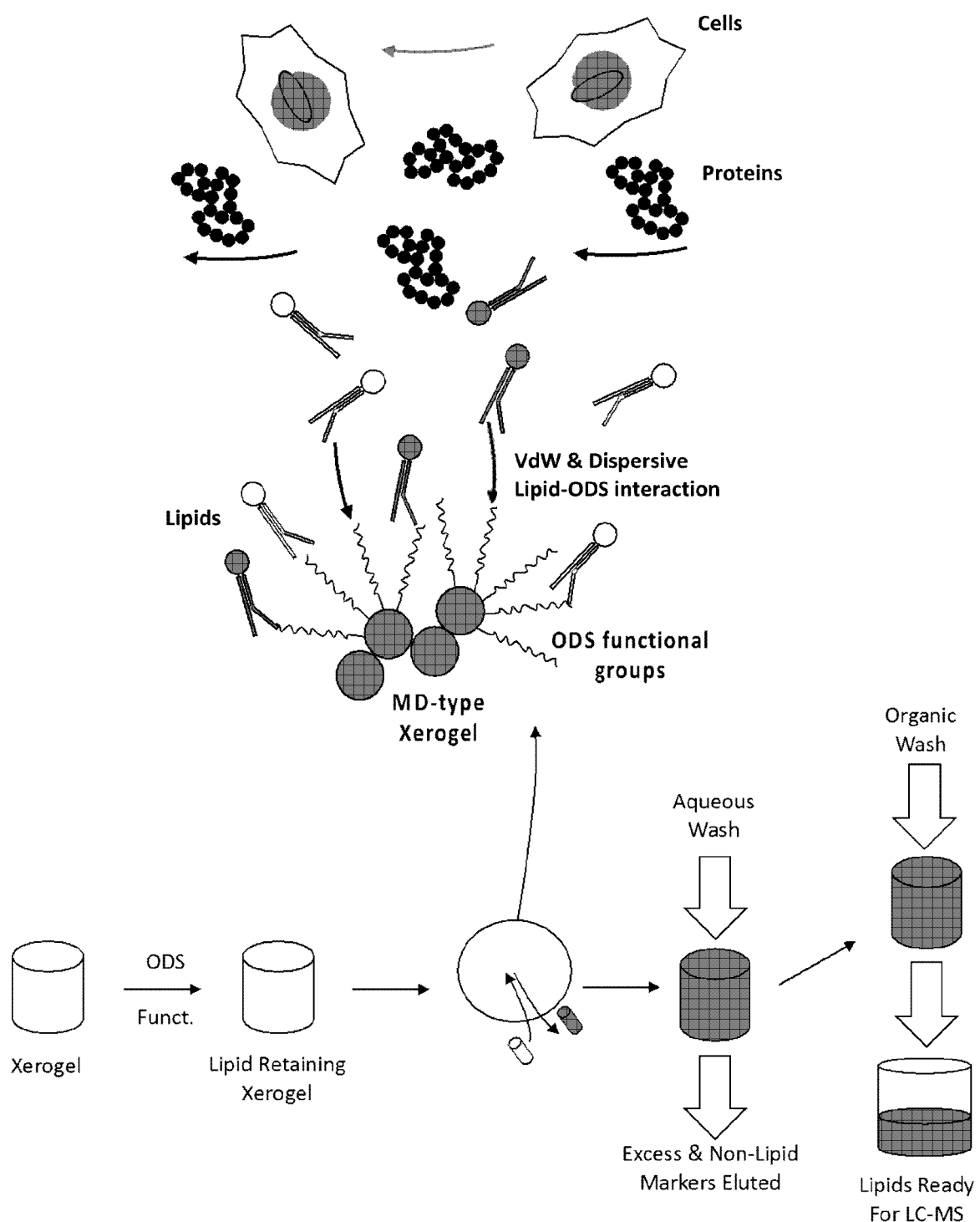
FIG. 23: Proposed clinical application of ODS-functionalised xerogel for preferential lipid extraction from the nasal epithelial fluid.

The silica-network chemical structure of the xerogels should allow direct transfer of previously used OTS solution treatment and SI-ATRP polymerisation of ODMA for surface ODS grafting. Indeed, depending on precursor selection, the presence of surface labile methyl groups renders their structure chemically identical to PDMS rods explored in Examples 1-8. The ability to incorporate surface thiol groups into the chemical structure by using thiol-presenting precursors during the sol-gel synthesis process enables the evaluation of thiolene surface-initiated polymerisation (TSIP) for the purposes of ODS surface modification. Given the porous and 'sponge-like' nature of xerogels, these experiments also focus on expanding their use for analysis by methods other than DESI-MS. The technique remains indeed a relatively novel instrument as opposed to broader MS-type systems such as LC-MS. Once a suitable and effective means of ODS xerogel functionalisation is explored and fully characterised, the experiments assess the viability of such devices in sample collection and preparation for analysis via LC-MS, as shown in FIG. 23.

Example 15 is the first of a series of experiments to explore the synthesis of block copolymers, specifically with Allyl Methacrylate (AMA). AMA monomers present two vinyl groups: a conjugated methacryloyl group and an unconjugated allyl group. The former is more reactive than the latter; polymerisation therefore occurs preferentially at the methacryloyl group, thus—depending on polymerisation conditions—leaving the allyl group unreacted and free to react. This unreacted allyl group is therefore hypothesised to be utilised as a means of synthesising P'R'MA-b-AMA block copolymers ex-situ in solution via CRP methods, for subsequent grafting onto MD-type xerogels via click chemistry. This method should therefore present an ideal means of grafting well-defined polymers to the surface of MD-type xerogels whilst minimalizing the impact on their material properties.

From a biological perspective, this series of experiments explores the concept of Dendritic Cell (DC) extraction. DCs are key immune markers, providing a clear indication of the underlying immune state. During an immune response, DCs are key response mediators. In turn, they are therefore key to understanding not only the body's response to pathogens, but also how to diagnose the condition caused by those pathogens.

A key issue in the clinical context thus far has not only been the extraction (particularly in known and reproducible quantities) of DC-SIGNs, but also their re-elution for analysis in a viable state. Strong pH or temperature variations or high salt-content solutions instantly kill the cells due to bilayer destruction. Key requirements to be satisfied in this work therefore include both the ability of the proposed material to successfully extract and retain DC-SIGNs and being able to viably re-elute them.

Mannose glycomonomer has been extensively reported to have a preferential affinity to DC-sign cells, typically binding to carbohydrate-rich DC-SIGN (CD209) and mannose receptor (CD206) cell surface receptor regions of DCs. Mannose glycomonomer conversion into reactive functional monomers such as methacrylate-class monomers and subsequently covalently bonded surface of extracting devices is hypothesised to yield the preferential method of extracting DCs from solution.

Mannose methacrylate synthesis is a laborious, complex and, crucially, low yield synthesis process; a means of increasing the yield of surface grafting reactions (as opposed to TSIP as explored in the previous series of experiments) is therefore desirable. The block copolymer method proposed above may be one way of achieving the desired objective—i.e. provide a means of optimising the yield of surface grafting mannose methacrylate monomers.

The experiments report the synthesis and surface grafting of mannose methacrylate to labile thiol-moiety presenting MD-type xerogels for the purposes of DC-SIGN cell extraction and viable re-elution. The concept of 'R'MA-AMA block copolymers with free vinyl groups for surface grafting of precisely defined solution CRP-synthesised polymers is examined first.

A means of extracting the diagnostically relevant dendritic cells by bonding mannose methacrylate onto the xerogel surface is thus provided.

The final series of Examples, starting at Example 19, serve as a final proof-of-concept for the evaluation of the extraction, retention and re-elution capacity for a final biomarker type: proteins. The capacity of this material to extract proteins is a first step towards achieving a POC testing device by transferring ELISA detection technology onto protein-extracting xerogels.

ELISA plates have been commonplace in biochemistry laboratories for decades, allowing the quantification of specific protein concentrations in a given media. Analysing the protein composition of the sputum extracted from TB infected patients via ELISA including the respiratory system has revealed key information in the disease's pathogenesis and biomarkers. Although the concept of ELISA plates allows straightforward protein identification, it requires pre-analysis liquid sample preparation—which in the context of the respiratory system implies the extraction of nasal or respiratory epithelial fluid, a key limiting factor to rapid respiratory diagnosis. The most likely explanation is the absence of sufficient evidence of diagnostically relevant markers including proteins in the respiratory system. This in turn is probably due to inadequate extraction and quantification methods.

The device proposed in Example 19 et seq, represents to the best of our knowledge the first approach of transfer of ELISA technology to a 'mobile' phase for in-situ protein fluid extraction for immediate post extraction analysis (without protein transfer onto an ELISA plate), which aims to lead to a fully-fledged POCT device which allows rapid diagnosis of respiratory disease.

From a surface chemistry perspective, the binding of antibodies on surfaces typically relies on the presence of surface thiol groups. Thiol moiety presenting xerogels have proven to be a promising and polyvalent platform for both lipid and cell extraction. The aim here is therefore to transfer the ELISA concept to the proposed xerogels by covalently binding primary detection antibodies on to the surface of the thiol-presenting silica xerogels. The resulting xerogel therefore presents itself as an alternative to ELISA type detection plates but critically allows the protein capture process to take place in-situ, avoiding the need to extract the relevant fluid from patients. The xerogels also have the added advantage of a much higher surface area due to the physical structure of the gel itself, potentially increasing their diagnostic capacity over their plate-based counterparts.

Example 1: ODS Functionalisation of Glass Slides

Materials

Glass microscope slides purchased from VWR and Svylgard® 184 PDMS monomer solution and crosslinker was purchased from Svylgard and used as delivered. Octotrichlorosilane (OTS), Aminopropyltriethoxysiane (ATPS), Bromoisobutiryl Bromide (BIBB), Triethylamine (EtNO3), Octadecyl Methacrylate (ODMA), Copper (I) Chloride, 4,4'-Dinonyl-2,2'-dipyridyl (DNBpy), Lineloic acid, Bovine serum, fluorescence labelled Bovine serum albumin, Tetrahydrofuran (THF) and Toluene were purchased from Sigma-Aldrich and used as delivered or purified using Alumina columns to remove inhibitors where needed. Fluorescence labelled 1,2-dioleoyl-sn-glycero-3-phosphoethanolamine (DOPE) was purchased from ATTO-Tec Gmbh.

Methods

Functionalising Glass with ODS

Figure 2:
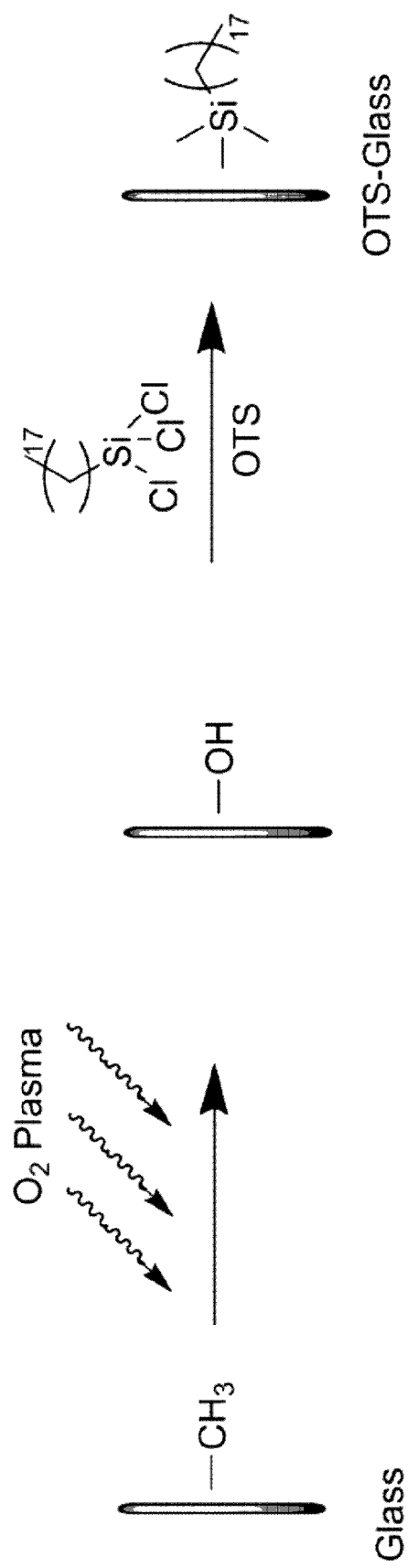
FIG. 2: Schematic of OTS treatment of glass or PDMS surfaces.

The first and most straightforward means of grafting the desired ODS groups on the surface is via OTS solution treatment, commonly used in industry for various applications and the basic outline of which is shown in FIG. 2. An adjusted version of a protocol used by Sneha et al was used [1]. Briefly, glass or PDMS surfaces were triple cleaned via sonication with d(H2O), EtOH and Acetone before being oxygen plasma treated for 5 minutes at 35 sccm of oxygen gas flow. The thus treated samples were then immediately washed with d(H2O) so as to remove the radicals formed during plasma treatment, leaving surface hydroxyl groups on the surface. The samples were then placed into a 0.1% OTS solution, the rest of the solution constituting of 20:80 Chloroform:Hexane solution for 5 minutes. Once removed, samples were immediately triple washed in chloroform so as to remove any unbound OTS molecules. Solution treated samples were then heat treated at 120° C. for an hour to remove any solvent or contaminants as well as promote OTS group interlinking.

Solution Polymerisation

Figure 3:
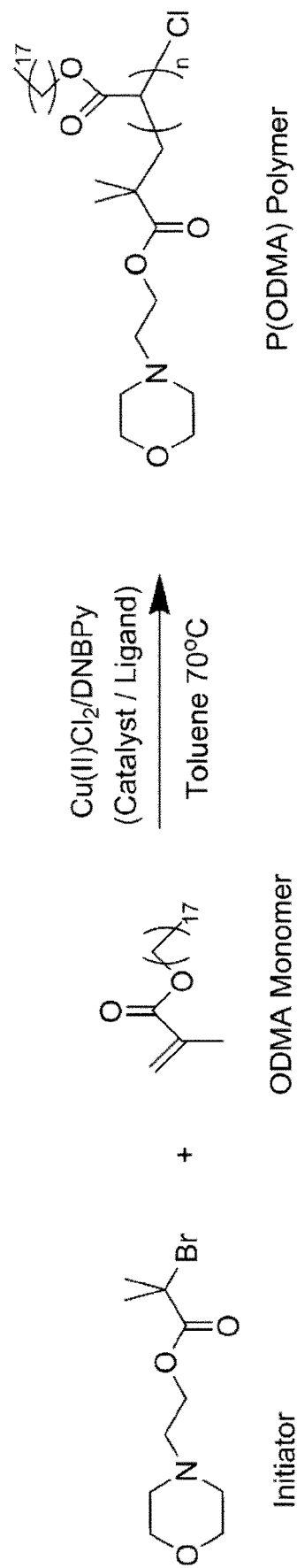
FIG. 3: Schematic of solution ATRP reaction process with ODMA monomer.
Figure 4:
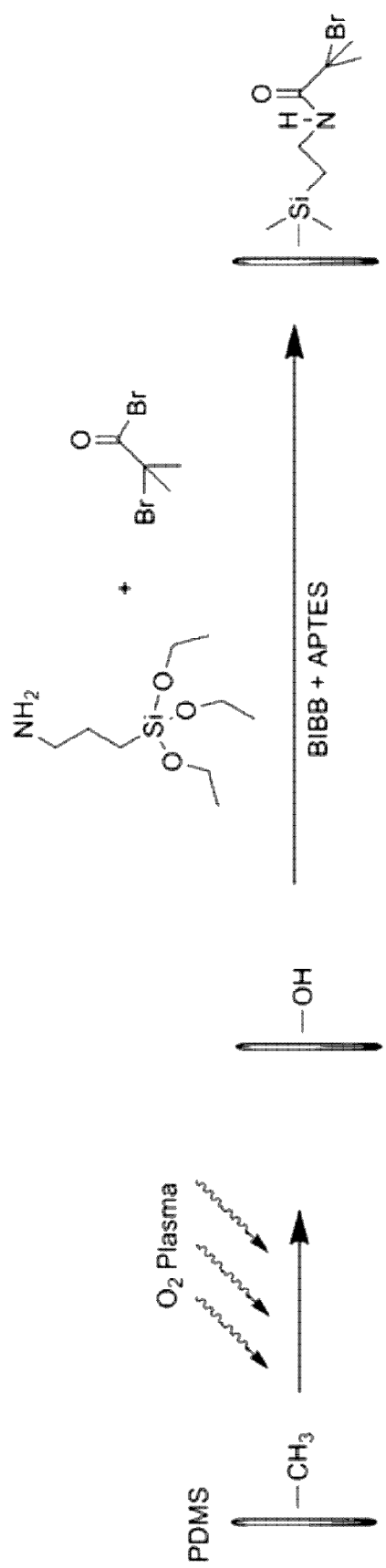
FIG. 4: Schematic of PDMS surface modification via grafting of bromine initiators for SI-ATRP.
Figure 5:
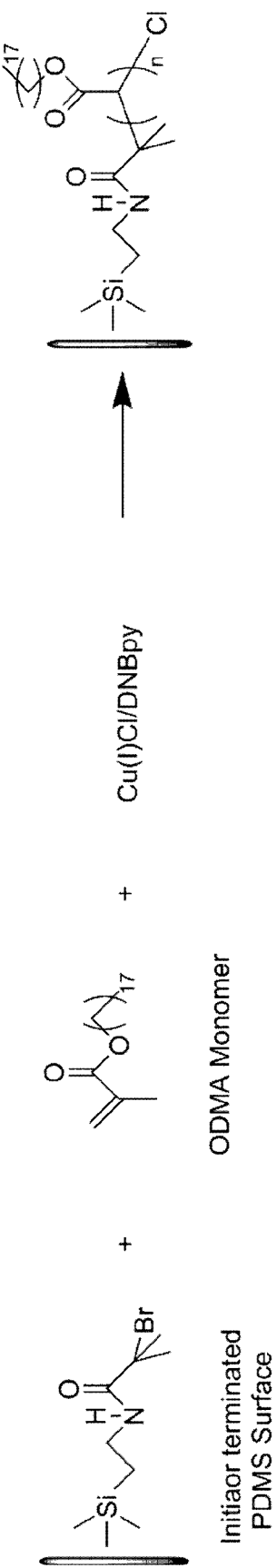
FIG. 5: Schematic of SI-ATRP reaction process from bromine functionalised PDMS rods for surface polymerisation of ODMA.

It is herein hypothesised that since ODS moieties are responsible for the preferential extraction of lipid-type biomarkers for physiological solution (as has been shown in ODS-silica column chromatography), increasing the density of those moieties should lead to an increased extraction efficiency. To accurately control the density of the relevant groups, an ATRP polymerisation process was used. The reaction scheme in solution is shown in FIG. 3, and follows previous work by Qin et al [2]. The protocol described below bases its quantities and molar ratios on a degree of polymerisation of 50, as shown in Table 1.

TABLE 1

Molar ratios of monomer, initiator, catalyst and ligand required for ATRP solution polymerisation.

| Monomer (ODMA) | Initiator (Me—Br) | Catalyst (Cu(I)Cl) | Ligand (DNBpy) |
|---|---|---|---|
| 50 | 1 | 1 | 1 |

Based on the above ratios, a typical solution ATRP reaction was performed using the quantities calculated shown in Table 2.

TABLE 2

Molar mass, molar quantities and theoretical masses calculated for the solution ATRP synthesis of ODMA.

| Reagent | Molar Mass | mmol | $m_{th}$ |
|---|---|---|---|
| Me—Br | 280.16 | 0.4 | 112.064 |
| Cu(I)Cl | 99 | 0.4 | 39.6 |
| DNBPy | 408.66 | 1 | 408.66 |
| ODMA | 338.57 | 20 | 6771.4 |

Cu(I)Cl (39.6 mg/0.4 mml) and 4,4'-Dinonyl-2,2'-dipyridyl (408.66 mg/1 mmol) were introduced into a Schlenk flask and subjected to a triple degas and vacuum cycle. Pure ODMA (6.771 g/20 mmol) was degassed with argon for 30 minutes in another Schlenk flask with 1.8 ml toluene. In a further small tube, Me-Br (112.064 mg/0.4 mmol) was degassed under argon with 0.2 ml toluene whilst in ice. Once degassed, the contents of the ODMA containing flask were transferred under vacuum via cannula transfer line into that containing the catalyst and ligand and degassed further. Once mixed, the ODMA, Cu(I)Cl and DNBPy solution was finally transferred under vacuum via cannula transfer line into the flask containing the Me-Br initiator and stirred till a homogeneous solution was obtained, and subsequently left to react for the desired amount of time at 80° C. Once reacted to the desired degree, the reaction was quenched by exposing to oxygen and diluting in THF before passing through a neutral $Al_2O_3$ column. The resulting phase was finally precipitated in MeOH, filtered and dried to obtain a dry precipitate used for characterisation. Aliquots for kinetic study were taken carefully using a degassed syringe at 1 h, 2 h, 3 h, 4 h and 5 h.

Surface and Biological Characterisation

The following characterisation techniques were used to assess the surface modification techniques performed:
FTIR, ellipsometry and WCA were used to characterise the modified surfaces.
$^1$H-NMR and GPC provided polymer solution characterisation.
Confocal microscopy, MTT cytotoxicity assay and DESI-MS analysis constitute the biological performance evaluation of the synthesised substrates.

Confocal imaging was used to preliminarily assess the extraction, retention and re-elution capabilities of the proposed ODS functionalised rods. Control and functionalised surfaces were subject to a treatment mimicking that of clinical proceedings. The prepared surfaces were soaked in 1:1 MeOH:d($H_2O$) overnight prior to assessment so as to condition the surface extraction groups as is common practice in reverse phased HPLC column preparation and dried prior to use. Once ready, samples were immersed into a 1 mg/L 488 nm fluorescent labelled DOPE lipid solution and 680 nm fluorescence labelled 1 mg/L albumin from bovine serum (BSA), with a 95:5 d($H_2O$):MeOH solvent ratio due to the limited solubility of lipid solutions in aqueous solution. Once immersed for 5 minutes, samples were withdrawn, and washed with d($H_2O$) and Folch solution (2:1 $CHCl_3$:MeOH). Fluorescence intensity measurements were taken using a Leica® SP5 MP/FLIM inverted confocal microscope.

Results

This Example reports the results of proof-of-concept tests of a device designed to extract lipid biomarkers from the nasal epithelium with DESI-MS enabled analysis. To this end, methods and technologies derived from column chromatography [4] and SPME [5] were transposed onto a device that combines the requirements of minimal invasiveness during sampling as well as those of the DESI-MS analysis set-up.

The first step towards assessing the feasibility of such a device was to determine whether functionalising a flat surface such as glass or PDMS coating with ODS could successfully extract lipids in sufficient quantities to be analysed under DESI-MS. Traditional methods of column chromatography rely on the high surface area of the ODS-coated nanoparticles for the high extraction efficiency. A flat surface inherently reduces that available extracting surface area. Glass was chosen as an initial step prior to PDMS due to its chemical resemblance to PDMS (from a silica network perspective), and yielding the same functionalisation potential. OTS surface treatment is regularly used both in research and industry, typically as surface resists or functional coatings in nanopatterning applications [6], yielding a straightforward and reliable means of grafting $C_{18}$ groups to the surface.

Figure 6:
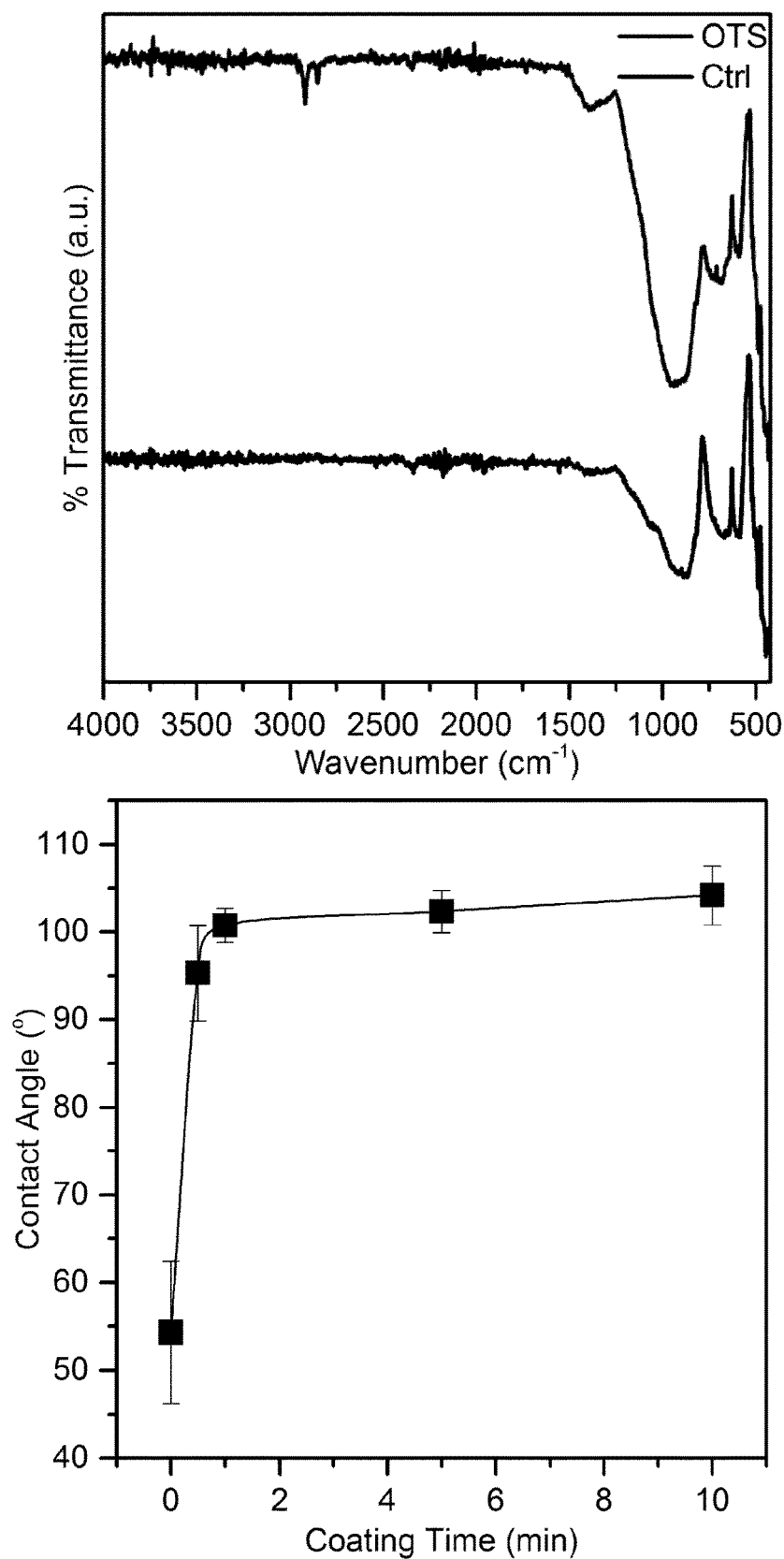
FIG. 6: a. Normalised FTIR in transmission spectra of OTS treated and control glass surfaces and b. Static WCA measurements for increasing OTS solution coating time of glass surfaces.

FIG. 6 shows the transmission FTIR spectra of both OTS treated and untreated glass surfaces. As can be seen from the clear difference between the two spectra in the 3000 $cm^{-1}$ range, the peaks at 2851 $cm^{-1}$ and 2920 $cm^{-1}$ correspond to symmetric and asymmetric stretching of C—H bonds [7]. This suggests that Octadecyl functional groups have been successfully grafted onto the glass. The broadening of the peak between 1250 $cm^{-1}$ and 900 $cm^{-1}$ can be attributed to the structural modifications incurred by the oxygen plasma treatment. Indeed, this region corresponds to Si—OH bonds (900 $cm^{-1}$ and 1060 $cm^{-1}$ corresponding to Si—O stretching in Si—OH and asymmetric Si—O—Si stretching in —[$(CH_3)_2$—Si—O]— bonds respectively).

The relatively poor signal-to-noise ratio in the 1500 $cm^{-1}$ to 2900 $cm^{-1}$ and 3000 $cm^{-1}$ to 4000 $cm^{-1}$ band ranges can be attributed to the glass structure disturbing the FTIR machine processing. Crushing the glass into a powder could be a means of reducing the noise, but was deemed unnecessary given the clear visibility of the relevant bands and early stage of the testing process. The successful surface ODS functionalisation is further confirmed by the static water contact angle measurements shown in FIG. 6b. Indeed, the plateauing out of the contact angle value towards 110° C. corroborates literature values [8]. The above results suggest the process can successfully be carried out by subjecting the surfaces to OTS solution treatment for only 10 minutes.

Example 2: First ODS Extraction Evaluation of Functionalised Glass

Results

Fluorescence Intensity Measurements

Having successfully functionalised glass surfaces with ODS (Example 1), the next step was to determine whether ODS surface groups grafted in such a way were capable of selectively extracting and retaining lipids whilst not extracting proteins from solution. It is key to the success of this proof-of-concept study that only the relevant biomarker (in this case lipids and fatty acids for lipidomics analysis) be extracted from solution, leaving proteins behind as the latter may hinder the analysis process. ODS coatings achieve this by preferentially attracting lipid type markers due to week interactions, larger elements such as proteins and cells requiring more specific binding [4, 9].

This was tested by introducing control and functionalised glass into a solution containing DOPE lipid and Albumin protein, both biomarkers being labelled with covalently-bonded fluorescence markers. The covalent bond between lipid and fluorescent marker is key as it guarantees that any fluorescence signal observed during analysis can be with certainty be attributed to the presence of lipids, and not leaching or separation of the fluorescent marker from the lipids themselves. Once extracted from solution, the slides were first washed off with water and then Folch solution. Fluorescence measurements were taken between the steps. The water wash aims to remove any unbound lipids that could lead to false readings, as well as more importantly water soluble undesired proteins. The Folch solution wash then aims to remove all bound lipids from the surface, the resulting lipid-only containing solution is then ready for other forms of analysis such as LC-MS or GC-MS. This two-step washing process closely mimics the intended clinical procedure. The concept of DESI-MS itself relies on the lipids being desorbed from the surface. It is therefore necessary to not only confirm the extraction capability of the surface, but also its ability to elute out the markers if so desired.

Figure 7:
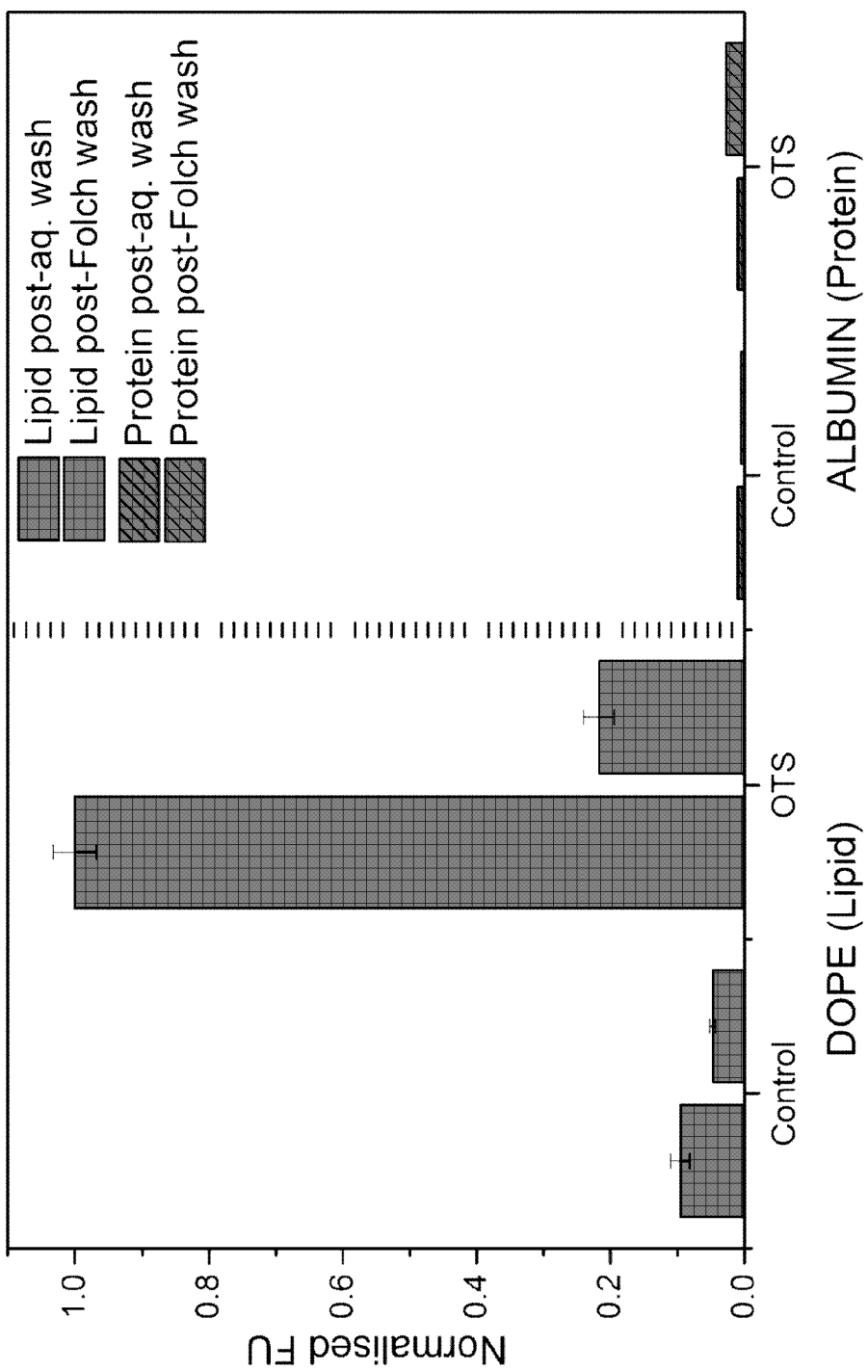
FIG. 7: Fluorescence intensity measurements of lipid and protein retaining capacity of ODS functionalised glass surfaces.

The data shown in FIG. 7 appears to confirm the lipid successive extraction, retention and elution capabilities of ODS functionalised glass. The signal corresponding to lipids extracted from the OTS treated surface post-aqueous wash is clearly much stronger than that of its unfunctionalised (control) counterpart. This confirms that the signal observed corresponds to markers extracted by ODS moieties and is not an artefact. Furthermore, the signal post-Folch wash in the case of OTS-treated surfaces is significantly lower than the pre-wash state, suggesting the capacity of the proposed surfaces to re-elute lipids, which have been extracted from solution previously.

It is however important to note that although there is a considerable reduction in signal between aqueous and Folch washing steps, the signal after the Folch washing step does not return to baseline, suggesting some retention of lipids on the surface. This would suggest a not 100% efficient re-elution process, which, in a clinical context, could indicate a certain percentage loss of biomarker or data. At this early stage though, this process can still be considered a successful proof-of-concept test. The slight difference in signal between post-aqueous wash and post-Folch wash for the control samples suggests there is some slight retention of lipids despite the lack of functional groups, but is considered negligible when compared to the ODS surfaces.

Whilst lipid retention is desired, protein retention should be avoided. This is indeed the case with both control and ODS surfaces, confirming the hypothesis that ODS functionalisation allows lipid-only retention as desired. The slight signal observable on the right-hand side of FIG. 7 can be considered to be artefact. The increase in intensity observed after a second washing step for OTS treated surfaces is clearly illogical, as further washing could not add any fluorescence to the considered system. This confirms the artefact nature of the value.

Towards DESI-MS Lipidomics Analysis

Fluorescence intensity measurements constitute the first successful step towards proving the suitability of ODS coated surfaces for lipidomics analysis using such surfaces specifically under DESI-MS analysis, which allows quasi-instant mass spectral imaging of a surface, a quality that has greatly accelerated its introduction into clinical and surgical practice. Demonstrating that ODS surfaces can extract, retain and re-elute lipids from solution suggests they should be able to yield a signal under DESI-MS analysis.

Figure 8:
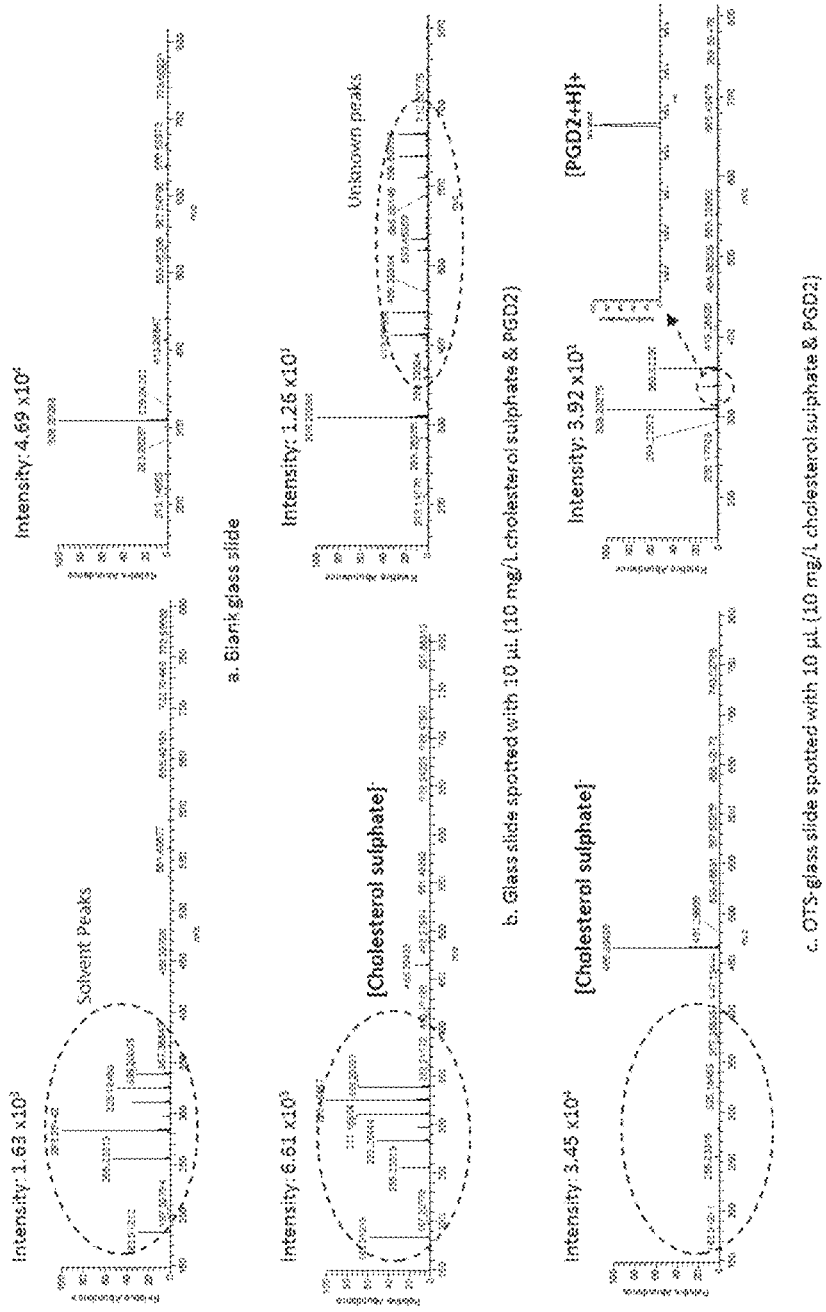
FIG. 8: Negative and positive ion mode mass spectra for OTS and control treated glass surfaces obtained via DESI-MS analysis.

FIG. 8 represents a series of mass spectra obtained via DESI-MS analysis. Successive spectra of blank glass, control (non-ODS coated) spotted with cholesterol sulfate and PGD-2, and an ODS coated glass slide equally spotted with cholesterol sulfate and PGD-2 are shown in FIG. 9a. through to 9c, in both negative (left-hand side) and positive (right-hand side) ion modes respectively. Cholesterol sulfate and PGD-2 chosen as suitable representative lipid molecules; cholesterol sulfate is one of the most abundant sterol sulfates, and has key physiological signaling roles in amongst others, blood clotting [10]. PGD-2 plays a critical role in the allergic inflammatory process, specifically in the interaction and co-ordinated action of mast and dendritic cells [11].

The peaks shown in FIG. 8a. are the result of the 95:5 MeOH:H$_2$O solvent mix, which is bouncing off the glass surface straight into the detector. In theory given the consistent mass positions of the solvent as shown here, it is possible to assume such peaks could be removed computationally during spectra analysis. However, in the interest of making the interpretation of results as straightforward as possible, the ideal mass spectra when analysing a surface with extracted biomarkers should be able to yield a signal without such solvent peaks appearing, or at least with a lower relative intensity than those of interest. Indeed, the higher the relative abundance of peaks of diagnostic interest, the more straightforward the analysis and results processing for diagnostic purposes will be.

FIG. 8b. shows the mass spectra obtained from DESI-MS analysis of a control glass (i.e. without ODS functional groups on its surface), which has been spotted with 10 µL of both cholesterol sulphate and PGD-2 solutions (both at 10 mg/L concentration). Although there are more peaks visible in positive mode relative to the spectra obtained from the un-spotted glass slides in FIG. 8a, these are too randomly distributed to be reliably assigned to either cholesterol sulphate or PGD-2. Indeed, a peak for PGD-2 would be expected at 353.27 m/z in positive mode, and cholesterol sulphate would not be expected to show any values in positive mode at all.

A slight peak in negative mode can be observed at 465.30 m/z, corresponding to cholesterol sulphate (cholesterol sulphate-H specifically), suggesting the presence and slight retention of the lipid standard on the surface. However, given that its relative abundance is only around 20% (compared to 65%-95% of relative abundance for solvent peaks), it can be argued that such a small peak does not constitute a suitable means of detecting standards. Indeed, the experimental set up here only contains two standards, each of which is observable in one ion mode each. Given the very low relative abundance of the cholesterol sulfate peak, such a signal would most likely be lost amongst other signals when analysing multi-component or clinical samples. This therefore confirms that glass slides are ill suited to lipid extraction for DESI-MS analysis.

In contrast, FIG. 8c. shows much higher relative abundance of cholesterol sulphate and PGD-2 respectively, particularly the former (as shown in the negative ion mode mass spectrum). In contrast to FIG. 8a. and b., the intensity 465.30 m/z peak associated with cholesterol sulphate when desorbed from OTS-treated glass has a relative abundance of 100%, with no peaks associated with the solvent visible at all. The much higher relative abundance of the lipid peak in the case of the ODS functionalized surface relative to the control therefore further confirms the trend determined from previous fluorescence imaging, namely that the ODS functional moieties on the surface allow increased extraction of lipids from a solution and therefore better analysis under DESI-MS relative to unfunctionalised surfaces.

This is can also be observed in the positive ion mode, with a slight peak visible at 353.27 m/z, but only under very fine axis visualisation parameters. It remains undetectable over a normal 0-1000 m/z range, in contrast to the cholesterol sulphate peak in negative mode which was clearly visible over the same range. This suggests a lower extraction capability of ODS glass for PGD-2 versus cholesterol sulphate. Given the unstable nature of PGD-2, it is more likely that the PGD-2 standard itself degraded during storage or use, leading to lower intensity readings during analysis.

A further element of comparison between control and ODS functionalised surfaces is possible noting the overall signal intensity between the two surfaces. Both un-spotted and spotted glass have an overall intensity of $1.63 \times 10^3$ and $6.61 \times 10^3$ respectively, compared to $3.45 \times 10^4$ for the OTS treated surface. This therefore suggests that the ODS surface allows both better lipid extraction and signal under DESI-MS and better resolution.

These results support the hypothesis that ODS surface functionalisation could be a suitable means of synthesising a DESI-MS specific POC device. The following work will focus first on transferring these techniques onto a more suitable application-related substrate (namely PDMS). The active extraction phase surface area will then equally be increased in the hope of in turn increasing the extraction capacity of the material, which in turn should increase the resolution of the desorption signal under DESI-MS.

Example 3: Solution ATRP

Results

Prior to considering a substitute surface for glass, the aspect of active extraction phase surface area was addressed. Although surface modification could be considered, with nano-porosity or nano-roughness being options, a more controlled means of testing the hypothesis that increased active surface yields better extraction signal under DESI-MS was desired.

Controlled polymerisation processes such GTP, RAFT and ATRP allow precise control of polymer chain length, particularly of methacrylate polymers [12]. ATRP is of particular interest due to its wide-spread use both in solution and surface-initiated, the latter allowing 'grafting from' surface polymerisation strategy, allowing the stable and controlled polymer growth [13]. Directly relevant to the proposed project, ODMA monomer represents an ideal candidate as it has a methacrylate backbone, therefore loaning itself to the ATRP process, and a $C_{18}$ functional group. The polymerisation of p(ODMA) via ATRP should therefore yield precise control of density of ODS moieties on the surface it is polymerised onto, allowing the investigation of the above proposed hypothesis of the correlation between active extraction phase surface area and signal.

Figure 9:
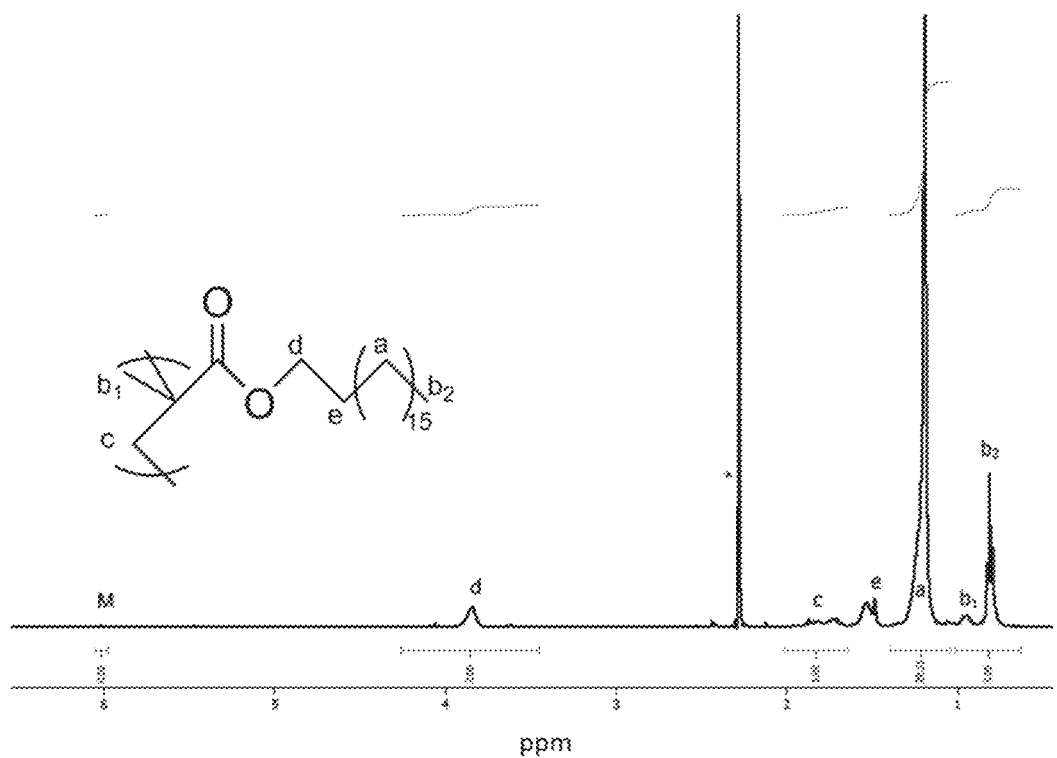
FIG. 9: 1H-NMR spectrum of p(ODMA) synthesised via ATRP in solution with a targeted Dp of 50.

The first step towards the surface polymerisation of ODMA via SI-ATRP is proving the ability to synthesize p(ODMA) in a controlled manner in solution. FIG. 9 is a proton $^1$H-NMR spectra of the completed solution-ATRP polymerisation reaction of p(ODMA), the polymer form of the ODS functional group to be used. Using peak integration, it is possible to determine the percentage conversion. Indeed, the relatively large peak that can be identified around 3.9 ppm corresponds to the first $CH_2$ group down from the oxygen that follows the carboxylic grouping along the $C_{18}$ 'brush' extending out of the polymer backbone. The peaks at 5.62 ppm in contrast correspond to the same $CH_2$ group but in the ODMA monomer. The ratio of the integration of the 6.1 µm peaks over the overall integration of both thus yields the percentage conversion of monomer to polymer as shown in $$\% \text{ conversion} = \left( \frac{\int \text{polymer} - \int \text{monomer}}{\int \text{polymer}} \right) \times 100$$

and subsequent calculations below. It is important to note that the peak denoted with an asterisk corresponds to acetone, most likely residual from the glassware cleaning process (FIG. 9).

$$\% \text{ conversion} = \left( \frac{\int \text{polymer} - \int \text{monomer}}{\int \text{polymer}} \right) \times 100$$

$$\% \text{ conversion} = \left( \frac{\int 2.00 - \int 0.02}{\int 2.00} \right) \times 100$$

$$\% \text{ conversion} = 99$$

Although not 100% conversion is obtained, it can be considered that 99% conversion proves successful polymerisation via ATRP of ODMA monomer.

TABLE 3

Number average molecular weight, weight average molar weight and polydispersity index determined via GPC for ATRP in solution of p(ODMA).

| $M_n$ (g/mol) | $M_w$ (g/mol) | Đ ($M_w/M_n$) | $M_{n\,th}$ |
|---|---|---|---|
| 2.18E+4 | 2.37E+4 | 1.087 | 1.8E+4 |

As shown in Table 3, a Đ of 1.087 suggests a controlled polymerisation process as desired. This combined with the observation of a fully homogeneous system during experimental proceedings suggest a successful ATRP reaction is occurring. The discrepancy between the theoretical and actual $M_N$ values obtained via GPC can be attributed to GPC calibration. Indeed, the GPC used was calibrated using PMMA that has a much smaller hydrodynamic radius than the p(ODMA) measured. As a result, the GPC system will generally over-estimate molecular weight values. This error is systematic, and therefore allows for comparison between measurements as shown here. Confirmation of the living nature of the polymerisation will be obtained using GPC methods during a kinetic study of the polymerisation reaction. A key characteristic of living polymerisation is its first-order kinetic behaviour, as shown in the equations below [14].

$$R_p = \frac{d[M]}{dt} = k_p[P^*][M]$$

$$\ln \frac{M_0}{M} = k_p[P^*]t$$

Figure 10:
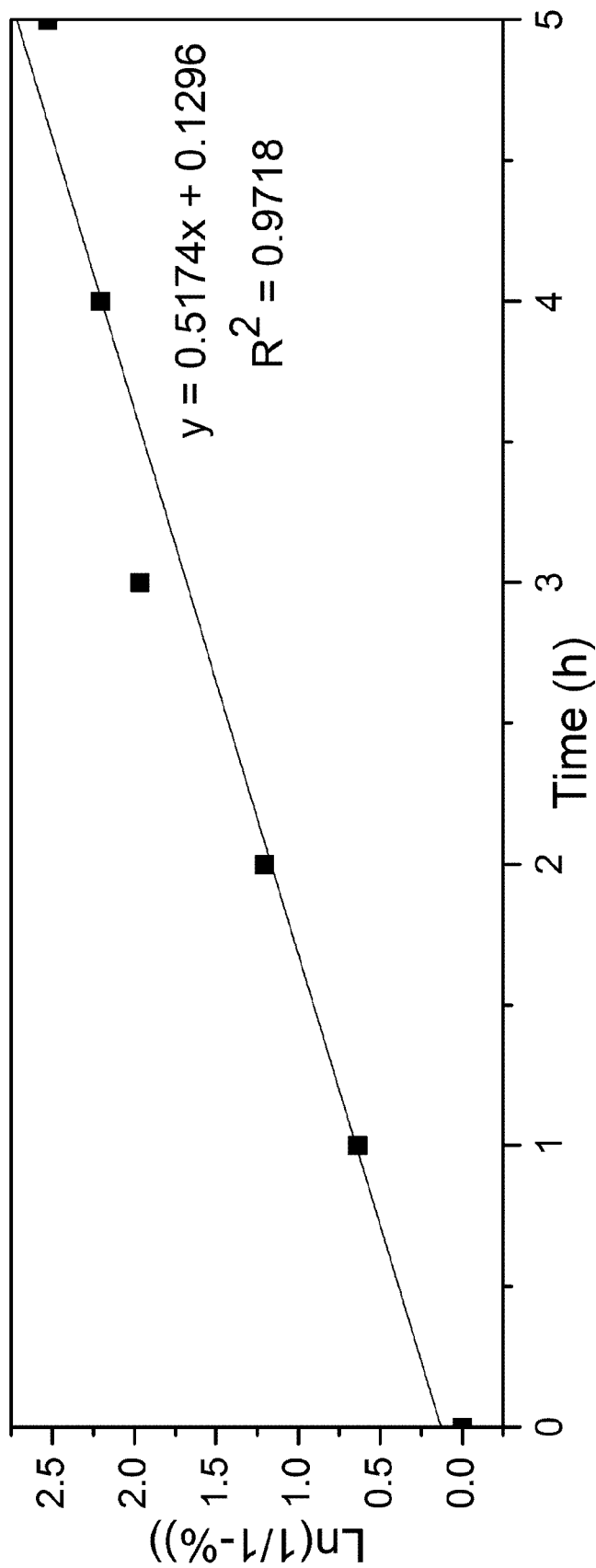
FIG. 10: Plot of ln([M]0/[M]) versus time (h) as a result of the kinetic study of the ATRP-mediated polymerisation of ODMA obtained from GPC data.

Therefore if [P*] is constant, a plot of ln([M]0/M]) should be linear. Plotting such a graph with the results obtained from the kinetic study of ATRP-mediated p(ODMA) polymerisation indeed yields such a linear trend, as shown in FIG. 10. Although a relatively linear trend can be observed in FIG. 10, it can also be argued that it follows a slightly parabolic trajectory. This may be due to experimental and/or measuring inaccuracies, but it is also possible that this slight offset could also be due to a decrease in concentration of active propagating species [P*] as a result of termination reactions or a contaminated catalytic system.

The second key characteristic of a living polymerisation is its pre-determinable degree of polymerisation. The equation below shows the linear relationship between the degree of polymerisation $DP_N$, number average molecular weight $M_N$ and monomer conversion percentage.

$$DP_N = \frac{M_N}{M_0} = \frac{\delta[M]}{[I]_0} = \frac{[M]_0}{[I]_0} \text{ conversion}$$

A plot of $M_N$ versus percentage conversion for a controlled living polymerisation should yield a linear plot. As can be seen from FIG. 11 with data obtained from GPC, this is the case for the considered reaction.

A further key characteristic of CRP methods is the narrow molecular weight distribution, manifested by a low Đ. Four key requirements exist for a narrow distribution to be achieved [14]:

The rate of initiation should exceed the rate of propagation

The exchange between species of different reactivity also exceeds that of propagation Chain transfer and termination are non-existent The rate of depropagation is much lower than that of propagation This in turn yields a Poisson-type distribution as shown by the equation below.

$$\frac{X_w}{X_n} = \frac{M_W}{M_N} = 1 + \frac{X_n}{X_n + 1}$$

Figure 11:
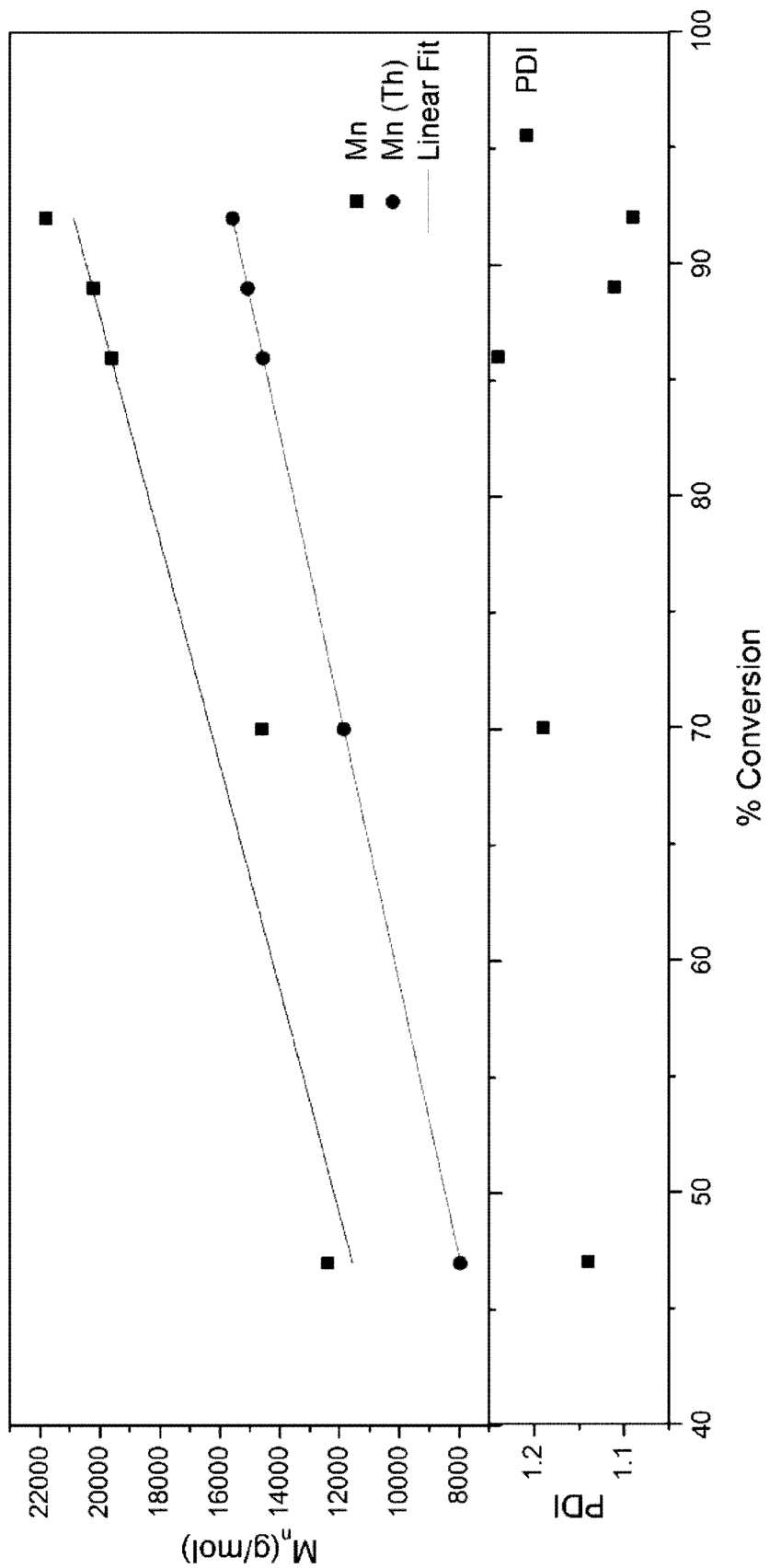
FIG. 11: Plot of MN and Đ versus percentage conversion (%) as a result of the kinetic study of the ATRP-mediated polymerisation of ODMA. Data was obtained from GPC and 1H-NMR.
Figure 12:
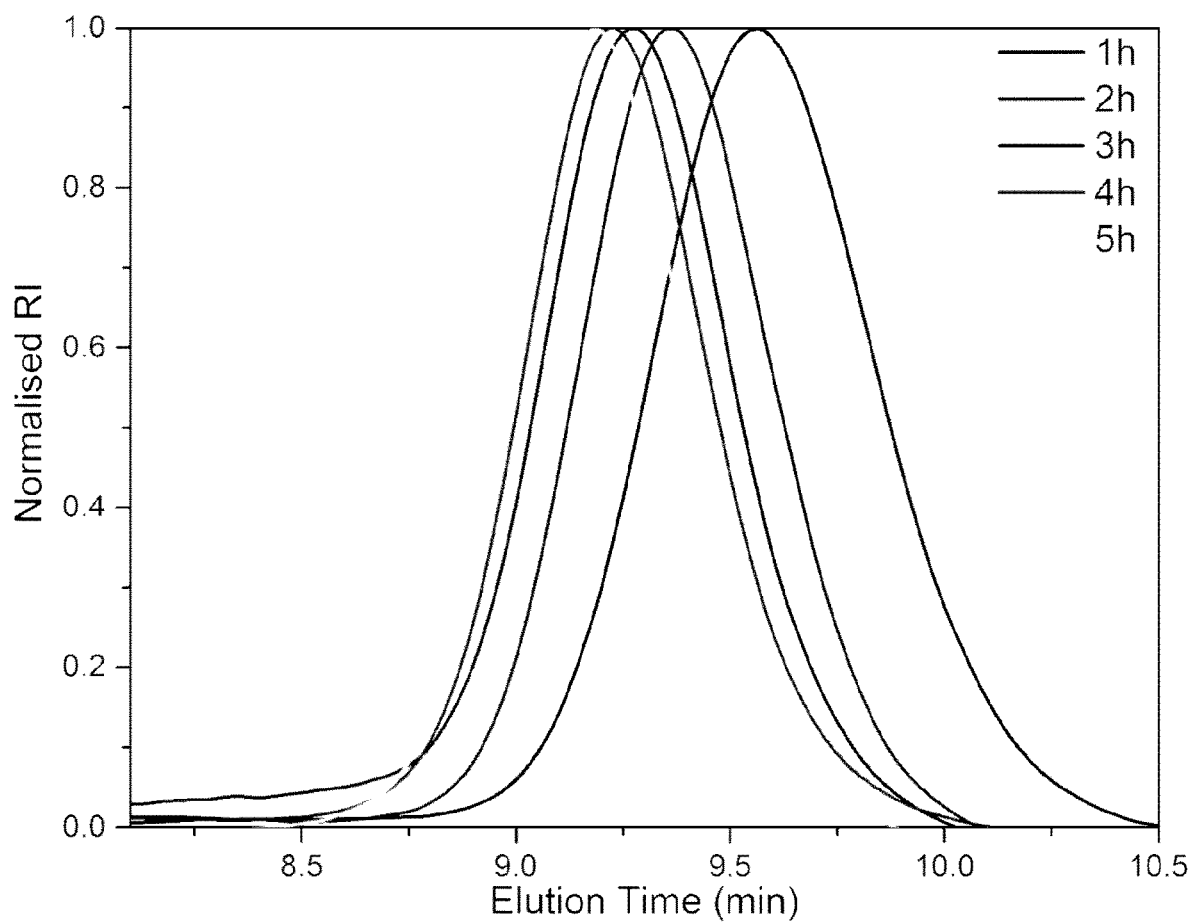
FIG. 12: Plot of normalised RI versus elution time (min) as a result of the kinetic study of the ATRP-mediated polymerisation of ODMA.

As can be seen from the above plot in FIG. 11, the Đ thus obtained from the reaction of p(ODMA) via ATRP remains below 1.3 throughout the kinetic, confirming further its controlled nature. A further confirmation of this reaction's living nature can be found in the plot of normalised RI versus elution time shown in FIG. 12. GPC data confirms an increase in molecular weight as a function of percentage conversion. Indeed, there is a clear negative shift in the elution time peaks as the polymerisation progresses. Larger elements require lower elution times as they are not retained by the porous beads in the GPC column.

The kinetic study confirms the controlled nature of the ATRP reaction protocol used. The next step is therefore to adapt the above protocol to surface initiated ATRP process, so as to use the advantageous properties of the controlled ATRP method to grow polymer chains in a controlled manner from PDMS substrate surfaces.

Example 4: Surface-Initiated ATRP from Modified PDMS (Post Functionalisation Surface Characterisation)

Methods

The reaction process of SI-ATRP follows a similar process to that of solution ATRP previously described, with adjustments being made given the initiator is now grafted to the modified PDMS rods and not in solution as was previously the case. As the polymer grown using SI-ATRP was grown on the surface of the PDMS, conventional GPC and NMR studies would not be able to quantify the reaction process. To mitigate this, a sacrificial Me-Br initiator was also introduced into the reaction mixture. The molar ratios and quantities used for SI-ATRP are shown in Table 4 below.

TABLE 4

Molar mass, molar quantities and theoretical masses calculated for SI-ATRP synthesis of ODMA from bromine modified PDMS

| Reagent | Molar Mass | mmol | $m_{th}$ |
|---|---|---|---|
| Me—Br | 280.16 | 0.4 | 112.064 |
| PDMS-Br | — | — | — |
| Cu(I)Cl | 99 | 0.4 | 39.6 |
| DNBPy | 408.66 | 1 | 408.66 |
| ODMA | 338.57 | 20 | 6771.4 |

For SI-ATRP synthesis, similarly to solution ATRP, Cu(I)Cl (39.6 mg/0.4 mml), 4,4'-Dinonyl-2,2'-dipyridyl (408.66 mg/1 mmol) and PDMS-Br rods were introduced into a Schlenk flask and subject to a triple degas and vacuum cycle. Pure ODMA (6.771 g/20 mmol) was degassed with argon for 30 minutes in another Schlenk flask with sufficient toluene to fully immerse the PDMS rods. In a further small tube, Me-Br (112.064 mg/0.4 mmol) was degassed under argon with 0.2 ml toluene whilst in ice. Once degassed, the contents of the ODMA containing flask were transferred under vacuum via cannula transfer line into that containing the catalyst, ligand and PDMS-Br rods and degassed further. Once mixed, the ODMA, Cu(I)Cl and DNBPy solution was finally transferred under vacuum via cannula transfer line into the flask containing the Me-Br initiator and to react for the desired amount of time at 80° C. Aliquots for kinetic study were taken carefully using a degassed syringe at 2 h, 4 h, 5 h, 7 h and 24 h. Once reacted to the desired degree, the reaction was quenched by exposing to oxygen and diluting in THF. The thus surface polymerised PDMS-p(ODMA) rods were removed from the solution, triple washed in toluene, dried and stored in a desiccator till use.

Results

Having successfully proven the suitability of the ATRP method for the polymerisation of ODMA, the next step was to transfer the process to a surface-initiated reaction. The aim was to grow ODMA polymers of controlled lengths from the surface of desired substrates. As previously mentioned in Example 1 however, initial investigations on glass need to be repeated on a clinically suitable material, such as PDMS.

PDMS is extensively used in a variety of clinical applications due to its biocompatibility, ease of synthesis and ease of functionalisation [15]. The latter property is of particular interest in this case. Its similarity to glass from a chemical and therefore functionalisation standpoint allows the direct transfer of glass surface modifications to PDMS. Its mechanical and cell-friendly properties also allow the synthesis of a device meeting clinical requirements for patient comfort and safety [15].

PDMS substrates were initially functionalised in similar fashion to glass substrates, i.e. with OTS solution treatment. As was the case for OTS functionalisation of glass in Example 1 and FIG. 6, and seen in FIG. 13, similar bands characteristic of successful surface grafting of ODS groups can be observed. Indeed, bands at 2851 cm$^{-1}$ and 2920 cm$^{-1}$ are clearly visible in contrast to the control PDMS substrate wherefrom they are noticeably absent [7]. OTS solution treatment therefore appears to be as successful at grafting ODS surface groups onto PDMS as glass, via the relatively straightforward process of oxygen plasma treatment and OTS solution transmission.

Figure 13:
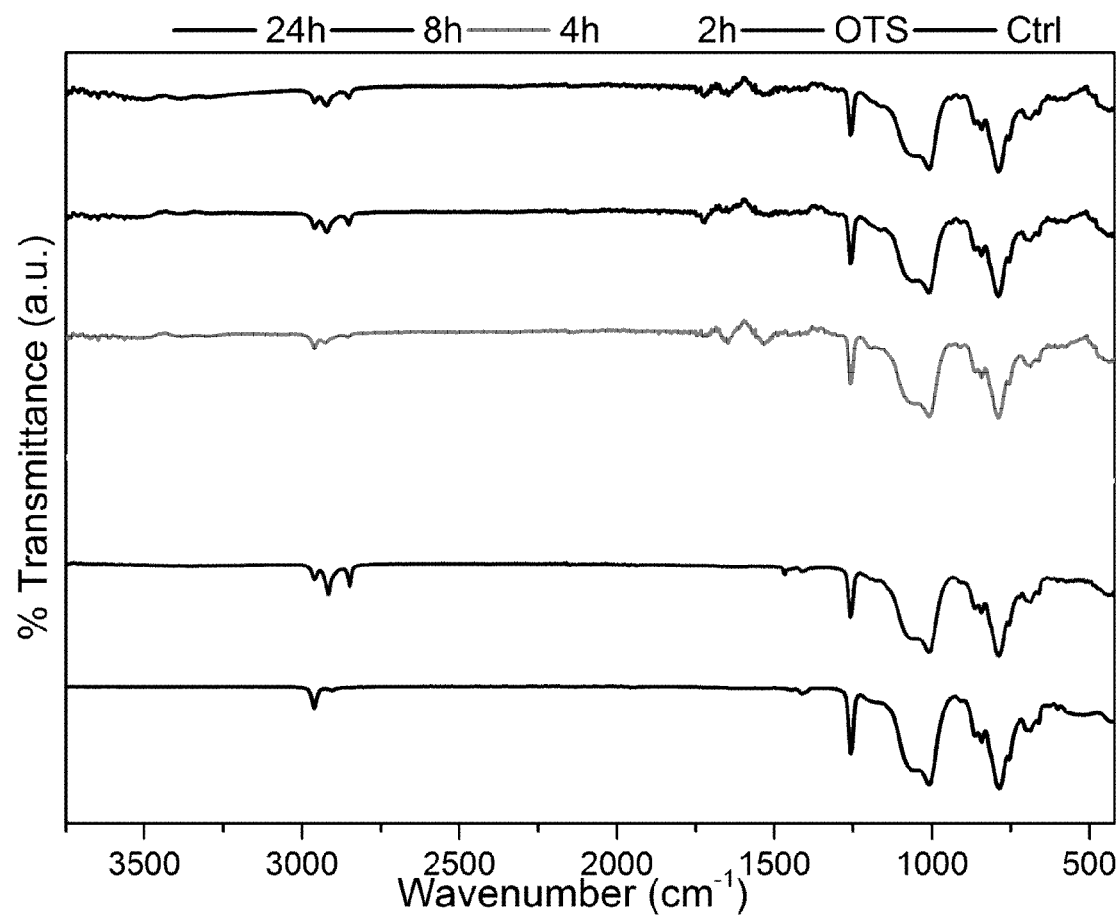
FIG. 13: Normalised FTIR in transmission spectra of unfunctionalised, OTS treated and SI-ATRP polymerised p(OMDA) at 2 h, 4 h, 8 h and 24 h.

ATRP in solution makes use of an initiator in solution to initiate the polymerisation reaction. In contrast surface-initiated reactions rely on the surface grafting of an initiator molecule from which the polymerisation reaction will occur [16]. This was achieved by successive oxygen plasma, APTES solution and BIBB solution treatments [17]. Once successfully modified, SI-ATRP was performed following a similar process to that in solution. Initial characterisation via transmission FTIR presented in FIG. 13 shows similar bands to those found in the case of OTS treatment at 2851 cm$^{-1}$ and 2920 cm$^{-1}$, characteristic of the presence of symmetric and asymmetric stretching of C—H bonds and therefore of ODS groups present on the surface of the PDMS substrate. The band present at 1750 cm$^{-1}$ corresponding to C=O bond stretching corresponds to that found on the methacrylate backbone, thus further confirming the successful surface polymerisation of ODMA monomer via SI-ATRP on the surface of PDMS [12].

The above FTIR signals confirms the successful surface modification and polymerisation of PDMS substrates with ODS groups either via OTS treatment or SI-ATRP of ODMA thus forming p(ODMA) on the surface from surface grafted bromine initiators, achieved via BIBB solution treatment. FTIR however only provides an indication of the end result of the polymerisation process. It does not provide any information regarding the kinetics of the reaction in-situ compared with the GPC and NMR investigations for solution ATRP of ODMA.

Surface grafting of the initiator onto the PDMS substrate and the polymerisation therefore by nature taking place on the surface implies that GPC and NMR investigations on the solution in which the polymerisation takes place would only provide information in theory on the consumption of the monomer as it polymerises on the surface, but not on the state of the polymerisation itself. Solid-state NMR or quartz crystal microbalance techniques [18] could provide means of precisely quantifying the SI-ATR, but as detailed by Yoo et al [3], a more straightforward means of characterising the state of polymerisation in-situ is to add a sacrificial solution initiator in the solution whilst the surface polymerisation is also occurring. Although as highlighted by Yoo et al, it is impossible to directly correlate the molecular weights and distributions obtained by this method, it does enable the evaluation of the kinetic profile and therefore the nature of the underlying surface polymerisation occurring in solution.

Figure 14:
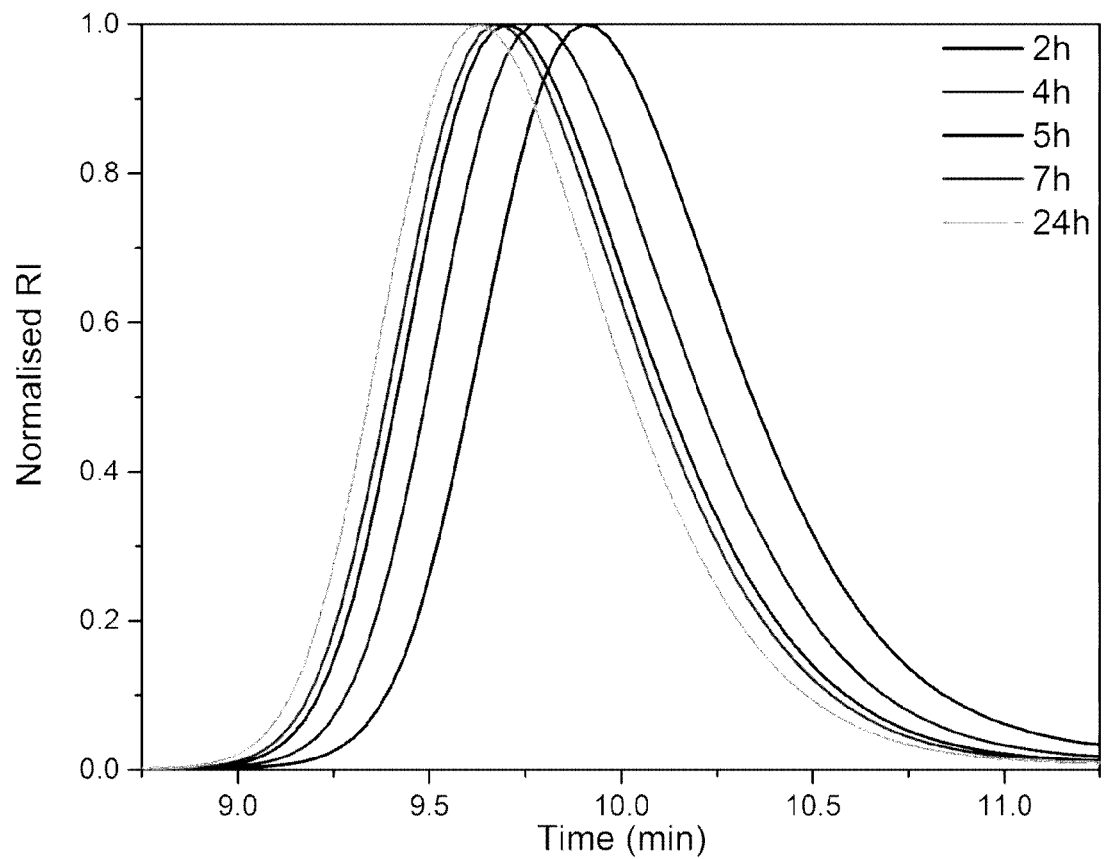
FIG. 14: Plot of normalised RI versus elution time (min) of the kinetic study of the SI-ATRP-mediated polymerisation of ODMA on the surface of PDMS substrates.

The normalised GPC signal of various time points over 24 hours presented in FIG. 14 suggests a steady increase in molecular weight as the polymerisation reaction proceeds. This is further corroborated by data presented in Table 5. Not only does the molecular weight steadily increase with reaction time, the Đ also stays below 1.2 throughout the reaction process. Although this data cannot conclusively prove that the underlying surface reaction is following the exact same progression, it does suggest that it is still a controlled polymerisation over the full reaction period, thus allowing the desired controlled growth of p(ODMA) from the surface of initiator-grafted PDMS.

TABLE 5

Number average molecular weight, weight average molar weight and polydispersity index determined via GPC for SI-ATRP of p(ODMA) as a result of kinetic study over 24 hours.

| Reaction time (h) | $M_N$ (g/mol) | $M_w$ (g/mol) | Đ |
|---|---|---|---|
| 2 | 1.08E+04 | 1.25E+04 | 1.15 |
| 4 | 1.28E+04 | 1.47E+04 | 1.15 |

TABLE 5-continued

Number average molecular weight, weight average molar weight and polydispersity index determined via GPC for SI-ATRP of p(ODMA) as a result of kinetic study over 24 hours.

| Reaction time (h) | $M_N$ (g/mol) | $M_w$ (g/mol) | Đ |
|---|---|---|---|
| 5 | 1.43E+04 | 1.65E+04 | 1.15 |
| 7 | 1.47E+04 | 1.69E+04 | 1.15 |
| 24 | 1.57E+04 | 1.83E+04 | 1.16 |

Figure 15:
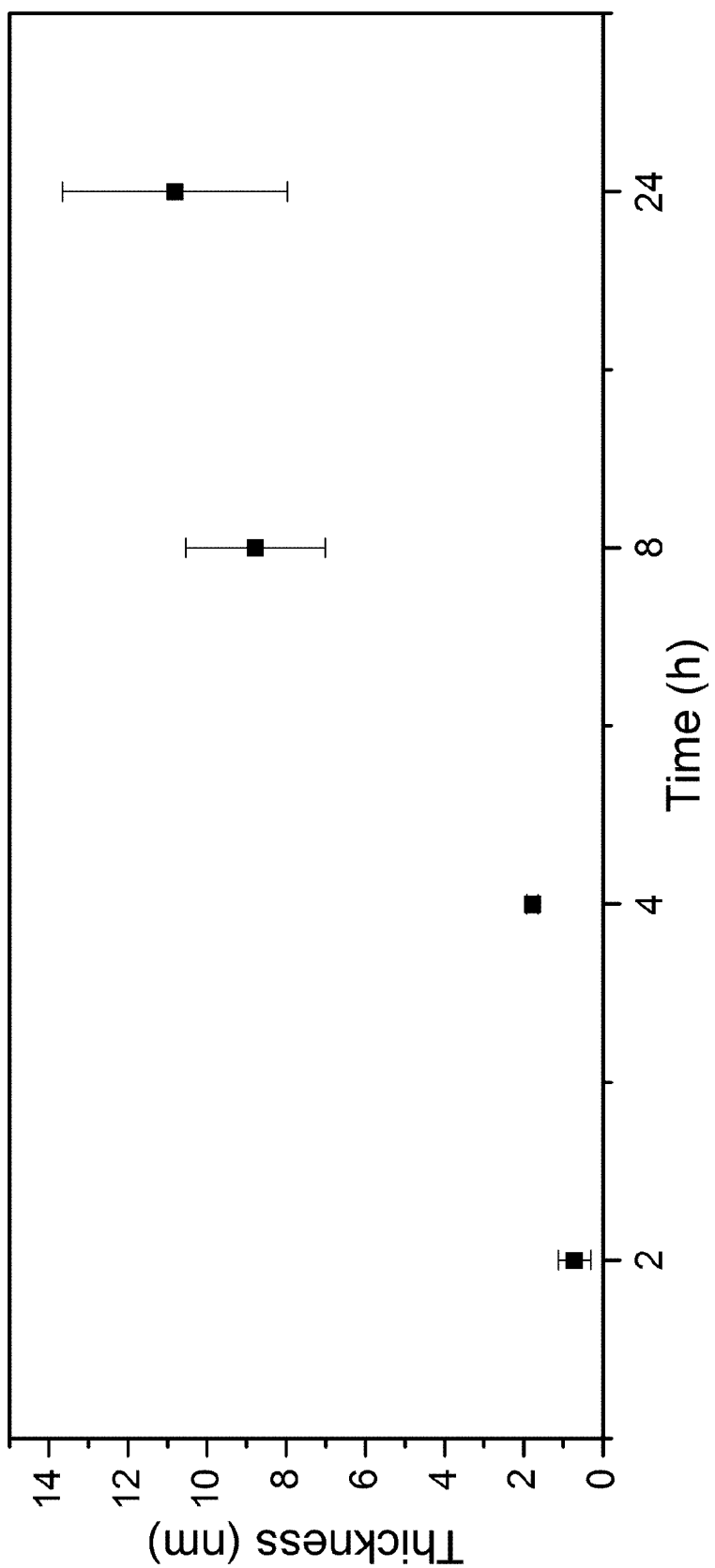
FIG. 15: p(ODMA) polymer brush thickness polymerised on the surface of PDMS substrates via SI-ATRP as function of reaction time.

Ellipsometry also provides a means of evaluating the surface polymerisation of p(ODMA) since it allows the quantification of polymer brush or film thickness. The trend observable in FIG. 15 of the measured polymer thickness on PDMS substrates appears to show a progressive increase in polymer layer or brush length with increasing polymerisation time, as logic and chemistry would dictate. The trend furthermore appears to show relatively steady thickness increase, with a plateauing out of the increase from the 8-hour timepoint onwards. This suggests that the reaction is tending towards full completion or monomer consumption within 8 hours, with much slower kinetics with increasing polymerisation time.

This trend is further corroborated by the previously shown GPC data in Table 5, as indeed the increase in molecular weight between the 4-hour and 7-hour of timepoint is of 1900 kDa as opposed to only 1000 kDa between 7-hour and 24-hour timepoints, i.e. a slowing down in polymerisation rate from around 630 kDa/h to around 60 kDa/h. It is important to note here that in contrast to measurements performed on glass, no WCA measurements were taken on PDMS. Since the innate contact angle of 105° for PDMS is close to that of ODS functional groups on the surface, WCA would not have provided conclusive information with regards to the functionalisation of PDMS surfaces with ODS groups via either OTS treatment of SI-ATRP.

Although it can be argued that none of the characterisation techniques used above can independently quantitatively characterise the surface polymerisation of ODMA via SI-ATRP, the combination thereof strongly points towards a successful controlled polymerisation of the relevant ODS functional group presenting monomers onto surface modified PDMS substrates, thus increasing the active extraction surface area relative to the monolayer coating of ODS provided by OTS solution treatment.

Figure 16:
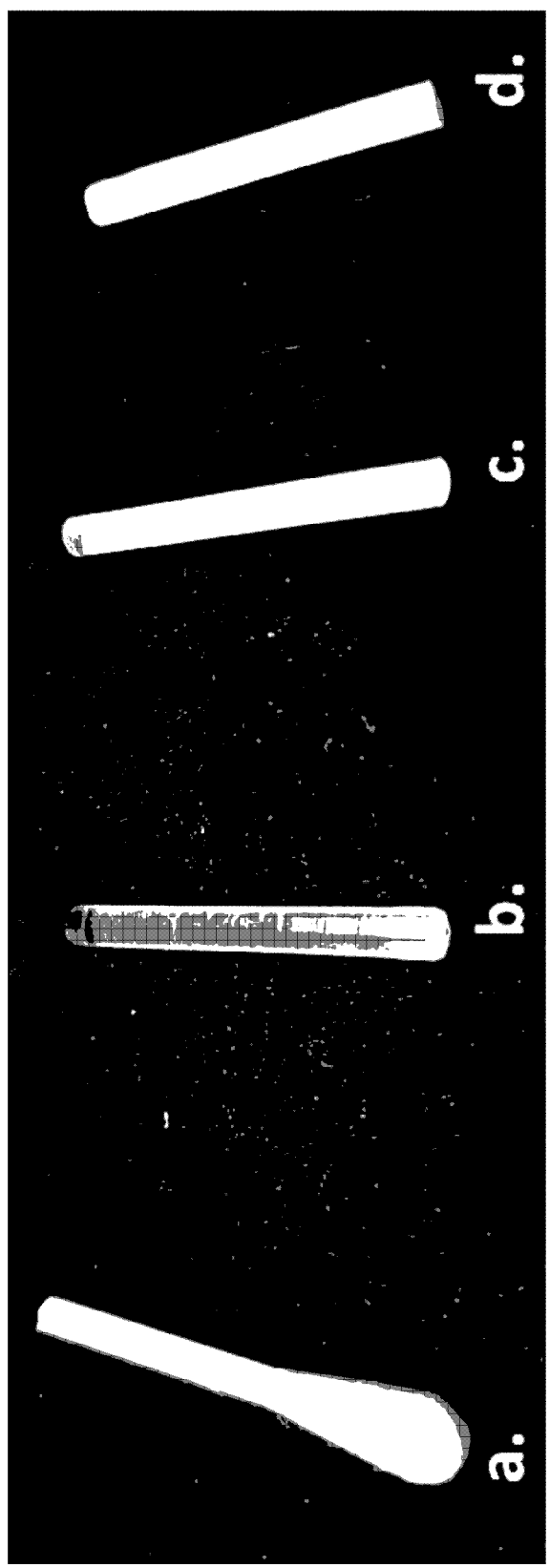
FIG. 16: Photos of a. cotton swab and b. pristine, c. OTS treated and d. 24-hour p(ODMA) SI-ATRP polymerised PDMS rods.

It is also important to note that the key physical characteristics of shape or stiffness did not change during any of the aforementioned functionalisation processes. This is of key importance when considering the clinical application of the proposed substrates. Cylindrical dimensions (or rods) offer not only a suitable shape for extraction within the nasal cavity, but are also ideal for fitting into catheters if the substrates were to be used in other parts of the body. The absence of any dimensional changes during the various functionalisation processes strongly suggests that shrinking or swelling considerations will not have to be made when designing or synthesising the rods. The initial shape cast will be maintained during the full process as clearly shown in FIG. 16.

Example 5: Surface-Initiated ATRP from Modified PDMS (Proof-of-Concept Extraction Assessed Via Fluorescence Intensity Measurements)

Results

Having thus shown it is possible to vary the surface concentration of ODS surface groups by polymerising ODMA via SI-ATRP, initial biological assessments were performed in order to determine whether increasing the density of ODS surface groups allows an improvement in lipid-type molecule extraction and retention from aqueous solutions. As performed in the case of the glass proof-of-concept study, the PDMS rods (OTS, various polymerisation time SI-ATRP functionalised and control PDMS rods) were introduced into a solution of 488 nm fluorescence labelled DOPE and 680 nm fluorescence labelled BSA in aqueous solution. Fluorescence intensity measurements were taken successively after an initial aqueous solution wash and after a Folch solution wash.

Figure 17:
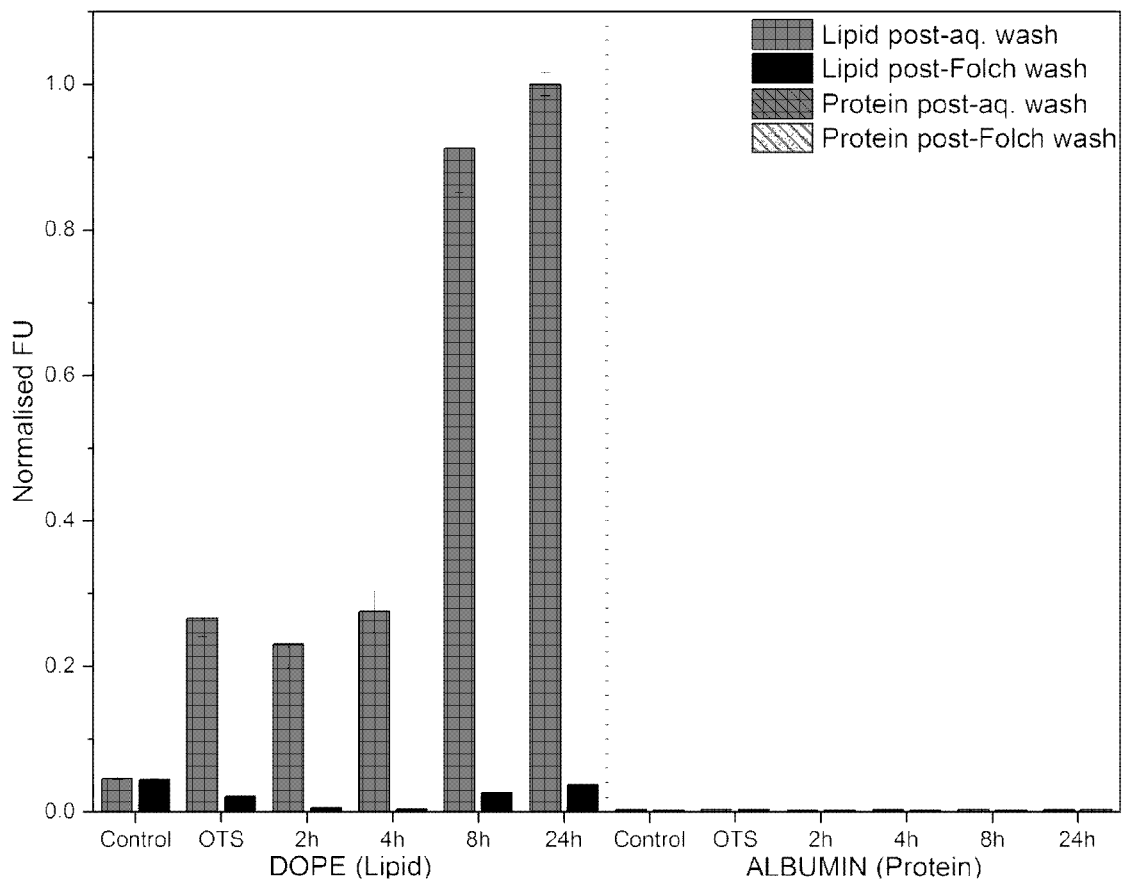
FIG. 17: Normalised fluorescence intensity measurements of lipid and protein retaining capacity of control and ODS functionalised PDMS surfaces via OTS treatment and 2 h, 4 h, 8 h, and 24 h SI-ATRP p(ODMA) polymerisation times.

Results of fluorescence intensity measurements are presented in FIG. 17. In similar fashion to the results obtained for similar measurements on ODS functionalised glass (FIG. 7), it can be observed that after the initial aqueous wash, the signal observed for DOPE lipids on PDMS rods functionalised with ODS is considerably more important than that observed for control PDMS. This again confirms the lipid extraction capability of ODS moieties thus grafted to PDMS. The signal for PDMS rods subjected to 8-hour and 24-hour SI-ATRP p(ODMA) reactions also is approximately 4 times higher than that associated with OTS solution treated PDMS. Given that by design the physical difference between the two substrates is the density of ODS groups (OTS by design theoretically only having a monolayer and SI-ATRP treated surfaces considerably more due to their polymeric nature) it would appear that the hypothesis of increasing the extraction surface area by means of surface polymerisation is herein justified.

Once washed with Folch solution, the fluorescence signal returns to near-baseline levels for all compositions, suggesting that, as desired, full re-elution of the lipids initially extracted from solution has been achieved. Although there appears to be marginally more signal post-Folch washing in the case of 8-hour and 24-hour reacted SI-ATRP PDMS rods relative to their 2-hour and 4-hour counterparts, the fact that the signal in the case of the former is similar to that of both OTS treated and control strongly suggest that near full re-elution of lipids from the PDMS rod surfaces has equally, as intended, been achieved.

In stark contrast to the signal observed for DOPE that of Albumin is near non-existent, with the only traces of signal being attributable to background noise. This is similar to results observed in FIG. 7. Indeed, as observed during actual experimental, the aqueous solution does not adhere to the hydrophobic surface of the PDMS rods regardless of functionalisation (i.e. control, OTS or SI-ATRP treated). However, whereas lipids show a chemical preference to bond to ODS surface groups, there is intentionally no specific surface interaction between the functionalised PDMS and the BSA other than the surface hydrophobicity. This is in accordance with literature where it has been shown that albumin surface coverage decreases with increasing surface hydrophobicity under similar adsorption conditions, as is the case here [19]. This allows the lipids to be extracted without any simultaneous extraction of BSA, as confirmed by the fluorescence intensity measurements shown in FIG. 17. This would again suggest that the proposed substrates can behave as lipid-type—or more generically, low molecular weight, hydrophobic—'species'-selective extraction tools, allowing faster diagnosis as only relevant markers are present on the surface of the propose device, with no contamination of much larger (and in this case irrelevant) proteins.

Example 6: Surface-Initiated ATRP from Modified PDMS (Towards DESI-MS Lipidomics Testing)

Results

The above fluorescence intensity measurements not only confirm the ability of surface-grafted ODS moieties to successfully extract lipids from an aqueous solution selectively (i.e. without protein extraction), but also suggest that the grafting of a higher density of those very ODS moieties onto the surface by means of SI-ATRP leads to an increased extraction efficiency of the surface to which they are grafted. As is the original intention of this project, the next step is to assess the desorption efficacy and therefore preliminary clinical relevance of the proposed rods for lipidomics analysis and eventually diagnostic purposes.

As previously explained, in addition to their mechanical properties and associated patient comfort benefits, a considerable advantage of PDMS substrates over glass is that they can be cast into desired shape. In this case, rods of 4 mm in diameter were chosen. The cylindrical shape allows for ideal insertion into the patients' nasal cavity (and any other orifice if a cannula is use), and also permits easy insertion onto a DESI-MS stage allowing rotational movement along the z-axis. This, as highlighted by Pruski et al [20], allows the setting of an optimal rotational speed for ideal desorption signal and therefore more precise analysis. Although in the case of Pruski et al this was found to be in the range of 101 RPM to 202 RPM, rotational speed was adapted to the PDMS substrate to around 60 RPM due to slight yet unavoidable axis tilt (as will be explained below).

Initial investigations on glass focused on two lipid-type components, cholesterol sulfate and prostaglandin D-2, and suggested the suitability of ODS group surface grafting of DESI-MS enabled lipidomics. In order to further test the concept of ODS surface modification in this case on PDMS substrates, linoleic acid was chosen as a proof-of-concept molecule due to its precursor role in cellular signalling; the biological communication pathway lipidomics aims to exploit for diagnostic purposes [21]. In order to quantitatively assess relative detection capacities of respective extraction surfaces, a concentration gradient of linoleic acid concentrations ranging from 0.1 mg/L to 100 mg/L was chosen, with the solvent once again being aqueous so as to mimic physiological conditions. Two different methods for DESI-MS analysis were chosen, specifically the time delay between the extraction step and analysis step. The results presented in FIG. 18A relate to samples, which have been directly transferred from the extraction and washing step to the DESI-MS analyser and directly analysed. In contrast, those presented in FIG. 18B relate to samples, which were frozen at −80° C. for 48 hours between extraction and analysis, mimicking a transport step to a centralised analysis facility.

Figure 18A:
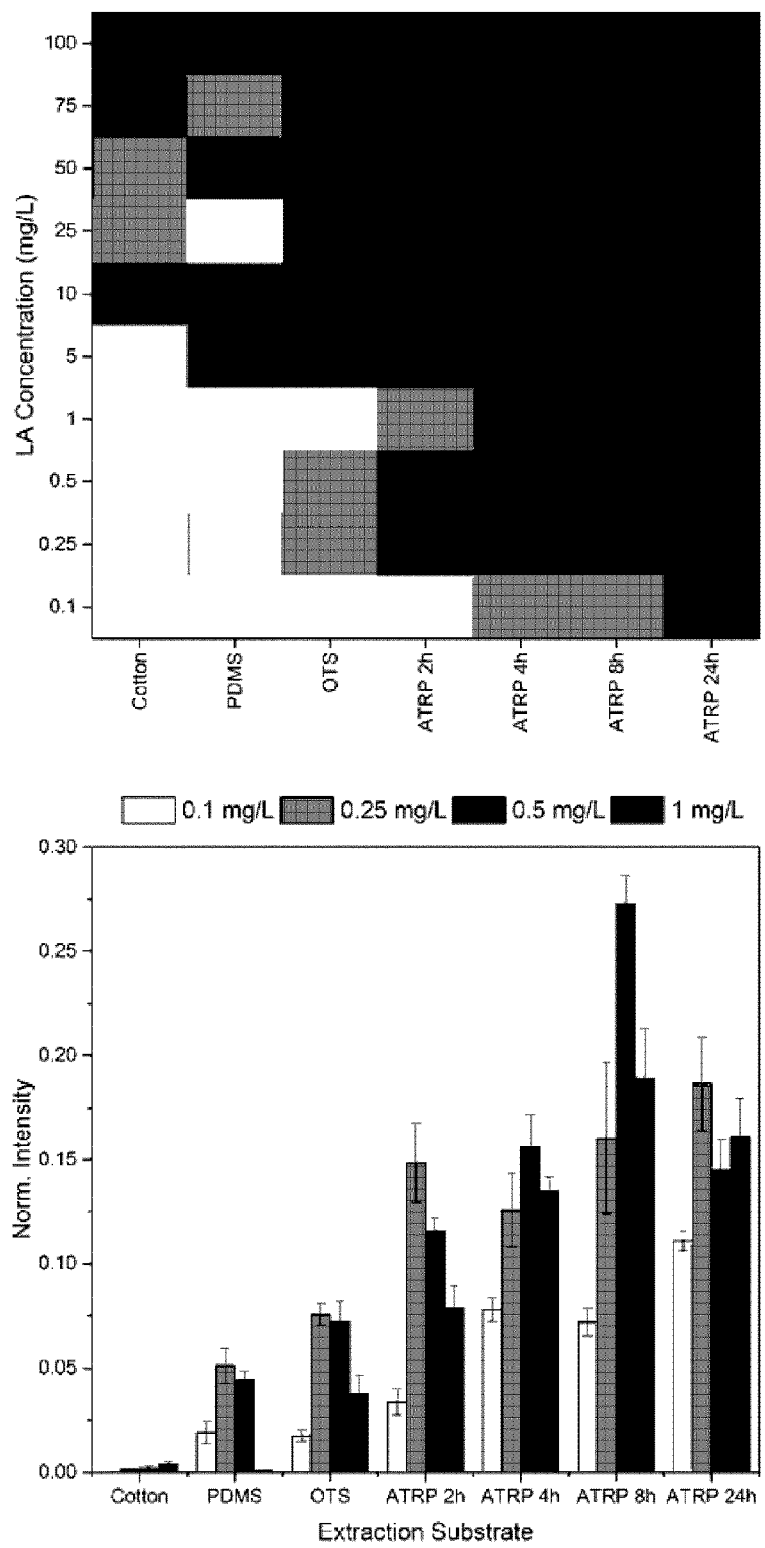
FIG. 18A: Normalised intensities heat maps and intensity plots of linoleic acid obtained via DESI-MS analysis of cotton, control and ODS functionalised PDMS substrates after a. direct analysis post 37° C. incubation.

The data presented in both FIGS. 18A and B show the normalised intensity of the peak corresponding to linoleic acid in negative ion mode, 279.23 m/z specifically, for each extraction phase tested over the concentration gradient from 0.1 mg/L to 100 mg/L. The first trend that can be identified from FIG. 18A is a relatively consistent correlation between signal and standard concentration, which is to be expected. This suggests that the synthesised extraction phases are able to extract in the 0.1 mg/L to 100 mg/L without achieving an extraction saturation limit. It further implies that the DESI-MS detection parameters used allow detection of linoleic acid over that concentration range.

It was initially hypothesised that increasing the surface concentration of ODS groups grafted onto PDMS substrates would yield increased extraction capabilities, and therefore provide greater signal resolution. Analysing FIG. 18A, this appears to be the case. Indeed, the normalised signal whilst desorbing from 8-hour and 24-hour SI-ATRP polymerised PDMS samples is higher than their shorter polymerisation time, OTS and pristine PDMS counterparts. Given the longer polymerisation times by nature imply an increased surface density of the ODS functional groups, these results strongly suggest the positive confirmation of the hypothesis. The relatively unsubstantial difference between 8-hour and 24-hour polymerisation time samples is in line with the surface characterisation results presented in Example 4, in which a plateauing of both molecular weights and polymer surface thickness were identified.

Figure 18B:
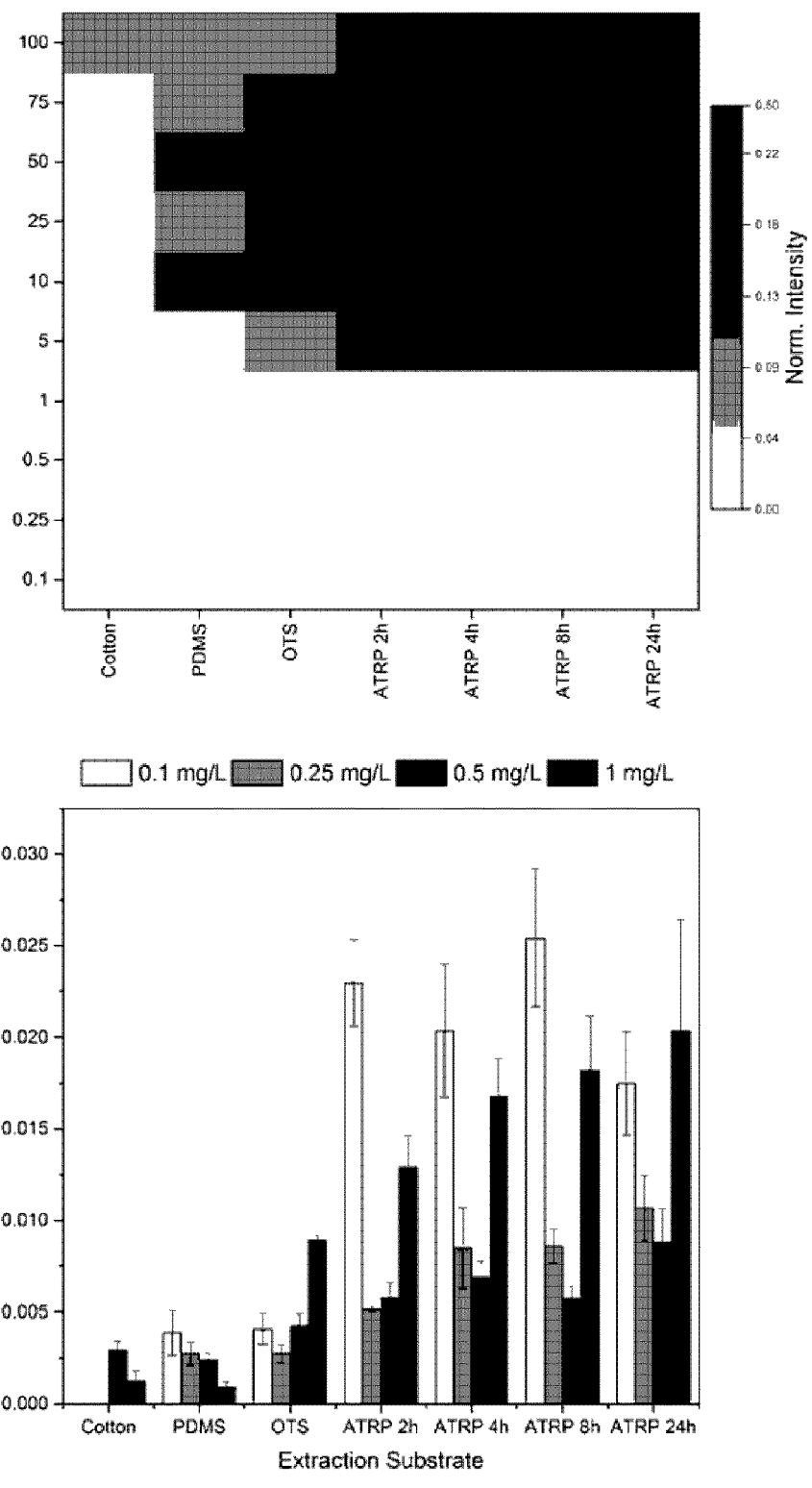
FIG. 18B: Normalised intensities heat maps and intensity plots of linoleic acid obtained via DESI-MS analysis of cotton, control and ODS functionalised PDMS substrates b. post 48-hour incubation in 80° C. freezer.

FIG. 18B presents similarly obtained normalised intensities for linoleic acid signal as desorbed from control and ODS functionalised surfaces, but in this instance subject to a 48-hour freezing period between extraction and DESI-MS analysis. As previously discussed, this intends to mimic the clinical context whereby the DESI-MS facility is within direct proximity of the facility or complex where patients are being diagnosed with the proposed rods. Samples in this case would be taken from patients and shipped to a centralised facility.

Several key immediate differences appear comparing FIG. 18A and FIG. 18B. First and foremost, it must be noted that peak intensity values are reached at 10 mg/L linoleic acid standard concentrations, after which the intensity values generally decrease. This is in clear contrast to FIG. 18A, where peak intensity was consistently reached for 100 mg/L. A possible explanation for this is lipid saturation. At high lipid concentrations (above 10 mg/L), it is possible that lipids are simply aggregating on the surface without truly adsorbing to the ODS moieties present on the surface. As a result of the freezing process, in contrast to the direct extraction previously described, the excess lipids are most likely aggregating further under cooling, and thus desorbing prior to analysis during the thawing process, thus leading to lower intensities than the 10 mg/L concentration standard. The fact the values for cotton in contrast to any PDMS substrates are directly correlated to standard concentration appear to corroborate this hypothesis, as the frozen standard would be protected in this case by fibrous cotton as opposed to being exposed as aggregates on the flat surface of the PDMS rods. This would equally explain why no such saturation concentration was observed in the direct extraction protocol, as excess lipids would be directly desorbed by the DESI sprayer, and further signal would be provided by the underlying physically ODS adsorbed layer underneath. Although in theory this could possibly imply the inaccuracy of the results, actual biological solutions will rarely contain such high concentration of diagnostically relevant lipids.

When considering the intensity values for 10 mg/L and lower however, the trends established from the direct extraction process presented in FIG. 18A remain true for those presented in FIG. 18B. Indeed, higher intensity values can be observed for SI-ATRP PDMS substrates relative to their OTS counterpart. However, there is much less progressive increase in intensity with increasing polymerisation time as had been observed for direct extraction, with values for 2-hour through to 24-hour polymerisation times being very similar. Given the proven physical change in polymer length, this would suggest the freezing process has a negative effect on the surface chemistry, possibly altering either the bonds between lipids and ODS moieties causing the former to desorb prior to DESI-MS analysis during the thawing process as previously hypothesised, or physically altering the p(ODMA) chains having the same effect.

A clear trend however that is in line with that established from the direct extraction protocol is the increased lower detection limit of OTS and SI-ATRP functionalised surfaces relative to cotton, yet again confirming the proposed PDMS modified substrates as viable improvements on current technology. The results presented in FIGS. 18A and B strongly point towards to the validation of the hypothesis that ODS surface functionalised PDMS provide suitable extraction and analysis qualities, and that increasing ODS surface group density by means of surface-initiated polymerisation equally allows for increased signal under DESI-MS.

Although a linear trend between ODS surface group density and signal intensity is identifiable, the correlation between standard concentration and signal intensity (independent of ODS surface group density) is less linear. For instance in FIG. 18A, extraction phases such as OTS or 2-hour SI-ATRP phases display what appear to be clear outliers from the trend at 50 mg/L and 10 mg/L, and 0.25 mg/L and 10 mg/L respectively. This can most likely be explained by a combination of systematic and experimental error due to the physical set up of the DESI-MS mounting methods. It proved difficult during experimental proceedings to mount the rods perfectly along the z-axis so as to avoid a variation in distance between substrate surface and the inlet of the DESI-MS. This often lead to a strong variation in signal intensity as shown from FIG. 19a, presenting the relative abundance expressed as a percentage during a typical PDMS rod analysis, specifically in this case that of SI-ATRP functionalised PDMS extracting from a solution of 1 mg/L linoleic acid.

Figure 19:
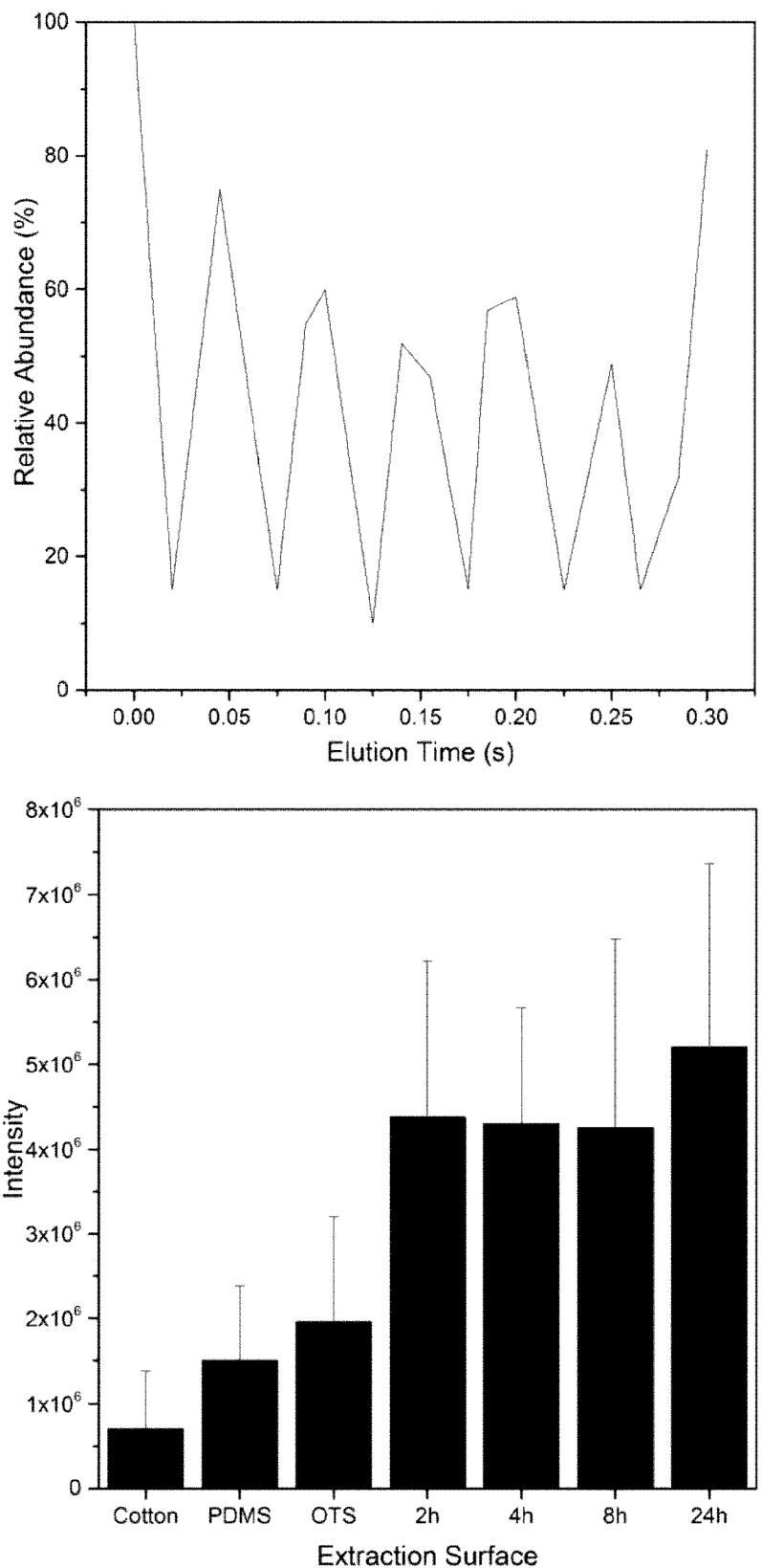
FIG. 19: a. chromatogram presenting the relative abundance vs analysis time spectrum obtained from the DESI-MS enabled analysis of 1 mg/L linoleic acid extraction via 24-hour reacted SI-ATRP PDMS and b. Average absolute overall intensity values for various extraction surfaces (times indicating SI-ATRP reaction time).

The signal varies considerably during rotation, presenting nearly 100% relative abundance signal in some instance and down to 20% relative abundance in others. This variation is the result of axis tilt, consistently varying the distance between the extraction rod and the DESI-MS detector. The peaks in abundance correspond to moments during which the extracting phase (or rod device) is being rotated in such manner that the surface is closer to the detector. This shorter substrate-detector distance allows greater desorption of surface molecules and therefore greater signal than moments where the rod is rotated further away from the detector, during which the signal is obviously lesser. Although the rotation presented in FIG. 19 is a one-off case, the trend repeats itself across most samples. Indeed, by its very nature, DESI-MS is a sensitive means of obtaining spectra; any experimental parameters altering this such as in this case even relatively small substrate-detector distance variations can have a considerable effect on the obtained results.

For this reason, data presented in FIGS. 18A, 18B, and 19a is plotted with normalised intensity as the y-axis as opposed to absolute intensity so as to minimise discrepancy resulting from experimental or set up induced error, thus maximizing the comparative potential of the results. Raw data was processed by using only data points corresponding to parts of the chromatogram (as presented in FIG. 19a) where the relative intensity is above a 75% relative abundance threshold. The thus obtained raw absolute intensity values associated with the linoleic acid peak at 279.23 m/z as measured in counts via analysis software was then normalised to the overall intensity of the spectrum (such as that presented on the left-hand edge of spectra in FIG. 20).

It is important to note however that the although above described normalisation process was used to most accurately compare the results across samples, the absolute intensity values presented in FIG. 19b highlight the fact that as ODS surface group intensity is increased, absolute intensity values of desorbed linoleic acid increase proportionally. Despite the large error values they display, it is clear that surface polymerised PDMS rods allow for much higher intensity values of desorbed linoleic acid than their OTS counterparts.

Figure 20:
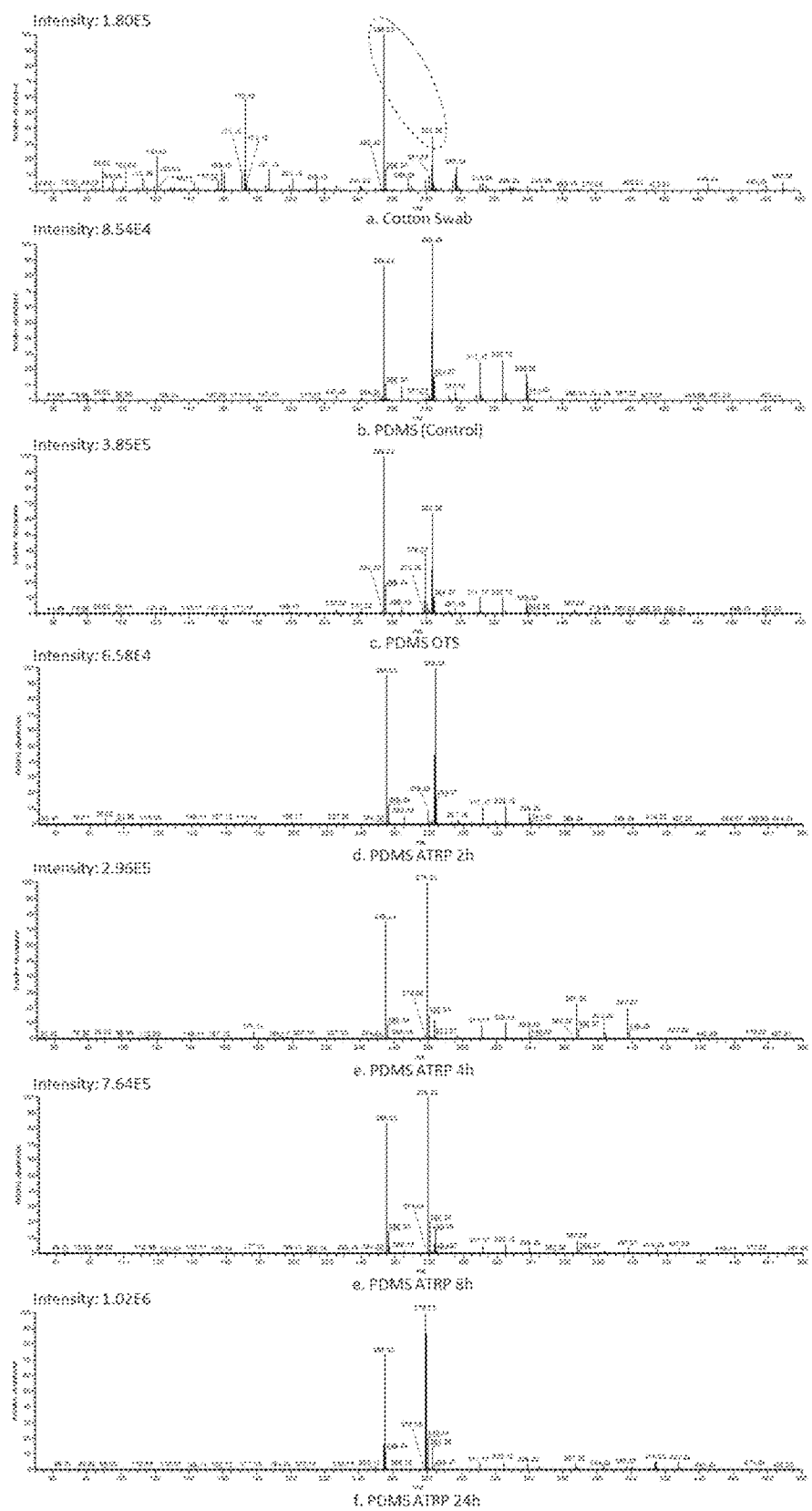
FIG. 20: Mass spectra for cotton, control and ODS functionalised PDMS substrates obtained after direct lipid extraction and desorption under DESI-MS from a 1 mg/L linoleic acid standard aqueous solution.

In FIG. 20, background peaks clearly visible in spectra obtained using cotton and control PDMS rods progressively disappear in favour of linoleic acid peaks, as the relative abundance of the latter increases with polymerisation time and therefore ODS surface density. Although therefore when presenting the results in such a way it conceals the actual extraction potential of SI-ATRP PDMS reacted rods relative to OTS and noticeably cotton substrates as clearly shown FIG. 20, it allows for the best comparison between substrates.

The most noticeable trend from these results is the increased intensity of measurements performed on ODS functionalised samples, OTS and various SI-ATRP reaction times relative to cotton; the current gold standard extraction substrate for such procedures. In particular, the PDMS substrates surface polymerised via SI-ATRP for 24 hours show an up to four-fold increase in signal at lower concentration ranges (0.1 mg/L) relative to OTS functionalised surfaces, and up to ten-fold increase in normalised signal relative to cotton at the same low concentrations. This strongly points towards ODS functionalised PDMS as a suitable improvement on cotton for such extraction and lipidomics analysis purposes.

Previous experiments using fluorescence intensity have assessed the successful extraction capacity of the ODS functionalisation relative to unfunctionalised PDMS. In this case however, the non-linear intensity profile of PDMS (most likely due to the systematic error introduced via off-axis tilt during rotation) renders the comparison between functionalised and control substrates slightly more complicated. However, the trend remains that ODS presenting samples have a higher intensity across the concentration scale than the non-linear profile exhibited by control PDMS, in particular when comparing to 8-hour and 24-hour SI-ATRP surface polymerisation times.

The initial premise of using a surface-initiated polymerisation method to grow polymer brushes of ODMA on the surface of PDMS rods was in order to assess whether increasing the ODS extraction phase surface area would allow greater lipid extraction from media and therefore better desorption signal, allowing better resolution and therefore better analytical and diagnostic potential. Comparing the various polymerisation time SI-ATRP p(ODMA) PDMS substrates relative to OTS solution treated PDMS, it is clear that the longer the surface-initiated reaction is allowed to proceed, the better the resulting desorption signal, with a clear improvement in signal at 8-hour and even more so 24-hour polymerisation times compared to OTS, with up to four-fold increase in signal intensity in the 0.1 mg/L to 0.5 mg/L range as observe in FIGS. 18A and B. A progressive increase in signal intensity at those concentration ranges can equally be observed to a lesser extent at 2-hour and 4-hour polymerisation times, confirming the correlation between polymerisation time and signal intensity. Given that the polymer characterisation techniques presented in Table 5 pointed towards a steady increase in polymer chain length, it can therefore be concluded that polymer chain length and signal intensity under DESI-MS analysis are directly correlated. The presented data does not however conclusively prove the increased extraction capacity of the thus functionalised surfaces; indeed, without having conclusive evidence of a stronger decrease in lipid concentration in the solution from which the lipids are extracted, it can only be concluded that longer polymer chains (and therefore increased ODS group surface density) increase the resolution and lower limit of detection under DESI-MS relative to both OTS functionalised, PDMS control and cotton substrates used in an identical manner.

Example 7: Surface-Initiated ATRP from Modified PDMS (Multi-Component Solution DESI-MS Testing)

Results

Figure 21:
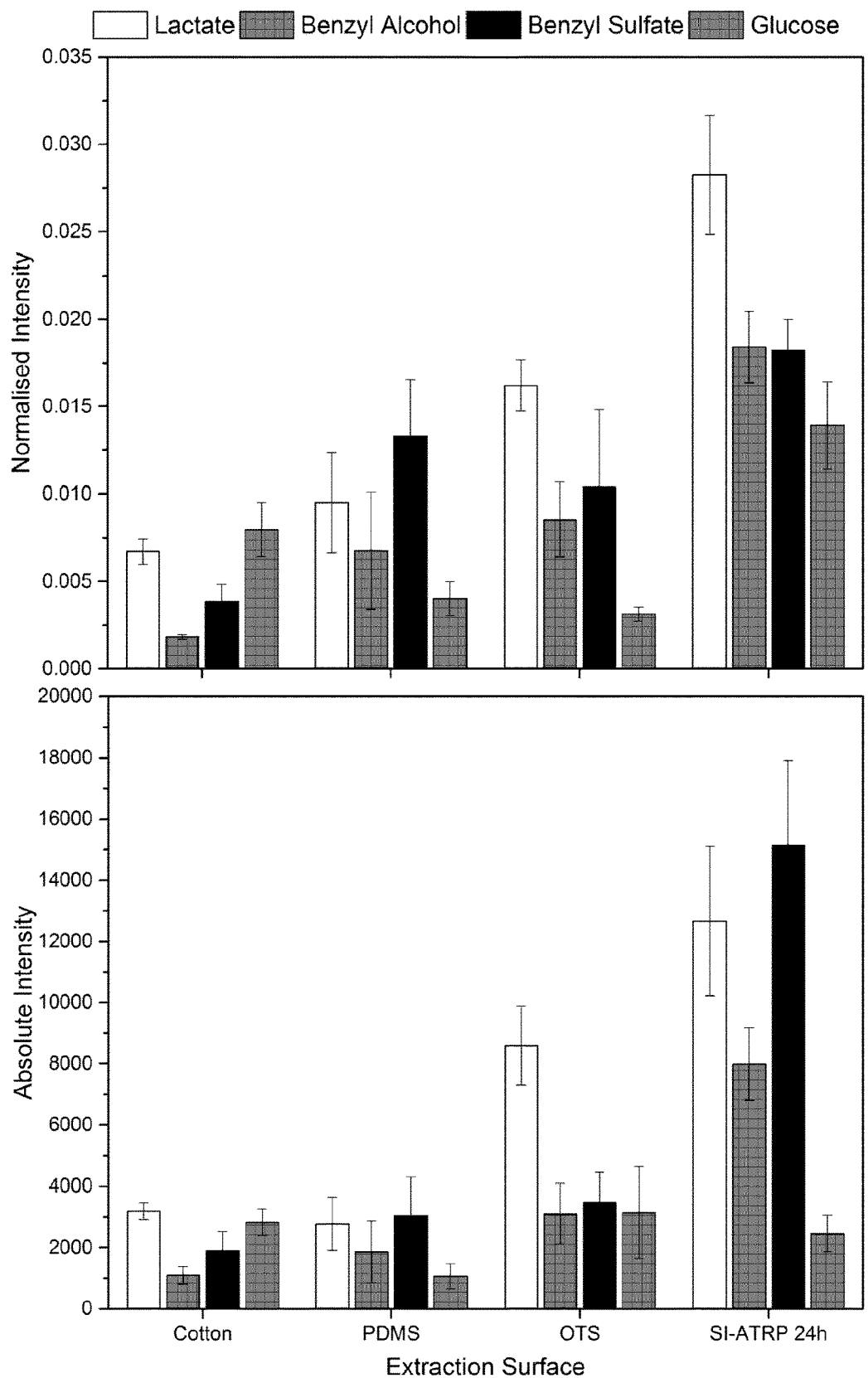
FIG. 21: Normalised (a) and absolute (b) intensities of lactate, benzyl alcohol, benzyl sulfate and glucose obtained via DESI-MS analysis of cotton, control and ODS functionalised PDMS substrates post extraction in bovine plasma solution.

Having established that direct extraction provided more consistent and reproducible results than the intermediate freezing method, a similar direct extraction process was performed on what was considered to be the first biological solution. FIG. 21 presents the normalised intensities of four lipid compounds successively extracted and desorbed under DESI-MS, notably lactate, benzyl alcohol, benzyl sulfate and glucose, naturally occurring and diagnostically relevant compounds [22].

A comparison of the normalised intensities relative to the extraction surfaces used, once again supports the previously-suggested trends of increased desorption signal with increased ODS surface group density as provided by SI-ATRP functionalised substrates relative to both OTS, control and notably cotton. In this case, only 24-hour polymerised PDMS substrates were selected, having previously demonstrated their high extraction potential relative to shorter polymerisation times, due to the longer p(ODMA) chains on their surface.

As previously explained, normalised signal has only been used in the thus far presented results for optimal comparative and analytical purposes. However, as highlighted by FIG. 19b, the absolute intensity values for OTS and increasing SI-ATRP treated substrates are orders of magnitude higher than those for cotton and PDMS control (unfunctionalised) substrates. Therefore, showcasing results in absolute intensities not only gives a better idea of what the results are like unprocessed, but also more specifically highlights the high potential of surface polymerised PDMS rods for lipid extraction and desorption under DESI-MS.

This is particularly clear from FIG. 21b. Although OTS solution treated substrates do not show considerably higher intensities for benzyl alcohol, sulfate and glucose than both PDMS control and cotton (with the exception of lactate that presents a three times higher intensity than the aforementioned controls), the 24-hour reacted SI-ATRP substrates shows a dramatic increase in desorption signal for lactate, benzyl alcohol and benzyl sulfate, particularly the former and the latter, with a fourfold and seven-fold increase in signal relative to cotton. Benzyl alcohol and particularly glucose however show much smaller increases in signal, that of glucose being comparable to that of cotton and OTS extraction phases. Given the much-increased extraction of lactate and benzyl sulfate, this suggests that benzyl alcohol and glucose have a lower affinity of $C_{18}$/ODS groups than the more successfully extracted lipids.

Regardless of the discrepancies detailed above, it must be noted that the proposed functionalised surfaces have successfully extracted various diagnostically relevant biomarkers from a biologically representative solution.

It can therefore also be concluded as discussed above both that surface-functionalised ODS groups suitable for the extraction lipids from an aqueous solution, and that increasing their surface density by means of surface-initiated polymerisation allow a greater desorption signal, most likely due to increased extraction from solution. It is also clear that ODS-functionalised PDMS is a better substrate than cotton for use in DESI-MS enabled lipidomics-based diagnostic techniques.

Example 8: Surface-Initiated ATRP from Modified PDMS (MTT Assay Cytotoxicity Testing)

Results

The results presented above strongly support the clinical potential of the proposed functionalised surfaces for DESI-MS enabled lipidomics analysis of biological fluid, including nasal mucosal fluid. In order to complete the picture of device clinical viability, it was key to establish the non-toxic nature of the thus functionalised devices. To this end, all proposed compositions were subjected to an MTT cell viability assay. Substrates were immersed in cell culture media for 1 hour, corresponding to the maximum amount of time such devices would be in contact with physiological media. Once removed, the cell intensity was measured after 1 hour and 24 hours, so as to determine the effect of the substrates on the cells they had come in contact with.

Figure 22:
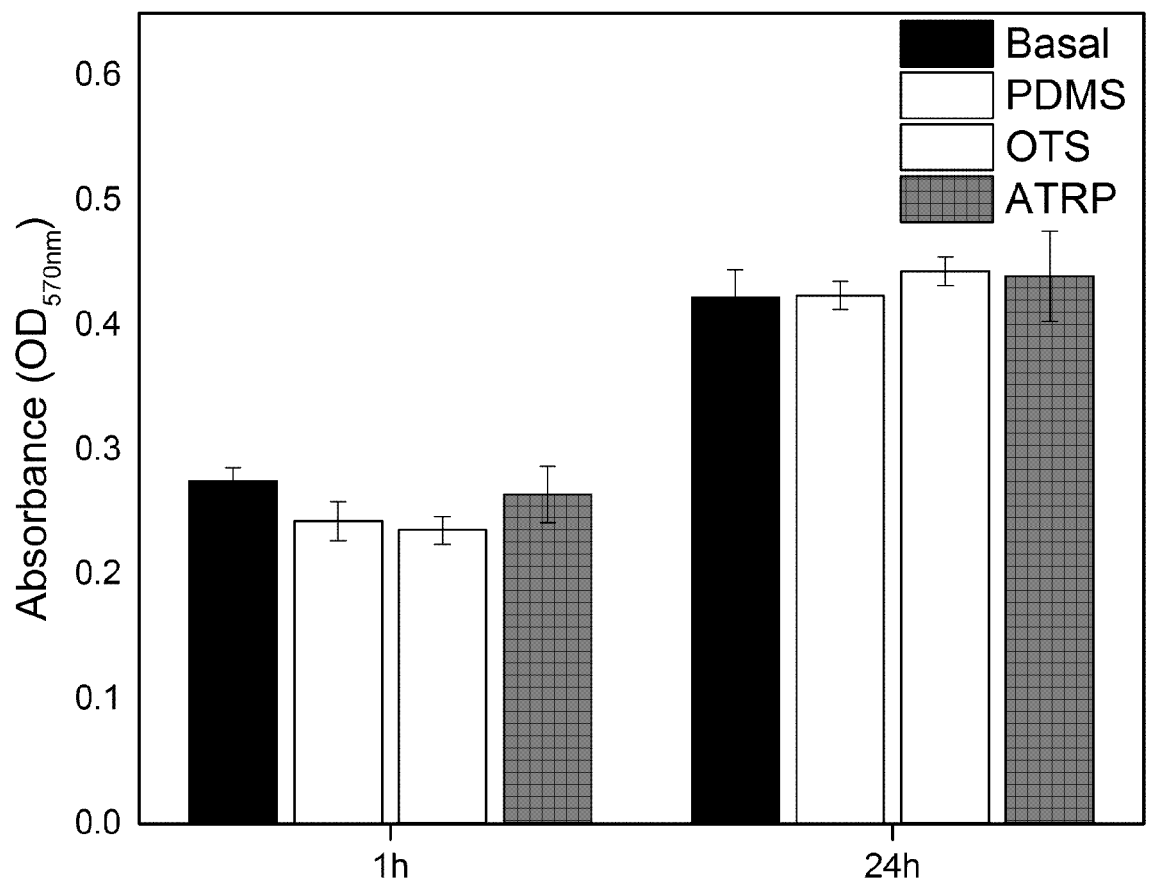
FIG. 22: MTT cytotoxicity assay for basal media, PDMS control, OTS and 24-hour SI-ATRP functionalised PDMS.

As can be seen in FIG. 22, comparing to basal absorbance levels, regardless of composition, no substrate shows any sign of causing any alteration to the cellular environment at both 1 h and 24 h timepoints. The minimal variation observable in absorbance values particularly at the 1 hour post exposure timepoint can be considered negligible, given that at the 24 hour post exposure mark the discrepancies are considerably reduced and any divergence at the latter time point are not correlated with the former. For instance, where at 1 h the OTS absorbance values is slightly lower than basal media and the lowest value of all four, at 24 h it is the highest value. Given the tests were performed on the same media (i.e. one same solution was tested at 1 h and 24 h, not separate experiments), it is clear the slight value discrepancies can be labelled as artefacts. MTT assays are a staple ISO standard testing method. Therefore, this suggests that the substrates and any functionalisation performed as suggested do not have any negative impact on the cellular media they come into contact with and are therefore safe for use.

Summary of Examples 1 to 8

The above presented work details the various stages of ODS functional group functionalisation onto the surface of silica-network based surface, namely glass and PDMS silicone. PDMS rods were synthesised into shapes that allowed both facile and effective introduction into patient mucosal linings (such as directly into the nasal cavity or other systems via cannula lines) as well as optimal desorption under DESI-MS. The ODS surface functionalisation by means of either OTS solution or SI-ATRP surface-initiated polymerisation have been shown to allow lipid extraction from aqueous solutions when using fluorescence labelled lipids and visualised under confocal microscopy. 24 h polymerised SI-ATRP rods displayed optimal lipid extraction and desorption under DESI-MS spectroscopy, crucially allowing a drastic increase in lower limit of detection relative to cotton swabs as currently used in DESI-MS-based procedures. This was shown to be the case both for single lipid model solutions as well as physiologically-approximating solutions, such as the bovine serum solution used here.

Crucially, none of the proposed substrates showed any signs of cytotoxicity when exposed to MTT assays, provisionally indicating their suitability for clinical implementation.

This constitutes what is to the inventor's knowledge the first reported work regarding substrates specifically designed with both clinical and analytical considerations in mind of nasal extraction and DESI-MS enabled analysis respectively. The PDMS rod-like substrates indeed satisfy the clinical requirements of facile introduction and analyte extraction and in-situ biomarker purification (as shown by the retention of lipids and elution of proteins in FIG. 17). Subsequent analysis requirements of speed and precision are satisfied by the DESI-MS enabled analysis, providing extensive data collection within a minute.

As shown by FIG. 20, it is possible to perform patient procedures and store the DESI-MS samples during transport and still obtain reliable results; specifically, 24 h polymerised SI-ATRP samples provide increased LOD relative to the currently used methods. In combination with their reduced substrate DESI-MS signature, this substrate best meets the requirements of this project.

As previously reported, an ideal 'gold standard' nasal fluid extraction device should aim to be sponge-like in both its soft and highly compressive nature as well as high surface area. The next experiments will therefore concentrate on an alternative silica network yet porous and flexible substrate in the form of xerogels. Given the successful nature of the ODS functionalisation methods proposed, the following Examples will therefore focus on a means of optimising ODS surface functionalisation on the proposed xerogel substrates.

Example 9: Xerogel Material Properties

Materials

Trimethoxymethylsilane (MTMS, 99%), Dimethoxydimethylsilane (DMDMS, 95%), (3-Mercaptopropyl)trimethoxysilane (MPTMS, 95%), N-Octadecyl methacrylate (ODMA), (3-Mercaptopropyl)methyldimethoxysilane (MPMDMS, 95%), Trichloro(octadecyl)silane (OTS, 90%), (3-Aminopropyl)triethoxysilane (APTES, 99%), α-Bromoisobutyryl bromide (BIBB, 98%), Triethylamine (99.5%), 4,4'-Dinonyl-2,2'-dipyridyl (dNbpy, 97%), Copper (II) chloride (97%), Hexadecyltrimethylammonium chloride (CTAC, 98%), Urea (99.5%), Acetic Acid (99.85%), 2,2'-Azobis(2-methylpropionitrile) (AIBN 98%), n-Hexane (95%), Anhydrous Chloroform (99%), Anhydrous Toluene (99.8%), 2-Propanol (99.5%) were purchased from Sigma-Aldrich and used as purchased unless otherwise stated. Phosphatidylglycerol (PG), phosphatidylinositol (PI), phosphatidic acid (PA), phosphatidylethanolamine (PE), phosphatidylserine (PS), phosphatidylcholine (PC), sphingomyelin (SM), and ceramide (Cer) were purchased from Avanti lipids.

Methods

Xerogel Sol-Gel Synthesis

Figure 24:
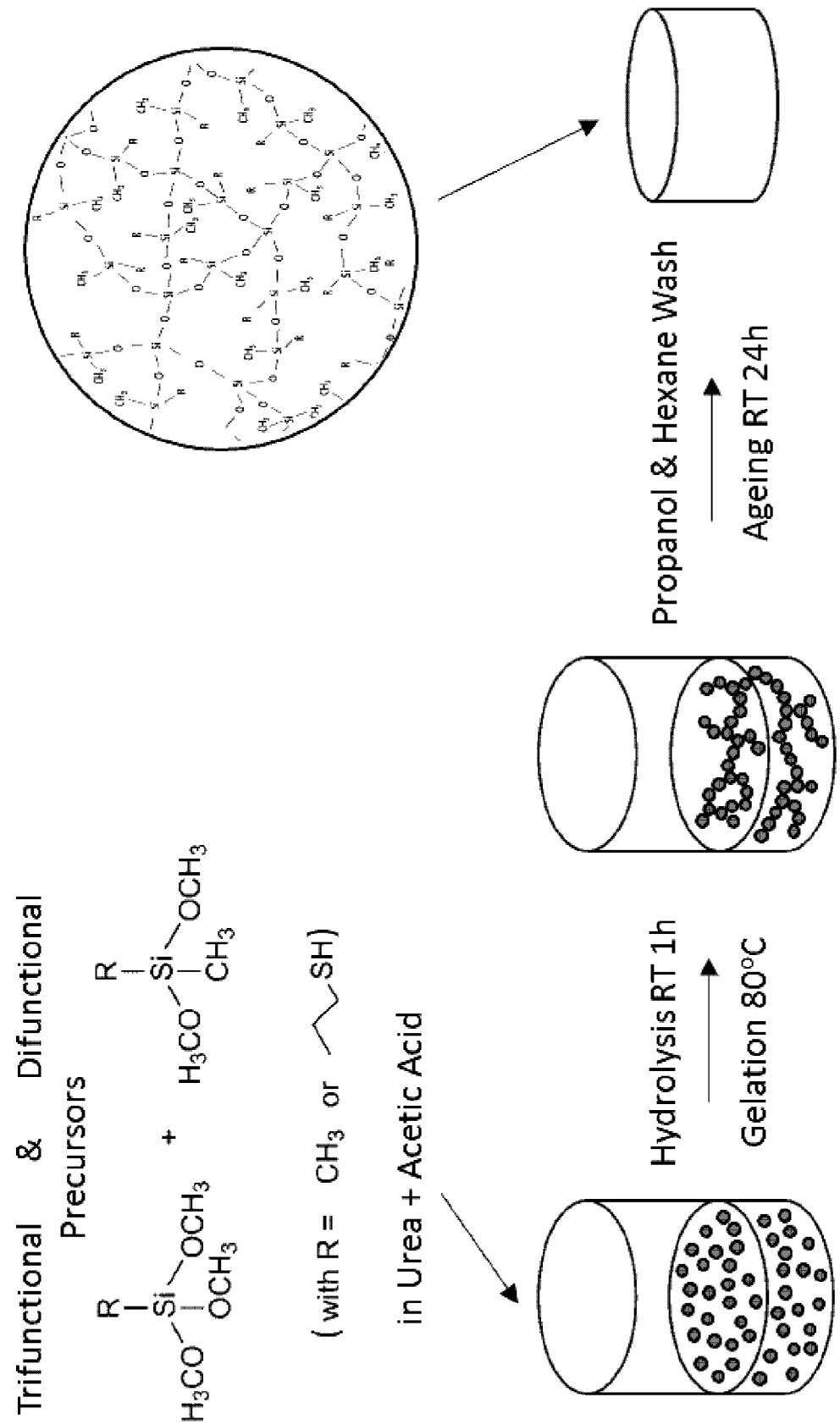
FIG. 24: Schematic of xerogel synthesis process.

Xerogel synthesis followed by the procedure described by Hayase et al. [23] and represented schematically in FIG. 24. Tri-functional and di-functional siloxane precursors (MTMS and DMeDMS) were mixed in a 3:2 molar ratio, 5 g of urea and 0.8 g of CTAC were added to 15 mL of 5 mM acetic acid solution and mixed at room temperature for 60 minutes to promote hydrolysis. Once hydrolysed, samples were poured into sealed containers and transferred to an 80° C. oven for 24 hours for gelation and network condensation. The resulting gels were then removed and soaked over 3 successive 8 hour periods in 2-propanol and n-hexane to wash out unreacted reagents. Once washed, gels were left to dry at room temperature (or in a 40° C. oven to accelerate the process) and stored in a desiccator prior to use or surface functionalisation.

Two main compositions were chosen based on the suitability of their mechanical properties for the proposed application and their post-functionalisation potential. Table 6 identifies their respective denominations and exact compositions.

TABLE 6

Denomination and composition of xerogels used henceforth

| Denomination | Siloxane precursor ratio | Urea (g) | CTAC (g) | Acetic Acid (mL) |
|---|---|---|---|---|
| N | MTMS:DMDMS | 5.0 | 0.8 | 15 |
| MD | MTMS:DMeDMS | 5.0 | 0.8 | 15 |

Results

Both N- and MD-type xerogels were therefore assessed prior to functionalisation with testing methods deemed to best illustrate their potential. The results are summarised in FIGS. 28A and B. It is key that the proposed xerogels offer significant advantages relative to the previously presented PDMS solid substrates to ensure patient comfort. Although the physical feel of the xerogels cannot be perfectly numerically assessed (and will be referred to henceforth despite its somewhat arbitrary nature), compression testing (with loading and unloading assessed) was determined to be the most suitable way to attribute a numerical value to this parameter.

Figure 28A:
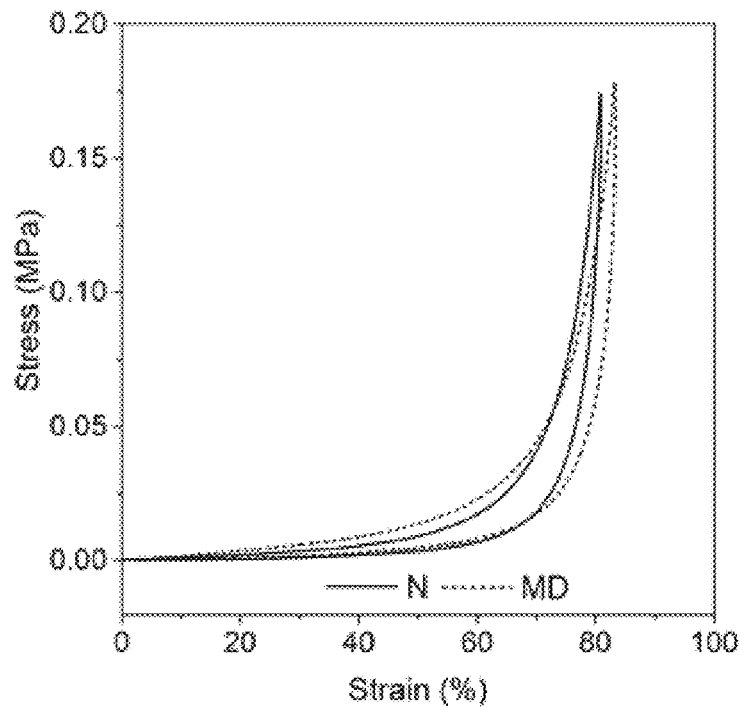
FIG. 28A: N- and MD-type xerogel innate (pre-surface functionalisation) material properties (a. loading and unloading curves under compression testing and b. fluid absorption capacity over time).
Figure 28A:
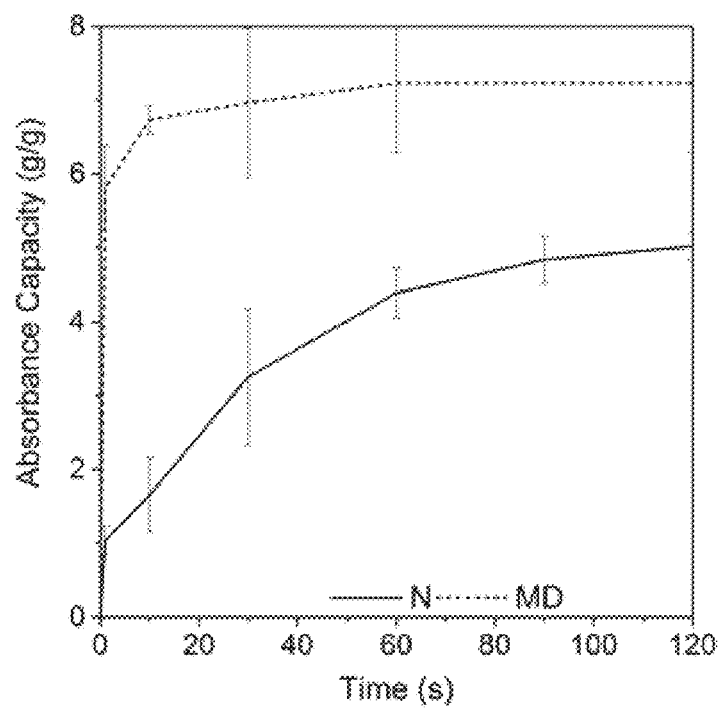
Figure 28B:
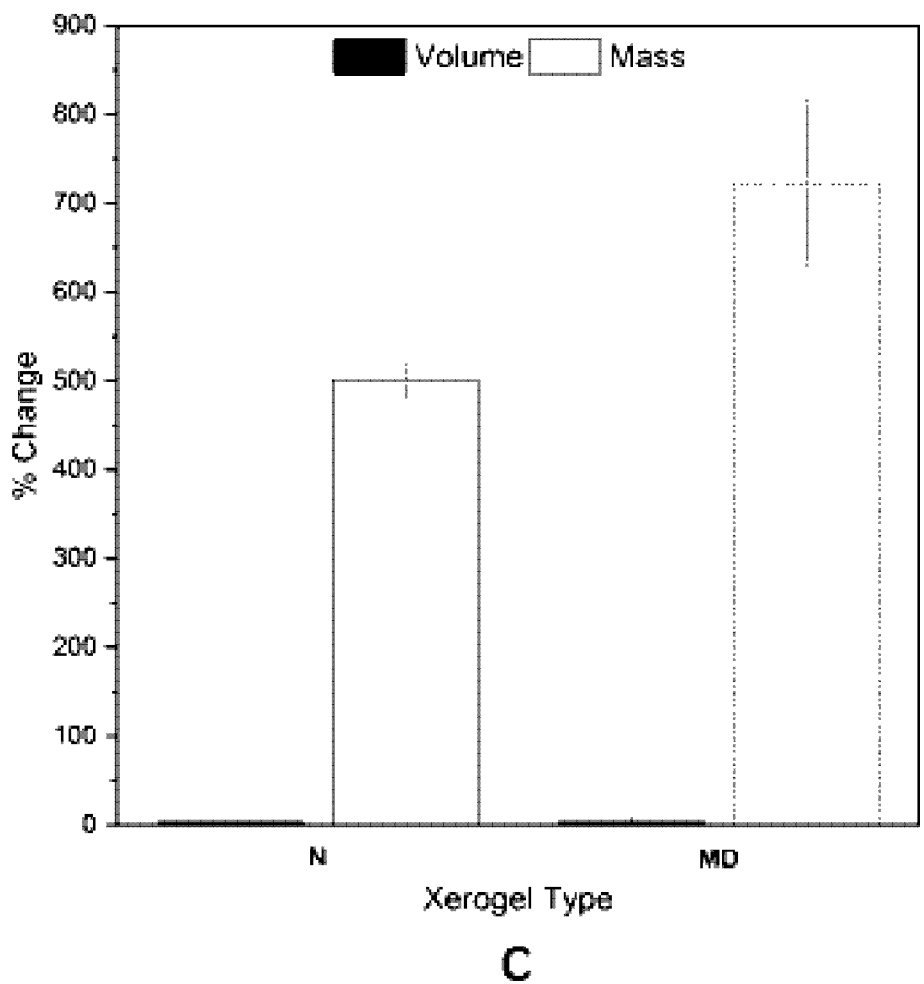
FIG. 28B: N- and MD-type xerogel innate (pre-surface functionalisation) material properties (c. volume and mass change after 1 minute of fluid wicking). Table showing average strain and stress values at 5 N recorded for both N- and MD-type unfunctionalised xerogels.

Loading and unloading stress-strain curves for both types of xerogels are shown in FIG. 28A(a) and average strain and stress values under 5 N load are also summarised in FIGS. 28A and B. Both N and MD xerogels follow a very similar loading and unloading pattern, achieving similar stress and strain values. The impressive flexibility and full recovery post-compression of the structures can most likely be attributed not only to the molecular structure of the gels (the long organic silica chains provide an element of structural rigidity sufficient to somewhat resist compression whilst allowing the 3D structure to be flexible) but also the high pore volume (which allows sufficient free space for the material to freely compress under load and recover once unloaded) [25].

The second concern with regards to substrate selection was its fluid wicking capacity. It is key that the chosen material allow biomarker-containing fluid to flow into the structure, so that the functional groups grafted onto the surface can perform their functional role (in this case, extracting and retaining lipids). As shown in FIG. 28A (a and b), both N and MD have at a minimum an approximately 5 g/g absorbance capacity within 120 seconds of fluid immersion. MD-type xerogels however perform better in this respect than their N-type counterparts, achieving approximately 7 g/g absorbance capacity within the 120 second timeframe as opposed to only approximately 5 g/g for the latter. This divergence is due to the varying chemistry of the xerogels. The thiol moieties of the MD variants result in a less hydrophobic substrate than the methyl group present in N-type variants.

Despite the variation, both can be considered to absorb or wick a sufficient volume of fluid to be suitable candidates for the prospective application of nasal fluid wicking. The lack of volume change (shown in FIG. 28A(b)) further confirms this suitability. Indeed, the lack of dimension change during the wicking process is key to the substrate viability, as any expansion could lead to the device being stuck in the patient's nose (or other orifice).

Scanning Electron Microscopy (SEM)

Figure 29:
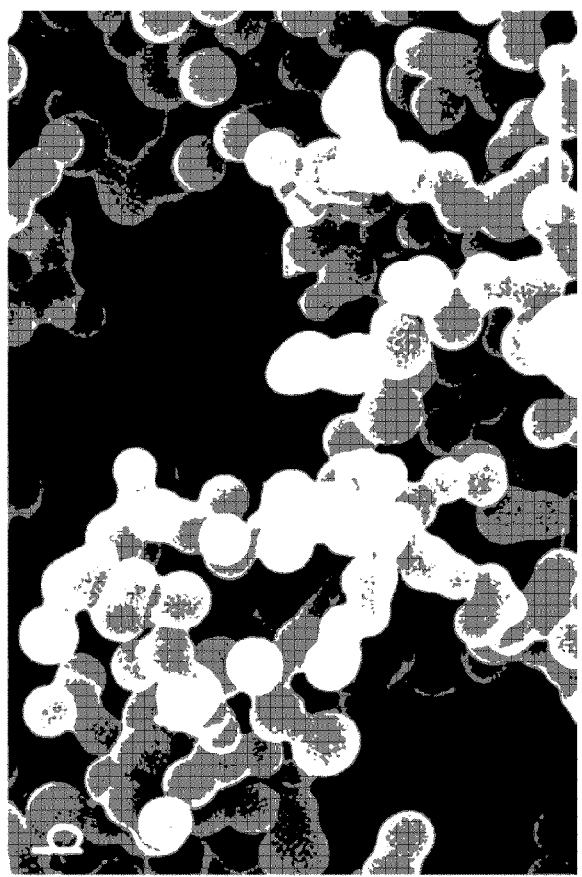
FIG. 29: Representative SEM images of N-(a) and MD-(b) type xerogel microstructure (scale bar 10 μm).
Figure 29:
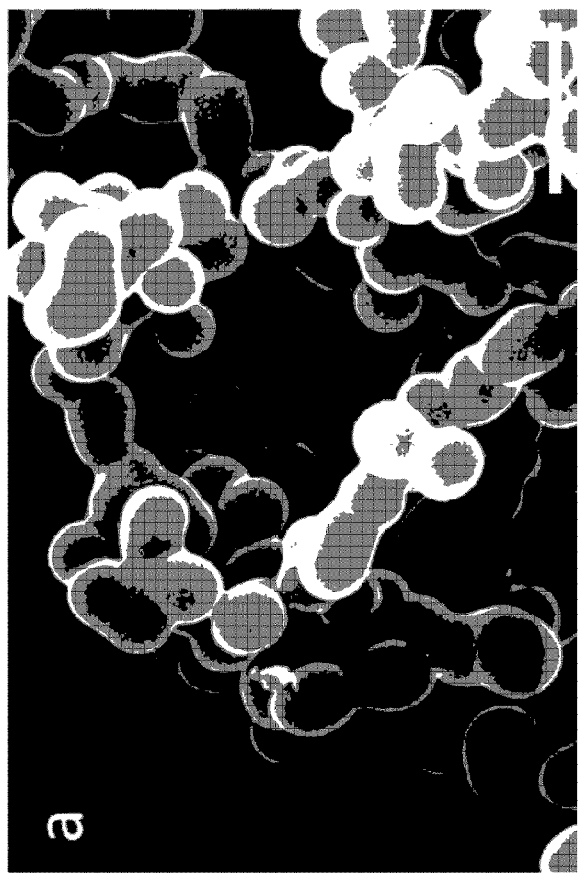

SEM imaging provides a means of investigating not only the respective xerogel microstructure, but also any variation thereof between siloxane precursor choice (i.e. N- vs MD-type) and during post-functionalisation processes. As shown in FIGS. 29a and b, both N and MD xerogel substrates consist of a colloidal aggregate type structure, characteristic of the sol-gel synthesis process [26]. This has two key advantages: first, a high material porosity, which allows the material to be highly absorptive (as shown in FIGS. 28A(b) and B(c)); and secondly, a very high surface area relative to flat surface counterparts. This high surface area also in theory applies a higher density of functional groups when the surface is functionalised (in this case with ODMA), in turn leading to a higher functional yield (such as lipid extraction) relative to flat substrates.

Comparing FIGS. 29a and b, both N- and MD-type structures appear relatively similar, with similar colloid and interconnect diameter size, in turn yielding similar material porosity size. This structural similarity appears to be reflected in the material properties shown in FIG. 28A(a), thus most likely indicating that the mechanical properties are correlated to colloid interconnect and not labile chemical moieties (i.e. thiol vs methyl groups). These SEM micrographs in combination with the previously tested physical properties therefore constitute what will be referred to in this report as benchmark material properties: i.e. properties to which any surface-functionalised xerogels will be compared to and assessed for suitability with regards to the considered application.

Example 10: Xerogel ODS (Octadecylsilyl) Surface Functionalisation

Figure 25:
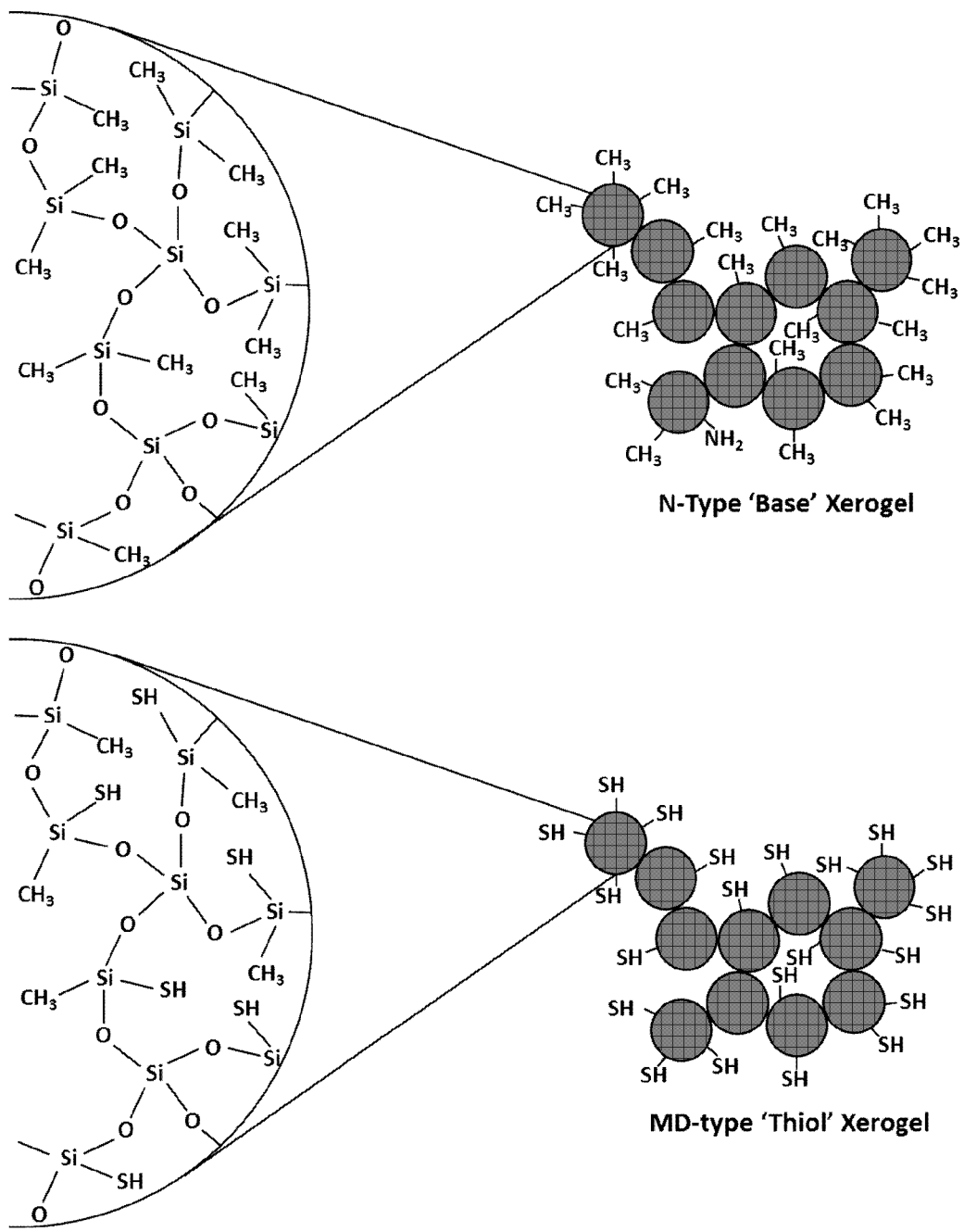
FIG. 25: Schematic representation of surface groups of N-type and MD-type xerogels.
Figure 26:
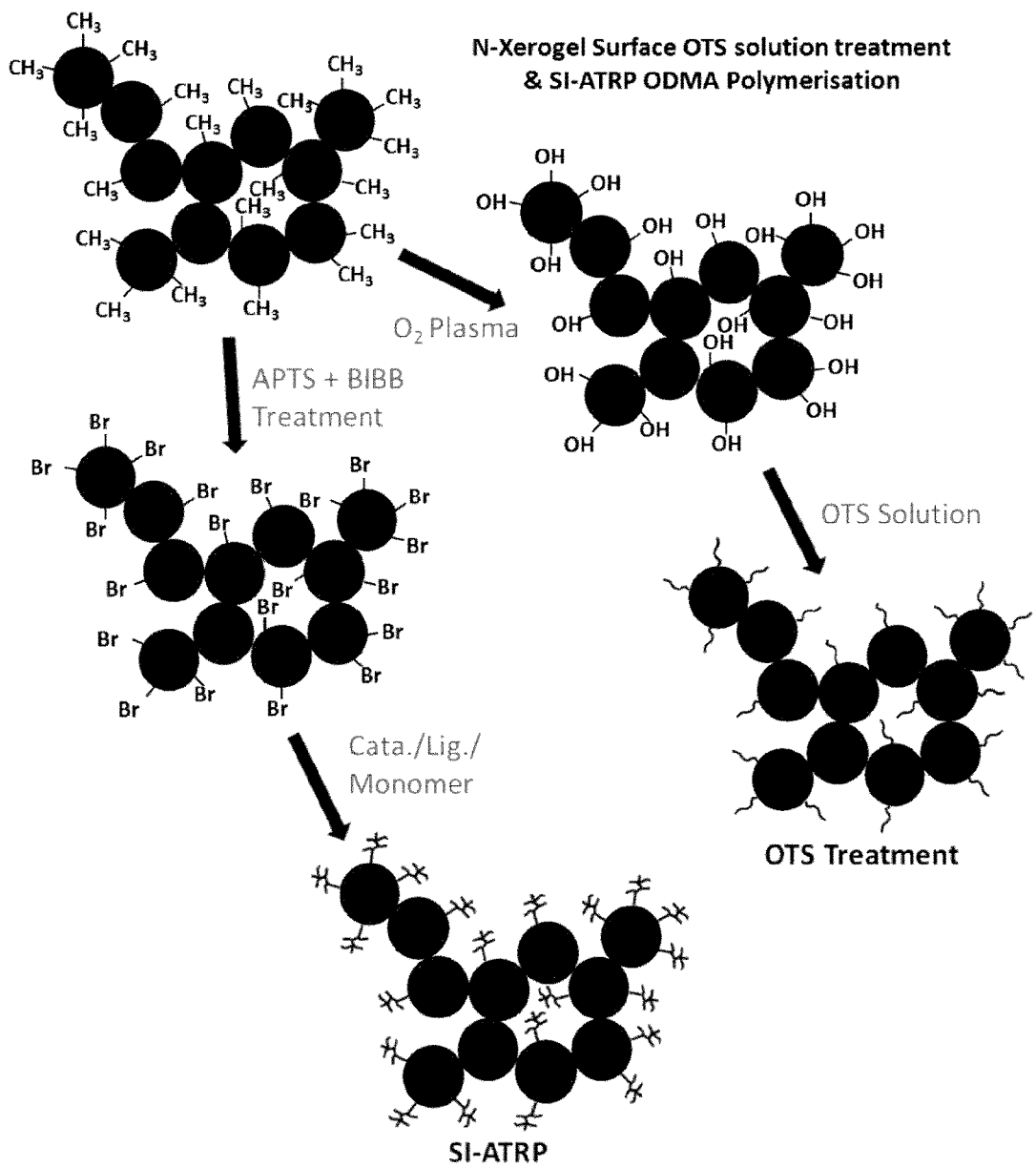
FIG. 26: Schematic representation of OTS, SI-ATRP and click chemistry surface modification of N- and MD-type xerogels.
Figure 26:
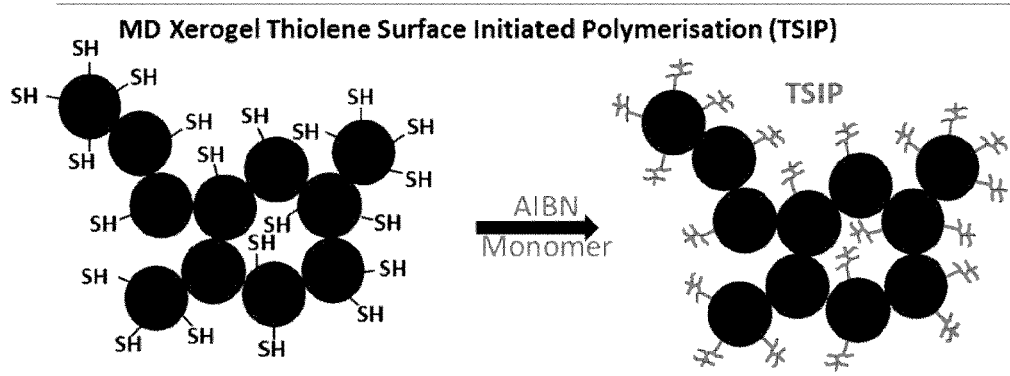
Figure 27:
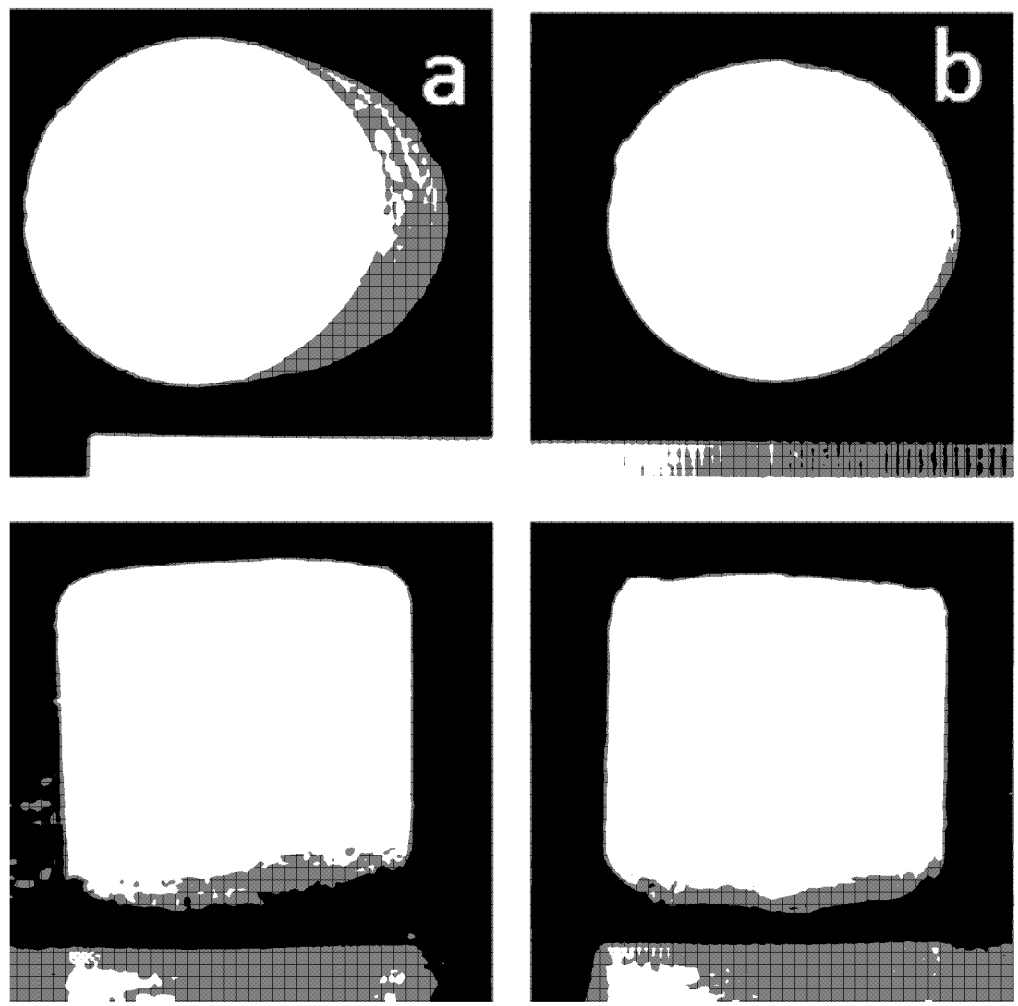
FIG. 27: Representative photographs of N-type (a) and MD-type (b) base xerogels.

As shown schematically in FIG. 25, N xerogels present surface methyl (—$CH_3$) groups, as opposed to MD xerogels with thiol (—SH). And as illustrated in FIG. 26, each composition lends itself to different surface functionalisations, using the following 3 processes: OTS solution treatment, SI-ATRP ODMA polymerisation and ODMA click polymerisation.

Example 11: OTS (Trichloro(Octadecyl)Silane) Solution Treatment

Methods

Xerogels were oxygen plasma treated for 5 minutes at 35 sccm flow rate to promote hydroxyl group surface formation. Samples were subsequently thoroughly rinsed with DI water, and left partially wet so as to promote OTS group adhesion. The OTS treatment was achieved by dipping the xerogels in a 100 mL 1:4 ratio chloroform:hexane solution, to which 0.8 mL of OTS was added. After 15 minutes reacting in solution, samples were removed and placed in a 110° C. oven for an hour to promote monolayer formation and crosslinking. Once removed, xerogels were triple washed with chloroform to remove any unreacted OTS.

Results

Figure 30:
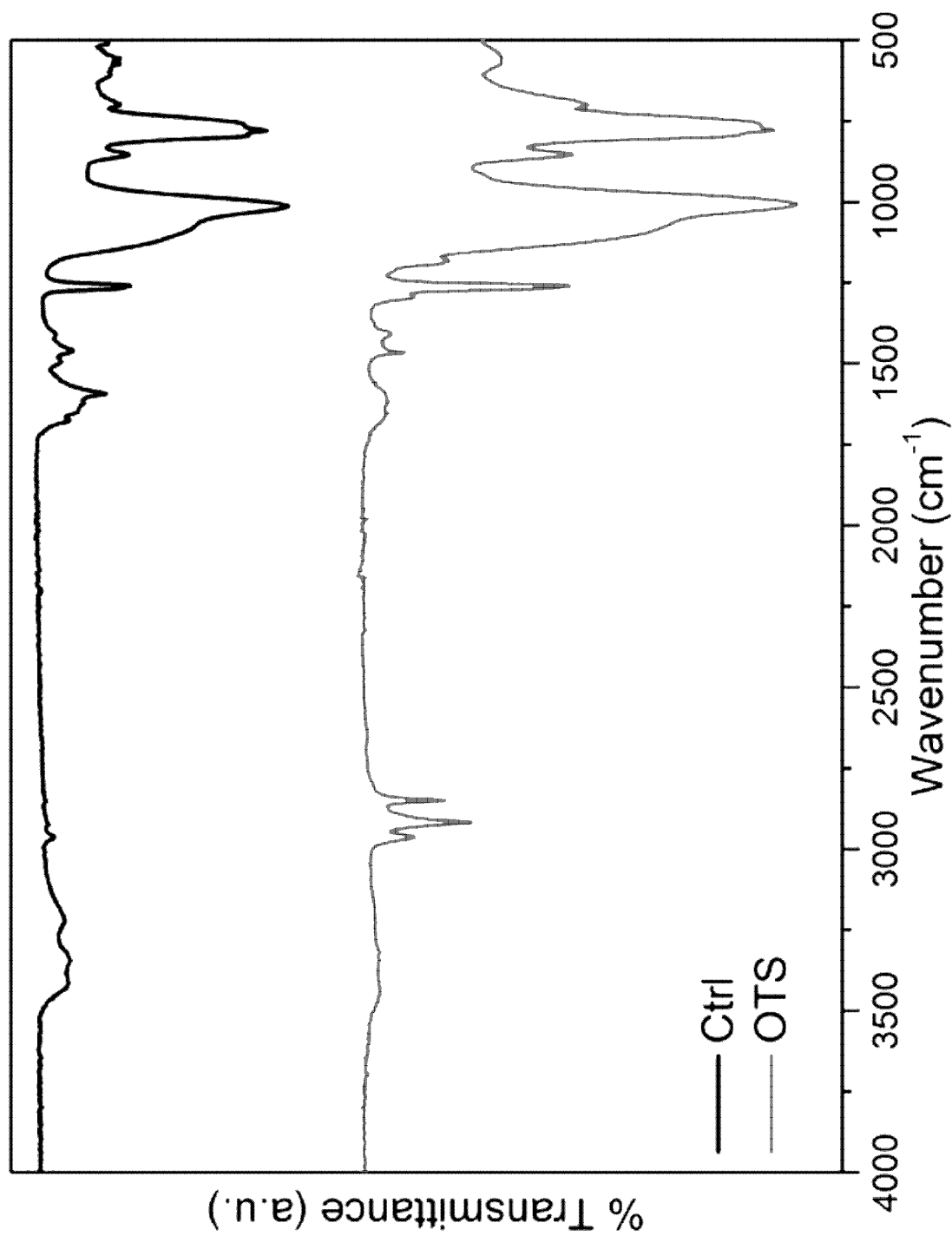
FIG. 30: FTIR of OTS surface functionalised and unfunctionalised (control) N-type xerogels.

The observed bands at 2820 $cm^{-1}$ and 2950 $cm^{-1}$ in the FTIR spectra of the OTS treated xerogel (red) in FIG. 30 correspond to symmetric and asymmetric bending of methyl groups (—$CH_3$), characteristic of ODS groups [27]. The OTS treatment of $O_2$ plasma treated N-type xerogels therefore allows the surface grafting of ODS moieties as desired.

Figure 31:
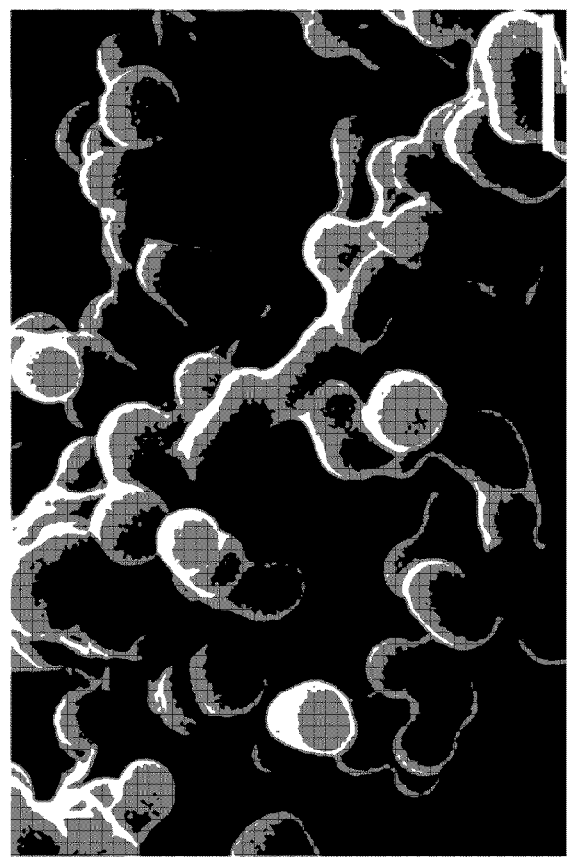
FIG. 31: SEM micrographs of control (a) and OTS surface functionalised N-type xerogels (scale bar=20 μm).
Figure 31:
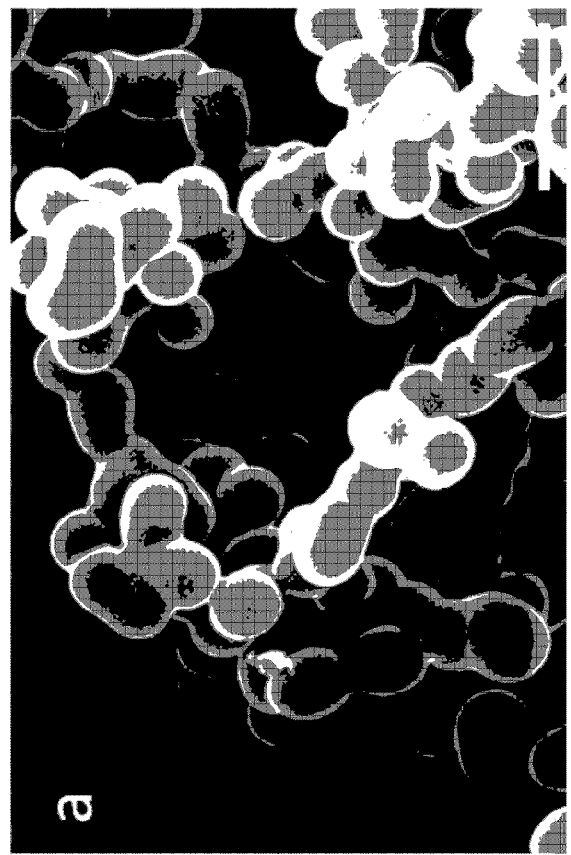

SEM imaging provides a first insight into the effect of surface functionalisation on the microstructure of the xerogels. The base N (and MD) xerogels have been determined to be suitable due to their innate high surface area, which is itself the result of the colloidal assembly-like structure. The micrographs shown FIG. 31 show no observable differences between control and OTS treated substrates. Colloid diameter and interconnect to not appear to vary, implying that at least from a microstructural perspective the microstructure is not affected by the functionalisation method used and is therefore still suitable for the desired application.

Compression testing constitutes the first physical and numerical assessment of any substantial variation between what has been identified as the ideal non-functionalised substrate properties and the ODS functionalised counterpart. The values shown in Table 7 show some indication of the OTS treated xerogel behaving differently under compression relative to its unfunctionalised N-type counterpart, the former reaching a strain value roughly 6% lower than the latter. This suggests that the OTS functionalisation stiffens the material, contrary to the intended requirements.

Figure 32:
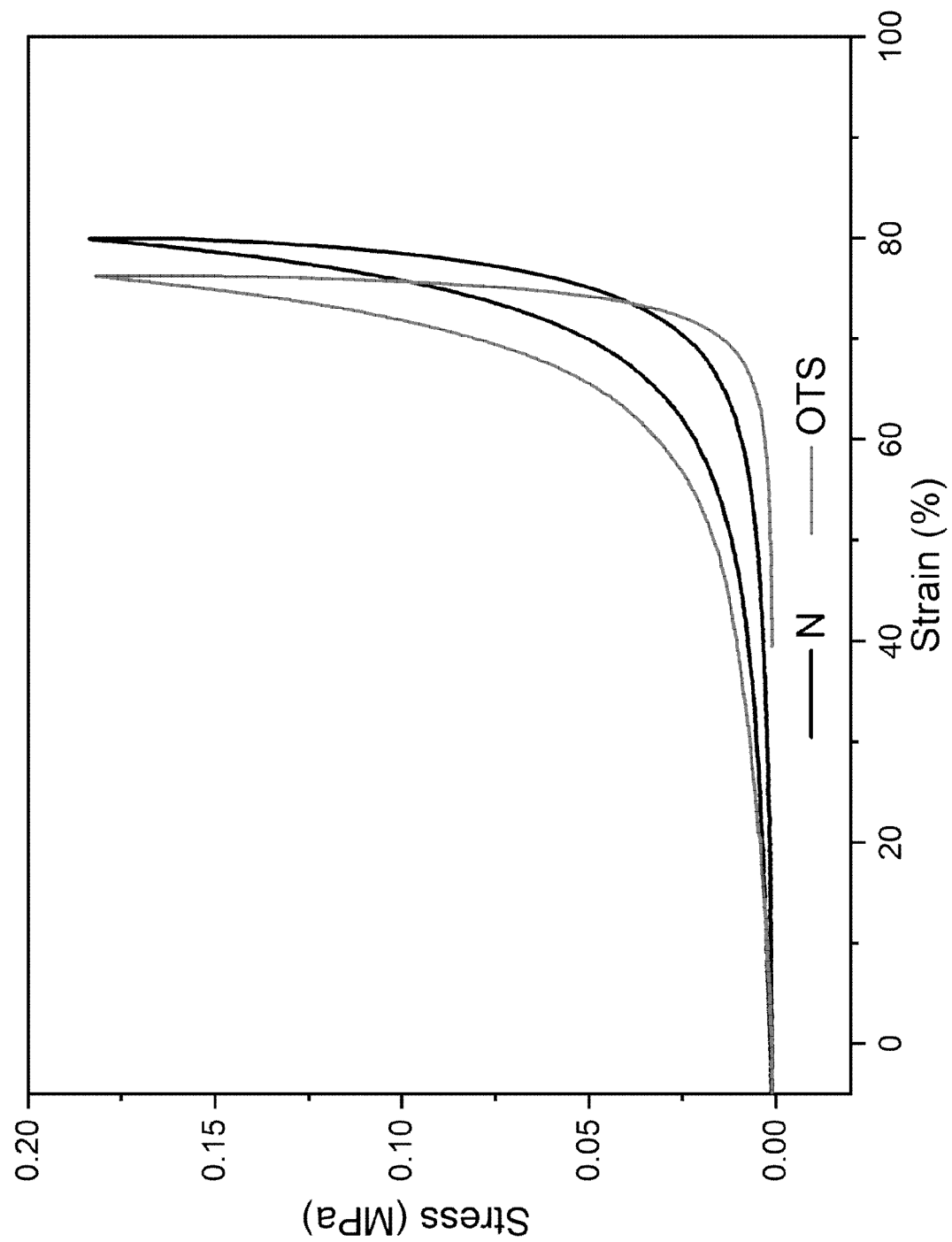
FIG. 32: Representative stress strain curve as a result of compression testing of control versus OTS functionalised N-type xerogels.

The representative loading-unloading stress-strain curves shown in FIG. 32 corroborate the values shown in Table 7. Not only is the curve for the OTS functionalised xerogel (red) shifted towards a lower strain, but also whereas the N-type control fully recovers upon unloading (shown by a return to zero stress and strain values), the OTS sample does not; the strain staying at 40% post unloading. This suggests the material has been permanently deformed during the compression process. This is confirmed by photographic evidence shown in FIG. 33. Post compression, the clear-cut edges of the material are no long recognisable, the material itself is clearly brittle and broken up and clearly not suitable for the considered application of fluid-wicking in a patient's orifice.

TABLE 7

Strain and stress values obtained for control vs OTS-functionalised N-type xerogels

| Composition | N | OTS |
| --- | --- | --- |
| Strain at 5N (%) | 80.45 ± 1.34 | 73.81 ± 2.32 |
| Stress at 5N (MPa) | 0.19 ± 0.04 | 0.15 ± 0.02 |

Example 12: SI-ATRP Functionalisation

Methods

N-type xerogels were oxygen plasma treated in similar fashion to the OTS process described in Example 11. The gels were then added to a 4% APTES Toluene solution to graft —$NH_2$ (necessary precursors to the SI-ATRP process), degassed and left to stir overnight at room temperature. Once reacted, samples were removed and triple washed with toluene to remove any unreacted ATPES. In order to graft the bromine surface initiators, N-ATPES xerogels were added to a 50 mL THF solution, to which 1.3 mL BIBB and 1.4 mL $EtNO_3$ were added dropwise under ice and stirring. Once degassed, the solution was left to react shielding from light overnight, resulting in N—Br xerogels ready for SI-ATPR polymerisation of ODMA.

N—Br xerogels, 10 mg of Cu(I)Cl catalyst and 70 mg dNBPy ligand were added to a round bottom flask and triple vacuumed and backfilled with argon. 5 g of ODMA monomer was added to 15 mL of toluene in a second round bottom flask, the contents of which were transferred once degassed to the initial flask containing the N—Br xerogels, catalyst and ligand. The reaction vessel was then heated to 80° C. under careful stirring (thus ensuring no damage to the xerogels from the magnetic stirrer) and left to react for the desired amount of time, typically 2, 4, 8 and 24 h. Once reacted, the xerogels were removed and triple rinsed with toluene to remove any unreacted reagents, left to dry, and stored in a desiccator till further use or analysis.

Results

The N-type xerogels were subject to multiple pre-polymerisation steps to surface functionalise initiator molecules from which ODMA ATRP-mediated controlled polymerisation can proceed. The SI-ATRP process was investigated because it offers a high degree of precision on the concentration of functional groups grafted onto the surface.

FTIR

Figure 34:
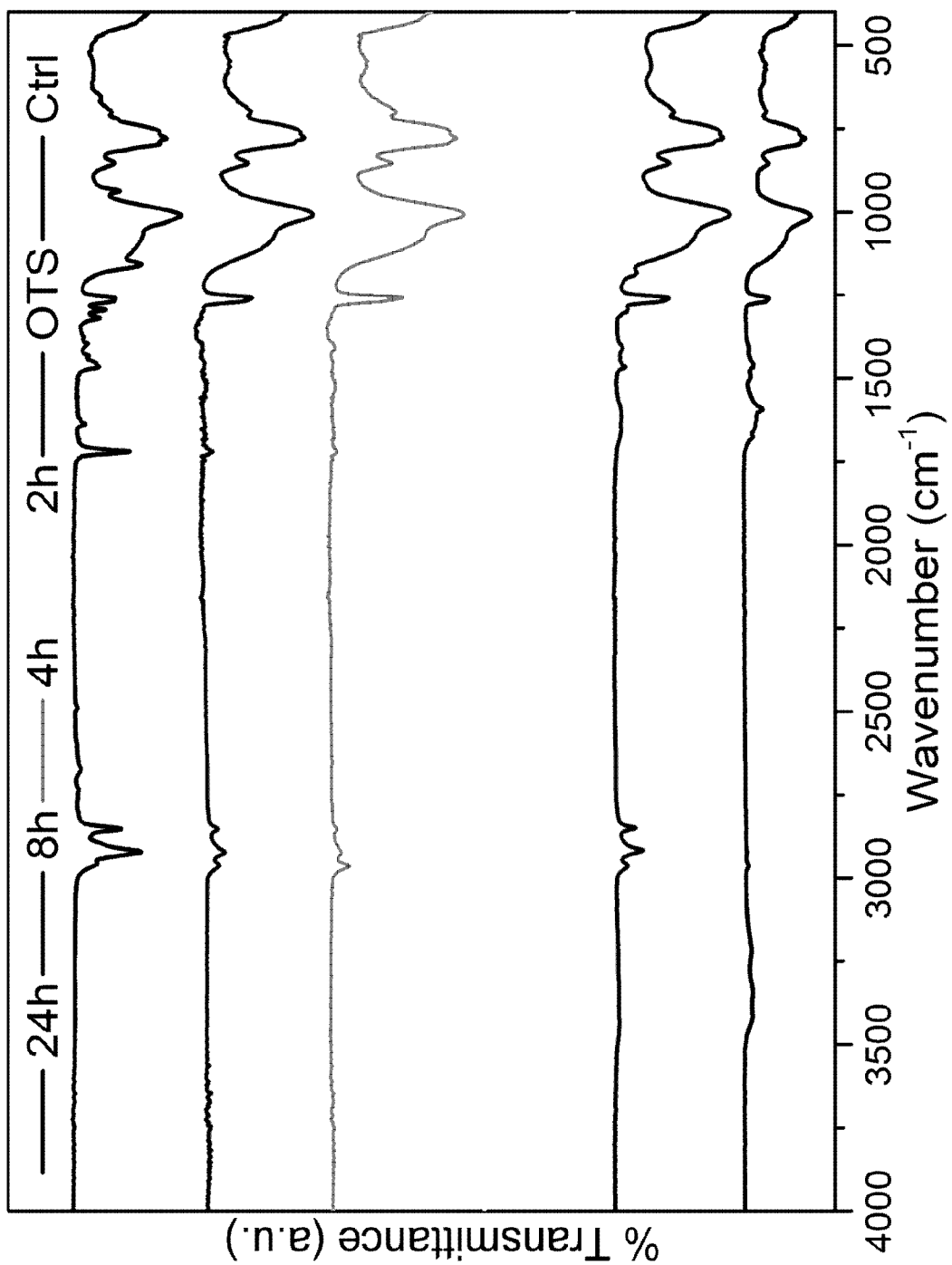
FIG. 34: FTIR of N-type control, OTS treated and 2 h, 4 h, 8 h, 24 h SI-ATRP ODMA xerogels.

Once again, FTIR was used to determine the presence of ODMA groups as a result of the polymerisation. Normalised transmission spectra for N-type control and various polymerisation time substrates are shown in FIG. 34, as well as OTS treated xerogel as a reference. The normalisation of the spectra also enables a semi-quantitative analysis of the amount of ODMA present on the surface.

Increasing polymerisation time should in theory allow longer polymer chains to grow, providing there is sufficient monomer. Comparing the ODMA characteristic bands at 2851 $cm^{-1}$ and 2920 $cm^{-1}$ over the various polymerisation times, it is clear that the intensity of these bands increases with increasing polymerisation time. Indeed, whereas barely any signal is observable at 2 hours, it is more discernible at 4 hours and 8 hours, and comparable to substrate bands in the 1250 $cm^{-1}$ to 400 $cm^{-1}$ region. This suggests as hypothesised not only that it is possible to form ODMA polymer chains from initiator-coated N-type xerogels, but also that increased polymerisation time yields longer ODMA polymer chains to form on the initiator-coated surface, as previously shown for PDMS substrates. A further confirmation of the successful nature of the proposed SI-ATRP process is the presence of a band at around 1730 $cm^{-1}$ corresponding to —C=O stretching. This therefore confirming the presence of surface-polymerised methacrylate type monomers, in this case ODMA [28].

Comparing the 24-hour SI-ATRP signal to that of the aforementioned OTS-treated xerogel, it also seems clear that the former yields a higher surface density of ODS groups than the latter as intended. Indeed, SI-ATRP allows the formation of polymer chains whereas OTS treatment only provides a monolayer coating of the treated surface. This should in turn lead to improved bio-functionality provided the thus functionalised substrate can provide satisfactory physical properties. However, given the semi-quantitative nature of the FTIR data, only the 24-hour SI-ATRP polymerised xerogel provides a higher density of ODS groups than the OTS sample. Shorter polymerisation times are unlikely to provide sufficient ODS to be worthy of further investigation, given the complex nature of their synthesis process.

SEM Imaging

Figure 35:
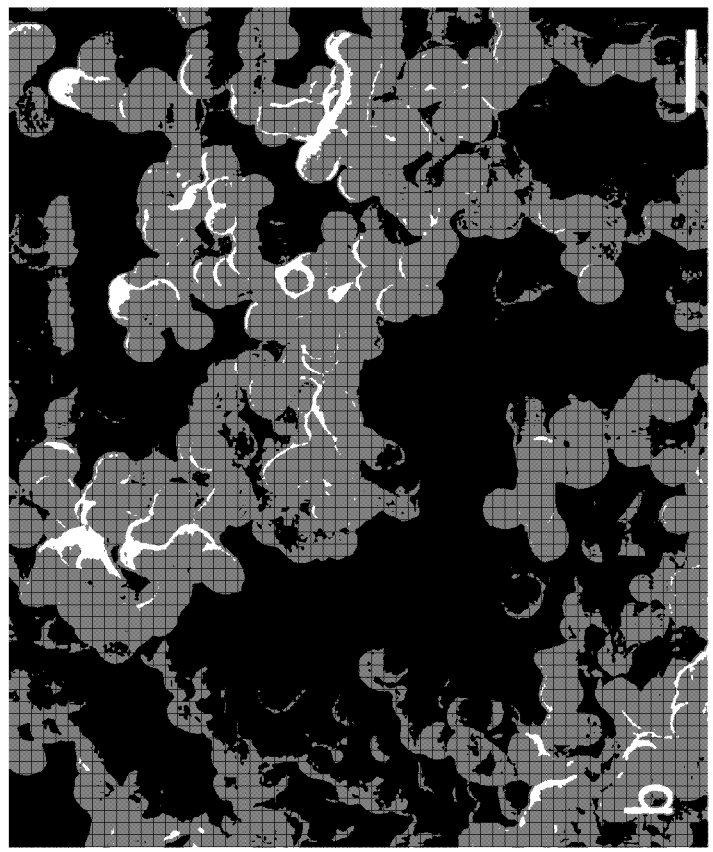
FIG. 35: Representative micrographs of N-type control (a) and 24 h polymerised SI-ATRP (b) xerogels (scale bar=10 μm).
Figure 35:
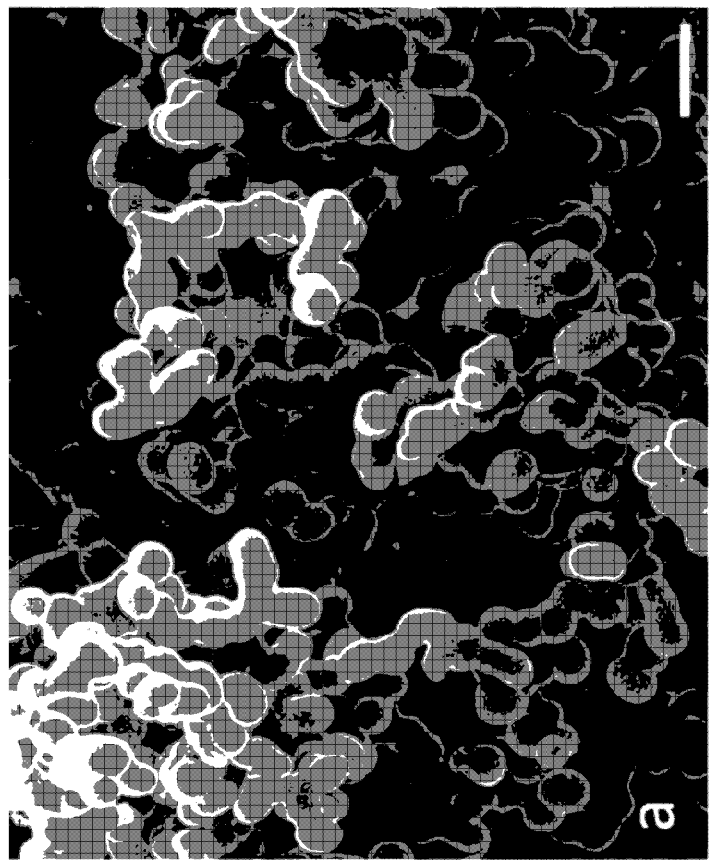

SEM imaging was once again used as a first means of assessing the impact of the ODS functionalisation process on the substrate microstructure as representative micrographs of N-type control and 24-hour SI-ATRP polymerised xerogels are shown in FIG. 35.

Figure 33:
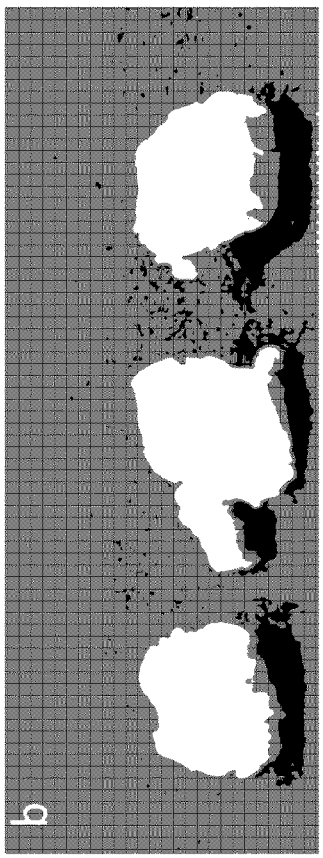
FIG. 33: Representative photos of OTS-functionalised N-type xerogels pre-(a) and post-(b) compression testing.
Figure 33:
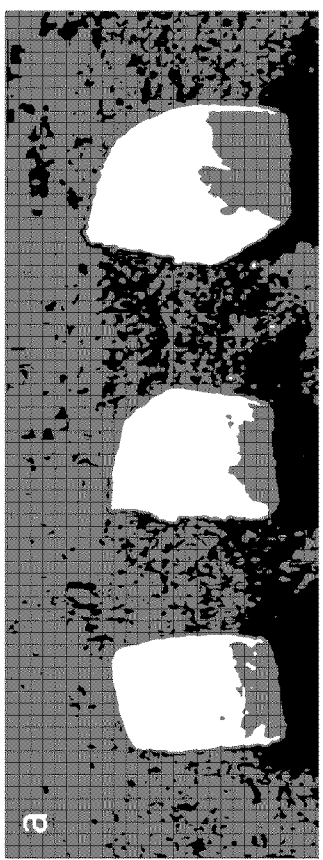

In similar fashion to OTS treatment shown in FIG. 33, the SI-ATRP polymerisation process does not appear to have an effect on the microstructure of the N-type control xerogels of whose surface it is modifying. Indeed, both colloidal structure and interconnect appear unchanged pre- and post-surface functionalisation, despite the higher density of ODS groups provided by p(ODMA) polymer chains.

Compression Testing

Figure 36:
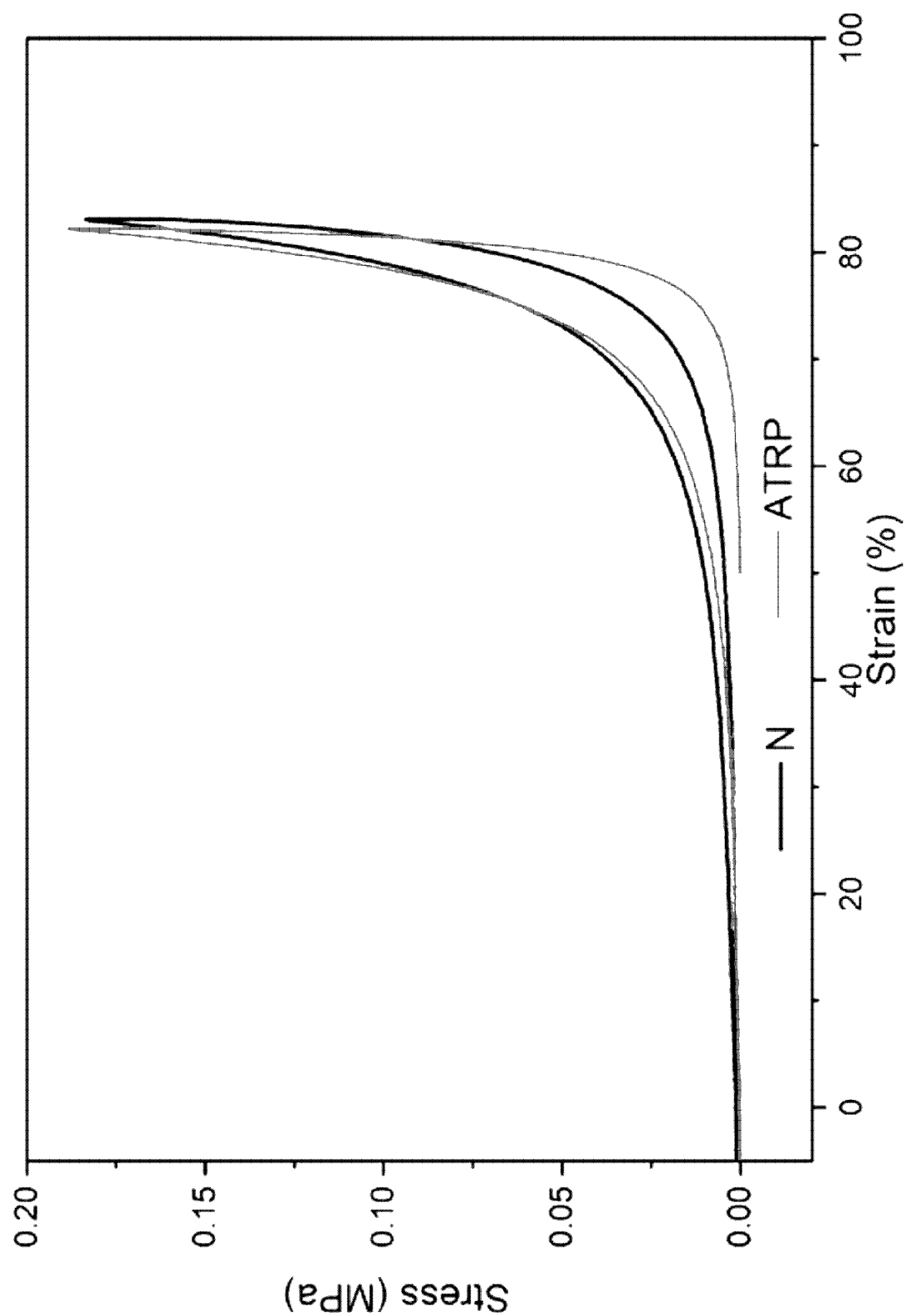
FIG. 36: Strain and stress values obtained from N-type and 24-hour ATRP SI-ATRP polymerised xerogels and representative stress-strain curves of N-type control and 24-hour SI-ATRP ODMA polymerised xerogels.
Figure 37:
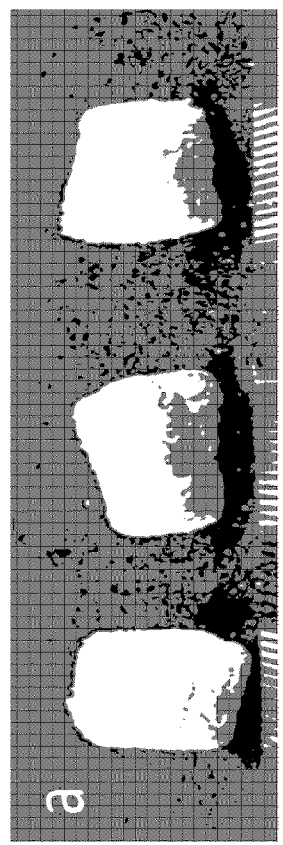
FIG. 37: Representative pre-(a) and post-(b) compression SI-ATRP xerogels with visible post-compression structural damage.
Figure 37:
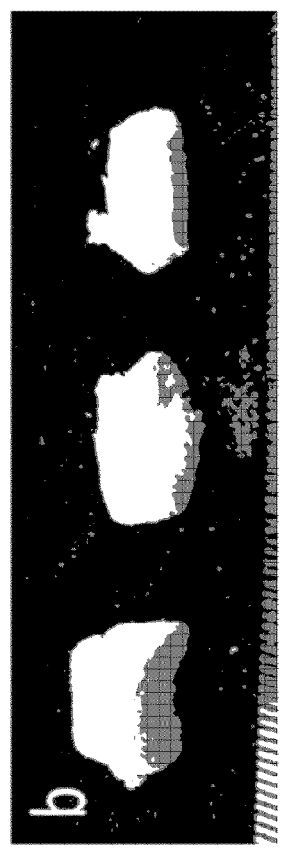

A more representative assessment of the material is given by compression tests as shown in Table 8 and FIG. 36. In contrast to OTS (Table 7), the strain values obtained at 5 N for ATRP and the N control xerogels are relatively similar, 2% and therefore their respective error margin. Stress values are also almost identical. The representative stress-strain curve in FIG. 36 corroborates the values during the loading to 5 N load phase. However, similarly to OTS, the unloading results do not follow the same trend as the N-type control. Once unloaded, 50% residual strain (even higher than the 40% in the case of OTS treatment) still implies a lack of full material recovery and therefore permanent deformation. Representative photographs pre- and post-compressive cycle shown in FIG. 38 clearly highlight the damage caused by the loading cycle.

TABLE 8

Strain and stress values obtained from N-type and 24-hour ATRP SI-ATRP polymerised xerogels

| Composition | N | ATRP |
| --- | --- | --- |
| Strain at 5N (%) | 80.45 ± 1.34 | 78.53 ± 0.46 |
| Stress at 5N (MPa) | 0.19 ± 0.04 | 0.19 ± 0.01 |

Figure 38:
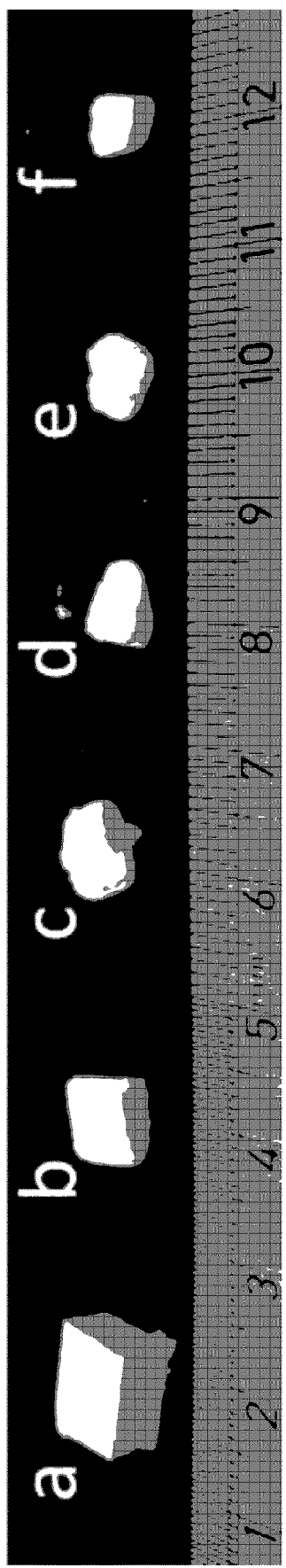
FIG. 38: Representative photographs of the effect of the various steps of the SI-ATRP surface polymerisation process (a. N-type control/pre-functionalisation, b. ATPES treated, c. BIBB treated, d. 2 h, e. 4 h and f 24 h timepoint SI-ATRP xerogels).

Beyond the lack of fully elastic behaviour like its unfunctionalised N-type counterpart, the various pre-polymerisation surface modification steps make the process not only time-consuming but also destructive, as shown by representative photographs taken after each process step (FIG. 38). Whereas the base N-type material appears to be clearly cut to shape, each surface modification step (required prior to any ODS surface modification) damages the substrate and causes significant material loss. The BIBB-xerogel (i.e. the surface-grafted initiator modified N-type xerogel (the initiators from which the p(ODMA) polymer grows during the SI-ATRP process, FIG. 38c) is already damaged beyond recognition. Although this damage could potentially be limited by more precautious experimental handling such as slower spinning speeds during reactions, the fact remains the process to prepare the substrates for polymerisation requires more than 48 hours, excluding substrate synthesis prior to that, and a further 36 hours of polymerisation, washing and drying time prior to any use.

Plasma Treatment Issue

Figure 39:
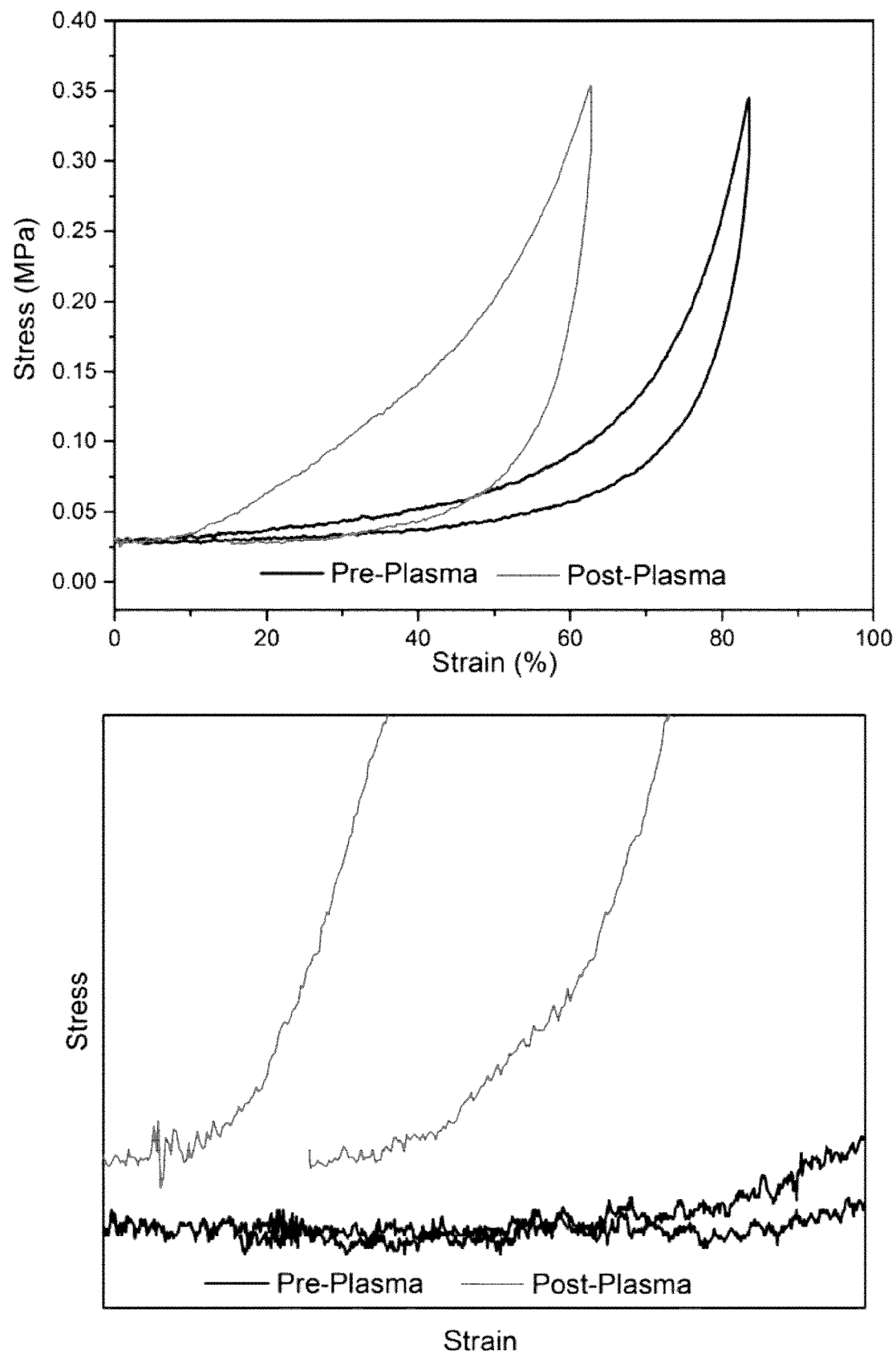
FIG. 39: Representative compression curves of pre- and post-O2 plasma treated N-type xerogel substrates (a. full range, b. focus on lack of recovery region).

As shown in FIG. 39, although both control and plasma-treated substrates reach similar stress values, there is a considerable difference in the strain percentage achieved at equal load in both materials, with plasma-treated samples achieving 60±2.04%. This, combined with yet again a lack of fully elastic behaviour (or permanent strain even when no load applied), seems to confirm that $O_2$ plasma treatment is the cause of the loss of material flexibility observed with both OTS and SI-ATRP modified samples. A possible explanation for this is the formation of new Si—O—Si bonds after plasma treatment. The resulting tetra-functional structure would cause the material to be less flexible than the original tertiary structure found in pre-treated samples, as shown in various compression tests. This hypothesis is further supported by the increased intensity of the bands around 1020 cm$^{-1}$ corresponding to Si—O—Si stretching, relative to those observed in N-type control substrates in FTIR tests (FIGS. 30 and 44) [26, 30].

Although the plasma treatment can therefore be identified as the first cause of the loss of material flexibility, it is important to note that subsequent ODS functionalisation by both OTS and SI-ATRP further worsen the issue. In both cases, higher values of residual strain (40% and 50% respectively relative to 18% for plasma treated only) are observed. Although some loss can be expected due to the material being coated with 216.19 g/mol $C_{18}$ chains (excluding the molecular weight of the grafting moieties for both OTS and the SI-ATRP process) which would be expected to increase the material stiffness due to steric hindrance of the $C_{18}$ chains, the significant loss in flexibility in both cases can most likely be attributed to the chemical processes of the methods themselves. Any residual surface silanol groups in the case of OTS treatment would result in reduced mechanical properties as observed, whilst the combination of APTES and BIBB treatment during SI-ATRP preparation steps significantly modified the surface, resulting in the further loss in mechanical properties which was observed.

It is therefore clear that a process that does not require the formation of hydroxyl (—OH) groups as a preparatory step for ODS surface functionalisation is required in order to retain the suitable mechanical properties of the base material whilst providing the desired functionality.

Example 13: SI-FRP Functionalisation—Physical Characterisation

Methods

Thiol-Ene Surface-Initiated Polymerisation (TSIP) of ODMA

MD-type xerogels were surface functionalised with p(ODMA) via TSIP. The direct surface-initiated polymerisation from surface thiol groups present on MD-type xerogels permits a more straightforward albeit less controlled means of surface polymerisation as compared to the above SI-ATRP, which requires several pre-polymerisation surface treatment procedures. The concentration of ODS groups functionalised to the surface was controlled by varying the initial concentration of ODMA monomer introduced into the reaction vessel whilst keeping other reagent ratios constant. ODMA concentrations evaluated were 0.05 g/mL, 0.10 g/mL, 0.15 g/mL and 0.20 g/mL.

In a typical reaction, six 10×10×5 mm cut MD-type xerogels (approx. 60 mg total weights), ODMA monomer in desired concentration, 20 mg of AIBN and 10 mL of toluene were introduced into a round bottom flask, degassed with argon for 30 min and left to soak overnight at 0° C. to allow monomer to fully soak through the xerogels whilst inhibiting the temperature sensitive AIBN mediated click reaction. The reaction vessel was then kept at 60° C. for 12 h. Once reacted, xerogels were removed and triple washed with toluene to remove any unreacted ODMA and AIBN and stored in a desiccator till further use.

Fluorescence-Labelled Liposome Synthesis

For confocal microscopy, fluorescence labelled solutions were made up in concentrations of 100 µg/mL in aqueous solutions. These were synthesised by diluting DOPE and DOPC lipids in organic solvent, re-evaporating and re-suspending in d(H$_2$O) to achieve the physiologically representative lipid concentration. These were fluorescence labelled by adding 0.5% final volume 0.2 mg/mL Alexa Fluor 488 labelled DOPC. 5% v/v 0.02 mM Laurdan was added to the lipid solution to fully characterise the structure of the liposomes thus formed.

To assess the extraction, retention and re-elution capacity of the various materials, samples were immersed in the aforementioned physiological-mimicking solutions for 5 minutes, before being removed and excess squeezed out softly. Aqueous washing was used to remove any excess unbound lipids and water soluble 'contaminants'. Samples were then placed in the top section of a Cornstar Spin-X centrifuge tubes with 500 µL of d(H$_2$O) and centrifuged at 6000 RPM for 5 minutes.

Organic solvent washing was used to fully elute out the lipids from the resulting lipid-only containing ODS-functionalised device. To do so, the previously aqueous-solution washed xerogels were placed once again in the top of Cornstar Spin-X tube, to which 500 µL of organic solvent (MeOH only, Folch solution (MeOH:CdCl$_3$ 2:1 v/v or CHCl$_3$ only depending on the protocol followed—specified during results analysis)) were added and centrifuged at 6000 RPM for 5 minutes.

Multi-Lipid Solution Synthesis

In order to assess the biofunctionality of the proposed xerogels, physiologically representative solutions of lipids were synthesised. PG, PI, PA, PE, PS, PC, SM and Cer were dissolved to 0.1 mg/L concentrations in CHCl$_3$ and mixed in equal ratios into one solution. Once fully homogenised, the lipids were dried via speedvac and re-suspended in aqueous solution made up of d(H$_2$O)/CHCl$_3$ 95:5 back to 0.1 mg/L concentration. Absorption, excess marker removal and re-elution procedures from the investigated xerogels (functionalised and control) were performed in similar manner to the method described above for fluorescence marker evaluation.

Functionalised Xerogel Characterisation

The functionalised xerogels were subsequently characterised following the 3-phase method:
  Phase I: FTIR
  Phase II: SEM, uniaxial compression and absorbance capacity evaluation
  Phase III: MTT assay, confocal microscopy and LC-MS measurements For material characterisation purposes, xerogels were loaded onto confocal plates and imaged under reflectance imaging, thus enabling full substrate surface material characterisation without the need for conductive substance coating required in SEM imaging.

For biological characterisation purposes, samples were immersed into a biologically representative solution, with the relevant biological species investigated labelled with fluorescent dye. The species was then visible under confocal microscopy by setting the laser to the corresponding wavelength.

Results

Having proven that the base PDMS-like N-type structure does not lend itself to methods already tested, the MD-type substrate was selected to attempt thiol-ene click chemistry surface modification. This approach is widely used and reported, and involves a straightforward and less stringent environment than others, all factors which are consistent with the key objectives of this project and make it an attractive approach to investigate. Surface thiol (—SH)

groups serve as initiator sites post-thermal activation, from which ODMA monomers homopolymerise till termination [31].

Figure 40:
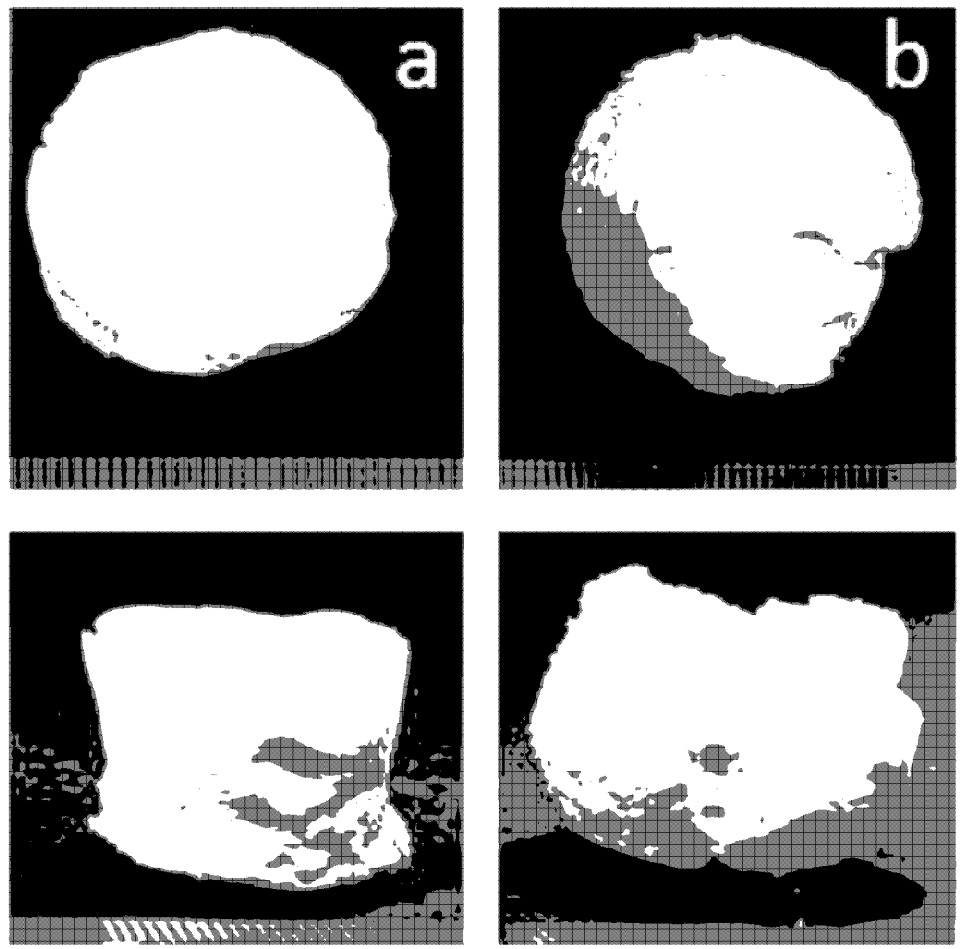
FIG. 40: Representative photographs of a. MeTMTS:DMDMS and b. MeTMS:DMeDMS xerogels (i.e. trifunctional mercaptosilane with normal difunctional and both tri- and difunctional mercaptosilane precursors respectively).

In this case, the MD-type xerogel (MTMS and DMeDMS precursors) was used as the base substrate. Although using two mercaptosilane-type precursors as opposed to only the di-functional alternative reported by Hayase et al, preliminary investigations on the substrates deemed the double-mercaptosilane precursor too brittle and difficult to cast to shape for the proposed use [23]. As can be seen in FIG. 40, thus synthesised samples shrink during the gelation and drying period and are too brittle to consider for use.

In order to investigate the effect of monomer concentration on the density of the ODMA surface grafted groups, a final concentration range from 0.05 g/mL to 0.20 g/mL was investigated in similar fashion to OTS and SI-ATRP surface functionalised samples to determine their suitability for the application and therefore further biological evaluation.

FTIR

FTIR was once again used as the first method for determining whether, and if so the extent to which the process allowed surface grafting of ODS by comparing normalised signals. First of all looking at the signal for control or pre-functionalisation MD-type xerogel, it is important to note the lack of thiol characteristic bands, which would typically be expected in the 2550-2600 $cm^{-1}$ [23, 32]. This is most likely due to their lower density relative to the predominant signal from the silica network and labile methyl groups originating from the trifunctional MTMS precursor, such as Si—O—Si asymmetric stretching at 1025 $cm^{-1}$ and multiple peaks associated to —$CH_3$ rocking in Si—$CH_3$ and Si—$(CH_3)_2$ in the region of 750-870 $cm^{-1}$. These corroborate original literature FTIR reports by Hayase et al (in which thiol groups were made visible by gold nanoparticles) [23, 24].

ODMA surface grafting via click-chemistry appeared to be successful. ODS surface groups can once again be clearly observed by the strong intensity of bands at 2851 $cm^{-1}$ and 2950 $cm^{-1}$, as well as that at approximately 1730 $cm^{-1}$ confirming the presence of carboxylic group on the surface and therefore successful grafting of ODMA onto the xerogel surface. In similar fashion to increasing polymerisation time for SI-ATRP, increased initial ODMA monomer concentration also appears to allow increased ODS surface groups density, the ODS characteristic bands indeed increasing in intensity with increasing concentration. This suggests that despite the lack of polymerisation control the grafting-from click-chemistry process provides, it is still possible to increase functional group concentration across the substrate surface by varying the initial condition molar ratios in favour of the desired monomer.

SEM

Successful surface modification should have minimal or no impact on the original microstructure of the base substrate, in this case MD-type xerogels. MD- and N-type xerogels (FIG. 29 and FIGS. 42a and b respectively) were already deemed to have similar microstructures, indicating that the microstructure is most likely responsible for the similar mechanical (compressive) properties of the xerogels as shown in FIG. 28A(a).

TSIP surface modified xerogels in the 0.05 g/mL to 0.15 g/mL appear to have similar microstructures to the MD-type unfunctionalised substrate on which they are based. However, the 0.20 g/mL concentration sample clearly differs from its counterparts, with a glue-like coating covering the colloidal structure. Given these micrographs were taken after thorough washing steps ensuring the removal of any unreacted or grafted ODMA, this suggests that at the highest initial condition concentration, the resulting molar ratio encourages longer polymers to form from the surface thiol group, resulting in the extensive coating observed. The resulting coverage appears to significantly reduce the surface area (since it is covering up the colloidal structure), but also strongly suggests that the resulting material will be much more brittle than its lower concentration counterparts given the high density of what appears to be p(ODMA), itself a brittle polymer at room temperature.

A more precise analysis of FIG. 42d however also points towards a slight modification in the substrate microstructure as a result of surface functionalisation. For example, in certain regions necking appears reduced and aggregate formation to have occurred in both cases suggesting again reduced available surface area and decreased mechanical properties.

Compression

Although similar microstructures have been hypothesised to lead to similar material behaviour under compression testing as established by comparing N-type and MD-type control xerogels, OTS and SI-ATRP processes have disproven that hypothesis on both accounts.

Figure 43:
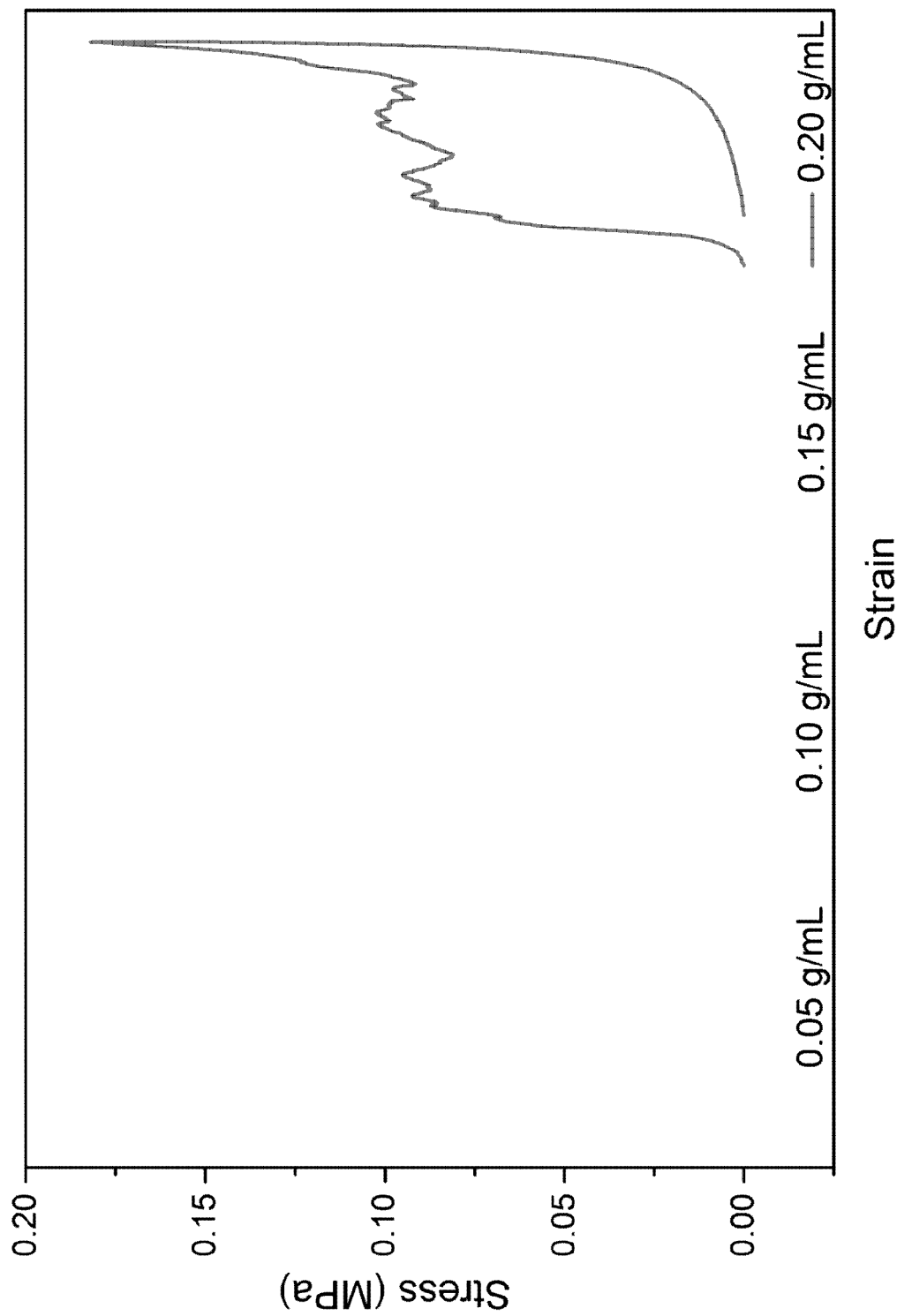
FIG. 43: Representative stress-strain curves for increasing initial condition ODMA concentration click-chemistry functionalised xerogels.

In the case of TSIP-modified samples, however, the hypothesis appears to be proven correct. SEM investigations suggest that the 0.05 g/mL and 0.10 g/mL concentration samples are closer to the control substrates than the 0.15 g/mL and 0.20 g/mL concentrations where the higher monomer concentration lead to aggregate and p(ODMA) surface coverage. The hypothesised increased stiffness of the former two samples relative to their two lower concentration counterparts is indeed confirmed by their behaviour under compression as shown by FIG. 43 and Table 9.

The 0.05 g/mL and 0.10 g/mL compositions indeed have strain and stress values closely matching those of the MD-type unfunctionalised xerogel, in the region of 80% strain and 0.20 MPa; trends also exhibited by their compression curves. At higher concentrations of 0.15 g/mL and even more so 0.20 g/mL, a significant reduction in strain (70.45±4.56% and 63.14±5.92% respectively) despite similar stress values indicate a more brittle material behaviour under compression. This is graphically well illustrated by their corresponding compression curves (FIG. 21), where an irregular loading pattern can be observed. This is most likely due to the excess p(ODMA) polymerised on the surface observed under SEM imaging (FIGS. 42d and e), where the brittle polymer causes cracking and brittle failure.

TABLE 9

Strain and stress values obtained for MD-type control, 0.05 g/mL, 0.10 g/mL, 0.15 g/mL and 0.20 g/mL ODMA concentration click-chemistry functionalised xerogels

| Composition | MD | Click - 0.05 | 0.1 | 0.15 | 0.20 |
| --- | --- | --- | --- | --- | --- |
| Strain at 5N (%) | 80.63 ± 2.19 | 78.82 ± 3.30 | 79.19 ± 7.07 | 70.45 ± 4.56 | 63.14 ± 5.92 |
| Stress at 5N (MPa) | 0.18 ± 0.03 | 0.20 ± 0.01 | 0.20 ± 0.02 | 0.20 ± 0.01 | 0.12 ± 0.11 |

Figure 44:
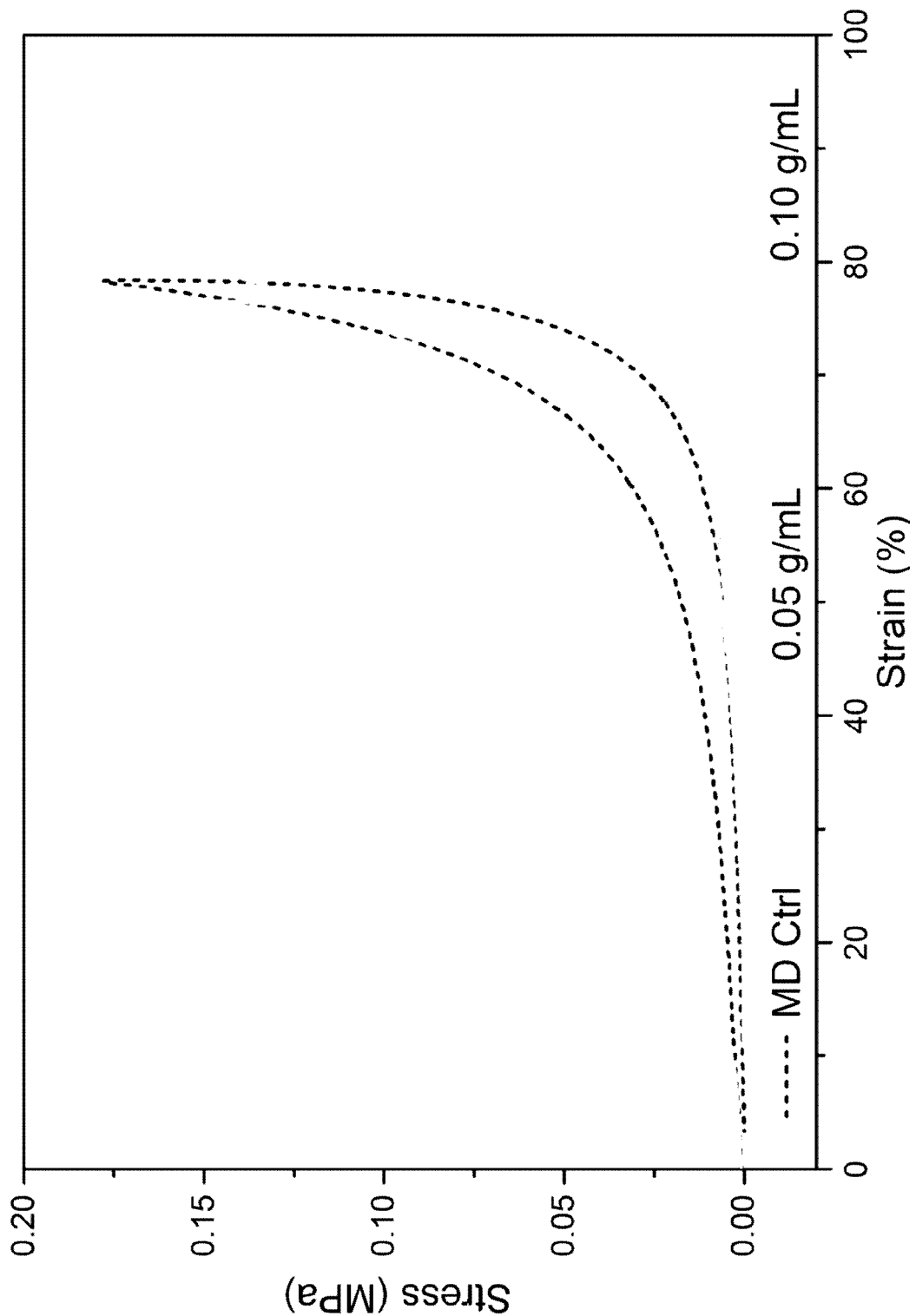
FIG. 44: MD-type control vs 0.05 g/mL and 0.10 g/mL initial condition ODMA concentration click chemistry surface functionalised xerogels.
Figure 45:
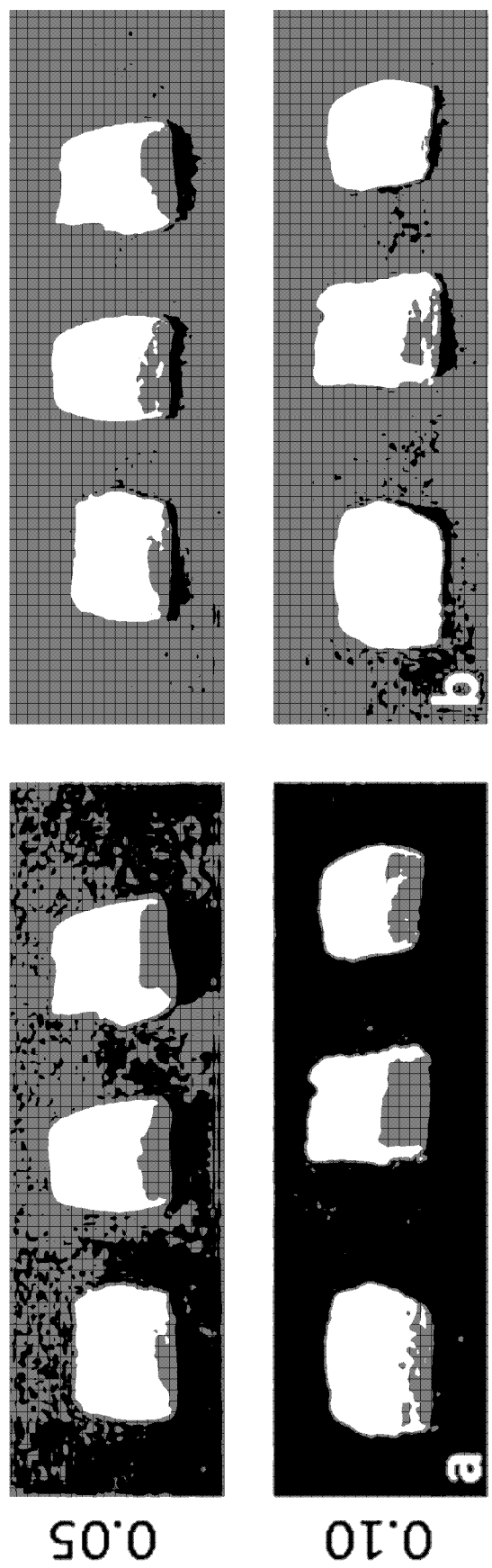
FIG. 45: Representative photographs of 0.05 g/mL and 0.10 g/mL click-chemistry functionalised samples pre- and post-compression testing.

The 0.15 g/mL and 0.20 g/mL samples therefore initially appear to represent the ideal candidates for the proposed application, with similar microstructures to the MD-type control on which they are based as well as similar mechanical properties (which are particularly clear from their compression curves compared to those of the MD-type control in FIG. 44). The slightly steeper stress response to increasing strain exhibited by the ODS functionalised substrates is most likely due to the surface grafted p(ODMA), which will inherently affect the compression characteristics of the material. Although present, the residual strain is drastically lower (approximately 10%) compared to OTS and SI-ATRP samples (40% and 50% respectively). Physical behaviour to the touch cannot distinguish between control and functionalised, and samples return to their original shape as shown by representative photographs in FIG. 45.

The satisfactory material properties, combined with their ease of synthesis through thiol-presenting mercaptosilane precursors, make these click-chemistry surface-modified xerogels the best candidates for the proposed application of lipid extraction from biological cavities.

Fluid Absorbance Capacity

Figure 42:
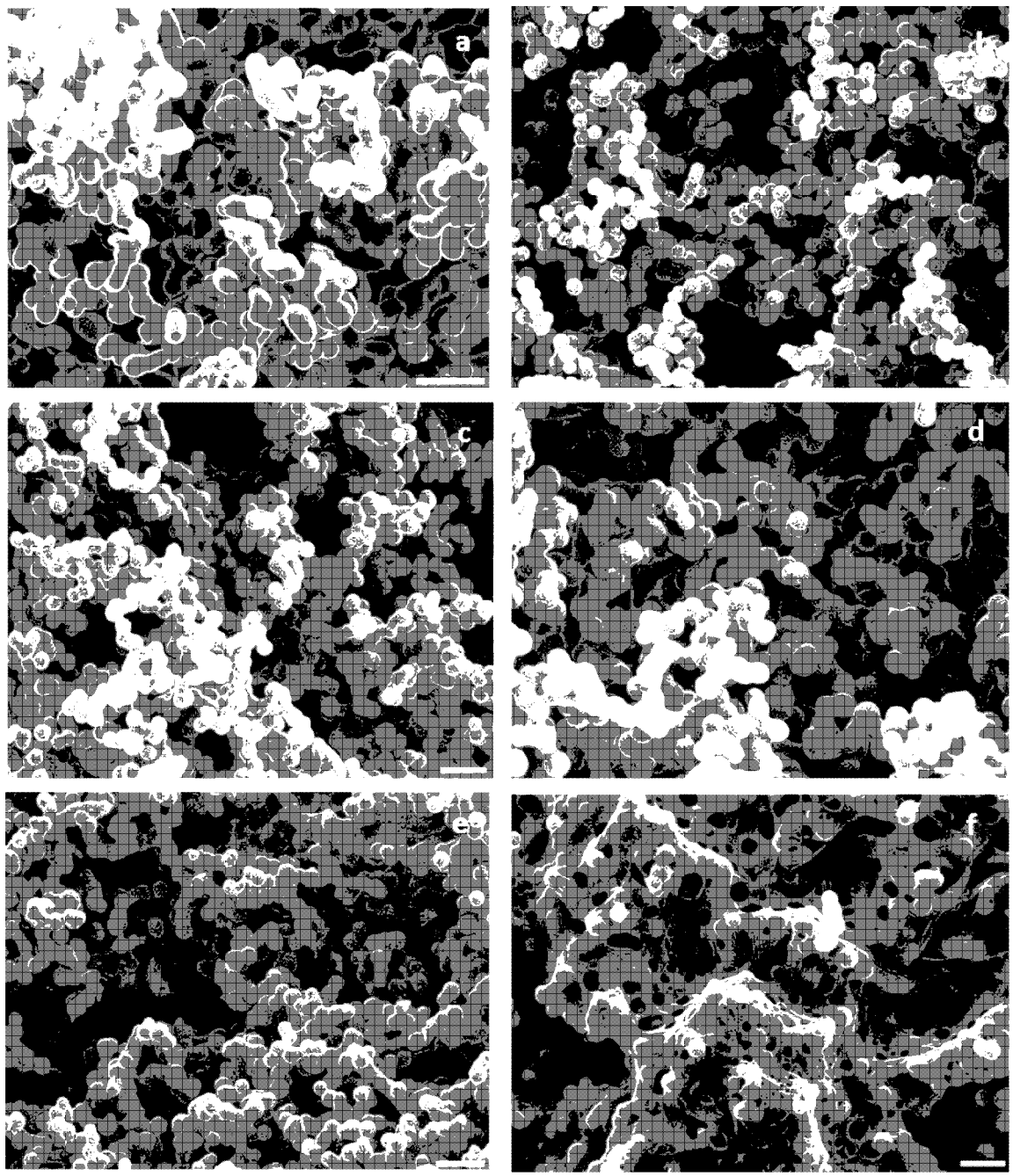
FIG. 42: Representative SEM micrographs of N-type control (a), MD-type control (b), 0.05 g/mL (b), 0.10 g/mL (c), 0.15 g/mL) (d) and 0.20 g/mL (e) initial condition ODMA concentration click-chemistry surface modified xerogels (scale bar=10 μm).
Figure 46:
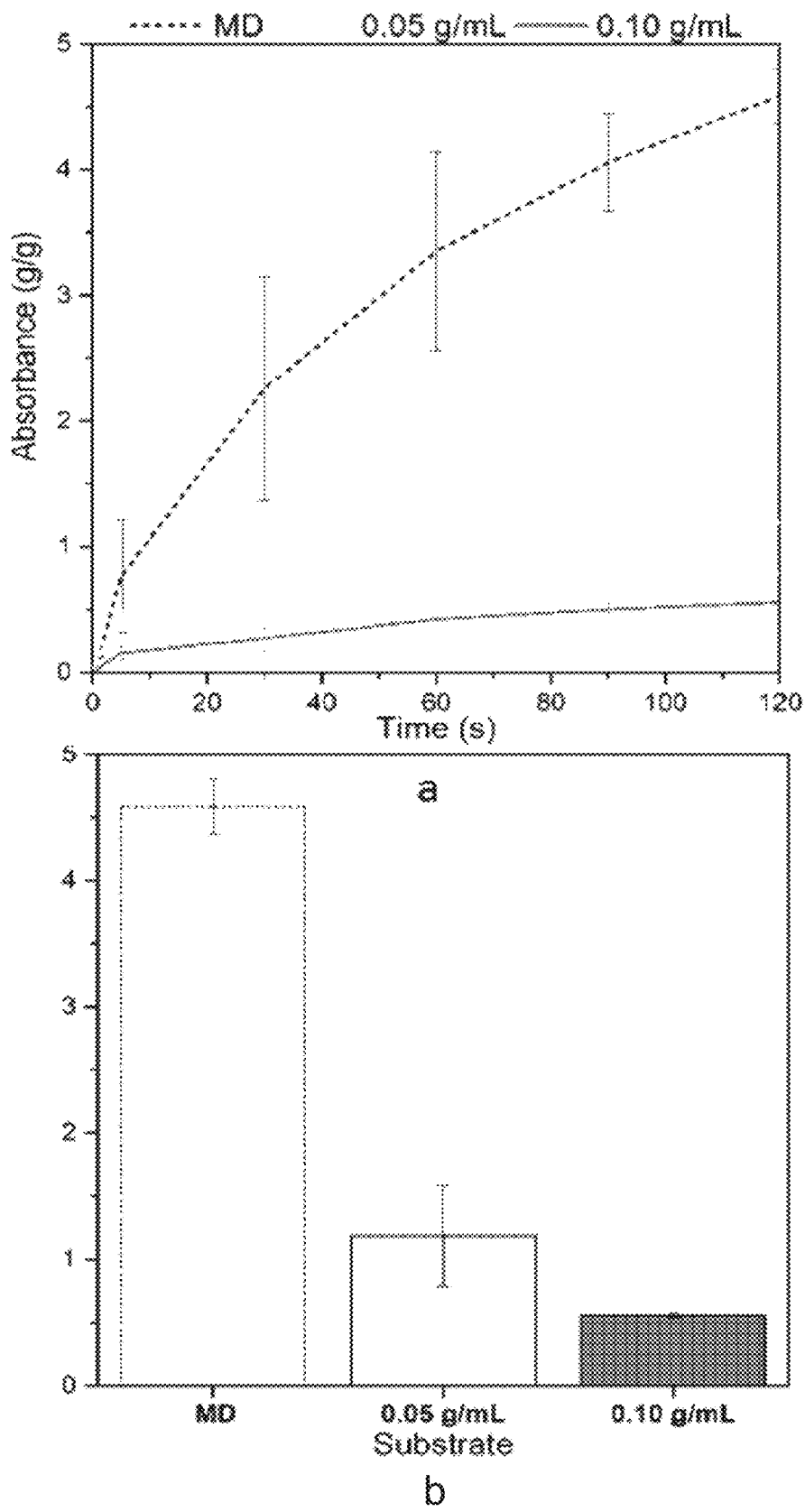
FIG. 46: Absorbance capacity of 0.05 g/mL and 0.10 g/mL click xerogels over time (a) and after 120 seconds (b) relative to MD-type control xerogels.

The absorbance trends and values shown in FIG. 46 indicate an inversely proportional correlation between ODMA concentration and absorbance capacity, as well as a drastically reduced absorbance capacity relative to control. This is expected given the highly hydrophobic properties of ODMA and p(ODMA). The wicking behaviour shown in FIG. 46*a* also indicates a slower fluid uptake than the unfunctionalised xerogels, and a reduced overall wicking capacity. Both can be again explained by the presence of ODS groups. Although the absorbance capacity of the 0.10 g/mL xerogel is almost at 0.6±0.02 g/g, almost $\frac{1}{10}^{th}$ at of that of the MD-type control xerogel (4.6±0.2 g/g), its 0.05 g/mL counterpart exhibits a lesser reduction in fluid absorbance: 1.2±0.4 (g/g) versus for MD-control (4.6±0.2 g/g). Although indeed a dramatic reduction in the absorbance capacity of the material, these values only reflect the fluid retained by the structure, but not the ability of aqueous fluid to penetrate the structure. Indeed, the structure still being porous regardless of functionalisation (as shown by FIG. 42) implies that although fluid may not be retained, it should still be able to flow through the structure, simply not be retained. Although not completely in line with the objectives, given the final application of the ODS functionalisation is to separate lipid constituents from their aqueous solution, the lack of fluid wicking capacity does not necessarily limit their biological activity. This is further explored and confirmed by cross-sectional images of the ODS functionalised xerogels, which reveal lipid extraction within the structure (and not only on the surface of the material), thus confirming that during manual handling (squeezing) of the material in the lipid solution, fluid was able to pass through the structure for lipids to interact with surface ODS groups.

This can be considered to still be satisfactory for the proposed application; in particular if the bio-specificity hypothesis of preferential lipid extraction is validated as the material should therefore be able to extract more lipid per unit volume than its unfunctionalised counterparts. ODMA thiol-ene surface-initiated polymerisation functionalised xerogels were therefore selected as the best candidates for the proposed project and, unless otherwise specified, the majority of subsequent time- and resource-consuming tests focus solely on this composition.

MTT Cytotoxicity Testing

Although suitable compressive and absorptive properties have thus far been confirmed, a final key requirement before proceeding to proof-of-concept biological testing is the material's cellular environment compatibility. Xerogels were immersed in ISO standard MTT assay solutions for 1 hour, and absorbance values at 570 nm taken 1 hour and 24 hours post-immersion in assay solution to evaluate the effect of the materials on the cellular environment. All results were performed relative to basal media control.

Figure 47:
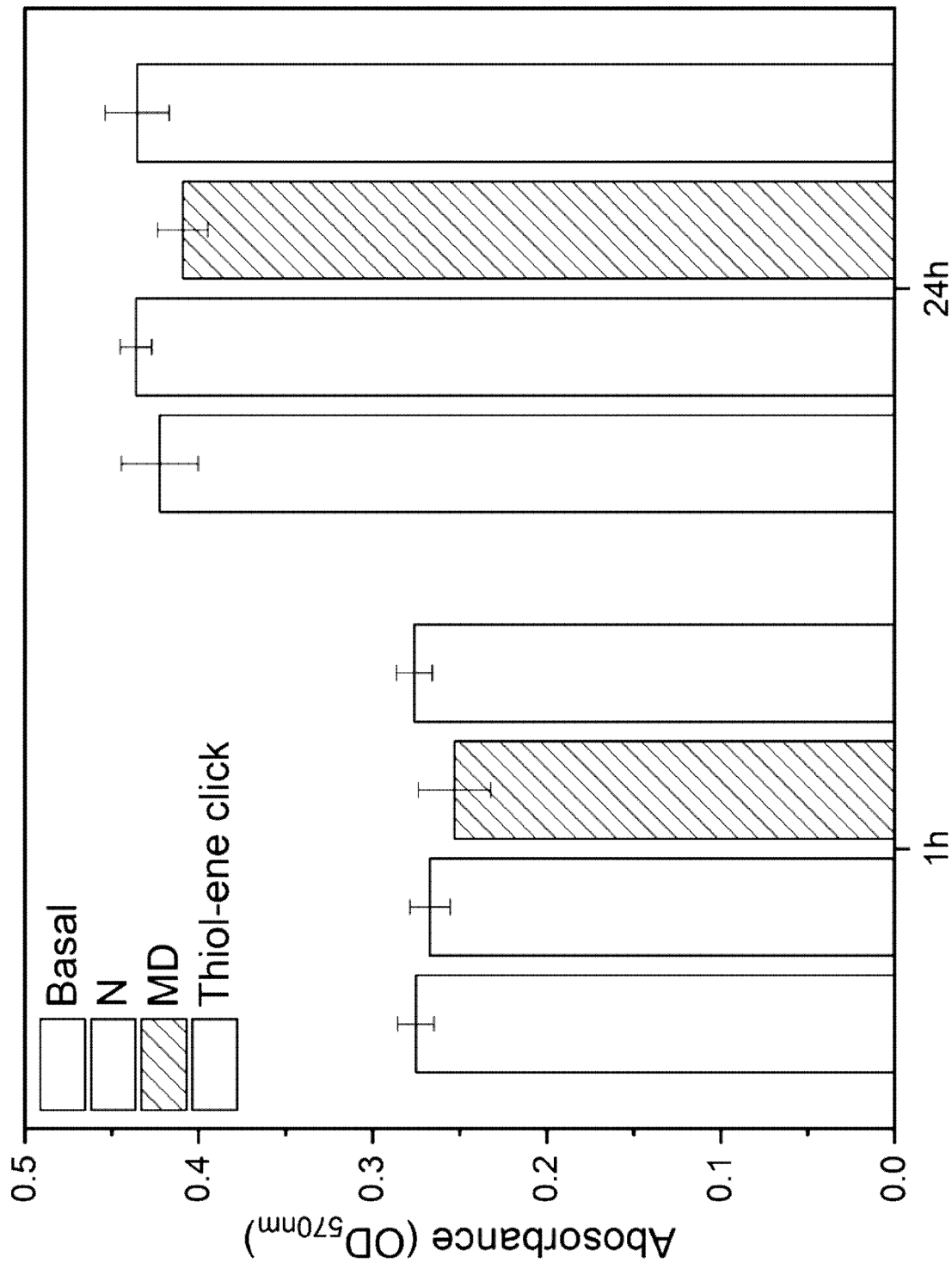
FIG. 47: MTT cytotoxicity testing of N-type, MD-type and ODMA thiol-ene click chemistry surface modified xerogels.

As is clear from FIG. 47, regardless of composition (N-type, MD-type or ODS functionalised by thiol-ene click chemistry), variations in absorbance values at both 1 hour and 24 hour timepoints are within each other's margins of error. The fact that absorbance values for both basal media and various xerogels are identical demonstrates that the proposed substrates are not cytotoxic, i.e. they have no impact on the cellular environment to which they are exposed to. This is of particular importance for the proposed application as any substrate effect on the biomarkers it is extracting would corrupt any post-extraction results. The fact that this does not occur further confirms these substrates are well-suited to the proposed extraction and diagnostic application.

Example 14: SI-FRP Functionalisation—Towards Biological Testing

Results

Fluorescence Testing

The aforementioned results have so far shown that the thiol-ene click chemistry functionalisation of xerogels (at a 0.05 g/mL initial ODMA concentration) is the best of the proposed options for surface grafting ODS groups onto the xerogels. Having successfully passed these tests, the material could therefore be further assessed for its biofunctional role. This proof-of-concept study was performed first of all using confocal microscopy, then by LC-MS.

a) Biological Solution Assessment

Confocal microscopy was used because fluorescence labelling allows for direct and impactful visual evaluation of the material's biofunctional performance (in this case lipid extraction and retention relative to controls) but also precise numerical analysis thereof.

Prior to testing the xerogels being studied, two controls tests were run that enable any subsequent tests to be fully representative. The first of these was a second structural evaluation using confocal microscopy in reflectance mode to confirm that the gold coating process used during SEM imaging was not obscuring any surface features. Reflection confocal microscopy allows a material to be visualised purely by lighting the material with a laser and analysing the reflected signal thereof, thus eliminating the need for any surface coating.

Figure 48:
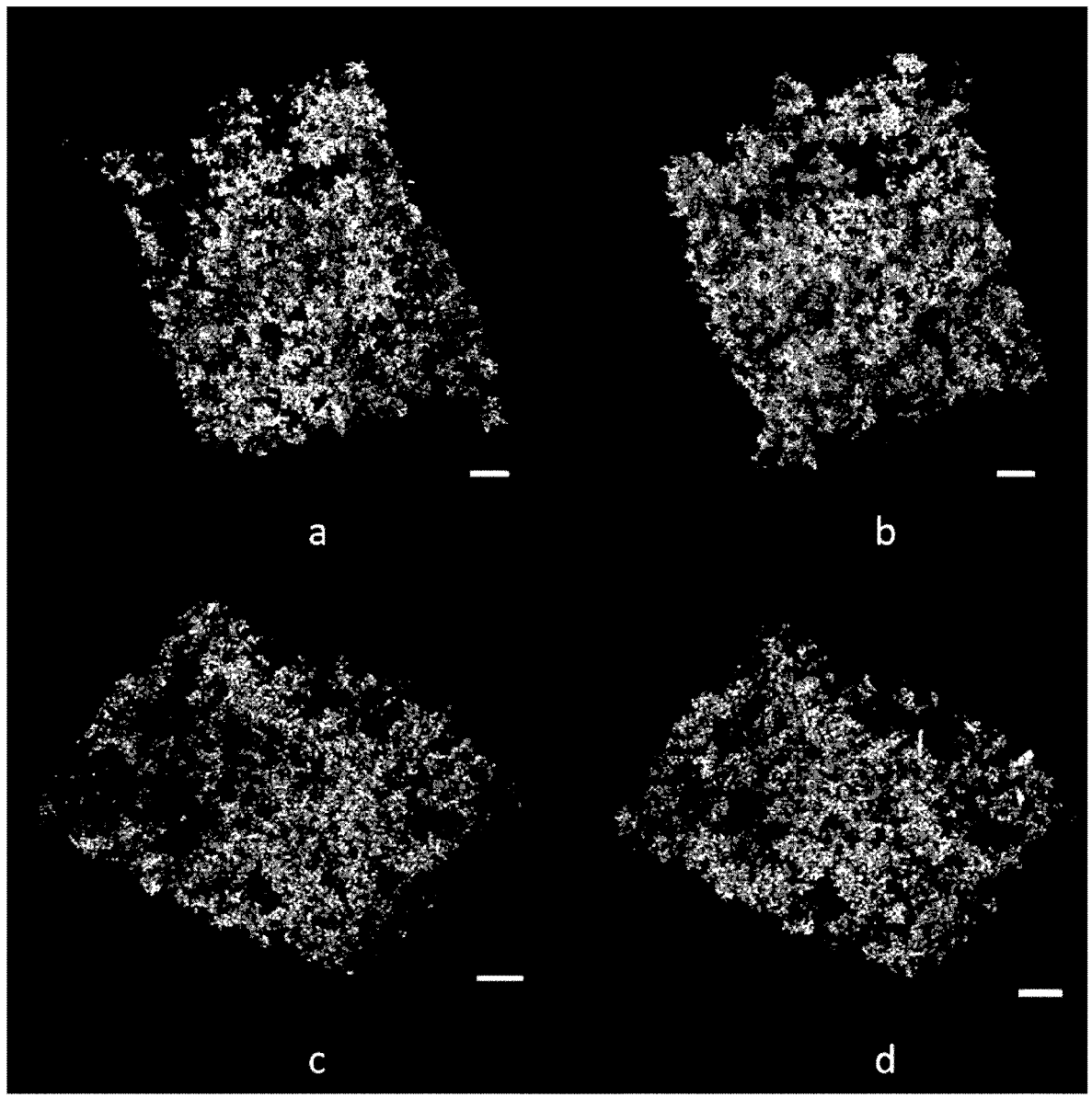
FIG. 48: Representative reflectance confocal microscopy images of N-type (a), MD-type (b), 0.05 g/mL (c) and 0.10 g/mL (d) xerogels (scale bar=10 μm).

As can be seen in FIG. 48, there are no clearly discernible differences between the various compositions, regardless of precursor selection (N- vs MD-type) or functionalisation (0.05 g/mL and 0.10 g/mL versus MD-type control). This confirms the conclusions drawn from SEM imaging, i.e. that both control (N and MD) are microstructurally identical and that ODS functionalisation does not have an effect on the microstructure of the substrate being functionalised. It also allows a visualisation of the structure without any fluorescence labelling, which can be referred to as a control surface for subsequent biological evaluation. The second control experiment was the evaluation of the biological models used for confocal microscopy so as to ensure the methods used were biologically representative.

Figure 49:
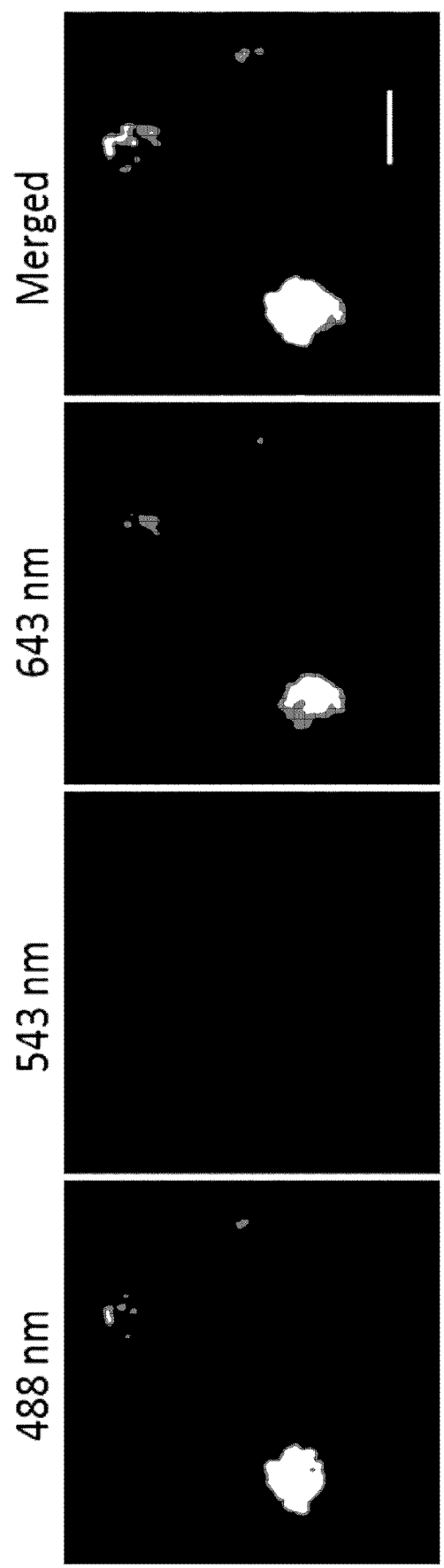
FIG. 49: Confocal microscopy micrograph of laurdan and 0.5% Alexa Fluor 488 labelled DOPE+DOPC liposomes, at 405 nm, 643 nm, 488 nm and (scale bar=20 μm).

This was done by adding laurdan to the DOPC:DOPE fluorescent liposomes, a technique, which allows for more precise structural investigation of the DOPC liposomes formed. Laurdan is a small lipid with low polar moment, but its polar moment can change direction more freely when in water (e.g. x y z axis) than when 'dry' (e.g. just x y) [33]. Results in change in emission spectra, 405 nm and 490 nm respectively, can therefore provide information on which state laurdan is in. As shown in FIGS. 49a and b respectively, both 405 nm and 490 nm channels are visible under relevant laser excitation, suggesting some laurdan molecules are exposed to an aqueous environment on the outer surface of the liposomes, whilst others remain more static within the liposome wall. The combination of this with the clearly visible spherical structure in FIG. 49 points towards the method used allowing the formation of liposomes as desired.

Figure 50:
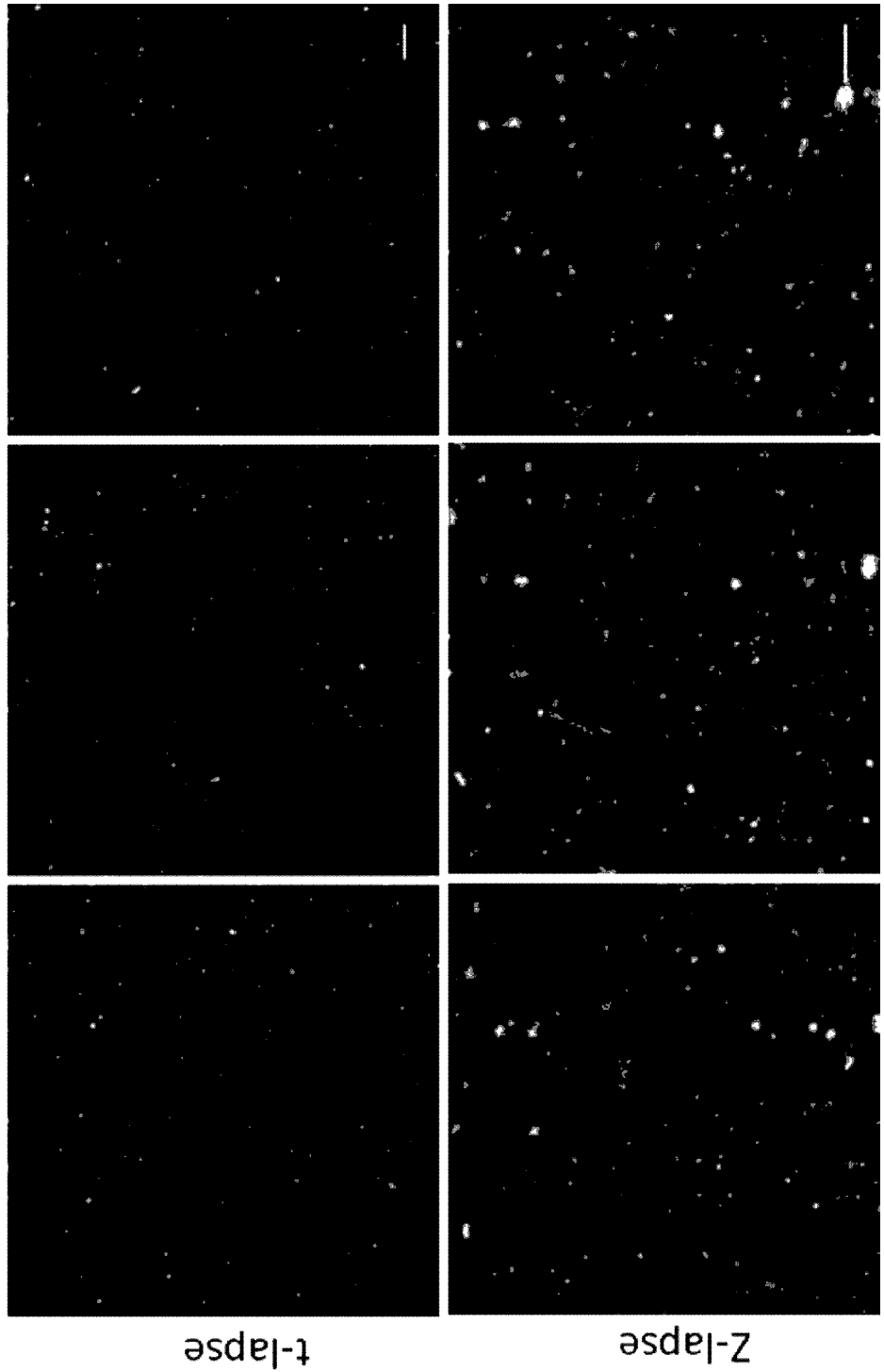
FIG. 50: Time and Z-axis lapse images (taken 10 s and 5 μm apart respectively) of DOPC 0.5% DOPE Alexa Fluor 488 labelled liposomes (scale bar=20 μm).

Given the aqueous media in which the liposomes have been formed, they would be expected to be mobile, as would be the case in physiological solutions, rather than being stuck on the glass. Liposome mobility within media is also key to their being successfully extracted from such media onto the surface-grafted ODS groups on the xerogels which are the subject of this work. Time and Z-lapse images shown in FIG. 50 confirm this mobility, with vesicles clearly moving through both axis. Given the concentration of DOPC initially used (100 µg/mL), the lipid-only containing solution can be assumed to be physiologically representative.

b) Lipid Extraction Assessment

Having established the physiological similarity of the fluorescent DOPC 0.5% DOPE lipid solution used, the extraction and retention capacity of the ODS xerogel was assessed relative to its unfunctionalised MD-type base substrate. N- and MD-type control xerogels only were used as control substrates; commercially available SAMs were assessed in prior work and have already been identified as non-biofunctional in terms of specific biomarker extraction (such as lipids in this case) and are therefore herein included.

The aim of the ODS functionalisation is to allow the extraction and separation of lipids from other biomarkers (such as proteins and cells) so as to allow minimal post-patient sample collection processing and separation steps. Indeed, current methods require either organic solvent lipid separation methods to extract the relevant lipids from the physiological solution they are contained in (e.g. nasal epithelial fluid), and/or centrifugation steps. Not only are these steps time consuming and therefore increase diagnostic time, but the substrates currently used do not provide standardisation of the lipid amounts extracted, thus yielding high inter-patient variability. The proposed xerogels through ODS functionalisation should therefore allow not only lipid retention, but through a known lipid absorbance capacity the possibility of developing a 'gold standard' extraction allowing directly quantifiable results to be obtained.

Extraction, lipid-selective retention and re-elution were assessed by immersing samples into the aforementioned physiologically mimicking solutions, and subsequently washing through with aqueous and organic solutions.

Figure 51:
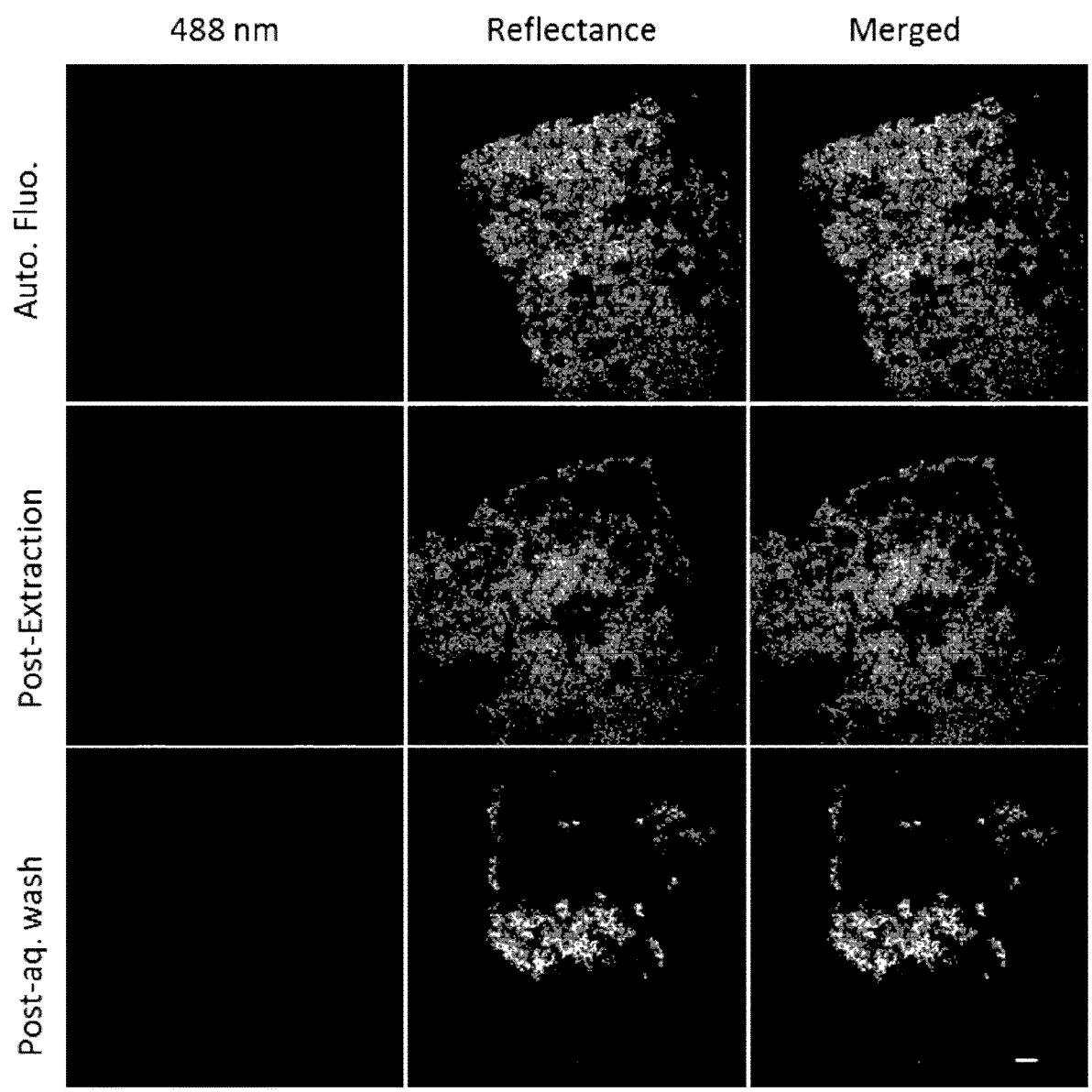
FIG. 51: Representative confocal micrographs of MD-type control xerogel substrates after autofluorescence assessment, dipping in liposome solution and post aqueous solution washing (scale bar=100 μm).

FIG. 51 showcases the followed protocol for non-ODS functionalised (control) MD-type xerogels. The lack of any signal in channel 1 in FIG. 51 indicates that at the set parameters, the substrate is not auto-fluorescent. This (conveniently) implies that any subsequent signal observed after dipping the substrate into the 488 nm fluorescence-labelled lipid solution directly indicates the presence of the lipids. Conversely, lack of signal implies no lipid presence in the substrate. This method was used for all substrates, control and ODS-functionalised.

A relatively large amount of fluorescence signal can be observed in FIG. 51b at 159.33±20.96 FSU, implying the presence of lipids on and within the structure. Indeed, all shown micrographs and subsequent fluorescence intensity measurements were obtained 10 µm from the surface so as to ensure results were not purely surface features, as well as to confirm that absorbed fluid was penetrating through the xerogel's porous structure and not staying on the surface. The presence of lipids here is to be expected, given the fluid-absorbing nature of the material as shown in FIGS. 28A and B, and FIG. 46. It is however important to note at this stage that the presence of lipids through the structure may simply indicate the presence of the aqueous solution containing them, as sample were testing directly after immersion and excess removal.

However, the complete lack of signal in FIG. 51c implies that any previously absorbed lipid during the wicking stage has not been retained by the material. This implies that the structure has no innate chemical preference to lipids of similar structure and physical properties to DOPE and DOPC. Although lipid markers or other biomarkers such as proteins may interact differently with the material, this points towards MD-type xerogels being suitable for use without ODS-functionalisation as they may allow such biomarkers through during elution. This may be crucial to other bio-functional separation roles considered for MD-type xerogel based devices. The lack of lipid presence post-aqueous wash rendered organic washing redundant and was therefore not performed on MD-type controls.

Figure 41:
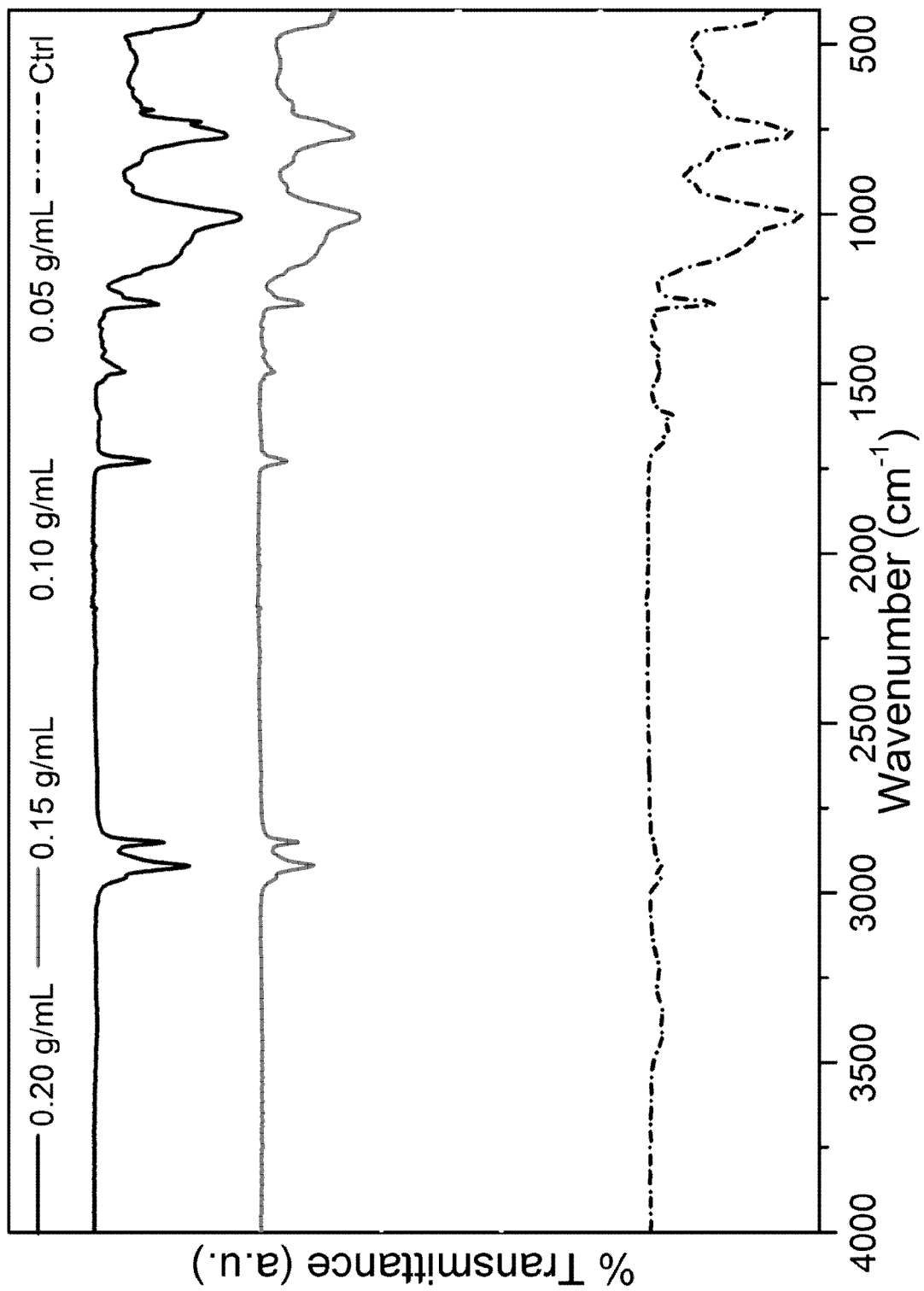
FIG. 41: Normalised FTIR spectra of MD-type control and increasing initial condition monomer concentration thiol-ene click chemistry functionalised xerogels.

The above results therefore confirm that without functionalisation, MD-type xerogels did not innately retain lipids during aqueous washing. FTIR results (shown in FIG. 41) however confirmed the presence of ODS surface groups in both 0.05 g/mL and 0.10 g/mL click-functionalised samples. The same lipid-wicking protocol was followed for both, the results of which are shown in micrographs in FIGS. 52 and 53, and in numerical values thereof in FIG. 54. Both 0.05 g/mL and 0.10 g/mL samples do not auto-fluoresce, in similar fashion to the MD-type control scaffold. The background values measured and shown in FIG. 54 can be attributed to background. The auto-fluorescence check furthermore allows the baseline background values to be determined, to which any subsequent fluorescence intensity can be qualitatively and quantitatively compared.

Figure 52:
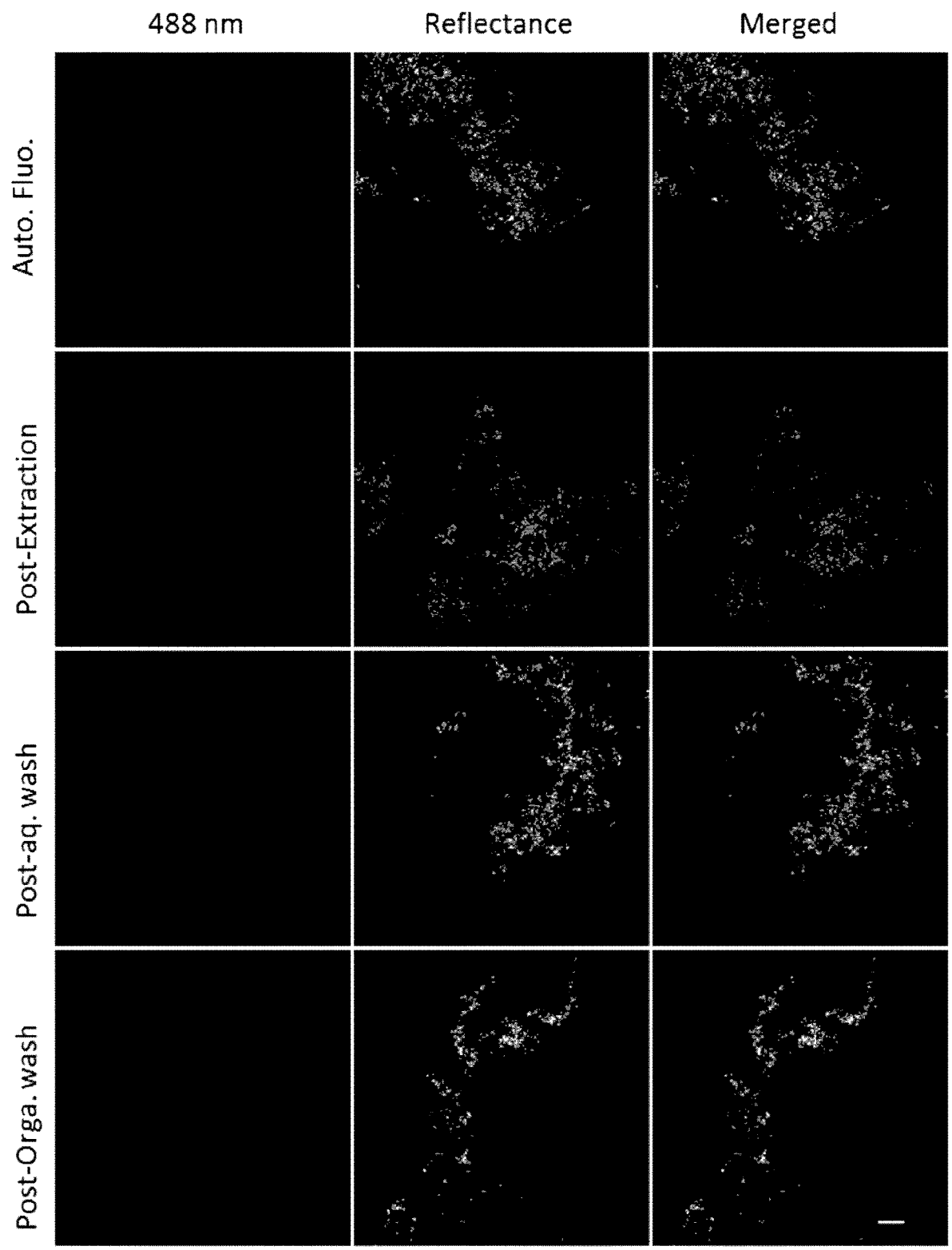
FIG. 52: Representative confocal micrographs of 0.05 g/mL ODMA concentration click chemistry surface functionalised xerogels after auto-fluorescence checking, dipping in lipid-only solution, post aqueous solution washing and post organic washing (scale bar=100 μm) (channel 1=488 nm only, channel 2=reflectance only, channel 3=overlay of both).
Figure 53:
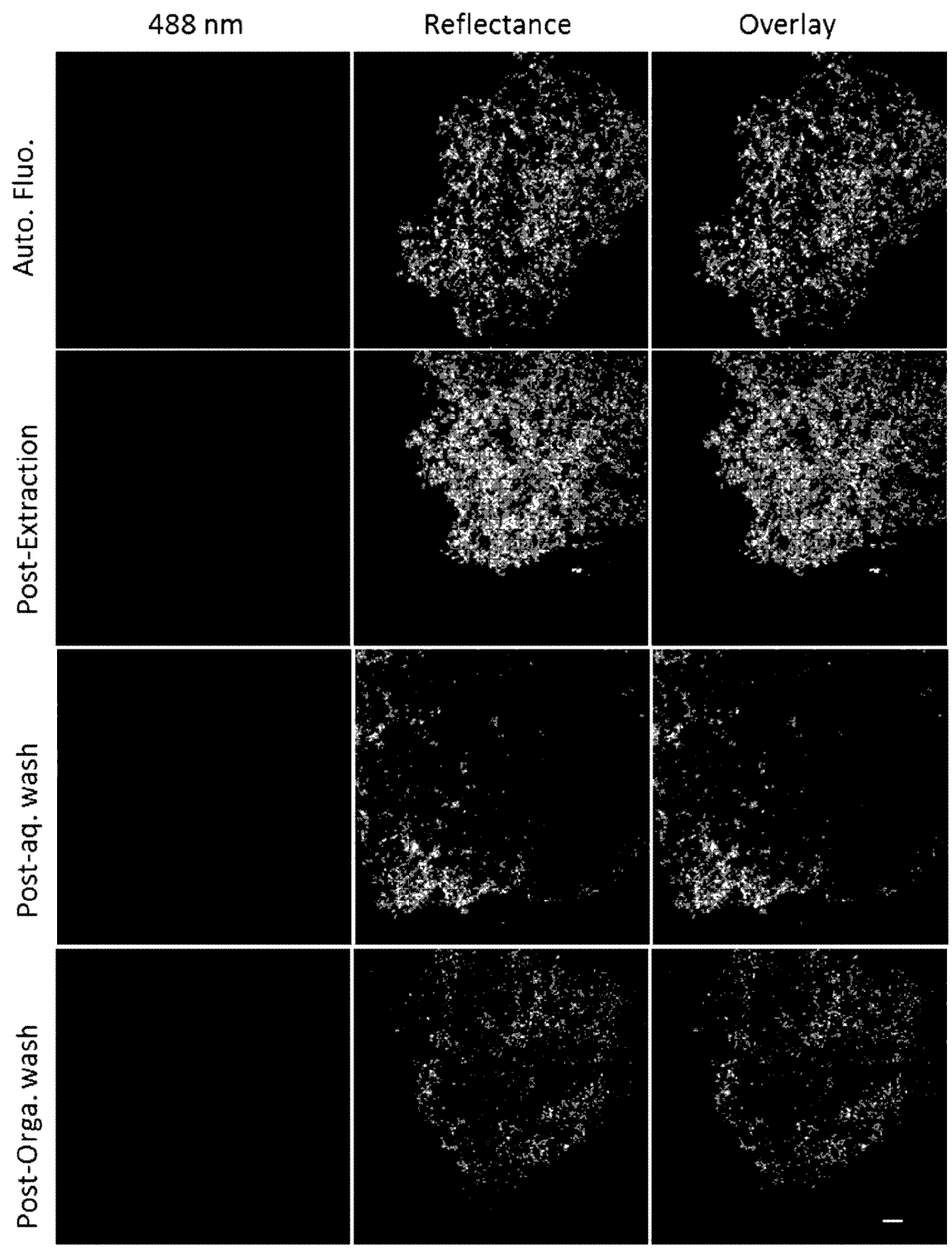
FIG. 53: Representative confocal micrographs of 0.10 g/mL ODMA concentration click chemistry surface functionalised xerogels after auto-fluorescence checking, dipping in lipid-only solution, post aqueous solution washing and post organic washing (scale bar=100 μm) (channel 1=488 nm only, channel 2=reflectance only, channel 3=overlay of both).
Figure 54:
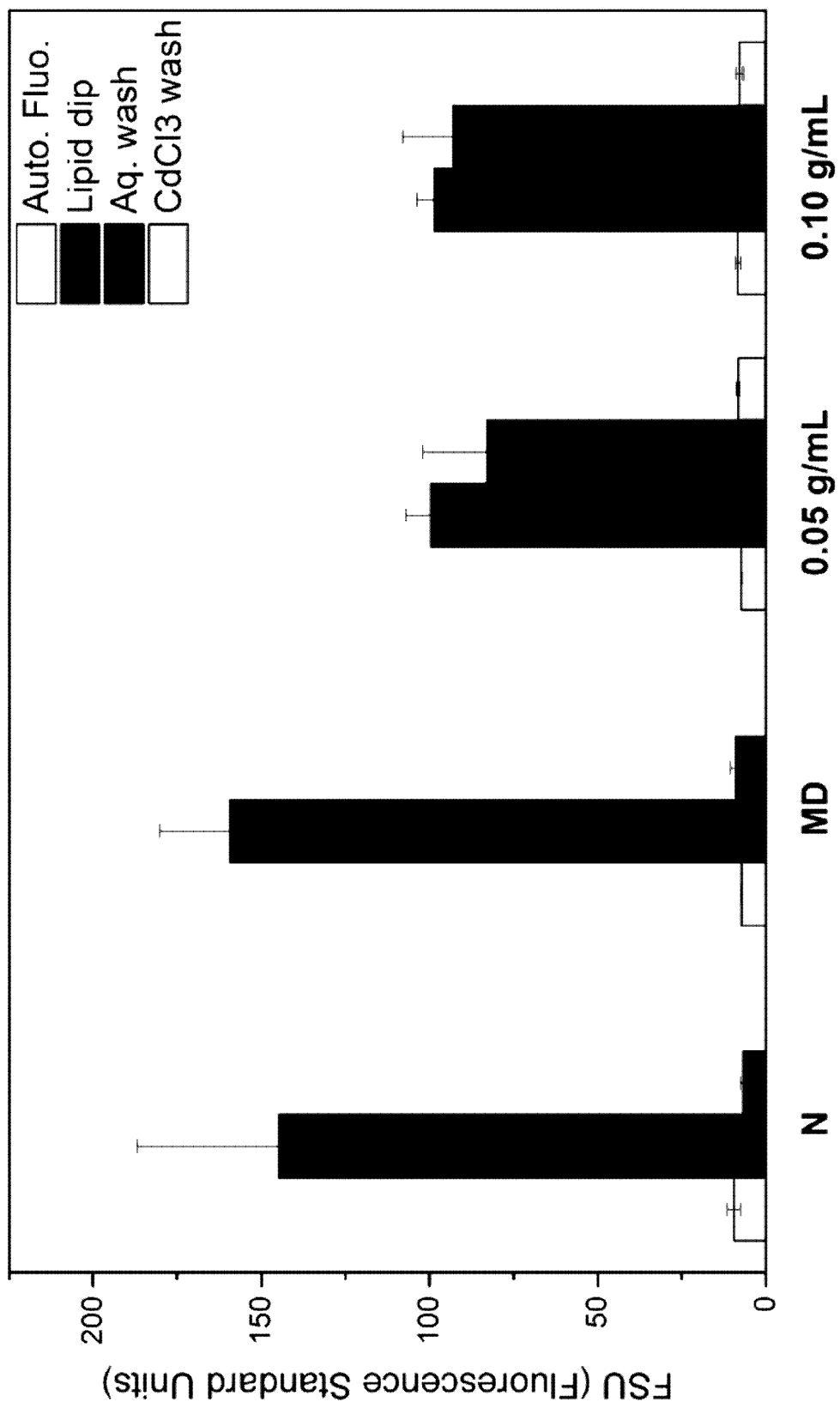
FIG. 54: Fluorescence intensity measurements taken during lipid adsorption, retention and re-elution testing of MD-type control, 0.05 g/mL and 0.10 g/mL ODS click-functionalised xerogels.

Post-wicking, both ODS-functionalised samples clearly indicate lipid presence within the structure, as seen by the red signal visible in the fluorescence channel in FIG. 52 and FIG. 53. The actual quantity of lipid adsorbed by the xerogels is however less than the MD-type control, at 98.51±5.21 FSU and 99.74±7.30 FSU for 0.05 g/mL and 0.10 g/mL respectively, compared to 159.43±20.96 FSU for the former. The increased hydrophobicity of the functionalised materials yields lower fluid absorption (FIG. 46) suggesting that less lipid is being absorbed into the structure. Although there is a reduction of approximately 60 FSU in lipid signal intensity, ODS-functionalisation clearly does not inhibit the ability of the material to absorb lipid-containing aqueous fluid. The over 90 FSU intensity difference between baseline and post-lipid wicking clearly indicates that the material is still suitable for purpose.

The major divergence between MD-type control and ODS-functionalised xerogels can be observed in the post-water washing step. Whereas the intensity observed in MD-type control returned to baseline post water washing, both ODS-functionalised samples exhibit fluorescence intensity at 93.08±14.82 FSU and 82.94±19.01 FSU for 0.05 g/mL and 0.10 g/mL respectively, as opposed to 8.96±1.60 FSU for MD-type control. The presence of fluorescence signal confirms the lipid retention ability of the ODS-functionalised materials during aqueous washing (designed to remove water-soluble elements such as proteins and cells.

Two further trends post-aqueous washing can be identified. First, a slight reduction in fluorescence intensity signal can be observed between the original lipid absorption and that measured after aqueous washing. This is most likely due to any non-surface bound lipid aggregates being washed away during the washing phase, as this step includes high RPM centrifugation. This in turn also confirms that the lipids which remain (and produce fluorescence signal) have an affinity for the surface-grafted ODS molecules. This minor divergence also falls within the original post-lipid-wicking step's margin of error for both 0.05 g/mL and 0.10 g/mL and is therefore not significant. Secondly, a slightly higher retention capacity for the 0.10 g/mL ODS-functionalised xerogel can be observed relative to its lower concentration counterpart, with a reduction in average signal of approximately 9 FSU. Although this could be explained by the most likely higher surface density of ODS groups in the case of the 0.10 g/mL samples relative to 0.05 g/mL, not only is this difference in surface group concentration impractical and relatively irrelevant to measure given the clear functionality of the proposed materials, but the divergence in average values falls within the respective samples' error margins, once again making the divergence inconclusive for these purposes.

The final organic solvent step is designed to elute out any lipids in the devices, water-soluble contaminants and unbound lipids having been removed in the previous step so as to provide the 'cleanest', diagnostically relevant and repeatable lipid extraction process. As can be observed from FIGS. 52 and 53, the micrographs obtained after this organic solvent washing step indeed appear to, as desired, to fully re-elute the previously adsorbed lipids, with no fluorescence signal visible. This visual trend is confirmed by numerical results shown in FIG. 54, with a clear return to approximately 7 FSU of fluorescence intensity. The auto-fluorescence measurements performed prior to any lipid extraction process confirmed such values to be attributable to background.

The above-presented results therefore appear to prove the successful nature of ODS surface functionalisation onto MD-type xerogels by means of click-chemistry for the proposed project. Indeed, the ODS-functionalised substrates retain to a significant degree their fluid-absorbing capacity, whilst retaining lipids during an aqueous washing phase and complete re-elution of any lipids previous adsorbed onto the ODS groups during an organic washing phase.

LC-MS Evaluation

LC-MS is broadly accepted as the 'gold standard' status for broad spectrum, precise and high-throughput analysis technique, based on an extensive body of research and industrial utilisation. Evaluating the capacity of the proposed xerogel-enabled nasal fluid extraction method for downstream analysis with LC-MS systems is therefore a key step in proof-of-concept testing these materials for clinical use. In a clinical context, this process is intended to mimic the processes that would be performed prior to LC-MS analysis and the results thus obtained. Using a multi-lipid solution such as the one used here allows for further physiological approximation (as opposed to single-lipid solutions such as that used in the earlier fluorescence section), as well as providing an initial insight into the viability of using such scaffolds for analysis via LC-MS.

For this evaluation, ODS functionalised and control samples were immersed in a lipid solution containing physiologically representative concentrations of PG, PI, PA, PE, PS, PC, SM and Cer mimicking the process of nasal fluid collection. (Phospholipids, ceramides and sphingomyelines are key components of cellular signalling pathways; so using this type of mixture provides a reasonably good suitable physiological model of lipid constituents expected during clinical applications of the proposed materials for use via LC-MS [35, 36]). Substrates were then removed, washed through with aqueous solution to remove any unbound lipids, and then finally washed through with methanol in order to desorb all previously extracted lipids from the substrates. LC-MS was performed on the solution recovered from samples post-elution; such a solution being directly indicative of the lipid species extracted and the relative amounts of each of them.

The data is presented, analysed and interpreted below. Each of the lipid constituents used (PG, PI, PA, etc.) had previously been evaluated by the CSM research group in which the measurements were performed in, thus providing a clear reference data against which to compare the results obtained in this project. The data analysis procedure is briefly explained below with an example (in this case PC), so as to provide a better insight into the final results obtained and how best to interpret them.

Figure 55:
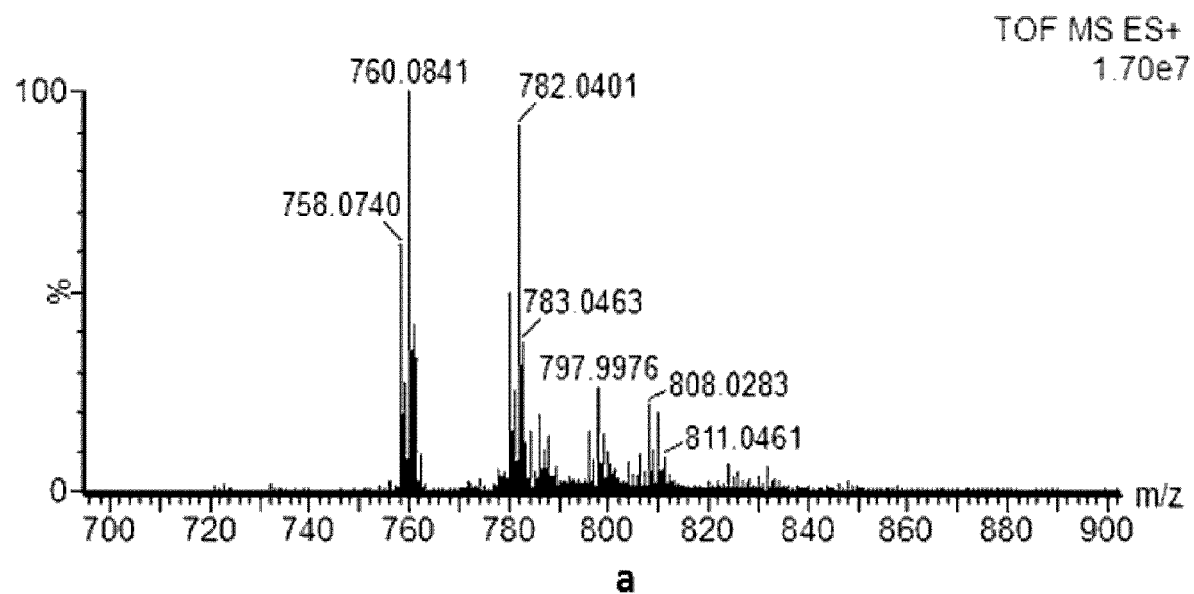
FIG. 55: ToF positive mode mass spectrum (a), PC composition positive mode m/z values (b) and relative abundance of lipid-ratio types (c) of PC used in LC-MS experiment.
Figure 55:
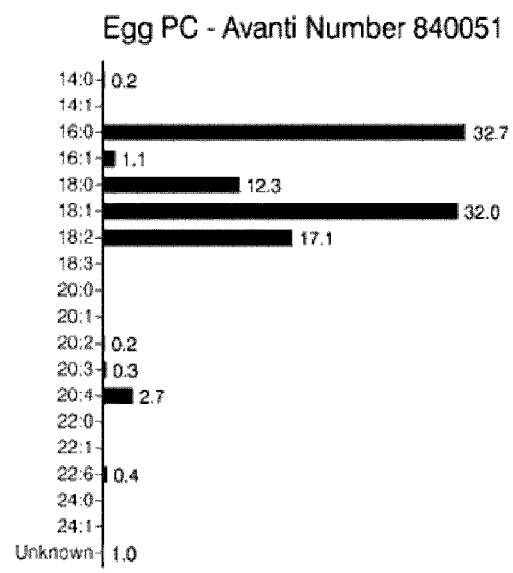

Each lipid species was previously analysed using LC-MS/MS (Liquid chromatograph-tandem mass spectrometry), and the relative amounts of each fragment recorded, as shown in FIG. 55. In contrast to LC-MS where only the m/z of the precursor ion of a given species is measured, LC-MS/MS allows m/z measurements of the by-products of said species. A first MS system analyses the precursor species ion, whilst a second fragments said ion and measures the m/z of the generated fragments. In practical terms, this allows for increased sensitivity and more information on the structure of the precursor ion [27]. This is key in applications such as the one herein described where various species present have close and possibly hard to distinguish m/z values.

The 3 most abundant fragment m/z values were thus extracted from data such as that presented in FIG. 55 and compiled into Table 10 for reference during LC-MS data interpretation.

TABLE 10

| | 3 predominant m/z values for each lipid species used in lipid solution for ODS xerogel LC-MS evaluation protocol | | | | | | | |
|---|---|---|---|---|---|---|---|---|
| M/Z + ve # | PG | PI | PA | PE | PS | PC | SM | Cer |
| 1 | 749.5328 | 887.5644 | 675.4959 | 718.5381 | 784.5123 | 760.5851 | 703.5748 | 648.6265 |
| 2 | 775.5648 | 863.5654 | 701.5116 | 716.5225 | 760.5123 | 782.5694 | 787.6687 | 548.3651 |
| 3 | 799.5484 | 889.5801 | 725.5116 | 744.5538 | — | 758.5694 | 801.6844 | 566.5483 |

Figure 56:
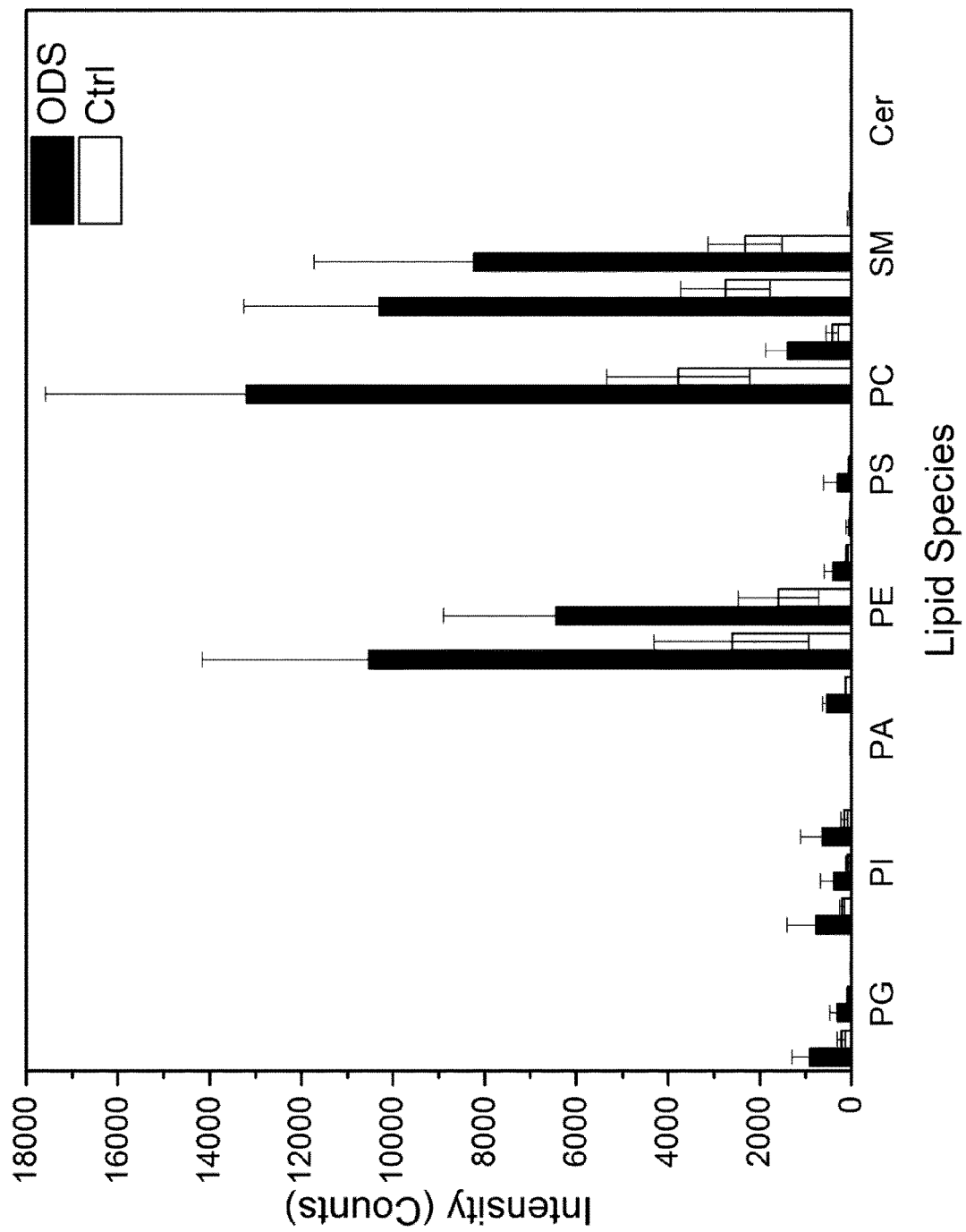
FIG. 56: Intensity measurements of various lipid species measured from ODS and control xerogel eluted samples via LC-MS/MS in positive mode.
Figure 57:
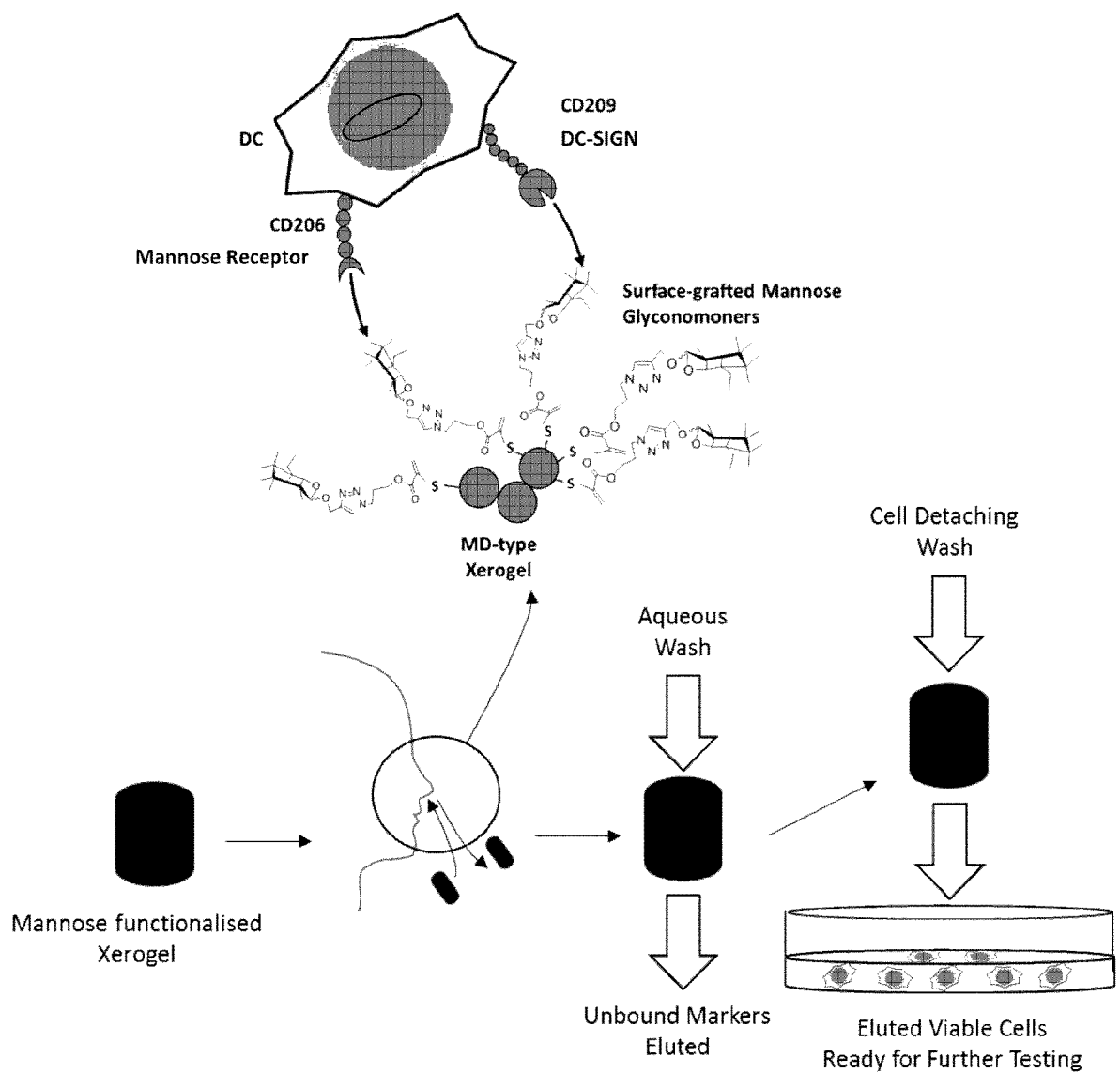
FIG. 57: Schematic representation of Mannose glycomonomer surface grafting onto xerogels functional concept; selective extraction and viable re-elution of Dendritic Cells enabled with preferential affinity of CD206 and CD209 surface receptors for Mannose groups.

FIG. 56 presents the thus compiled data for all lipid species, representing the intensity of various lipid fragments corresponding to each lipid type, measured from the solution eluted from the xerogels (ODS functionalised and control) after having been dipped in the lipid solution and washed through with aqueous solution. These values therefore give a clear indication of what was recuperated from the xerogel post-sampling and post-elution; and show what the xerogels can extract and re-elute for analytical purposes.

The first observable trend from FIG. 56 is the abundance of certain species (PE, PC and SM) relative to those which are less abundant or absent (PG, PI, PA, PS and Cer). This can partially be explained by the reduced abundance of such lesser present lipid species fragments in positive ion mode as opposed to negative. PE, PC and SM are zwitterionic phospholipids, thus abundantly visible in both modes, positive and negative [38]. In contrast, though PG, PI, PA and PS are reported to present fragments in both modes, most of them are present in negative mode and therefore not visible in the obtained scans. PC for instance is composed of 18:2, 18:1, 16:0, 18:3 and 18:0 ratio moieties in 68%, 12%, 10%, 7% and 3% proportion respectively. However, only 16:0 and 18:0 moieties are detectable in positive mode, the rest only visible in negative mode, hence the low signal abundance for PC.

Comparing ODS and Control obtained samples, it seems clear that regardless of lipid species, the signal obtained from solution eluted from ODS-functionalised samples is significantly higher than that from control sample-eluted solutions. This implies that lipids were more abundant in the solution eluted from ODS samples than control. Having proven by means of confocal imaging that ODS-functionalised xerogels extracted and retained more lipids than their control counterparts (FIG. 54), these results further confirm the suitability of ODS functionalisation of xerogels for lipid extraction from aqueous solution and subsequent selective re-elution. These results further support the suitability of the proposed protocol for clinical implementation, the xerogels clearly allowing a simplification of the downstream processing (post sampling) for high-throughput and conventional analysis via LC-MS.

Summary of Examples 9 to 14

Xerogels herein presented based on those reported by Hayase et al fulfil the missing criteria from their PDMS counterparts, their sol-gel synthesis method providing the porosity desired and ideal mechanical properties. Crucially, this is achieved whist retaining the silica network used for post-functionalisation on PDMS.

The ability to vary xerogel precursors during the sol-gel synthesis method enables the tailoring of surface labile groups; whilst a MDMS-DMDMS precursor mix forms a structure chemically similar to PDMS with labile methyl (—CH3) groups, using mercaptosilane precursors allows the synthesis of xerogels with labile thiol groups. Through careful ratio and compositional selection, xerogel with surface thiol groups were synthesised with identical or even improved material properties.

Surface thiol groups were subsequently used as an alternative to SI-ATRP for surface-initiated polymerisation of ODMA. By varying the initial monomer and thermal initiator concentrations, compositions with starting concentrations of 0.05 g/mL and 0.01 g/mL were determined to have similar surface densities of ODS groups whilst retaining suitable compressive mechanical properties.

Biological evaluations further confirmed the suitability of TSIP xerogels, with MTT assays confirming their non-cytotoxic nature. Confocal fluorescence measurements confirmed the lipid extraction and selective elution capabilities of the proposed material. Finally, LC-MS measurements enabled a first insight into the ability of such ODS functionalised xerogels to fit into a full clinical procedure—from sampling to sample analysis—during which the performance of ODS presenting xerogels vastly exceeded that of their unfunctionalised counterparts.

The xerogels and the associated ODS functionalisation have therefore been proven in their earliest prototype stages to be an effective means of sampling nasal fluid, and simplifying downstream processing.

The xerogels herein proposed should serve not only as substrates for ODS functionalisation towards lipid extraction, but also offer a multimodal platform for extraction of specific makers such as DCs and specific proteins. Functional groups extracting such biomarkers have the potential to be functionalised by means of thiol-ene based surface grafting. The next experiments explore such processes from both a material and biological perspective, in turn further validating the concept of MD-type xerogels as suitable polyvalent platforms for the desired clinical aims.

Example 15: Allyl-Based Block Copolymers

Materials

Trimethoxymethylsilane (MTMS, 99%), Mercaptopropyl)methyldimethoxysilane (DMeDMS, 95%), Hexadecyltrimethylammonium chloride (CTAC, 98%), Urea (99.5%), Acetic Acid (99.85%), Sodium azide, 3-Bromo-1-propanol, Diethyl ether, Magnesium sulfate, Triethylamine (EtNO3), Hydroquinone, Methacryloyl chloride, Sodium hydroxide, Methanol (MeOH), Copper(II) sulfate pentahydrate (CuSO4.5(H¬2O)), (+)-Sodium L-ascorbate, D-(+)-Mannose, Propargyl alcohol, Dichloromethane (DCM), Copper (II) chloride (97%), Copper(I) Bromide (99.99%, CuBr), Ethyl α-bromoisobutyrate (98%, EBrIB), 2,2'-Azobis(2-methylpropionitrile) (AIBN 98%), N,N,N',N'',N''-Pentamethyldiethylenetriamine (PMDETA), n-Hexane (95%), Anhydrous Chloroform (CdCl3, 99%), Anhydrous Toluene (99.8%), Acetone, Hydrochloric acid, Propanalol, Hexane, Anhydrous Tetrahydrofuran (99.9%, THF), 2-Propanol (99.5%), DAPI and SiR fluorescent stains were purchased from Sigma-Aldrich and used as purchased unless otherwise stated. Human THP-1 cell line, rhGM-CSF, rhTNF-α, rhIL-4, FCS, RPMI 1640, L-glutamine, 100 IU penicillin, streptomycin, ionomycin and foetal calf serum (FCS) were purchased from rndsystems.

Methods

Xerogel Synthesis

Xerogels with labile thiol moieties were synthesised followed previously described sol-gel Example 9. Briefly, tri- and di-functional precursors (MTMS and DMeDMS) were added to a solution containing urea and CTAC and stirred to promote hydrolysis at room temperature for an hour. The resulting clear solution was poured into moulds, sealed and placed at 80° C. for 24 hours for gelation and network condensation. The resulting xerogels were subsequently removed, triple rinsed with propranolol and hexane to remove any unreacted reagents and left to dry and stored in a desiccator till use.

Block Copolymer ATRP Synthesis

Figure 58:
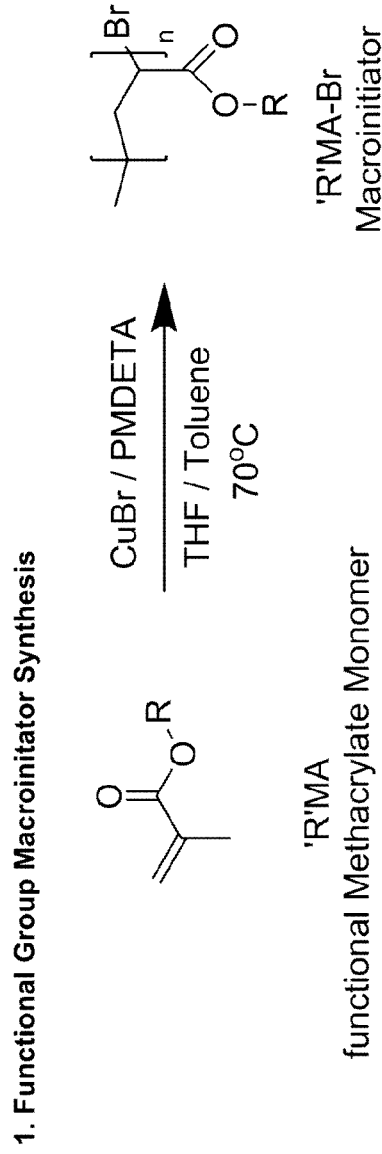
FIG. 58: Reaction schematic of 'R'MA-AMA ATRP synthesised block copolymer.
Figure 58:
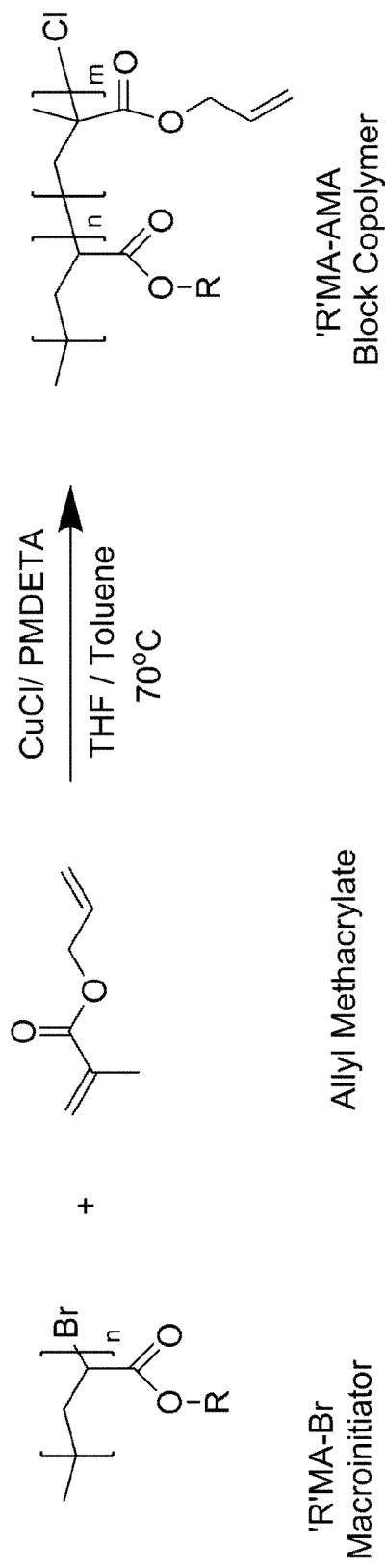

Block copolymers of functional group presenting monomers ('R'MA with R desired functional group) and double vinyl group presenting allyl methacrylate monomers (AMA) were synthesised following the protocols first reported by Paris et al [41, 42] and is schematically shown in FIG. 58.

Molar quantities and ratios were calculated depending on desired chain lengths. For a typical block copolymerisation reaction, 'R'MA monomer was reacted in bulk to form the p('R'MA)-Br macroinitiator from which surface-grafting p(AMA) polymer is grown. 'R'MA monomer, PMDETA ligand mixed with CuBr catalyst and EBrIB initiator were degassed in three separate round bottom flasks. The degassed monomer was transferred to the PMDETA-CuBr mix via cannula transfer. The resulting solution once homogeneous was further transferred to the EBrIB containing flask via cannula transfer, and reacted for the desired amount of time at 70° C. The reaction was stopped by exposure to air and quenching with $CdCl_3$. The resulting polymer was purified by precipitation in cold hexane and re-dilution into THF. The process was repeated three times to optimise polymer purity. Molecular weight and polydispersity index (Đ) were assessed via GPC and $^1$H-NMR.

A similar process was followed for block polymerisation of p('R'MA)-b-(AMA). Having determined the molecular weight of the p('R'MA)-Br macroiniator synthesised above, desired amount thereof was dissolved 50% v/v in anhydrous THF and degassed for 20 minutes. AMA monomer and PMDETA mixed with Cu(I)Cl were degassed in separate flasks, and mixed and transferred to the macroinitiator solution via cannula transfer. Purification, molecular weight and Đ procedures and assessments were performed as above.

Results

Solution Characterisation

Thiol-ene click chemistry provides an effective means of surface grafting desired methacrylate-base monomers, but the control on the density of surface groups thus attached remains low, or difficult to characterise. Surface-initiated polymerisation has already been shown to be difficult when using the proposed xerogels as substrates, as the SI-ATRP process of ODMA surface-initiated polymerisation proved. It is therefore proposed to synthesise controlled polymers ex situ via ATRP, allowing the straightforward synthesis of well-defined polymers through the well-reported controlled polymerisation method. These can then be grafted onto the surface of MD-type xerogels, shown to have the most suitable physical properties even post-functionalisation. Surface grafting was made possible by using the unreacted vinyl group on allyl methacrylate (AMA) units. Indeed, AMA has two double bonds: a conjugated methacryloyl group and an unconjugated allyl group. Due to varying reactivities, the former will preferentially react to form the polymer backbone, leaving the latter labile and free to react with surface thiol groups on the MD-type xerogel, thus allowing the surface grafting of well-defined block copolymers [42]. This varying reactivity only holds true however for low conversions; indeed, beyond a certain point, both vinyl groups will react, leading to crosslinking reactions, a common application of AMA polymerisations [45].

Given the time-consuming and low-yield synthesis process of mannose methacrylate, block copolymers were synthesised using methyl methacrylate (MMA) as a proof of concept 'functional' ('R'MA) monomer. The protocols used were based on the extensive work on allyl-based ATRP and block copolymer reactions by Paris et al [41, 42]. Two block copolymer ratios were investigated:

[MMA]:[I] 200:1 and subsequently [AMA]:[PMMA-Br] 600:1 (as reported by Paris et al)

[MMA]:[I] 20:1 and subsequently [AMA]:[PMMA-Br] 10:1

The aim of these varying ratios is not only to vary the 'functional' (in this case MMA) polymer chain length, but also to investigate the correlation between the number of AMA groups and surface grafting efficacy. Indeed, the surface grafting of thus synthesised block copolymers relies on the unreacted or labile nature of the unconjugated allyl groups on the p(AMA) block of the polymer to be able to react with surface thiol groups for click-reaction to occur.

Figure 61:
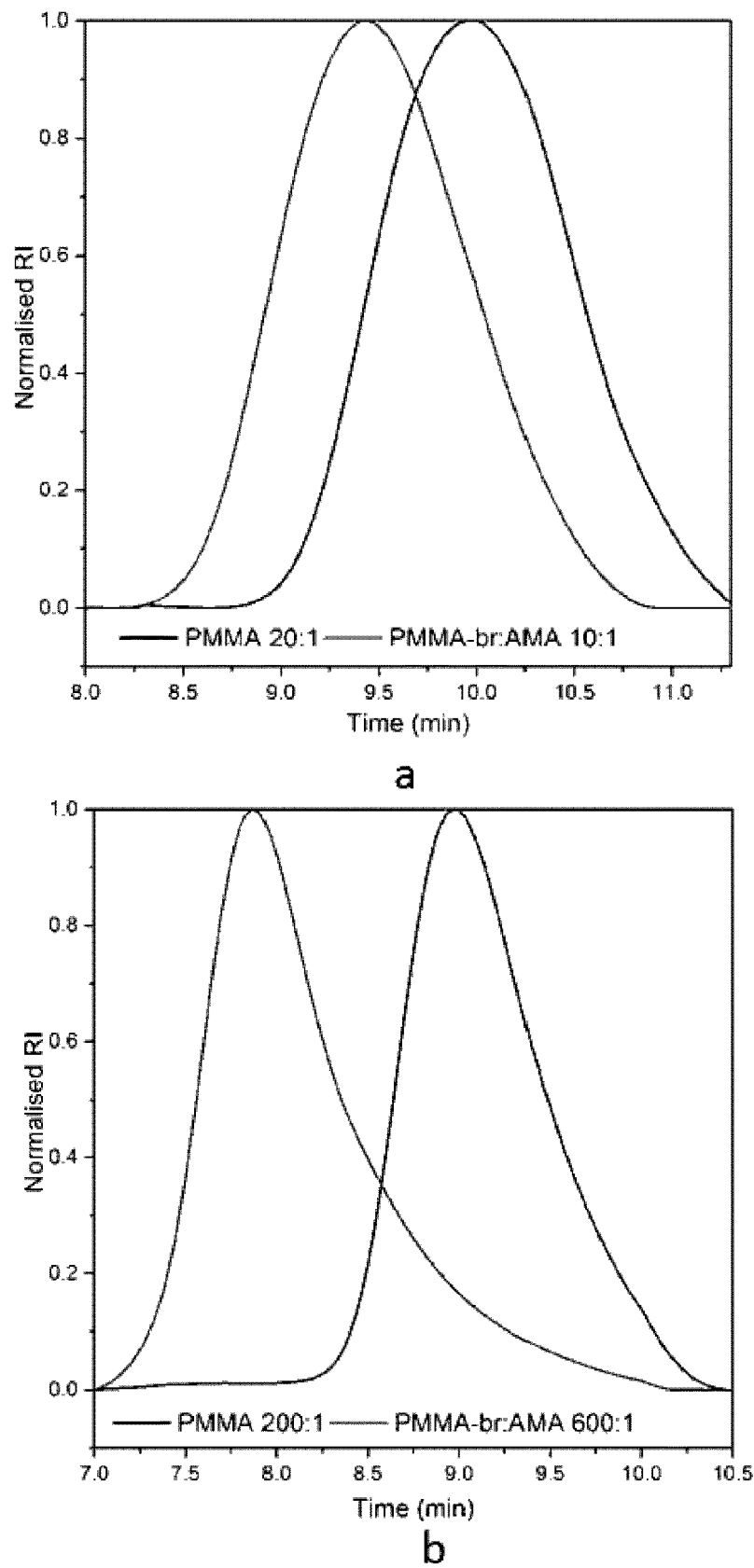
FIG. 61: Normalised elution signals obtained from GPC data of PMMA-Br macroinitiator (black) and PMMA-b-AMA block copolymers (red) for 200:600:1 (a) and 20:10:1 (b) [MMA]:[AMA]:[I] ratios respectively.

As can be observed in FIG. 61, block copolymerisation is confirmed by the shift to lower retention time of the block copolymer curve relative to the macroinitiator curves, implying an increase of polymer molecular weight. This is expected given the process of block copolymerisation involves the addition of a second p(AMA) polymer chain to the initial PMMA-Br chain. It can also be observed that the shift to higher molecular weights appears less significant for the 20:10:1 ratio copolymer than the 200:600:1 counterpart, suggesting that fewer repeating units are polymerised from PMMA-Br macroinitiators.

This is confirmed by the data presented in Table 11, where it is clear that not only does the reduction in molar ratios allow the synthesis of smaller polymers, but that it also results in a reduced PMMA:AMA ratio. It can also be observed from the GPC data that Đ is lower for higher $M_W$; indeed, the 200:1 ratio synthesised PMMA-Br has an $M_W$ of $1.10 \times 10^4$ g/mol and a Đ of 1.24, as opposed to $M_W$ and Đ values of $3.29 \times 10^3$ g/mol and 1.54 respectively. This follows theory; indeed, the monomer to initiator [M]:[I] defines the degree of polymerisation $DP_N$. Thus increasing the [M]:[I] ratio increases $DP_N$. $DP_N$ however is also defined as the ratio of number average molecular weight $M_N$ to monomer molecular weight $M_{monomer}$. Increasing the $DP_N$ in turn increases $M_N$. Đ being defined as the ratio of weight average molecular weight $M_W$ to number average molecular weight $M_N$ thus implies that an increased [M]:[I] ratio lower Đ, as observed [46]. MMA is a highly reactive species and reacts quickly in solution. Although dissolving in either polar or non-polar solvents may slow down reaction kinetics, doing so may result in broader $M_W$ values (i.e. increased Đ) due to a decrease in the deactivation process [47]. Careful selection of an appropriate catalyst/ligand system is key to optimal polymerisation control in CRP methods, with mixed ligand/catalyst systems of bromine and chlorine types for initiator and catalyst molecules respectively yielding the best results [47]. As this type of mixed system has already been selected in the presented work, improved polymerisation control yielding narrower molecular weight distributions can most likely be achieved by increasing [M]:[I] ratio whilst reducing polymerisation duration to retain low polymer molecular weights.

A key characteristic of CRP methods is the 'living' nature of polymer chains such that they retain their activity and thus their ability to be used as macroinitiators for block copolymerisation reactions [46]. This was performed here by adding AMA monomer to solution of dissolved PMMA-Br and copolymerised to form PMMA-b-AMA block copolymers. PMMA-Br macroinitiators were dissolved due to the solid nature of PMMA.

Figure 62:
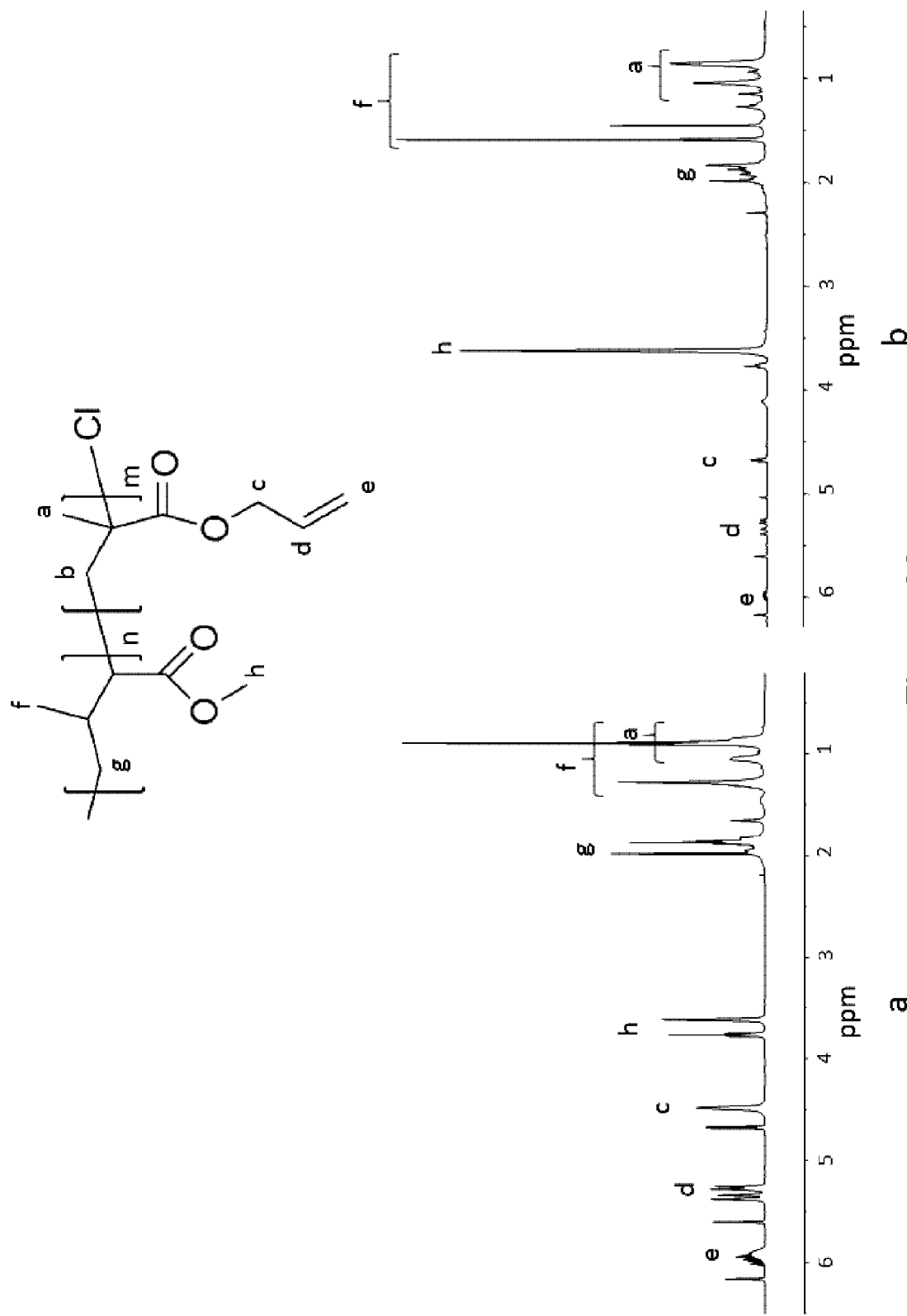
FIG. 62: 1H-NMR of 200:600:1 (a) and 20:10:1 (b) MMA:AMA block copolymers.

It can be observed that after the polymerisation of the AMA block in the case of 200:600:1 ratio, the Đ increases (Table 11). This is most likely due to the large number of AMA repeat units polymerised as the second block grows, leading to possible secondary reactions (such as cross-linking, branching or cyclopolymerisation reactions). Indeed, although peaks visible at approximately 5.9 ppm in $^1$H-NMR (FIG. 62a) suggest that the allyl pendant group on the PAMA chain remain unreacted, small amounts of cross-linking are still possible even if not fully visible under $^1$H-NMR. The reduced reactivity of the allyl group relative to that of the methacryloyl group does not hinder it from reacting; being prone to secondary Ð-increasing reactions at conversion rates over 20% [42, 42]. Though conversion was theoretically kept below 20% by reproducing experimental protocols detailed by Paris et al, reactions herein presented may have exceeded this value, resulting in a small number of secondary reactions occurring and causing the increased Ð observed.

In an attempt to reduce this risk, shorter chains were synthesised by drastically reducing the initial molar ratios to 20:10:1. Although this resulted in an increase in Ð for the PMMA-Br macroinitiator at a Ð of 1.54, the subsequent block copolymerisation reaction with AMA reduced the overall polymer Ð down to 1.43. The increase in Ð for the smaller 20:1 [M]:[I] blocks relative to their larger 200:1 [M]:[I] counterparts as aforementioned is simply due to the change in monomer/initiator ratio. The subsequent decrease in Ð once 20:1 [M]:[I] PMMA-Br macroinitiator was reacted with AMA in [M]:[I] ratio from 1.54 to 1.43 is most likely due to low conversion of AMA; as aforementioned, lower conversions minimise the probability of secondary reactions occurring. The PAMA blocks grown from PMMA-Br macroinitiators thus having a narrower molecular weight distribution implies by definition that the Ð value of the block will decrease with increasing block molecular weight; indeed, block copolymers have a higher molecular weight than their macroinitiator starting point. Critically, as seen by the $^1$H-NMR spectrum in FIG. 62b, peaks at approximately 5.9 ppm suggest the unreacted nature of allyl groups as desired for the subsequent surface grafting of block copolymers to MD-type xerogels via click-chemistry.

confirms the presence of the blocks, the band highlighting the carboxylic groups of both PMMA and PAMA in the respectively polymer blocks.

It can be observed that the intensity of the COOH band for 200:600:1 appears less intense than that of the 20:10:1 group. Although normalised data can only lead to semi-quantitate analysis, the difference in intensity could suggest a lower density of surface grafted groups for the former than its lower ratio counterpart. This could be due to multiple factors. The 200:600:1 block is firstly a factor of 10 longer than its 20:10:1 counterpart, at around 44 kDa as opposed to 3 kDa. This could result in the block not being able to travel through the structure as easily, resulting in its grafting only to the surface rather than the entire structure like its smaller counterpart. Another key difference between the two blocks is the number of AMA repeat units per chain. Whereas the 20:10:1 chains have on average 2 AMA units, the 200:600:1 blocks have on average 150. The sheer difference in numbers implies that the 200:600:1 blocks are far more likely than their smaller counterparts to either crosslink between chains or between themselves during the AIBN-mediated surface grafting process than the smaller counterparts. It therefore seems clear that shorter chains and fewer AMA repeat units promote better surface grafting.

SEM investigation gives a straightforward insight into the material's microstructure and a direct assessment of whether the surface grafting procedures have an effect thereon or not. The innate physical properties of MD-type xerogels having been determined to be best suited to the proposed application, surface functionalisation processes should have minimal effect on the material whilst providing biological functionality.

The overall trend when observing the micrographs of both control and block copolymer surface grafted is that surface grafting has little effect on the surface structure of the xerogel. Colloidal assembly-like structure is still present, and thus similar pore sizes can be observed. In similar fashion to previous surface functionalisations, this suggests

TABLE 11

Molecular weights and estimated number of repeat units for both 600:200:1 and 20:10:1 PMMA-b-AMA block copolymers as determined from GPC measurements

| | PMMA-Br | | | | PMMA-b-AMA | | | Repeat Units | |
|---|---|---|---|---|---|---|---|---|---|
| [MMA]:[I] | Mw (g/mol) | Mn (g/mol) | Ð | [AMA]:[I] | Mw (g/mol) | Mn (g/mol) | Ð | MMA | AMA |
| 200:1 | 1.10E+04 | 8.92E+03 | 1.24 | 600:1 | 4.44E+04 | 2.90E+04 | 1.53 | 90 | 150 |
| 20:1 | 3.29E+03 | 2.14E+03 | 1.54 | 10:1 | 3.42E+03 | 2.38E+03 | 1.43 | 20 | 2 |

Surface Grafting Characterisation

Transmittance FTIR was the first technique used to assess whether the surface grafting reaction of block copolymers via thiol-ene click reaction had been successful. Recorded intensities were normalised relative to systemically most abundant band within the MD-type xerogel substrate, i.e. that corresponding to Si—O—Si stretching at 1025 cm-1, so as to maximise the comparative potential of FTIR measurements.

Figure 63:
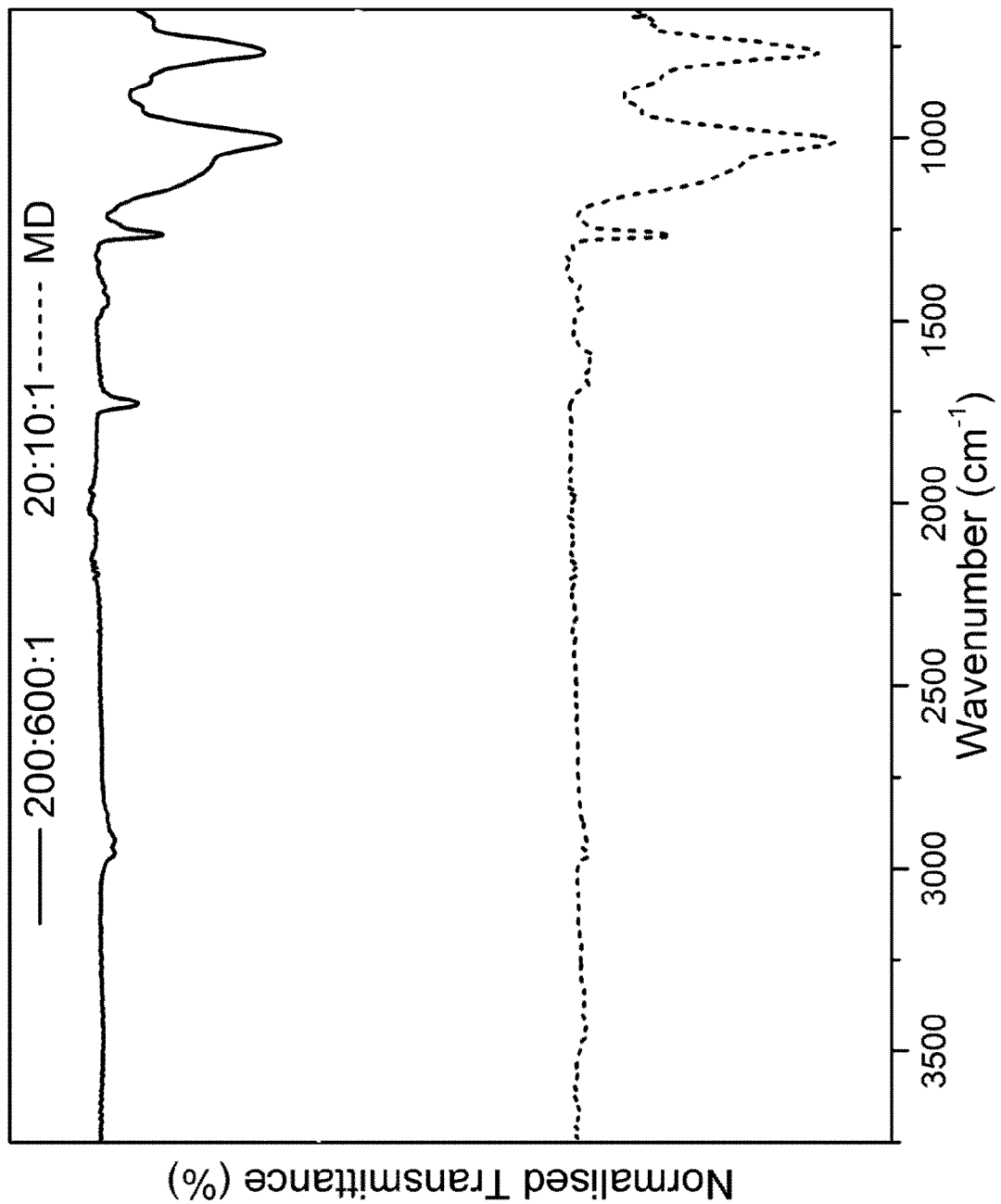
FIG. 63: Normalised FTIR transmittance spectra of MD-type control, and surface grafted 20:10:1 ratio and 200:600:1 ratio respectively PMMA-b-AMA block copolymers.
Figure 64:
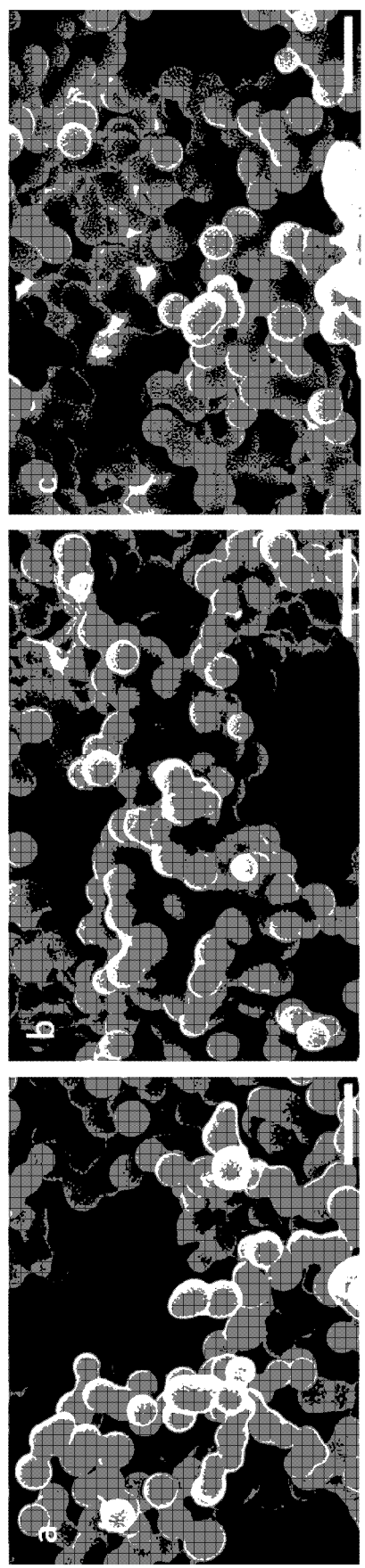
FIG. 64: Representative micrographs of MD-control (a), 200:600:1 (b) and 20:10:1 (c) MMA-b-AMA block copolymer grafted xerogels (scale=10 μm).

As can be seen in FIG. 63, there is a clear difference in the spectra obtained from the unfunctionalised MD-type control and surface grafted block copolymers. Indeed, in both surface grafting cases, a clear band at around 1730 cm-1 is visible, corresponding to COOH stretching. Its presence at this stage that the proposed method is suitable for application and worthy of subjecting to further investigation.

Figure 65:
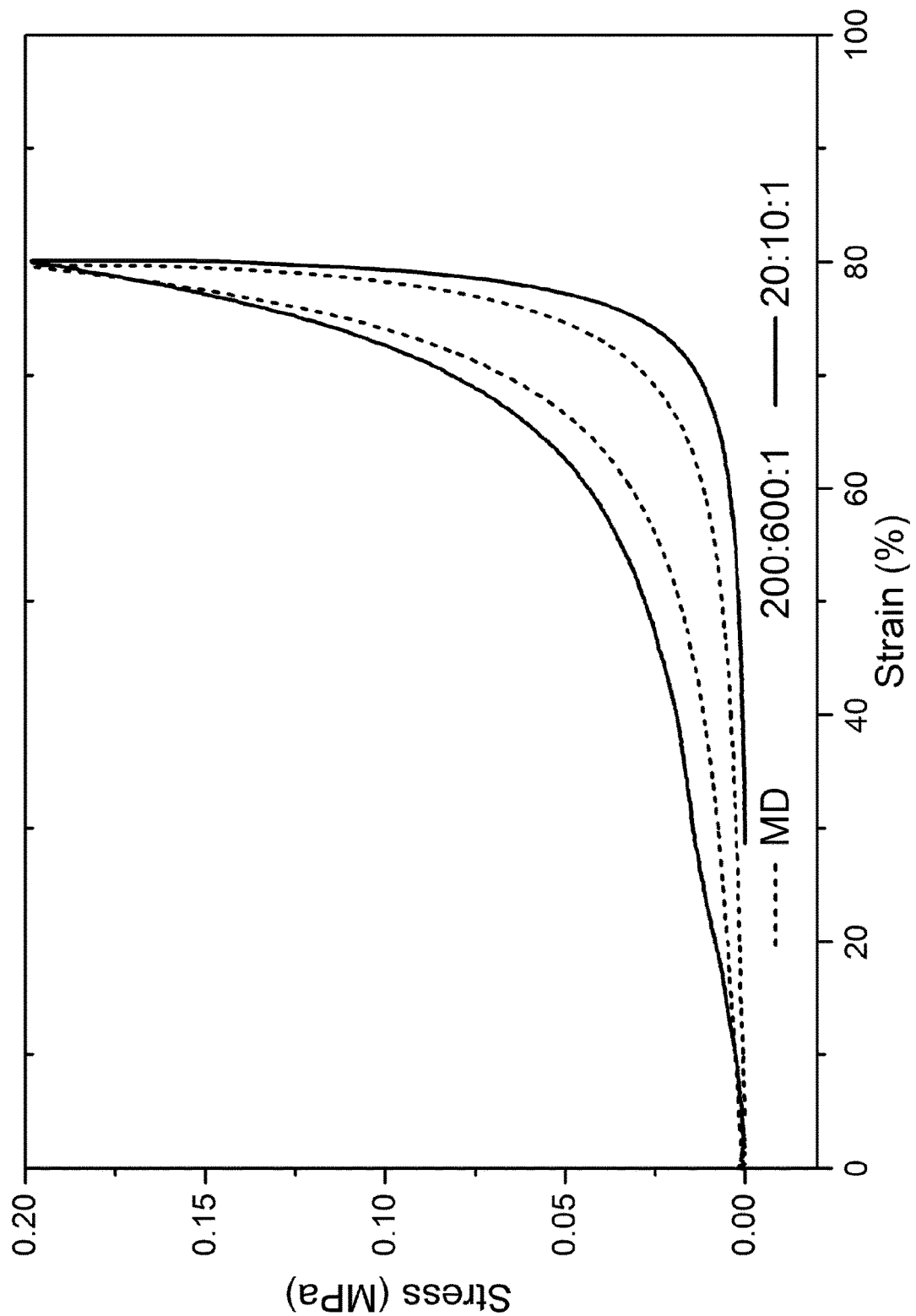
FIG. 65: Representative stress-strain curves of MD-type control and 200:600:1 and 20:10:1 MMA:AMA ratio respectively block copolymer surface functionalised xerogels.
Figure 66:
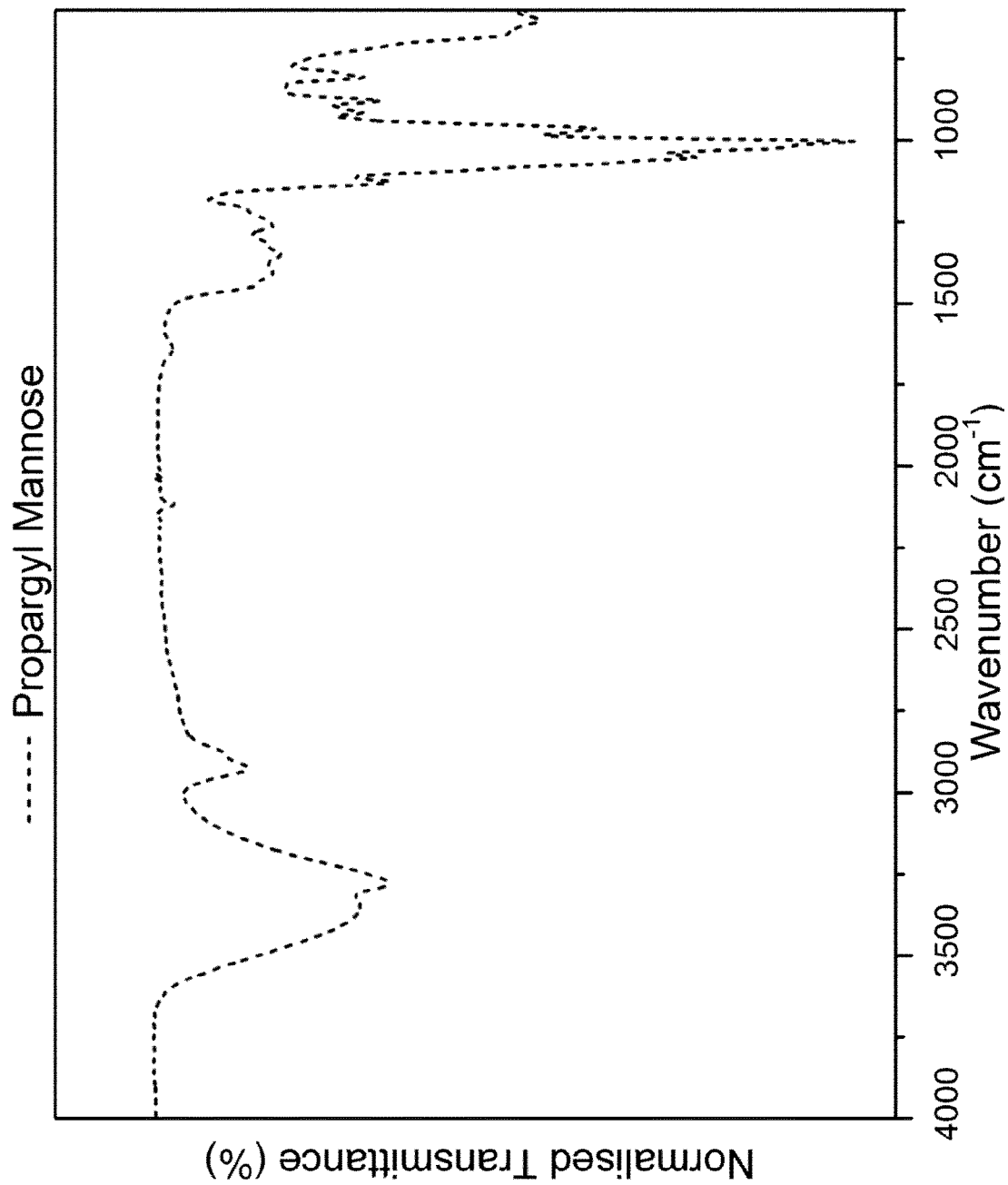
FIG. 66: Normalised transmittance FTIR signal of propargyl mannose.

Compression testing revealed a much greater difference between samples than had been revealed by the SEM investigations, as shown both in FIG. 65 and Table 12. The 20:10:1 ratio block surface functionalised xerogels exhibit relatively similar loading and unloading curves to its unfunctionalised MD-type counterpart. Both reach similar strain values under 5 N load at 80.63±2.19% and 74.68±4.9% (control and 20:10:1 block functionalised respectively). Residual strain can be observed for the block functionalised material at approximately 30% strain, due to the slight deformation caused by surface functionalisation with relatively large or long polymer chains. Despite the slight residual strain, the material seems to retain suitable mechanical properties (and cannot be differentiated to the touch), suggesting the suitability thus far in the testing process of short and low AMA repeat unit number surface grafted ATRP synthesised block copolymers.

TABLE 12

Strain and stress values at 5N of MD-type control and 200:600:1 and 20:10:1 MMA:AMA ratio respectively block copolymer surface functionalised xerogels

| Sample | MD | 200:600:1 | 20:10:1 |
|---|---|---|---|
| Strain at 5N (%) | 80.63 ± 2.19 | 41.20 ± 14.84 | 74.68 ± 4.9 |
| Stress at 5N (MPa) | 0.18 ± 0.03 | 0.21 ± 0.02 | 0.19 ± 0.01 |

Xerogels functionalised with the much larger 200:600:1 block copolymers however lead to instantaneous material failure under compression testing, as is clear from the rapid increase in strain under load shown in FIG. 65. This is corroborated by maximum strain values of 41.20±14.84% at 5 N as shown in Table 12. This is immediately felt to the touch as post functionalisation xerogels are solid blocks, as opposed to the soft and pliable material desired and obtained during other surface grafting processes, including that with 20:10:1 blocks, as explained above. Both the sheer length and the high likelihood of allyl group crosslinking within the structure during the surface grafting step are causes of the brittle behaviour of the material. Both 'R'MA and AMA polymerisations require very low conversions to ensure good polymerisation control; in turn implying low polymer yields (typically 20% and 6% for PMMA and PAMA reactions respectively).

Example 16: Characterisation Methods for Mannose-Functionalised Xerogels for DC-SIGN Capture and Extraction Once characterised and grafted onto MD-type xerogels, characterisation methods were used as follows:
Surface functionalisation assessment via FTIR.
Material property assessments via SEM, uniaxial compression testing.
Implementation assessments via wicking capacity, MTT assays and dendritic cell capture protocols.
Mannose functionalised and control samples were immersed into iDC and mDC containing solutions, the cells having been re-suspended in PBS so as to mimic physiological conditions. Fluorescence was achieved by staining cell nuclei with DAPI nucleic acid stain, adding 100 uL per 300 uL of cell solution, and exciting with a UV light laser a 405 nm. Actin cell filaments were stained with SiR, excited with a 643 nm laser (thus emitting at 674 nm). The far-red spectrum emission thus avoids any possible autofluorescence from DAPI staining, allowing clear differentiation between nucleus and actin.

Example 17: DC-Stripping Mannose Functionalised Xerogels

Methods

Figure 59:
FIG. 59: Synthesis of Mannose methacrylate monomer.
Figure 59:
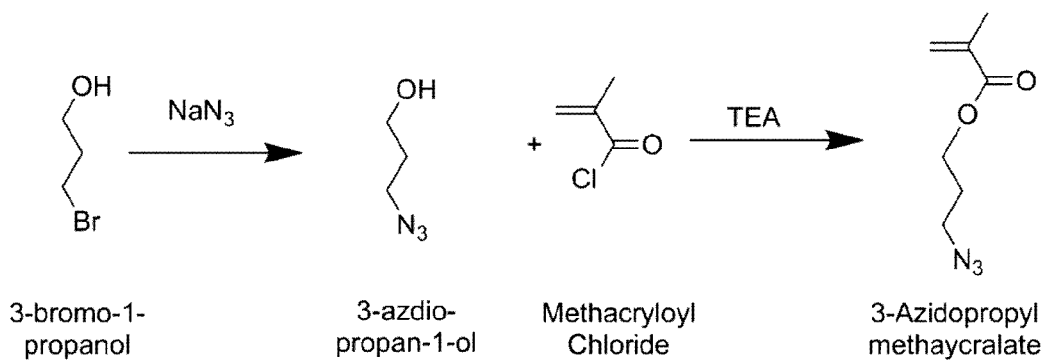
Figure 59:
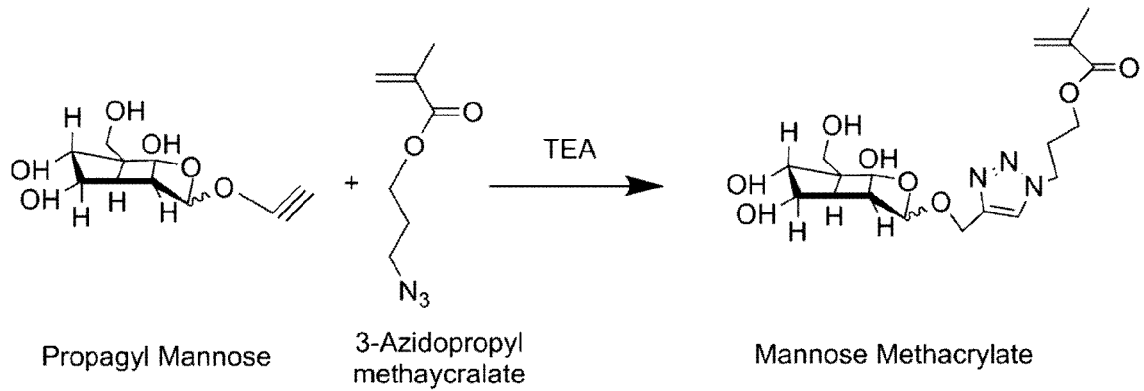
Figure 60:
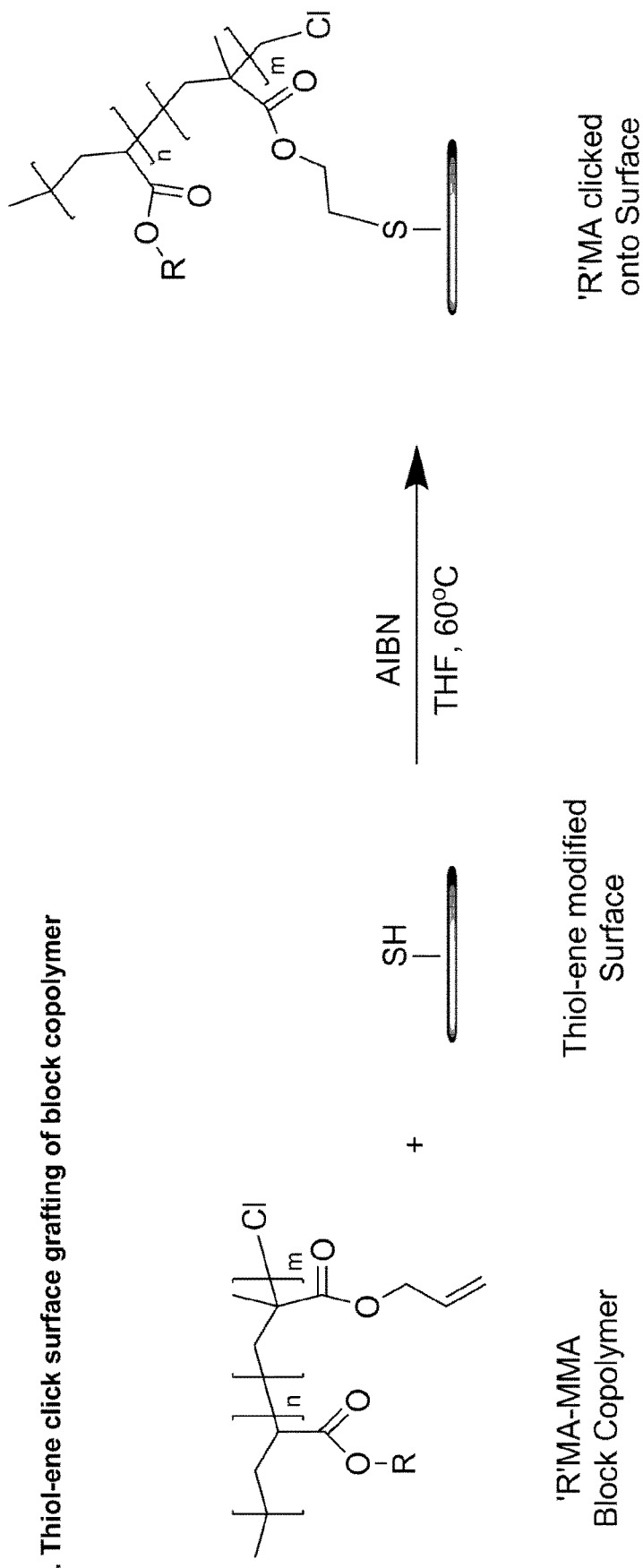
FIG. 60: Surface grafting of allyl based block copolymers to MD-type xerogels.

Mannose Methacrylate Glycomonomer Synthesis
The synthesis of the cell-binding mannose-presenting glycomonomer followed the methods reported by Zhang and shown schematically in FIG. 59. D-mannose and propargyl alcohol were reacted to form propargyl mannose. This was then reacted with 3-azidopropyl methacrylate, itself a product of the reaction between 3-azido-propan-1-ol and methacryloyl chloride. The process of each step is described below.

D-mannose and propargyl alcohol were added to a round bottom flask in 1:5 molar ratio respectively, degassed with argon and reacted at 65° C. for 10 hours. Unreacted propargyl alcohol was removed using a 8:1 chloroform:methanol column. Residual solvents were removed by rotary evaporation and freeze-drying. The final product thus obtained was stored at −80° C. till use.

3-azidopropyl methacrylate was synthesised by reacting 3-azidopropan-1-ol with methacryloyl chloride. The former was itself synthesised by mixing 3-bromo-1-propanol with sodium azide in 1:1.6 molar ratio respectively into a solution of 5:1 acetone/d($H_2O$) and reacted overnight at 70° C. Unreacted solvents were removed by washing with diethyl ether and solvents removed by rotary evaporation.

The thus formed 3-azido-propan-1-ol was mixed with TEA and methacryloyl chloride in a 3:4.2:3.6 molar ratio and reacted at 0° C. overnight. The resulting solution was filtered to remove ammonium salts, washed with HCl, d($H_2O$), 5 wt. % aqueous NaOH and d($H_2O$) sequentially and dried with magnesium sulfate. Residual solvents were removed under vacuum yielding a yellow liquid of 3-azidopropyl methacrylate.

The methacrylate functionalisation of D-mannose was therefore achieved by reacting propargyl mannose with 3-azidopropyl methacrylate. The two reagents were further mixed into a solution of $CuSO_4 \cdot 5H_2O$ and (+)-sodium L-ascorbate in a molar ratio of 1:1.1:0.06:0.07, finally added to a solution of MeOH/H2O in 2:1 v/v ratio and reacted for 24 hours at 25° C. Excess 3-azidopropyl methacrylate was removed by column separation and solvents removed by rotary evaporation. The thus obtained product was freeze-dried and stored at −80° C. till use.

Results

Mannose Methacrylate Synthesis
The synthesis procedure of the cell-stripping mannose methacrylate glycomonomer is schematically described in FIG. 59. $^1$H-NMR and FTIR were used to characterise the various synthesis steps as detailed below. The synthesis can be split into two steps: mannose moiety preparation and methacrylate group preparation. The first in the process was to synthesise propargyl mannose by reacting D-mannose with propargyl alcohol. Key bands as identified by FTIR and shown in FIG. 10 of OH, C≡C—H and C≡C around 3450 cm-1, 3300 cm-1 and 2200 cm-1 respectively confirm the successful synthesis of propargyl mannose.

Figure 67:
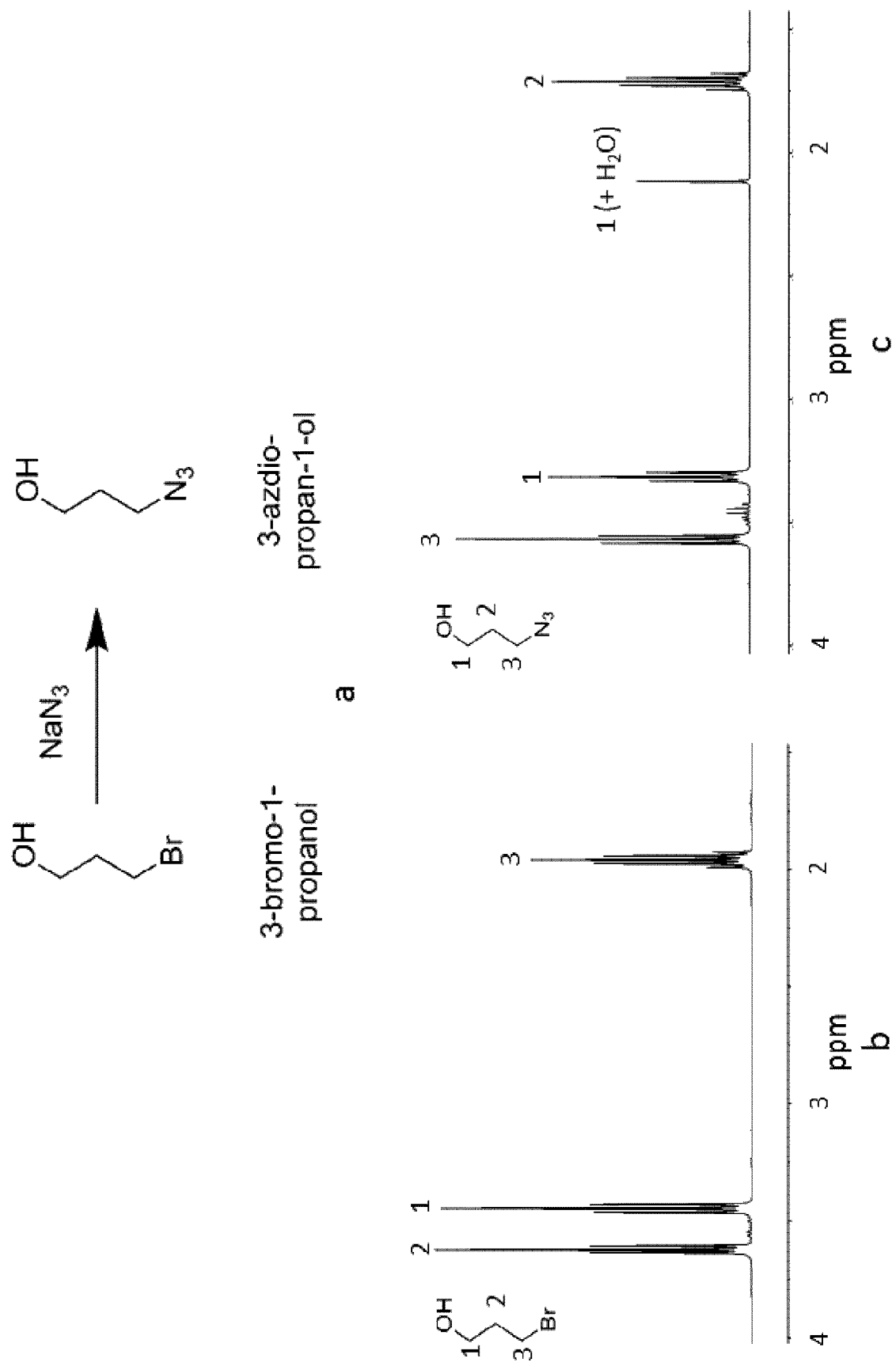
FIG. 67: Schematic (a) and 1H-NMR of 3-bromo-1-propanol (b) reaction with sodium azide to form 3-azido-propan-1-ol (c).

Having modified the mannose in this way so that is was ready for methacrylate functionalisation, the methacrylate group section was then synthesised. The first step was the conversion of 3-bromo-1-propanol to 3-azido-propan-1-ol, the azide moiety of which will serve as the bridging group between the mannose and methacrylate functional groups. As shown by $^1$H-NMR spectra in FIGS. 67a and b, the shifting of peak 3 confirms the conversion of bromine into azide due to the latter's higher electronegativity.

The second step consisted of reacting the aforementioned azide-presenting moiety with the methacrylate component of the system, which will in turn allow the final product to either be polymerised or more importantly to be surface grafted as desired via thiol-ene click reaction to the surface groups of MD-type xerogels. The relevant peak shifts shown in FIG. 67 demonstrate the successful synthesis of 3-azidopropyl methacrylate.

The final stage was therefore to react 3-azidopropyl methacrylate with propargyl mannose to form D-mannose methacrylate (MaMA). $^1$H-NMR shown in FIG. 69 corroborates $^1$H-NMR spectra reported in literature [48]. Comparing to the spectrum of propargyl in FIG. 68, peaks between approximately 3 and 4 ppm corresponding to hydroxyl groups (themselves characteristic of mannose region) are clearly visible in FIG. 69. Meanwhile, peaks around approximately 6 ppm confirm the presence of the methacryloyl group as provided by the previous reaction with methacryloyl chloride; confirming the methacrylate nature of the thus synthesised product.

The above results confirm the successful synthesis of a methacrylate form of the desired mannose glycomonomer. The purpose of producing it in a methacrylate form was to polymerise it in block form, i.e. forming PMaMA-b-AMA block copolymers. That allows synthesis of defined-length functional mannose methacrylate polymers that would subsequently be grafted to the surface of MD-type xerogels via click-reaction of the free allyl groups on the PAMA portion of the block.

Surface Grafting of Mannose Methacrylate onto Xerogels

Figure 70:
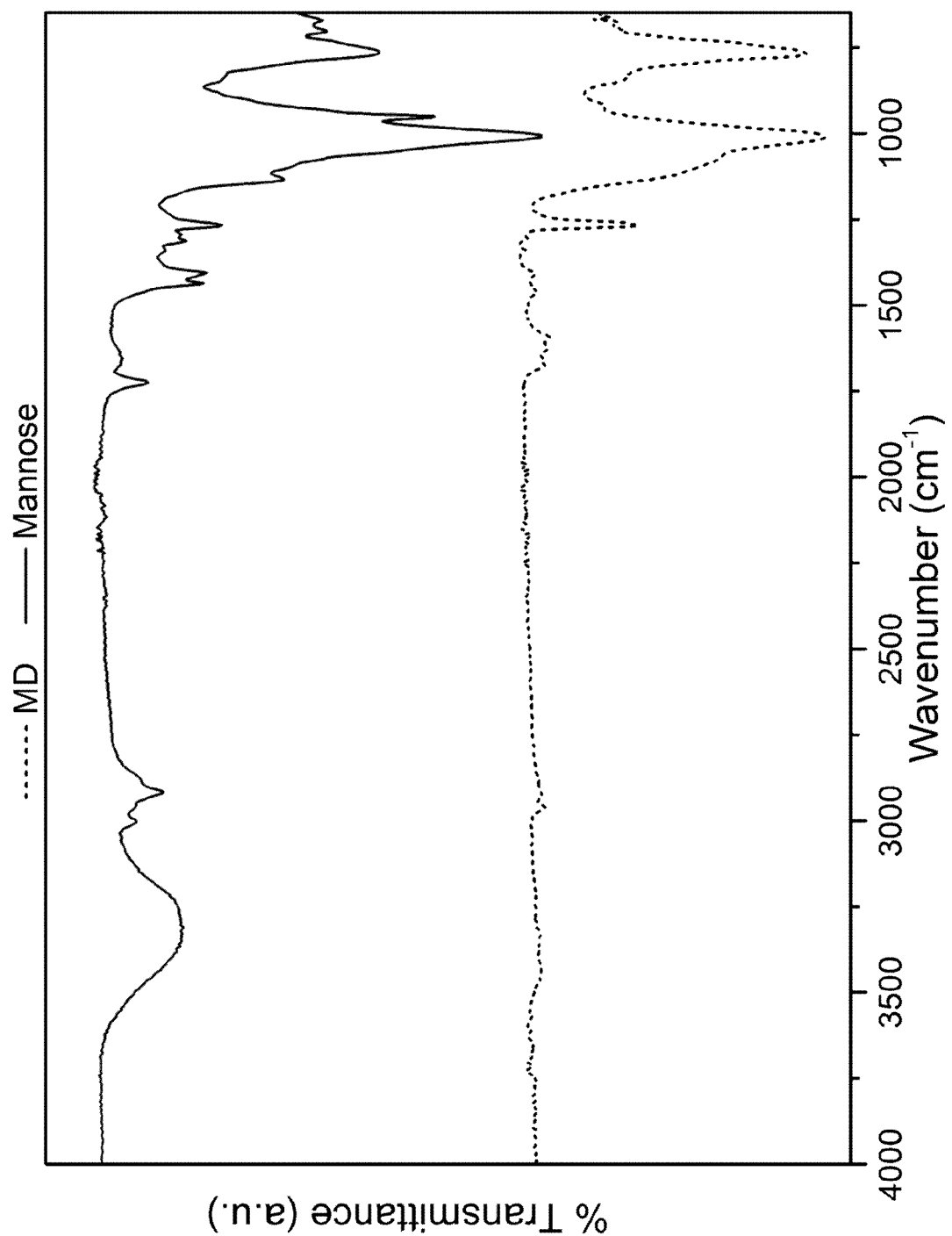
FIG. 70: Normalised transmittance FTIR data of MD-type control and mannose methacrylate surface-functionalised xerogels.
Figure 71:
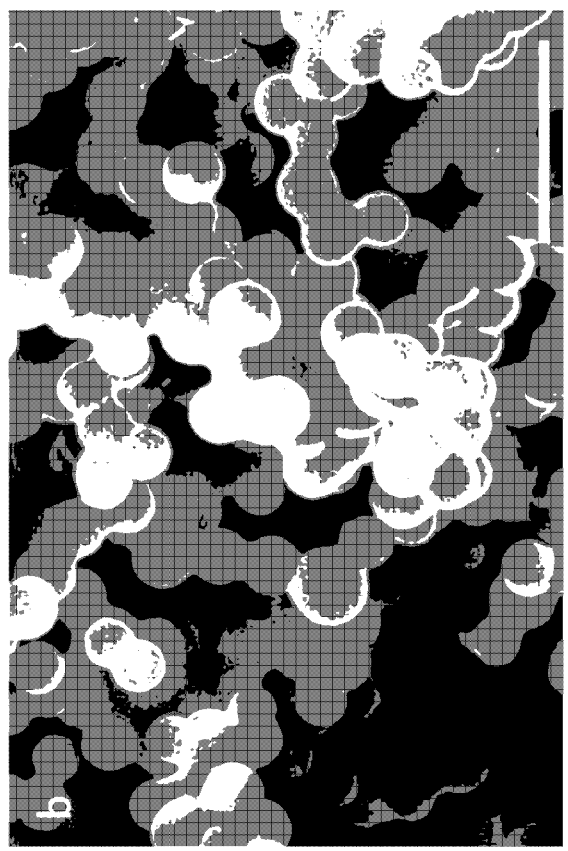
FIG. 71: Representative SEM micrographs of MD-type control (a) and mannose functionalised (b) xerogels (scale=10 μm).
Figure 71:
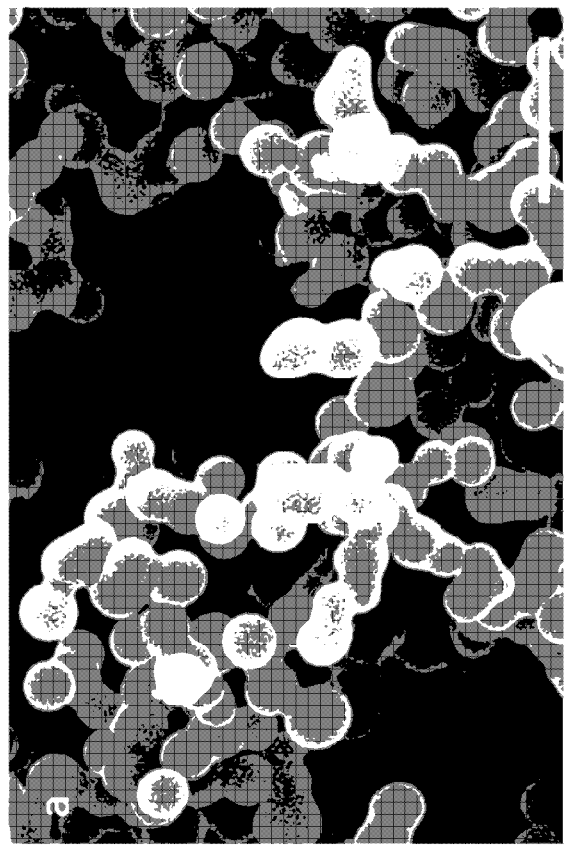

Normalised transmittance FTIR spectra of both MD-type control and mannose methacrylate surface functionalised xerogels are shown in FIG. 70. In similar fashion to previous surface grafting procedures, a clear difference between control and surface functionalised substrates is visible. Bands visible in the mannose-functionalised substrate around 3300 cm-1 are characteristic of hydroxyl group, directly identifying the high density of such groups in the mannose groups. Furthermore, the band at approximately 1730 cm-1 characteristic of COOH groups is visible, confirming the presence of the desired monomers on the surface. The presence of these bands after rigorous substrate washing and crushing clearly confirms the grafting of mannose groups across the substrate's surface.

SEM imaging reveals relatively similar microstructures, with the colloidal-assembly structure characteristic of the sol-gel substrate synthesis process visible pre- and post-mannose surface functionalisation. However, the latter shows regions of increased aggregation with less clearly defined colloids, with a semblance of a denser surface coating. It is possible that this surface feature is due to localised increased mannose methacrylate density via polymerisation. The lack of polymerisation control during thiol-ene click chemistry processes is a possible cause for this despite the controlled conditions under which this process was performed.

Figure 72:
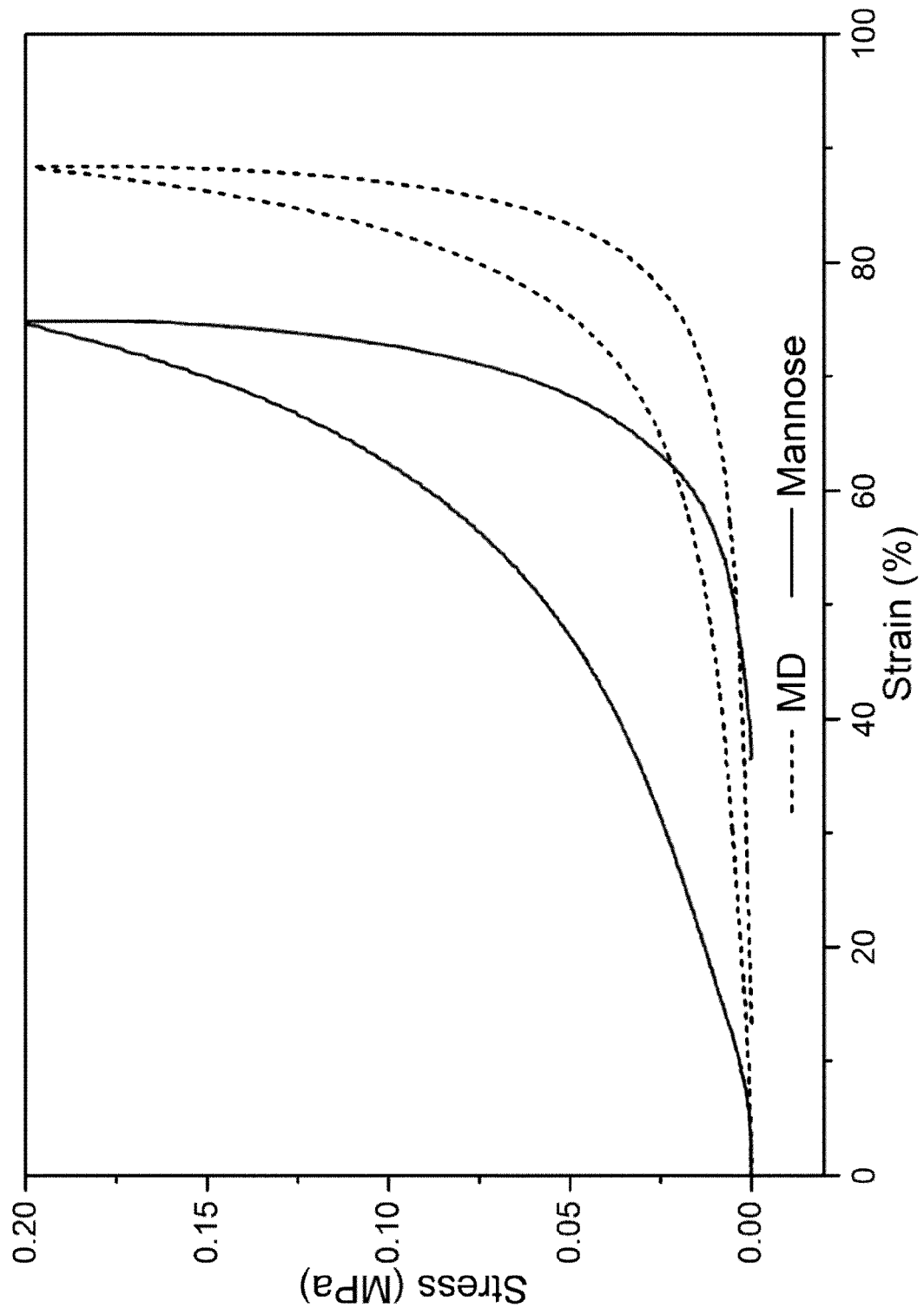
FIG. 72: Representative stress-strain curves for both MD-type control and mannose functionalised xerogels and table showing strain.

Compression testing identified some differences in the functionalised material's response to compressive load relative to its control counterpart. Indeed, in similar fashion to previously tested surface functionalised materials, mannose xerogels show a steeper loading curve, lower maximum stress values and residual strain once the compressive load is removed, indicating permanent deformation, as reported in FIG. 72 and Table 13. It is important however to note that whereas previous surface functionalised substrates (via block copolymer or ODS surface grafting) displayed a brittle failure, mannose functionalised materials appear to deform permanently without brittle failure, in similar fashion to putty. The cause of this can be found in the surface-grafted polymers' thermodynamic states under ambient conditions. Poly(mannose methacrylate) displays visco-elastic behaviour under ambient conditions as opposed to the solid brittle nature of P(ODMA) and P(MMA) in previously disclosed.

TABLE 13

Strain and stress values obtained for MD-type control and mannose functionalised xerogels

| Composition | MD | Mannose |
|---|---|---|
| Strain at 5N (%) | 80.63 ± 2.19 | 71.57 ± 2.83 |
| Stress at 5N (MPa) | 0.18 ± 0.03 | 0.20 ± 0.01 |

Figure 73:
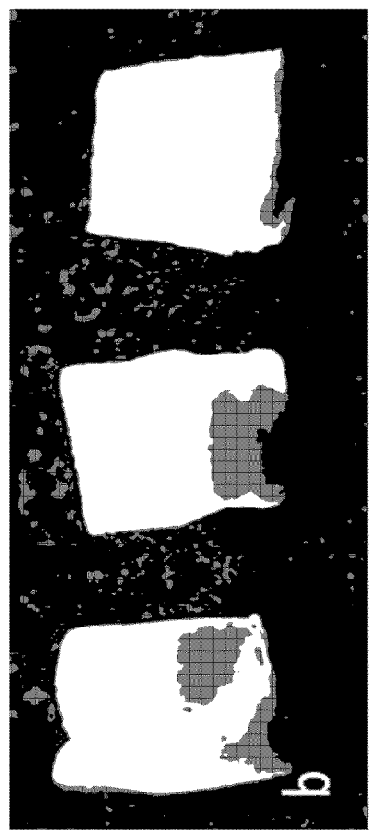
FIG. 73: Representative pre-(a) and post-(b) compression testing photographs of mannose methacrylate functionalised xerogels.
Figure 73:
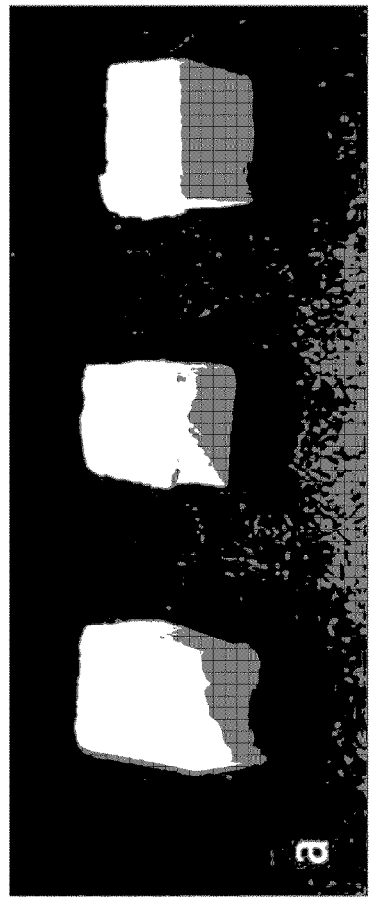

Although subject to permanent deformation, the material does not appear to deform dramatically to the touch and remains suitable for the proposed application, as shown by representative pre- and post-compression testing photographs in FIG. 73.

Figure 74:
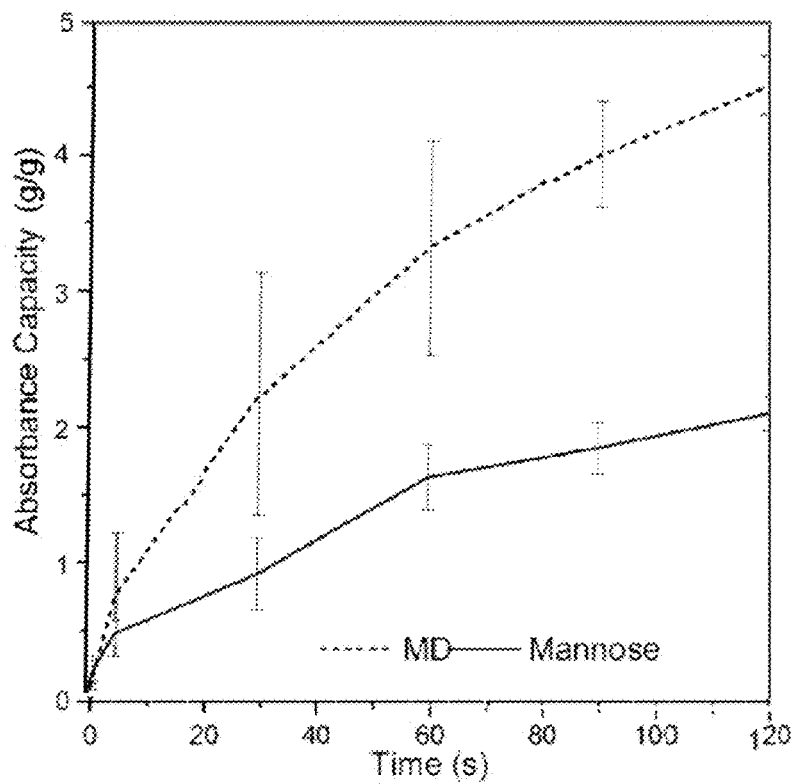
FIG. 74: Absorbance capacity of MD-type control and mannose functionalised xerogels over 120 s fluid exposure (a) and absolute absorbance after full 120 s (b).
Figure 74:
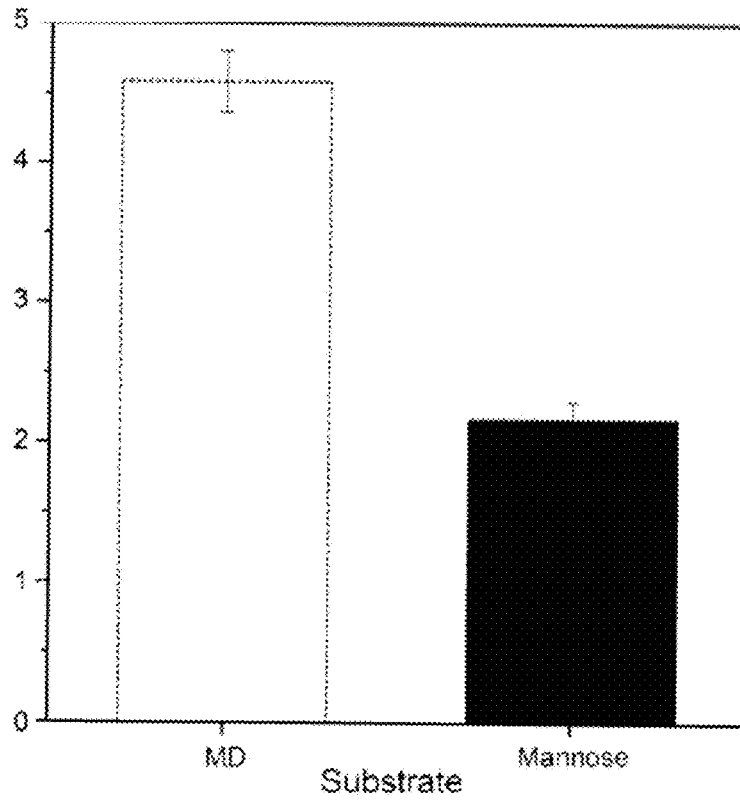
Figure 75:
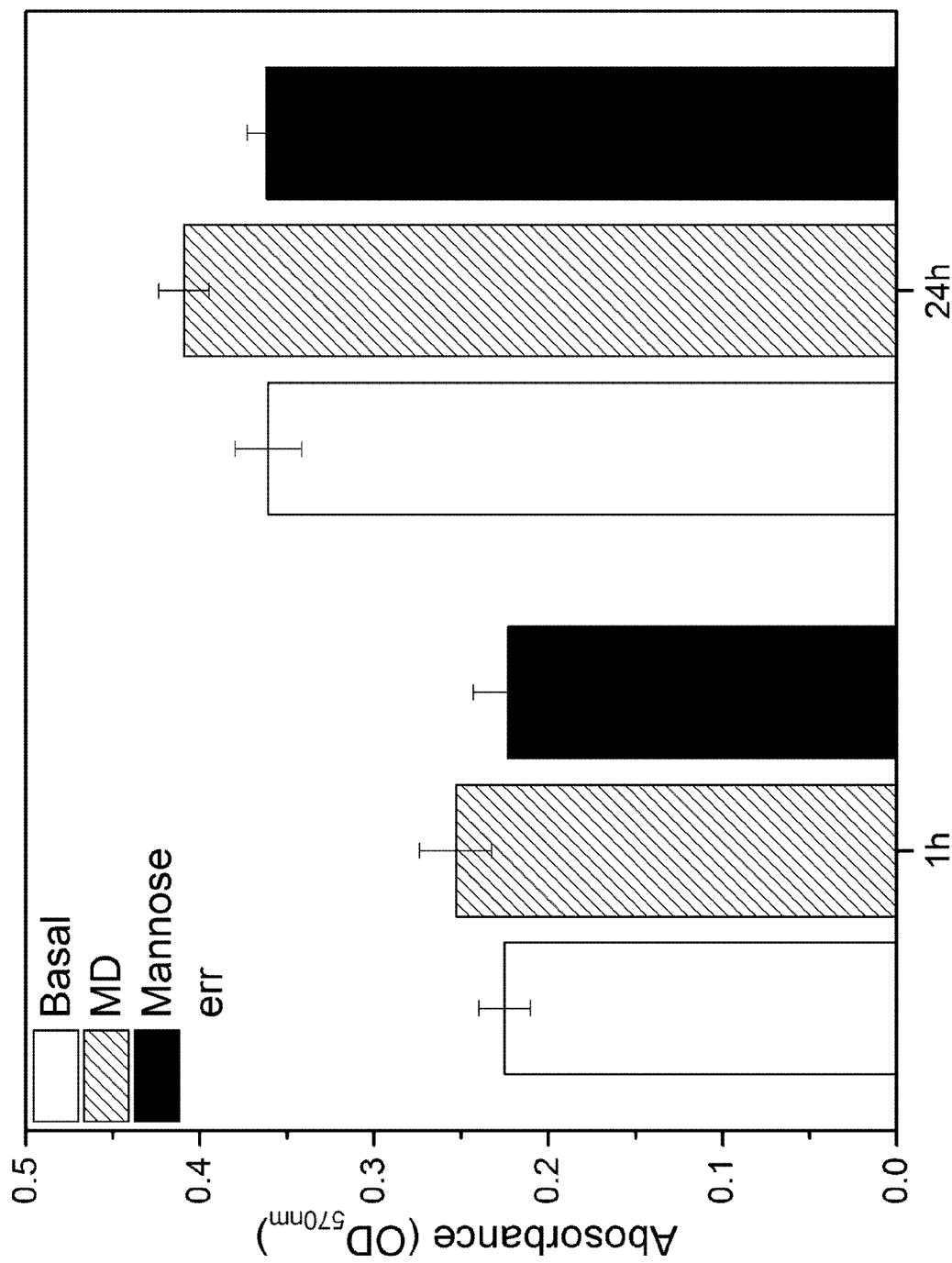
FIG. 75: MTT cytotoxicity assay measurements for basal media and MD-type and mannose functionalised xerogels.

Uptake testing (FIG. 74) showed that surface functionalisation with mannose methacrylate improves rather than impedes the material's innate aqueous fluid absorption properties due to mannose-methacrylate (and specifically the hydroxyl groups on the mannose moiety). MTT cytotoxicity assays presented in FIG. 75 showed no indication that mannose functionalisation has any effect on surrounding cellular media after 1 or 24 hours, in similar fashion to results obtained from similar testing for ODS-functionalised xerogels. This indicates that the functionalisation should not have an effect on the DCs to which the xerogel is exposed nor its ability to extract from the solutions to which it is exposed. This in turn implies that if the functionalised material is (as desired) able to extract DCs from solution and re-elute them, the material should not have any adverse effect on said cells whilst they are captured within it.

Example 18: DC Cell Extraction Evaluation

Methods

DC-containing solutions were prepared by differentiating THP-1 monocytic leukemia cell lines following the protocol reported by Berges et al; the differentiation procedure was performed by Dr. de la Serna and Dr. Garcia [44].

THP-1 cell lines were grown by immersing them in tissue culture media changed every 48 hours and maintained at 37° C. in a 5% CO2 humidified atmosphere incubator. Tissue culture was made up of RPMI 1640, 2 mM L-glutamine, 100 IU penicillin and 100 µg/mL streptomycin. Immature DCs (iDCs) were differentiated by re-suspending harvested THP-1 cells into culture media supplemented with 10% FCS at a concentration of $2\times10^5$ cells/mL, 1500 IU/mL rhIL-4 and 1500 UI/mL rhGM-CSF, and further cultured for 5 days. Mature DCs (mDCs) were differentiated by similarly re-suspending harvested THP-1 cells into serum- and FCS-free culture media at a concentration of $2\times10^5$ cells/mL.

In both cases, cytokine solution composed of rhIL-4 (200 ng/mL=3000 IU/mL), rhGM0CSF (100 ng/mL=1500 IU/mL), rhTNF-α (20 ng/mL=2000 IU/mL) and 200 ng/mL ionomycin were added to the cell culture media, and further cultured at 37° C. in a 5% CO2 humidified atmosphere incubator till experimental use. DCs were stained with DAPI and SiR for nuclear and actin fluorescence visualisation purposes prior to any characterisation.

Once THP-1 derived cells fully characterised for differentiation into either iDC or mDC, the extraction and re-elution characteristics of the mannose-functionalised xerogels were assessed by immersing both mannose-functionalised and control xerogels in identical iDC or mDC solutions for 10 min, ensuring maximum liquid structural absorption by compressing the gels with tweezers. Gels were squeezed and dried on filter paper to remove excess fluid, and imaged under 405 nm and 643 nm laser excitation laser so as to identify both nucleus and actin fibres of adsorbed cells (if present). Cell re-elution was performed by soaking cell-extracting xerogels in accutase cell detachment solution at 37° C. for 30 min and briefly centrifuged over filter Eppendorf tubes to remove cells. The cells extracted in this process were then re-suspended in cell culture media for further imaging and viability assessment under confocal imaging.

Results

Mannose-presenting glycomonomers were selected in this application due to their selective affinity to DC-SIGN surface markers on DCs. In similar fashion to previous biological characterisation sections, the mannose-functionalised xerogels were tested for such biomarker affinity. It was first necessary to confirm the successful differentiation of THP-1 derived cells into iDCs or mDCs prior to any material adsorption and extraction testing. This was achieved by staining cells with DAPI nuclear fluorescence markers and SiR actin staining, thus allowing clear visualisation of the cell structure under confocal microscopy.

Figure 76:
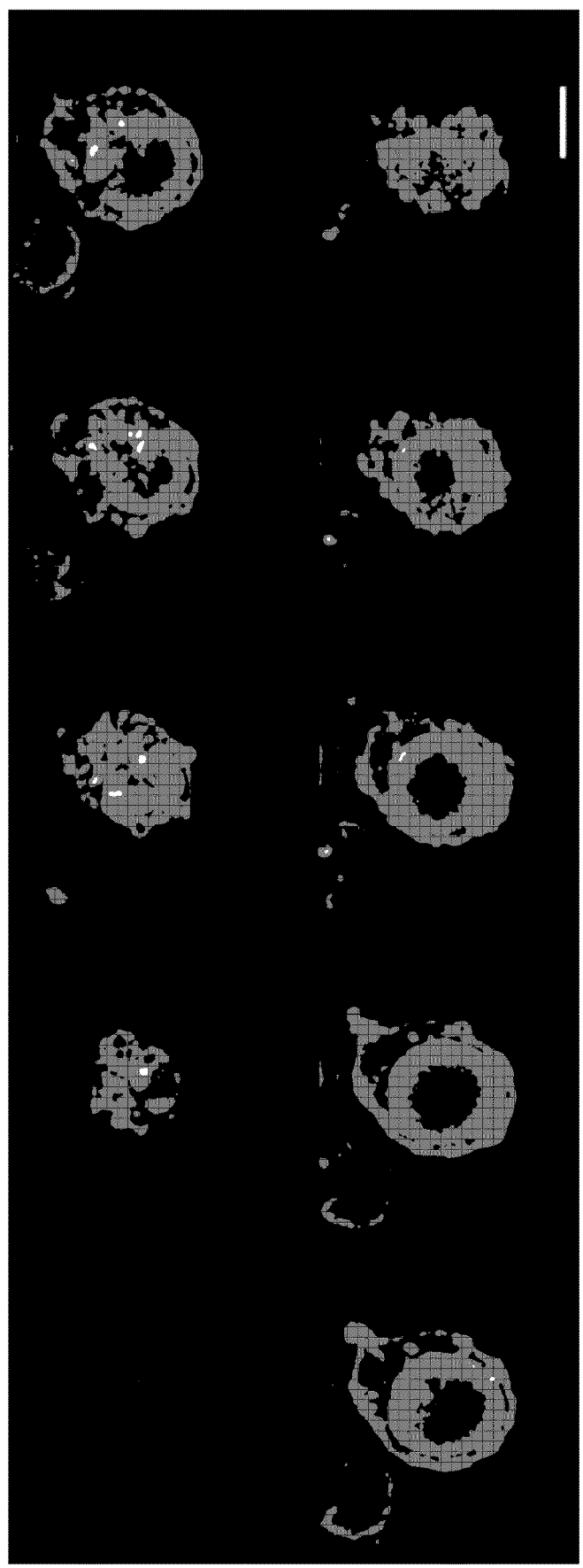
FIG. 76: Z-stack sectioning of THP-1 line derived iDCs in suspension visualised under confocal microscopy with 405 nm and 643 nm laser excitations (scale=10 μm).
Figure 77:
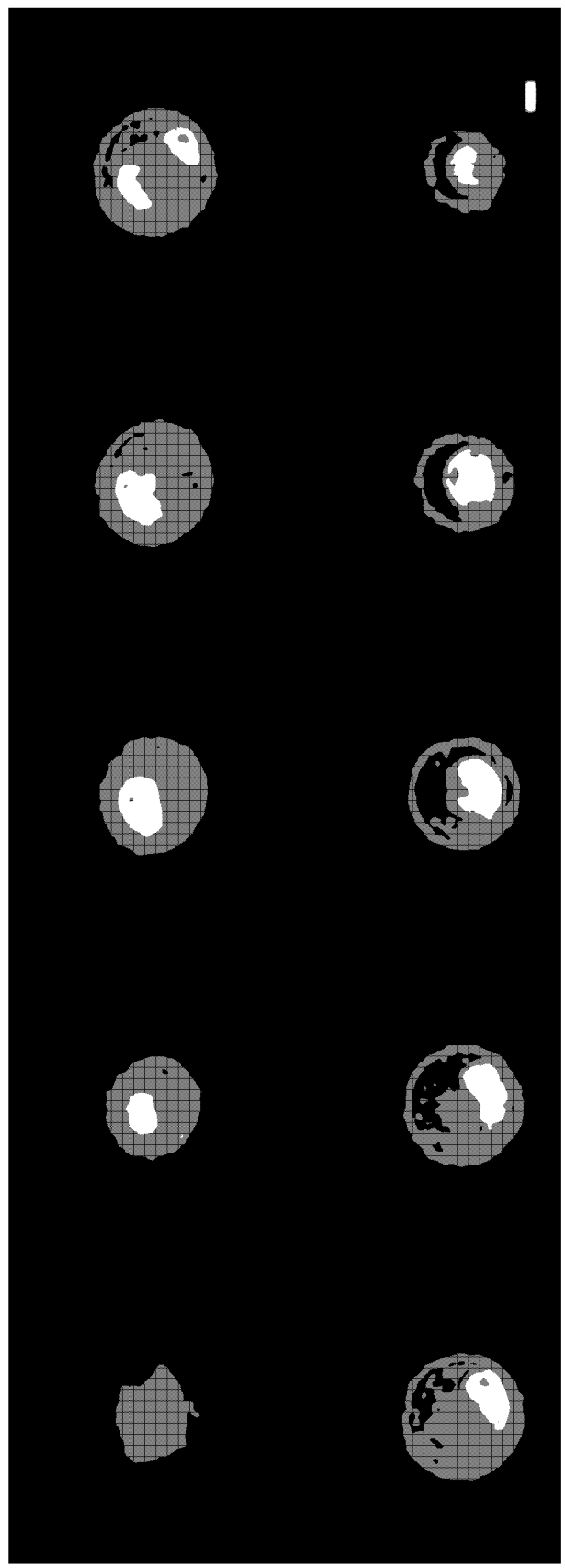
FIG. 77: Z-stack sectioning of THP-1 line derived adherent 'm'DCs visualised under confocal microscopy with 405 nm and 643 nm laser excitations (scale=10 μm).
Figure 78:
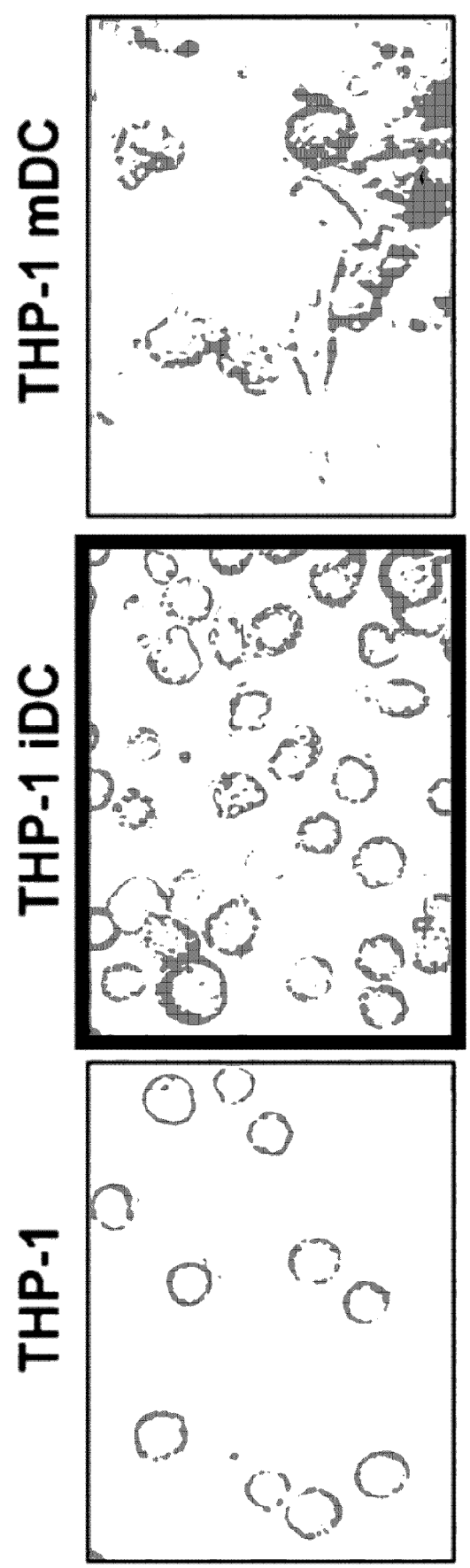
FIG. 78: Widefield microscope micrographs of THP-1 cells in native monocyte (a), iDC (b) and mDC (c) states. Reproduced with permission from Berges et al [22].

Representative micrographs of the DCs obtained from the differentiation protocol are shown in FIGS. 76 and 77, and can be compared to the micrographs shown in the original work by Berges et al (from which the THP-1 differentiation protocol was used). The comparison between experimental and literature cell micrographs strongly suggests the successful differentiation of THP-1 cells into immature DCs (iDCs). Indeed, in both FIGS. 76 and 77, cell shape is circular with spherical components on the cell membrane, otherwise referred to as ruffled and lobular cytoplasm with spikes and semi-circular extrusions [44]. As shown in FIG. 78, undifferentiated THP-1 cells present no such membrane artefacts with only a smooth cell membrane visible; fully mature DCs (mDCs) indeed present characteristic dendrite-like cell membrane elongations, which are clearly not visible in neither FIG. 76 nor 77.

A difference between differentiated cells was however observable. In total, THP-1 cells were derived in 4 flasks subject to identical treatment. Despite identical treatment, the innate variability of cell work results in some marginal observable differences. Whilst cells presented in FIG. 76 were observed in suspension, those in FIG. 77 were found stuck to the bottom of the incubation vials. Structural differences can also be observed, specifically cellular diameter. Suspension cells indeed appear to have an average diameter of approximately 10 μm as opposed to the roughly 25 μm of the adhesive cells. DCs indeed increase in size and adherence capability during their maturation process [49]. However, full maturation is typically characterised morphologically by the formation of dendrites as shown in FIG. 78. In contrast, dendrites are clearly not visible in FIG. 77. It is therefore likely that the former cells are in a transitional state between immature and fully mature. To distinguish between them, this report will refer to the cells presented in FIG. 77 as 'mature' DCs ('m'DCs), and to their smaller counterparts referred to as immature DCs (iDCs).

Despite the slight difference in cell morphology, the key common factor between iDCs and 'm'DCs is their clear differentiation away from THP-1 monocyte state without full differentiation into mature DCs. This is of paramount importance for the proposed mannose-based extraction of DCs. The key difference in immature and mature states is commonly defined as the cell surface expression of CD206 (mannose receptor) and CD209 (DC-SIGN) markers: immature cells present them, whereas fully mature DCs do not. This is commonly assessed by fluorescence marker-labelled dextran endocytosis. Dextran molecules act as ligands for CD206 and CD209. If the cell surface receptors are present, the fluorescent dextran is endocytosed by the iDC, and are detected by visible and measurable in fluorescence intensity measurements. Lack of signal establishes the cells as mDCs [50, 51]. Results presented by Berges et al clearly indicate dextran uptake for iDCs, confirming the expression of desired cell surface receptors.

The expression of such surface groups is key to the proposed functional extraction process hypothesised via xerogel mannose surface functionalisation. Indeed, if the cells used for extraction evaluation do not present any mannose receptors, there is no biochemical reason for them to have any particular affinity for the functionalised xerogels. The morphological assessment of the differentiated cells as iDC and non-fully mDC cell types confirms their suitability to the proposed extraction evaluation protocol.

Figure 79:
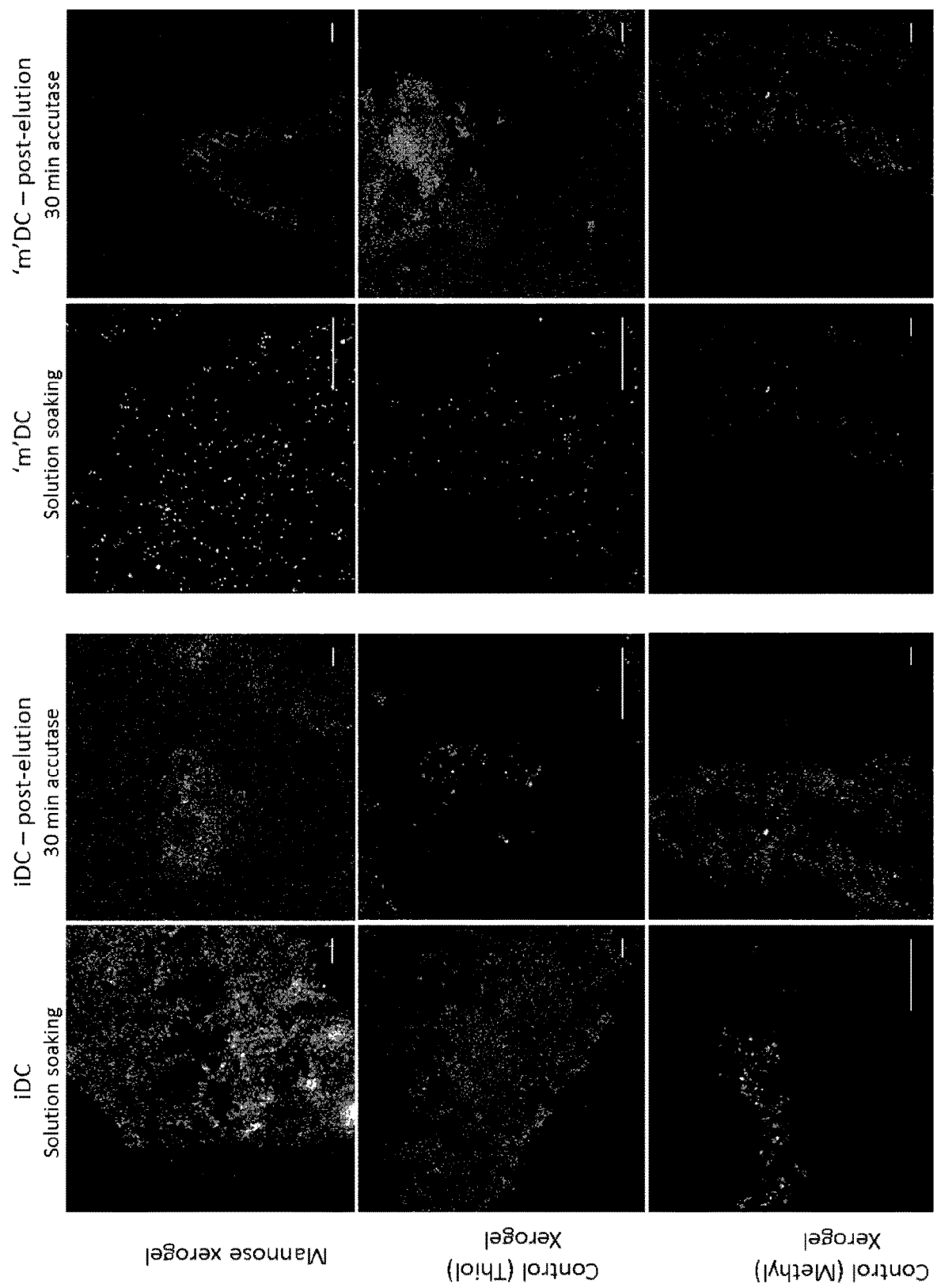
FIG. 79: Representative micrographs of mannose-functionalised and control (MD-type and N-type) soaked in iDCs and 'm'DCs solutions and post-accutase soaking (scale=100 μm).

Having confirmed the suitability of cell types for the proposed application, both cell lines were subject to extraction, retention and re-elution from mannose and control xerogel investigations, the results of which are presented in FIG. 79. It is important to note that results remain preliminary and though repeated, only constitute an initial insight into the selective affinity for extraction purposes of the mannose functionalised xerogels. Further work will be required before any firm conclusions can be drawn.

Functionalised and control materials were introduced to iDC and 'm'DC containing solutions for 10 min, at the start of which they were repeatedly compressed to ensure fluid inflow into the substrates. Xerogels were then removed, rinsed through with abundant aqueous solution to remove any unbound marker and dried to remove excess fluid prior to confocal imaging. Once assessed for cell presence, cells were re-eluted by introducing into an accutase solution at 37° C. for 30 min, the accutase acting as a mild detaching agent. Accutase was used as a milder alternative to the conventionally used trypsin in an attempt to preserve the cells for post-elution evaluations, as it was feared that the latter would cause too much stress to the cells, resulting in their death prior to any investigation.

Comparing FIG. 79 with FIGS. 76 and 77, it is clear that no red signal is visible in the former micrographs. As has been explained, DCs were stained with both DAPI and SiR for nuclear and actin filament visualisation respectively. Unfortunately, due to the innate properties of the proposed xerogels, the wavelength used to stimulate SiR fluorescent dye (643 nm) resulted in xerogel material autofluorescence, rendering it impossible to distinguish between signals associated with the structure and those associated with the actin filaments. In contrast, the DAPI-exciting 405 nm laser fortunately did not cause any autofluorescence; DC presence within the material was therefore assessed by 405 nm emission signal, whilst the structure was visualised in sequential reflectance mode so as to avoid any false-positive fluorescence readings as well as background interference.

Analysing the results of experiments performed on iDC cell types, it is clear from the post-extraction process that iDCs have been retained by both thiol control and mannose functionalised material, as made visible by the blue signal; and that, in contrast, no such signal is visible from the methyl control sample. Though iDC extracted from mannose-functionalised samples is desired, it was not expected from thiol control samples due to their lack of functional groups. However, the presence of cells post-extraction from thiol samples combined with the complete absence thereof in the case of methyl control samples suggested that the cause is hydrophobic material effect as opposed to functional group affinity. Mannose functionalisation has also proven the fluid wicking capabilities of the material as shown by FIG. 74. iDC extraction in this context appears to be due to the material being able to wick through its structure any iDC-containing that happens to be left behind after excess liquid removal. N-type xerogels being more hydrophobic by nature do not allow as much fluid to penetrate the structure, thus extracting fewer iDCs.

Although hydrophilic material properties are presumed to be important for iDC extraction, it is possible that the surface mannose groups are interacting specifically with iDCs through CD206 and CD209 affinity (as initially hypothesised) to retain them. Re-elution was therefore catalysed using a mild detergent, accutase. Xerogels were placed in an accutase solution for 30 min and subsequently centrifuged over Cornstar filters to remove any bound iDCs. As can be observed from FIG. 74, this elution process appears to be effective, with no DAPI signal visible post-elution. Though both MD-type and mannose-functionalised xerogel indicate iDC extraction capabilities, the key fact remains that the designed re-elution protocol allows them to be eluted out of the structure for further analysis.

To this end, having proven that iDCs are clearly being eluted from the structure post accutase and centrifuging, the ideal-follow on experiment from this would be the visualisation of thus recovered iDCs in solution, ideally obtaining micrographs similar to those presented in FIGS. 76 and 77. However, despite multiple attempts, only trace amounts of signal were observed when re-suspending and visualising the cells at 405 nm. The results are therefore not presented. The lack of any defined signal and only residual floating DAPI staining could indicate cell destruction, possibly through both accutase treatment being too aggressive or the physical stress of removal from cell culture media, laser light exposure (during visualisation under confocal microscope), detergent treatment and centrifugation. However, it is also possible that the manual handling only affected the fluorescence marker, the iDCs therefore being viable but not visible without their staining agent under fluorescent light. Re-staining the eluted solution with DAPI may allow for any removed nuclear staining to once again be visible. Failing that, a means of staining actin fibres without resulting in extracting material auto-fluorescence or alternative nuclear staining may provide a further insight into post-elution cell viability status.

The difference in cell maturity is highlighted by the combination of FIGS. 76 and 77 and the physical (suspension versus adhesion) presentation of THP-1 differentiated cells. In order to assess whether maturity status has an effect on extraction capabilities via the proposed functionalised and control xerogels, 'm'DCs were subjected to identical treatment as that described above for iDCs; the results of the process are presented in FIG. 79.

In contrast to iDC extraction behaviour, the material hydrophobicity hypothesis therefore does not hold for 'm'DCs. Indeed, DAPI signal is only visible in mannose-functionalised xerogels, with no nuclear-staining signal visible in either thiol- or methyl-control samples. Although confirmation of full cell type difference can only be assessed by surface marker expression such as IL-12, IL-27 and CD14 [52], both iDC and 'm'DC cells in this case are presumed to be in the pre-mature stage. They therefore still present CD206 and CD209 cell surface receptors, the receptors with specific affinity to mannose groups. If therefore identical from a differentiation or maturation perspective, the only difference highlighted by comparing FIGS. 76 and 77 is the physical size difference, 'm'DCs being larger than previously examined iDCs.

Preferential extraction of 'm'DCs by mannose-functionalised xerogels is therefore most likely due to CD206/CD209-mannose affinity, whilst the lack of retention by MD-type xerogels in this case may be due the increase in size. Due to increased diameter, it is possible 'm'DCs are simply more susceptible to aqueous solution washing, the material hydrophilicity not being sufficient to retain them during such a washing step, resulting in their being eluted out by the flow of the solution. Elution protocol proved once again to be successful in the case of 'm'DCs, accutase and centrifuge procedures allowing the desorption of previously extracted cells from the mannose xerogel. If the hypothesis of 'm'DC extraction from solution and retention during aqueous washing being mediated by CD206/209, mannose specific affinity is accurate, then the full re-elution via accutase treatment confirms the ability of the method to desorb cells bound through such affinity-based extraction systems.

Despite their increased size, imaging of eluted cells once again was not possible, with only mildly discernible features being visible under confocal imaging (not shown). Repeat DAPI staining and alternative actin staining are again proposed as means of further evaluating the viability of eluted cells upon further work.

The above results overall indicate that mannose functionalisation allows the extraction, retention and re-elution of DCs as desired, regardless of iDC or 'm'DC state. However, as highlighted by iDC investigations, mannose group extraction capabilities were not fully confirmed, as MD-type xerogels subjected to identical treatment and cell exposure also presented iDC extraction and retention capabilities. The extraction, retention and re-elution protocol was therefore retested on mannose-functionalised and MD-type xerogels, but with reduced iDC exposure time, 5 min in this case. The results of the adjusted extraction protocol are presented in FIGS. 80a and b.

Figure 80:
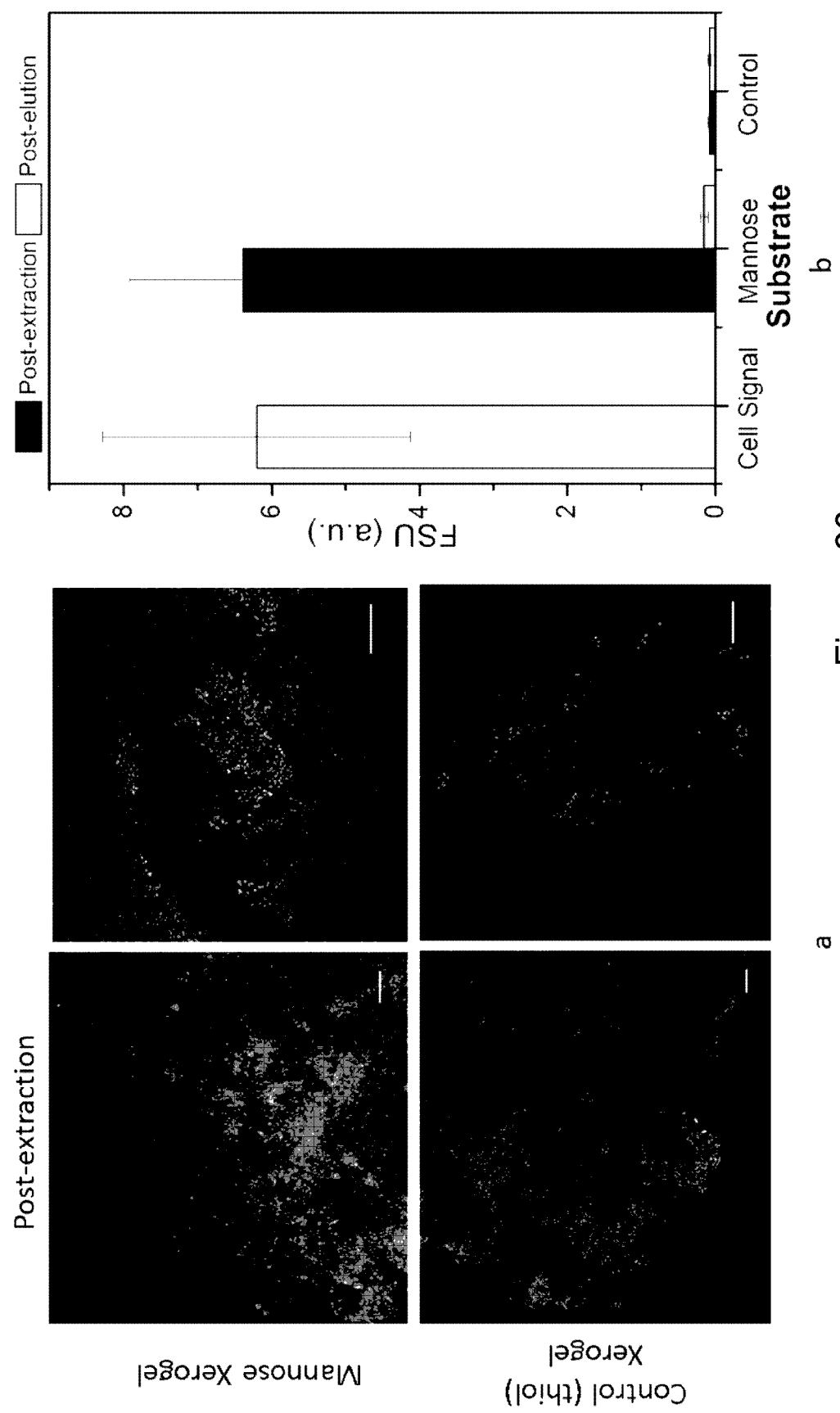
FIG. 80: Representative micrographs (a) of post-DC extraction and (b) post-accutase elution of mannose functionalised and control (MD-type) xerogels and fluorescence intensity measurements of DC-nucleus associated signal post DC extraction and elution for mannose and control xerogels (scale bar=100 μm).
Figure 81:
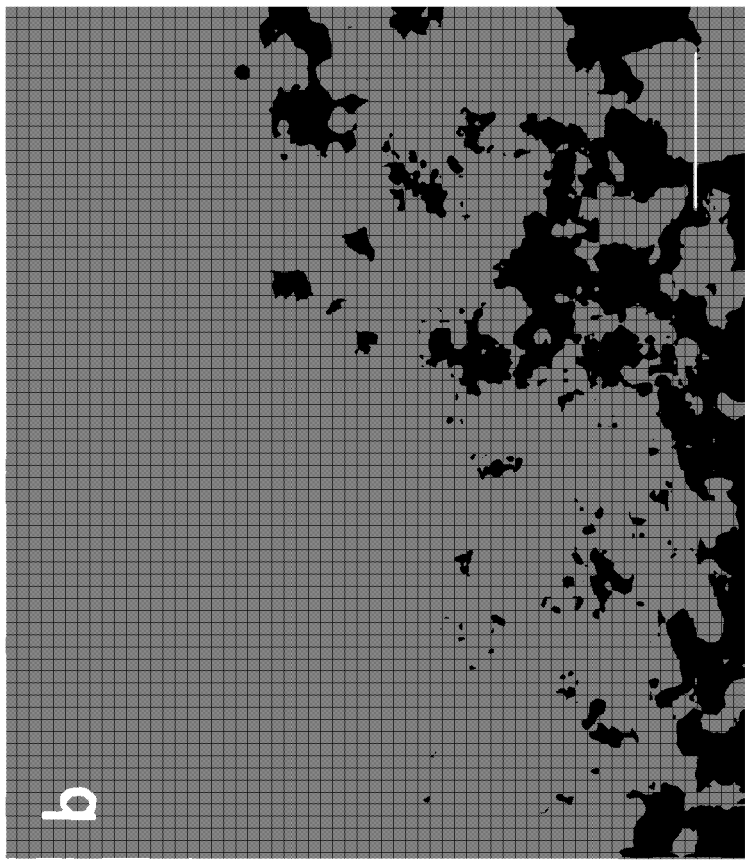
FIG. 81: Representative widefield fluorescence micrographs of Mannose-functionalised (a) and MD-type control (b) xerogels post 5 min DC solution soaking time (scale bar=100 μm).
Figure 81:
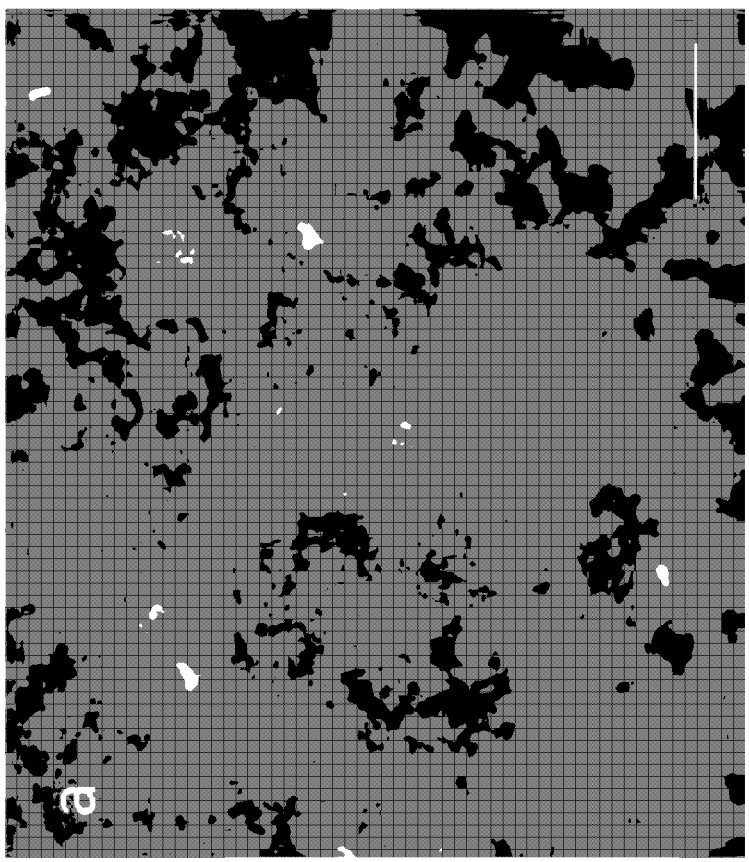

The key observable difference between FIG. 80 and FIG. 79 is that MD-type control xerogels in the former no longer show signs of iDC extraction when subjected to the reduced exposure and immersion time of 5 min. However, despite the reduced time, iDCs are still visibly extracted by the mannose-functionalised substrates, with clearly more visible iDC cell nuclei visible. The presence of iDCs post-extraction and washing in mannose xerogels and absence thereof in the thiol-control case was re-confirmed using widefield fluorescence microscopy as shown in FIG. 81 (due to the conflicting results between FIGS. 80 and 79). However, widefield images confirm the presence of iDCs in mannose samples as highlighted by regions of high contrast white points, and a complete lack thereof in MD-type xerogels when subjected to identical treatment. This clearly confirms that simply due to the reduced exposure time, only mannose group presenting xerogels were able to extract and retain iDCs from solution.

Subsequent elution using the same protocol as that used for the results shown in FIG. 79 yielded similar elution as previously observed. Indeed, post accutase-mediated elution, no DAPI signal is visible under 405 nm laser excitation, confirming the elution of the previously extracted cells.

Numerical analysis of the fluorescence signal associated with DAPI staining intensity further confirms the iDC extracting nature of mannose functionalised xerogels relative to their MD-type control counterparts, as shown in FIG. 80b. DAPI signal post-extraction (and aqueous solution washing) for mannose xerogels is 6.38±1.53 FSU as opposed to 0.15±0.01 for control, values attributable to background fluorescence. The intensity values extrapolated from presumed cells on the surface of the mannose xerogels also matches the cell signal intensity of DAPI-stained nuclei previously measured, at 6.21±2.08 FSU. The similarity in fluorescence intensity values strongly suggests that the values obtained from xerogel substrates are not simply artefacts or somehow desorbed or leached DAPI stain, but are attributable to the presence of cell nuclei within the gels; thus confirming numerically the preferential iDC extraction capabilities of mannose functionalised xerogels relative to MD-type xerogels.

The aim of the devised experimental procedures described in FIGS. 79 to 81 was to assess whether mannose functionalisation of MD-type xerogels enabled mannose-DC affinity based extraction from aqueous solution, thus yielding improved DC extraction relative to unfunctionalised material.

Although some differences between cell types obtained post THP-1 differentiation were observed in FIGS. 76 and 77, it is clear by comparing their morphology to literature that both of them present signs of being in an iDC state, with the latter of the two cell types most likely being closer to maturity than the former.

Evaluating iDCs for mannose xerogel extraction indicated that mannose surface functionalisation of xerogels allowed for improved extraction and retention of iDCs regardless of their maturity (i or 'm') relative to MD- and N-type controls. An exposure time of 5 min to an aqueous solution containing DCs was established as being sufficient time for functionalised xerogels to extract the cells, and subsequently re-elute them.

The proposed xerogels show promising signs of achieving the desired purposes of DC extraction and re-elution from physiological fluids such as nasal fluid.

Summary of Examples 15 to 18

These results therefore prove that although wicking materials as currently used for SAM materials in clinical practice may allow biomarker extraction including DCs, the herein proposed material not only matches such extraction capabilities but allows for a dramatic increase thereof due to its surface functionalisation potential.

Although the 'R'MA-b-AMA block copolymer for the surface grafting concept was only evaluated on PMMA-based block copolymers, the successful nature of both block synthesis and subsequent surface grafting pave the way towards the successful nature of such CRP methods being possible for the functionalisation of the proposed xerogels, were the biofunctional need for CRP polymer synthesis to arise. In this case, TSIP provided a reliable and functional means of grafting mannose methacrylate without the need for a CRP-based method.

The above section therefore shows the ability of MD-type xerogels to be functionalised with functional methacrylate-based groups to achieve DC extraction. These xerogels have therefore been shown to be suitable platforms for both lipid and cell extraction, and to that extent to have delivered their initially hypothesised promise.

Example 19: Surface Grafting of Detection Antibody

Materials (3-mercaptopropyl)methyldimethoxysilane, trimethoxysilane, ethanol, N,N-Dimethylformamide, rabbit and goat anti-human anti-collagen I antibody, human collagen type I and V, rabbit anti-human anti-interferon alpha antibody and AEC staining kit were purchased from Sigma Aldrich® and used as delivered unless otherwise specified. N-maleimidoburyryl-oxysuccinimide ester (GMBS), rabbit and goat anti-interferon alpha antibody, mouse anti-collagen I antibody, goat anti-mouse IgG H&L alexa fluor 488 nm labelled antibody, recombinant human Interferon alpha protein, anti-Interferon alpha antibody were purchased from Thermo Scientific.

Methods

Xerogel Synthesis Via Sol-Gel Process

The MTMS-DMDMeS synthesis was identical to that described in detail Example 9. Briefly, MTMS and DMDMeS were mixed in a 3:2 v/v ratio, in a solution of 5 mM acetic acid, with urea and CTAC as catalyst and phase separation avoiding agent respectively. Once hydrolysed under stirring for an hour, the sealed solution was transferred to an 80° C. oven for 24 hours for gelation and ageing. Once removed, the thus obtained xerogels were rinsed with primary alcohol and hexane repeatedly to remove any unreacted agents, left to dry and stored in a desiccator till use.

Surface Grafting of Antibodies

The surface post-functionalisation of the thiol-presenting gels were functionalised following established protocols typically used for the preparation of glass plates in ELISA assays. Typically, glass surfaces were modified to graft thiol groups on its surface. This initial process was followed when proof-of-concept testing glass to confirm the suitability of the proposed protocols, specifically using the method described by Bhatia et al [61]. Briefly, glass slides were treated with a 2% (3-mercaptopropyl)trimethoxysilane toluene solution for an hour in inert atmosphere post oxygen plasma treatment for 10 minutes at 30 sccm oxygen flow rate. Slides were then rinsed with toluene to remove any unbound MeTMS.

Using the thiol-precursor synthesised xerogels inherently removes the need for this precursor step, as thiol groups are by design present on the surface of the gel. This reduces the number of functionalisation steps thus saving time.

In order to covalently bond the capture antibody to the surface of the xerogels, an intermediary heterobifunctional crosslinking compound was used, as is the established method in surface preparation requiring antibody immobilisation for biosensing applications. Briefly, the underlying concept relies on the ability of heterobifunctional crosslinkers to covalently bond to both the surface thiol groups on the substrate to be reacted, and then to the carbohydrate region of the antibody [62].

Figure 84:
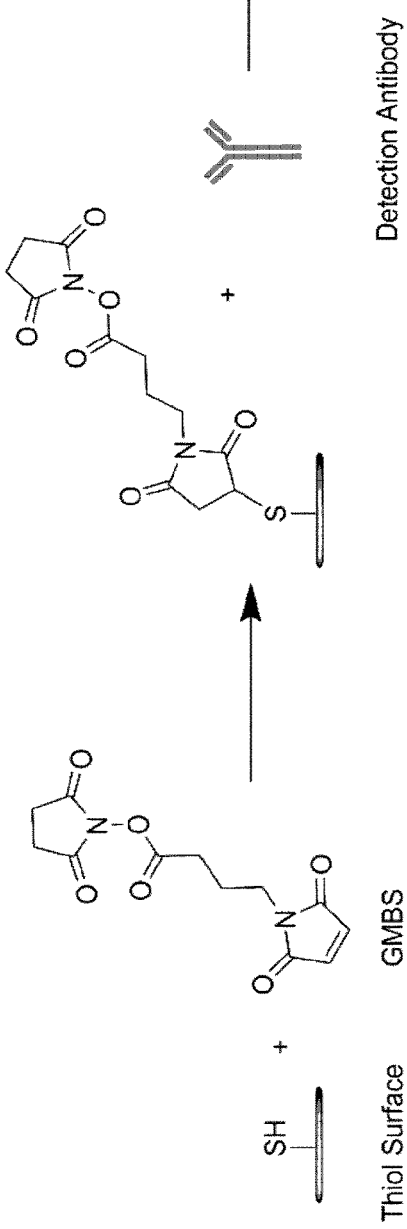
FIG. 84: Schematic representation of the primary detection antibody surface grafting protocol using a GMBS heterobifunctional crosslinker.

The surface grafting protocol followed that described by Shriver-Lake et al [62] and described schematically in FIG. 84. A commonly used crosslinking agent, GMBS, was dissolved in minimal DMF to final 2 mM concentration in EtOH, to which the thiol-presenting substrates (glass slides or xerogels) were introduced and soaked in an inert environment overnight. Once reacted, the substrates were abundantly rinsed with EtOH and PBS to remove any unbound GMBS.

To graft the capture antibody to the surface-reacted GMBS crosslinker, the GMBS functionalised substrates were placed in a 0.05 mg/mL solution of the relevant antibody in PBS and left to react overnight. The resulting surfaces were ready for protein extraction, stored at 4° C. till use, and used within 2 weeks of grafting. It is important to note that the detection antibodies were selected to have a different binding specificity from those of the detection antibody so as to avoid false positive reactions, achieved by varying the species the antibodies were derived from.

Characterisation Techniques

Antibody grafted xerogels were characterised with the following techniques following previously explored 3-phase evaluation:
SEM
Uniaxial compression
Absorbance capacity testing
MTT cytoxicity evaluation
Sandwich ELISA Results The first step in prototyping the suggested protein extracting xerogels was to assess the feasibility of transferring the ELISA-based technology from commercial plates to silica based networks. This was done by testing the functionalisation process on glass before testing on xerogels, when assessing ODS surface functionalisation. Glass surfaces were treated with MTS and GMBS solutions to provide reaction sites for capture antibody bonding. Fluorescence labelled antibodies were then covalently bonded to the surface. Any fluorescence signal obtained as a result therefore confirms the presence of the capture antibody, in turn confirming the successful nature of the suggested protocol for surface grafting of antibodies that can then be used for the ELISA type extraction, capture and analysis process. The control is this case was a non-GMBS functionalised MTS treated glass slide.

Figure 85:
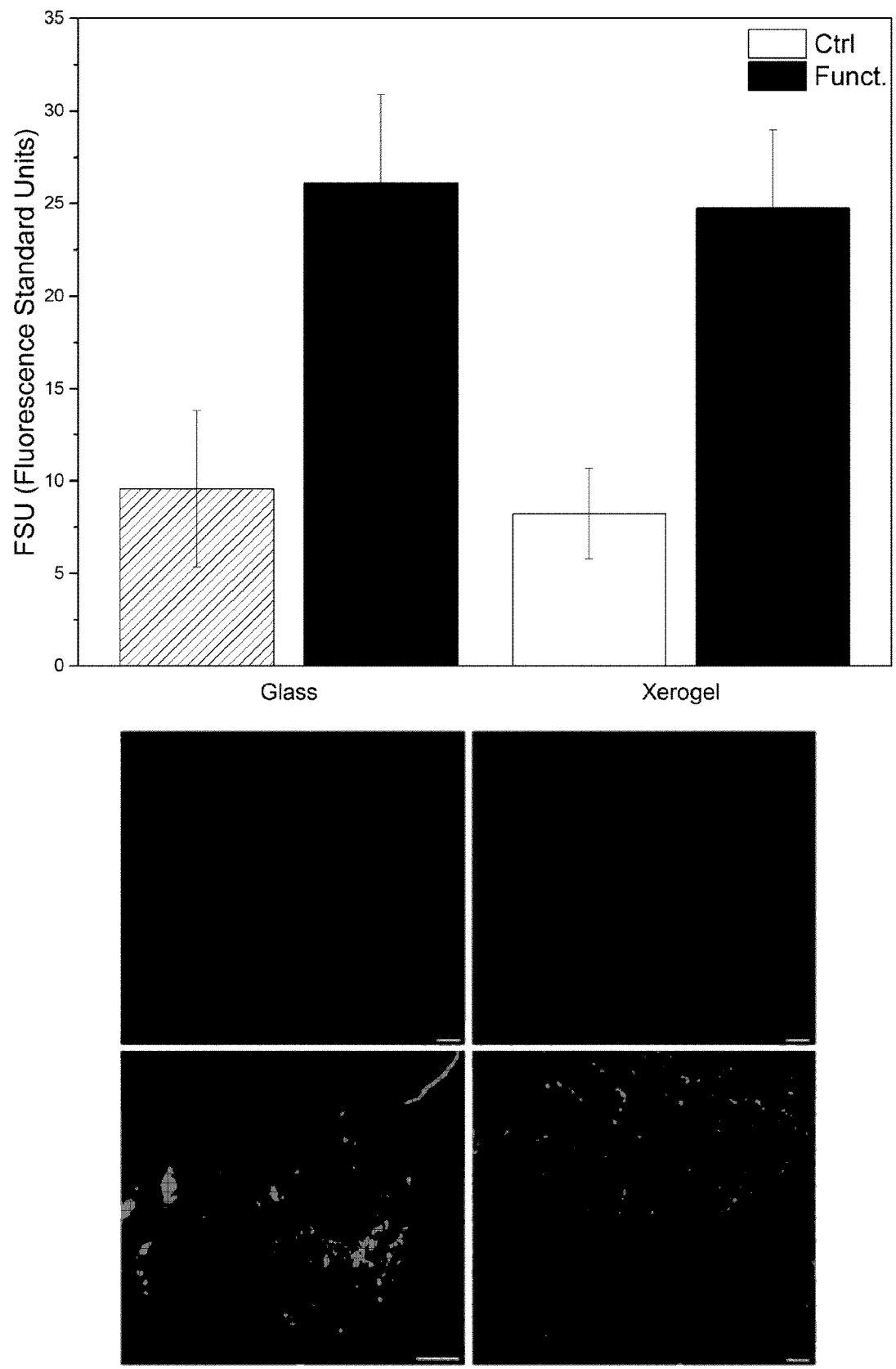
FIG. 85: a. Control and fluorescence labelled detector antibody functionalised glass and thiol-xerogel substrates and b. corresponding representative micrographs (scale bar=100 μm).
Figure 86:
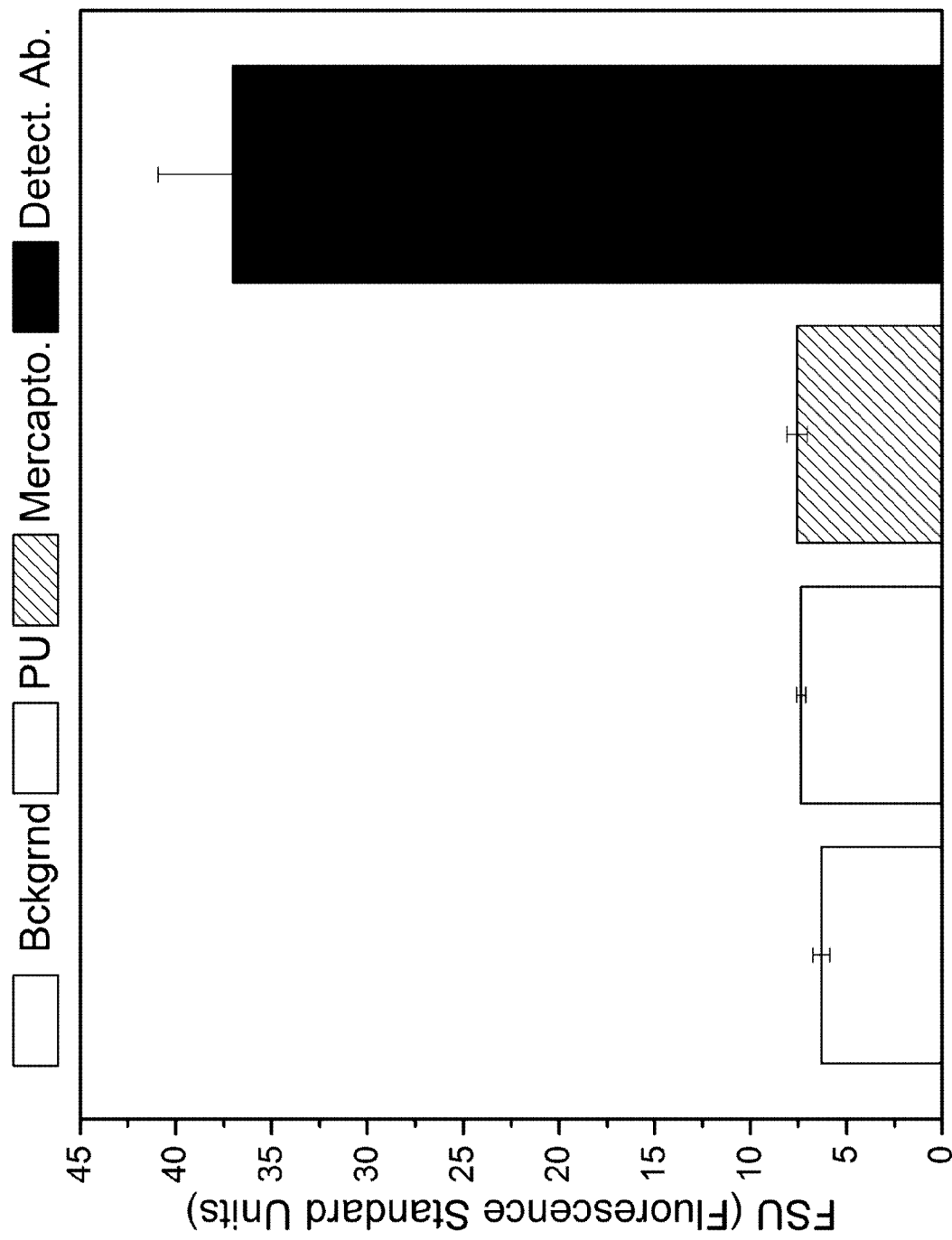
FIG. 86: Fluorescence intensity measurements of various control versus detection-antibody functionalised substrates.

As shown in FIG. 85, a clear increase in fluorescence signal was observed in the case of the full MTS and GMBS glass treatment prior to antibody grafting, confirming the successful nature of the full surface modification and grafting process. This is further confirmed by the lack of fluorescence signal for the control (i.e. non GMBS-treated glass); an observation, which also demonstrates that GMBS is the key step in allowing the antibody onto be grafted onto the surface. The fact that an intensity is recorded (in this case 9.8 FSU) is attributable to the autofluorescence of the background, and not relevant fluorescence from the grafted antibody. The comparison to background signal for reference across these fluorescence intensity measurements is shown in FIG. 86. No control was done without MTS treatment due to both the very common nature and therefore assumed reliable nature of the reaction. The fluorescence micrographs give a graphical confirmation of the clear difference between functionalised and control surfaces, with a clear pattern visible in the case of full functionalisation clearly not present in the case of control. The surface pattern was consistently observed across multiple samples, but its cause is unclear. It is suggested that it is due to glass topological effects, themselves due to etching as a result of the cleaning process prior to functionalisation. Cleaning with acetone and subsequent drying may have caused grooves or lines on the surface, exacerbated under fluorescence due to the angle of observation or illumination. Intensity measurements were taken with this in mind and larger representative sections (as opposed to individual points) analysed in an attempt to mitigate what appears to be an artefact.

Having established that glass slides for ELISA type testing can be successfully prepared, the same process was repeated on thiol moiety presenting xerogels. The presence of thiol groups with the xerogel by design mitigates the need for the additional MTS treatment step performed on glass, thus reducing the synthesis or grafting time, adding to the list of advantages of the proposed xerogels. The results presented in FIG. 85 are again in line with those observed on glass. Indeed, a considerable divergence between fully functionalised and control xerogels can be observed, with a clear increase in fluorescence signal for the functionalised material. The control here again is a non-GMBS treated thiol xerogel.

The micrographs of the xerogels give further graphical evidence to the successful nature of the grafting, as well as highlighting the microstructure of the xerogel. The fact the structure is visible to such an extent also strongly suggests uniform grafting. Any blank areas seen in FIG. 85b are due to the combination of the uneven microstructure of the xerogel and lack of extensive depth of field of the confocal microscope used, rather than being the result of a localised functionalisation phenomena, as can be seen when going through a z-axis profile view of the xerogel. When considering that the experimental process includes rigorous washing steps to ensure the elution of any unbound antibody from the surface, it is possible to conclude from the presented results that the capture antibodies are indeed bound to the surface of the desired xerogel by means of GBMS difunctional crosslinker.

The non-artefact nature of this successful functionalisation is further confirmed by the results presented in FIG. 86. The same protocol of antibody surface functionalisation using GMBS as a crosslinker between the substrate surface and the antibody was repeated on polyurethane, mercaptosilane precursor substrates with and without GMBS treatment. As is clear from the fluorescence intensity measurements, only the full functionalisation process allows the fluorescence-marked antibodies to be bound to the surface, as compared to the other surfaces which possess no chemical anchor points for this to occur. FIG. 86 shows the similarity of intensity values between background and control substrates, which, as has been explained, confirms the lack of any desired surface antibodies as opposed to minimal amounts due to partially successful surface grafting as the absolute values would suggest. In short, non-zero values do not constitute proof of antibody grafting, but represent the numerical value of innate equipment background intensity or instrumentation. This is further confirmed by the very low error margin, which in turn confirms the successful antibody xerogel surface grafting by means of GBMS crosslinker and antibody solution soaking.

Example 20: Physical Properties of Capture-Antibody Functionalised Xerogel

The protocol followed proves that it is possible to graft antibodies onto the surface of the thiol moiety presenting xerogels and to use them as capture antibodies for ELISA-type analysis. It is key to investigate the effect that such modifications have on the physical properties of the resulting xerogel relative to its innate advantageous properties to ensure they retain the patient comfort benefits. Particularly because the reason xerogels were chosen as base materials were the characteristic properties of high flexibility, absorbance capacity and cellular environment compatibility.

Figure 87:
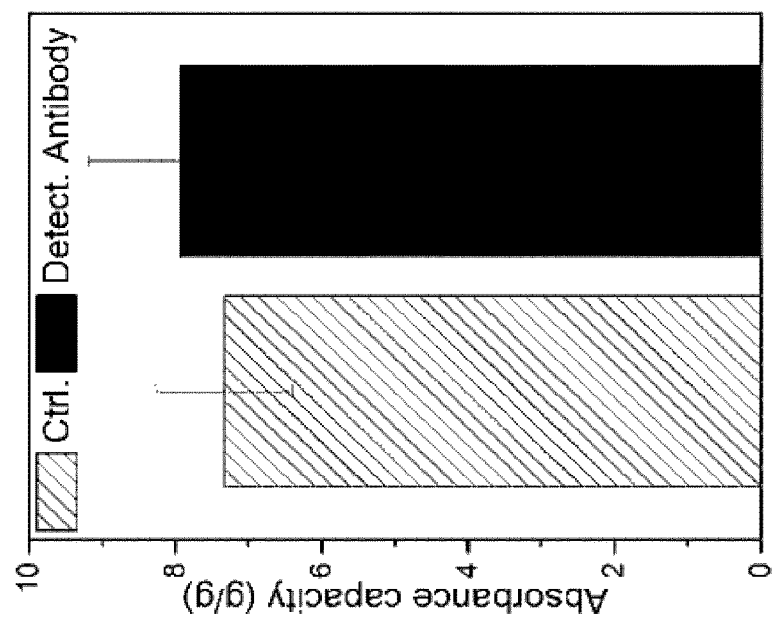
FIG. 87: a. Fluid absorbance capacity and b. cyclic/static compression testing of control and detection antibody functionalised xerogels and table showing strain and stress values under 5 N of load for both MD-type control and Anti-Col I functionalised xerogels.
Figure 87:
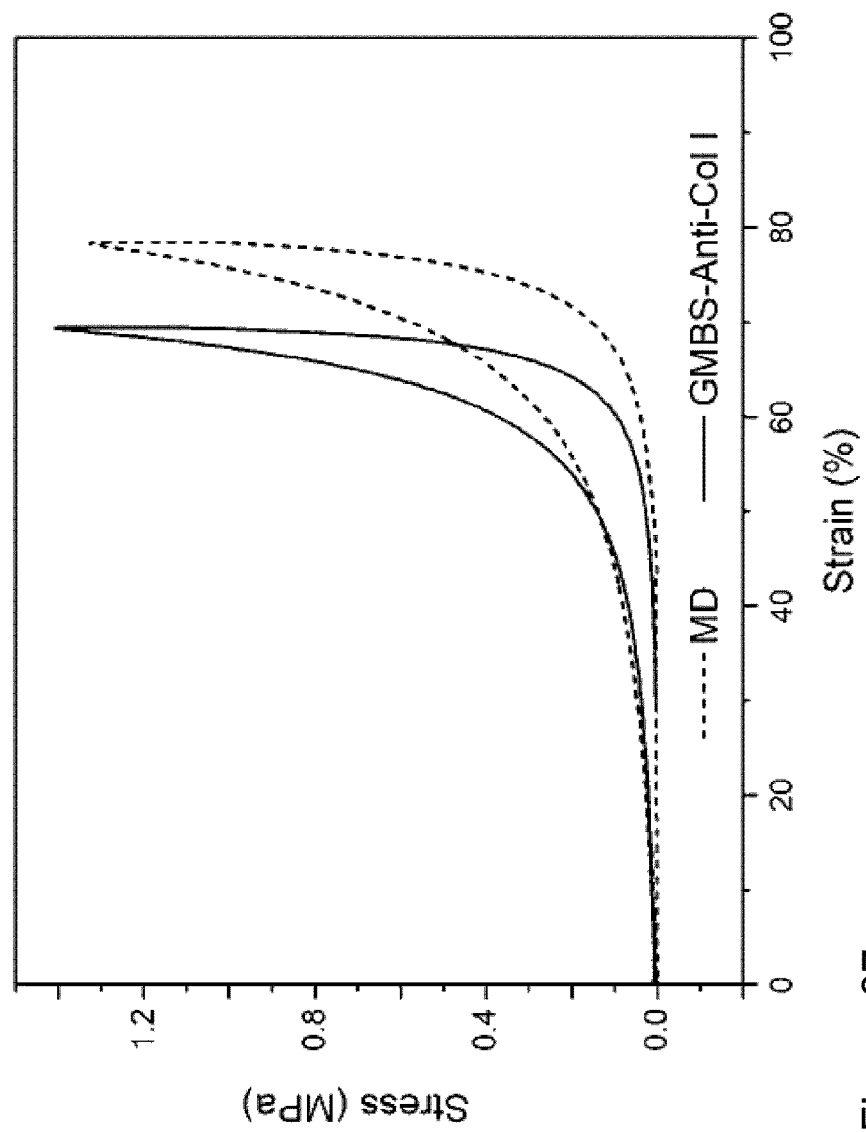
Figure 88:
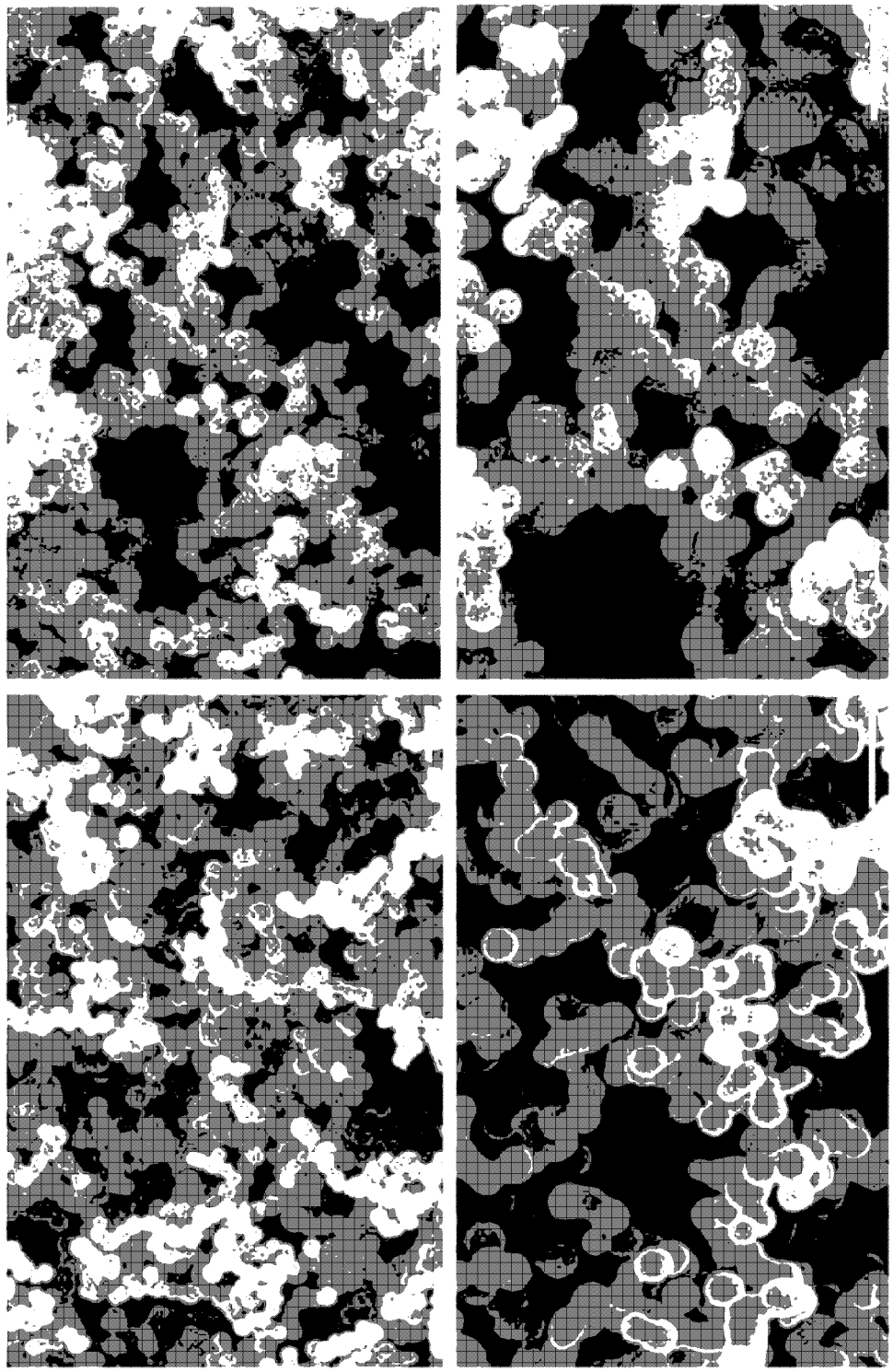
FIG. 88: SEM micrographs of unfunctionalised and GMBS—capture antibody functionalised xerogels (scale bar=10 μm).

FIG. 87 presents the results of absorbance capacity and compression testing for both original control thiol xerogels and their full detection antibody functionalised counterparts. Comparing the fluid uptake capacity of the control and functionalised gel, not only does the proposed functionalised composition allow similar orders of magnitudes of fluid uptake, but also appears to perform slightly better than its control counterpart, with the absorbance capacity increasing on average from 7.2 g/g to 7.6 g/g. Regardless of the upward divergence in uptake, it is clear that the process of binding antibodies to the xerogel surface via GBMS di-functional crosslinkers does not affect the ideal uptake properties the base composition exhibits.

The fact that antibody functionalisation does not affect the key properties of the xerogels can also be observed in the case of mechanical testing. Over the considered tested range, the stress strain curves of both control and antibody-grafted xerogels remains, for the purposes of the considered application, effectively identical.

There is a slight increase in stiffness in the case of the functionalised xerogels relative to the control composition. This can most likely be attributed to the use of GMBS crosslinkers to bond the antibodies to the surface. Defined as having a spacer with a of length of 7.4 Å suggests the structure itself is relatively rigid. This will therefore reduce the mobility of the structure under compression, leading to the slightly higher compression values observed.

However, the slight increase in stiffness exhibited by the antibody surface grafted xerogels is not sufficient to suggest radically different performances in the context proposed, and cannot be identified any other way than numerical analysis. The two compositions are indeed indistinguishable to the touch and under general manual handling. The values also closely match those obtained by Hayase et al in their studies of various composition xerogels including similar length groups on the xerogel surface, pointing towards the suitability despite functionalisation of the material [63].

TABLE 14

Strain and stress values under 5N of load for both MD-type control and Anti-Col I functionalised xerogels

| Sample | MD | Antibody |
| --- | --- | --- |
| strain at 5N | 59.60 ± 1.84 | 52.48 ± 2.10 |
| stress at 5N | 0.17 ± 0.01 | 0.21 ± 0.02 |

A key characteristic of the xerogels is their cell compatibly, or more specifically the lack of cellular environment disturbance as previously shown by the MTT cytoxicity assay protocol. It is particularly important in the context of diagnosis that the device proposed does not affect the biological environment it is being exposed to and extracting from. Any effect on either would not only corrupt the results by killing cells or biomarkers, but also put the patient's health at risk.

Control and functionalised compositions were immersed in ISO standard MTT cell assay media for an hour and removed. The cell media was tested 1 hour and 24 hours after the removal of the xerogels and compared to basal media. 1 hour of immersion was chosen as this is likely to be the upper time limit for the proposed devices to be placed within the nasal cavity of patients. 24 hour time point (for post cellular media contact cell viability measurements) was chosen as the longest post-exposure time point, as in can be considered that cell death would have occurred within that time frame.

Figure 89:
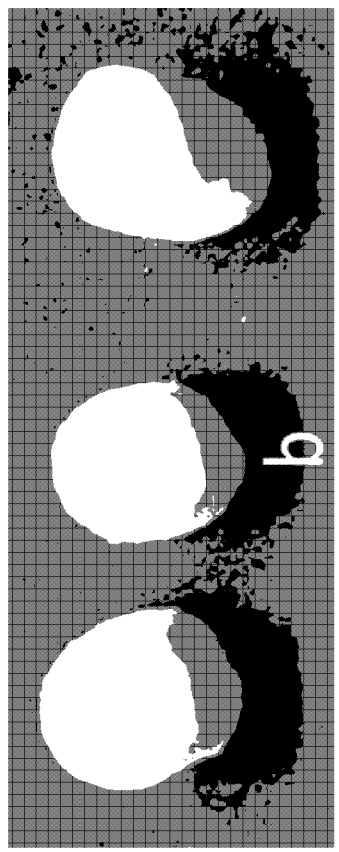
FIG. 89: Representative photographs of anti-Col I functionalised xerogels pre-(a) and post-(b) compression testing.
Figure 89:
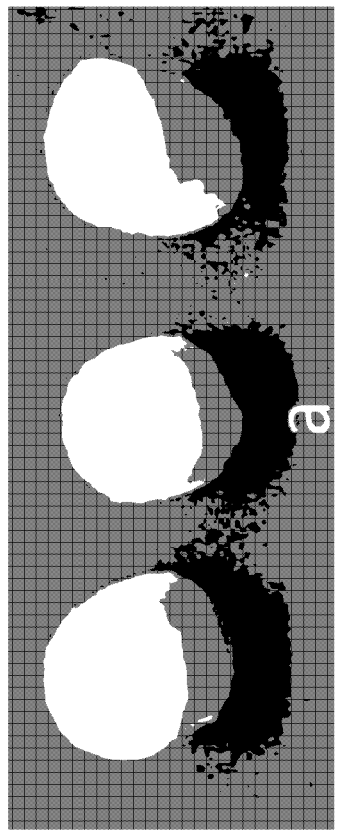

In similar fashion to MTT assays conducted on previous ODS and Mannose surface functionalisations, it is clear from FIG. 89 that the considered antibody surface functionalisation does not have any effect on the cellular environment it is exposed to. Indeed, at both 1-hour and 24-hour post exposure to cellular media, the absorbance values measured at 574 nm are between 0.25 and 0.27, and 0.42 and 0.44, respectively. The slight variation in measured absorbance values can be considered negligible. For instance, the lower measured absorbance values for the antibody functionalised xerogel relative to control (0.25 vs 0.27 respectively) cannot be considered as anything but artefact, given that the same solution tested after 24 hours shows a lower divergence and almost identical values. The data demonstrates that the proposed functionalisation process does not affect the cellular environment to which it is exposed.

Several important points are confirmed by the data presented so far. First, that protocols used on glass surfaces for ELISA plate preparation can be successfully used on the proposed thiol xerogels. Secondly, that the proposed xerogels (due to their thiol presenting moiety composition) eliminate a step in the grafting process, thereby reducing synthesis time and possible experimental error. And thirdly that, once grafted onto the surface, the functionalisation process does not affect the innate advantageous properties of the base material, namely their being an absorptive, soft and pliable, and cell friendly material.

Example 21: Protein Marker Capture and Sandwich ELISA Detection Method

Results

Having established the successful nature of sample preparation, the next step was to characterise the biomarker extraction and analysis potential of the functionalised xerogel by submitting it to sandwich ELISA protocol.

Figure 82:
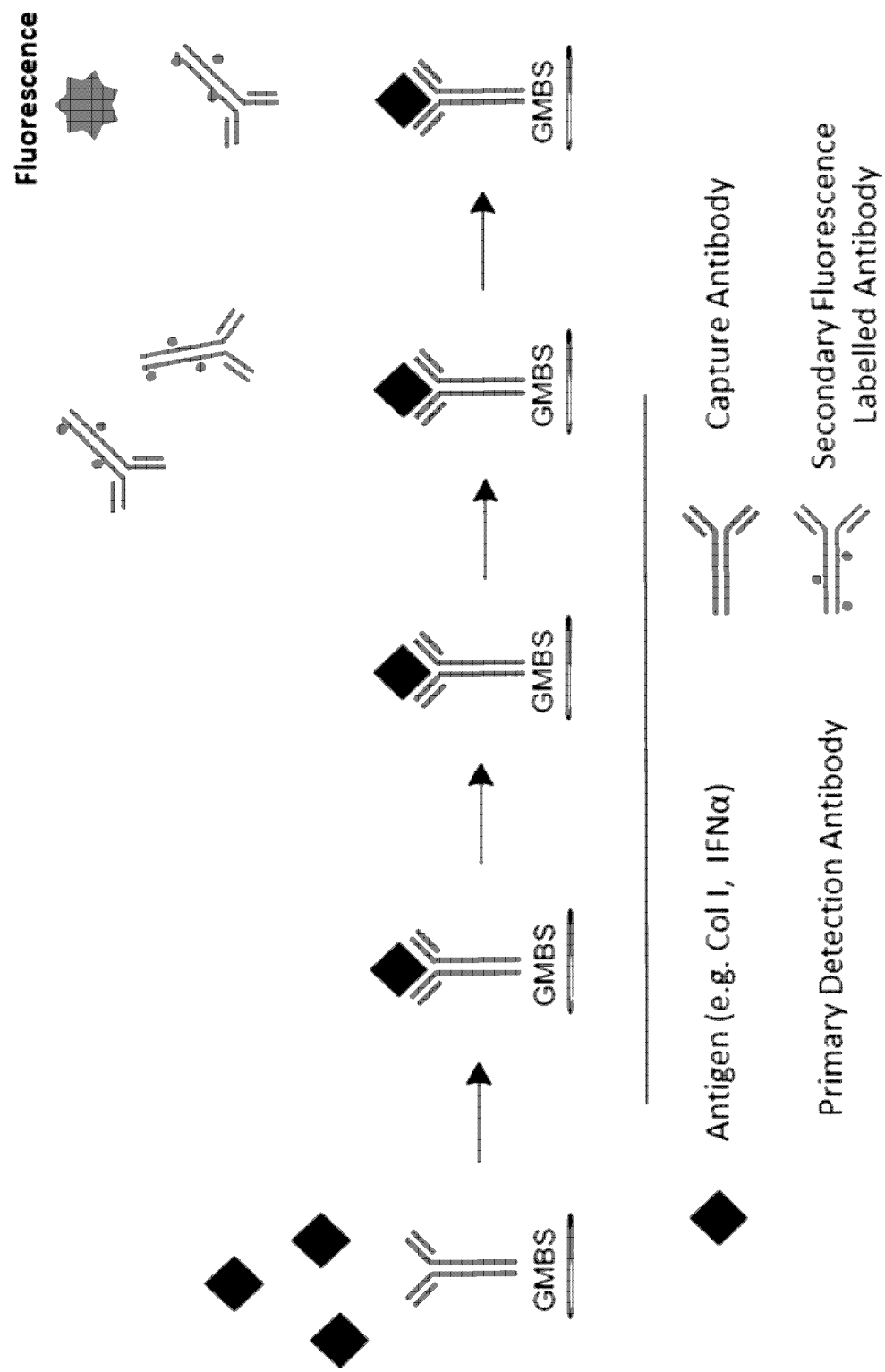
FIG. 82: Schematic representation of the Sandwich-ELISA detection process to be performed on proposed xerogel surfaces.
Figure 83:
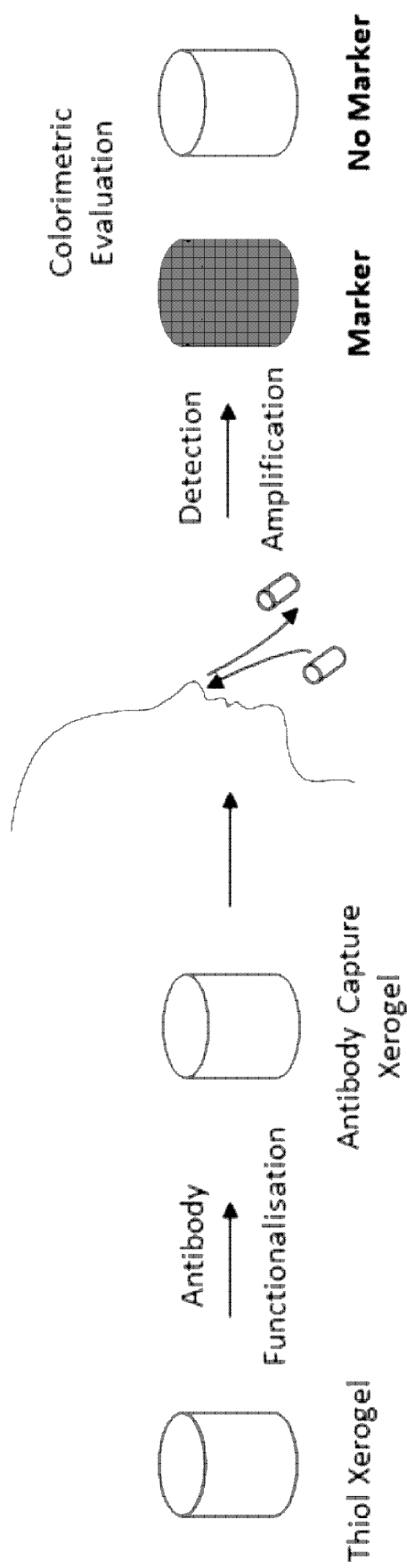
FIG. 83: Protein marker capture and detection via functionalised xerogel concept.

The concept of the ELISA process rests on the specific nature of the antibody-antigen binding reaction. As shown in FIG. 82, the capture antibody on the surface should be specific to the biomarker of interest, to enable the detection reaction of that biomarker when captured from the physiological fluid. The first step towards confirming that the process typically performed on flat surface is a transferrable to the proposed xerogels is therefore to conduct a full sandwich ELISA procedure so as to ensure not only the possible detection of the relevant biomarker, in this case collagen I, but also the lack of any false positives were the same xerogel to be placed in a solution with no relevant marker.

As has been explained, once capture-antibody functionalised, the xerogels were immersed in a solution containing a biologically representative concentration of biomarker. Collagen type I, though not biologically relevant for the purposes of respiratory diagnosis, served as a readily available and known substitute within the group in which the research was conducted for the proof-of-concept testing detailed below. Collagen type V was selected as the control biomarker, being of the same family but a different type therefore allowing to test the level of specificity of the capture antibody. Choosing two completely unrelated protein families (such as collagen and interferon as opposed to collagen type I and V for instance) was deemed to be too generic; differences in protein types such as that between interferon α and interferon β can be correlated to bacterial vs viral infections respectively. Being able to distinguish between different protein types within a protein family is therefore key to the diagnostic aim of these xerogels beyond simply being able to distinguish between different protein families.

Collagen type I detection antibody functionalised xerogels were immersed in solutions of both collagen type I and collagen type V diluted to 25 µg/mL overnight, triple washed through with 0.2% tween solution to remove unbound antigen, and immersed into mouse anti-human anti-collagen I detection antibody. If and only if collagen I is present on the surface, having been captured by the surface-grafted rabbit anti-human anti-collagen I antibody, will the detection antibody form a complex and remain attached to the surface. This can then be visually quantified by means of the fluorescence labelled secondary detection antibody that forms a complex via specific interaction with the primary detection antibody. In short, the process described above should ensure to a high degree of certainty that any fluorescence signal is attributable only to a genuine positive result, i.e. the capture and detection via sandwich-ELISA process of collagen I.

Figure 68:
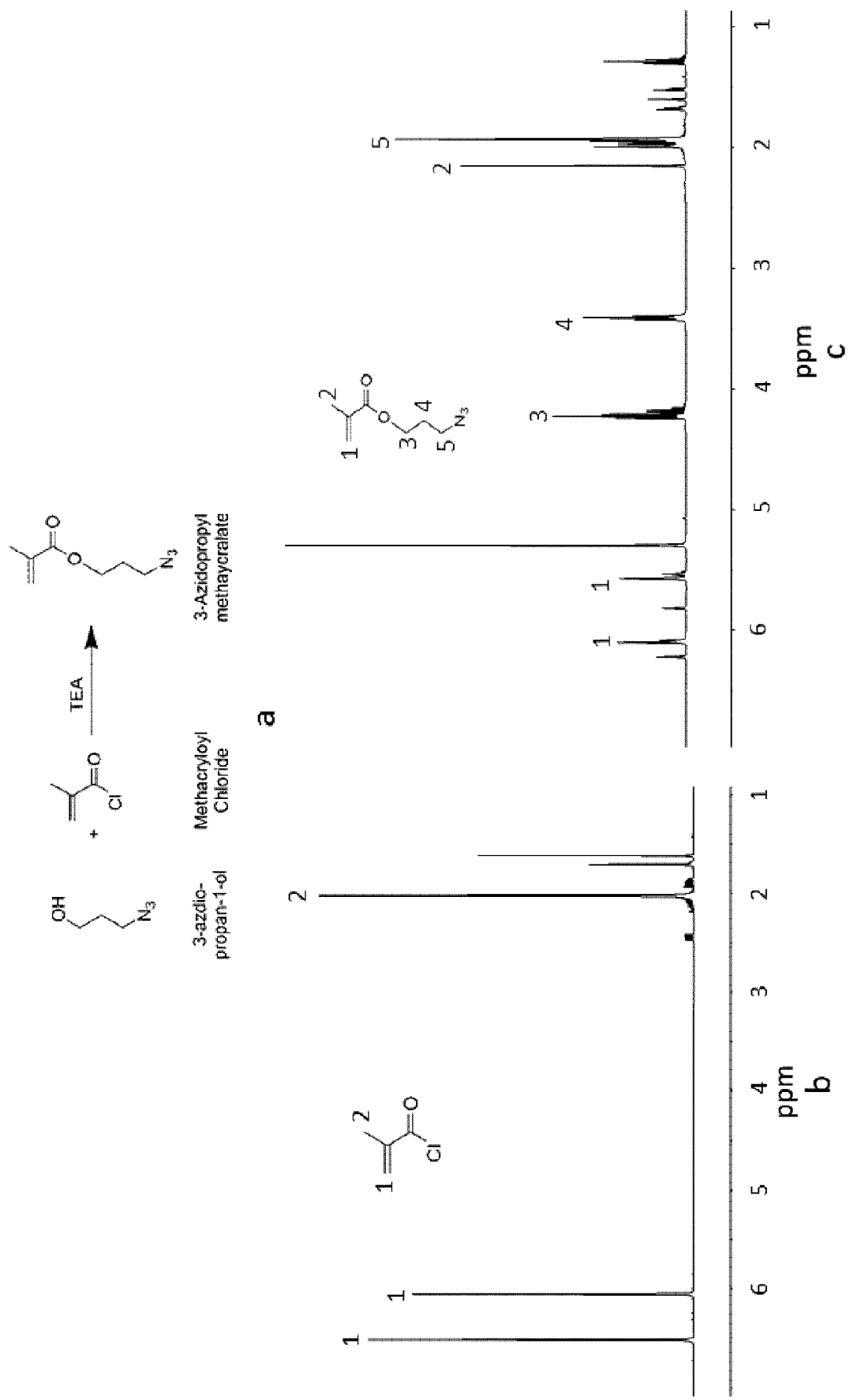
FIG. 68: Schematic (a) and 1H-NMR of 3-azido-propan-1-ol (b) reaction with methacryloyl chloride to form 3-azidopropylmethacrylate (c).
Figure 69:
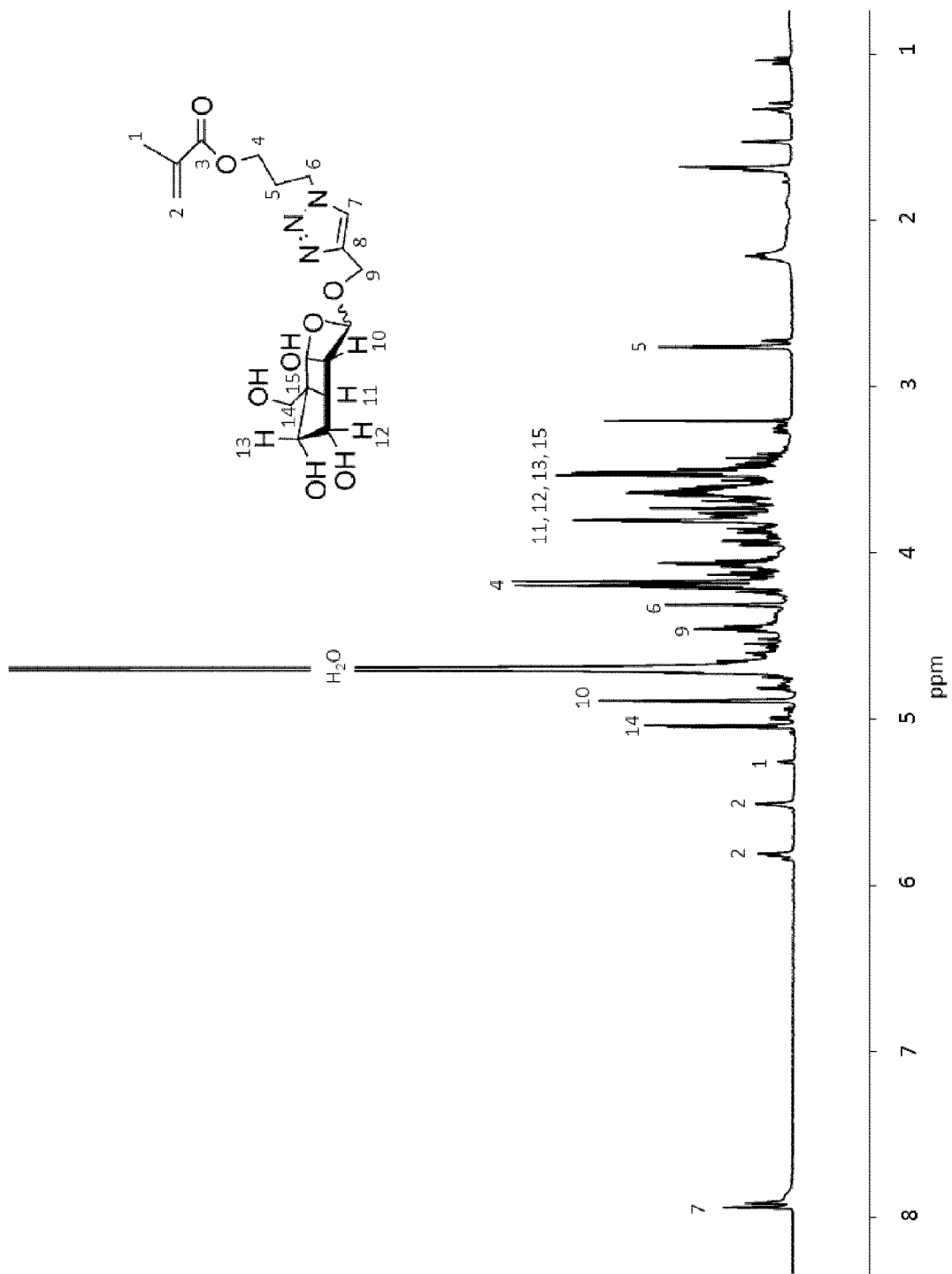
FIG. 69: 1H-NMR of D-mannose methacrylate as obtained from the reaction of 3-azidopropylmethacrylate and propargyl mannose.

The results of the process described in the previous paragraphs are shown in FIG. 68. As expected, a clear difference in fluorescence intensity signal is visible when comparing the collagen type I and collagen type V immersion results, with an over 4-fold increase in measured signal for collagen I versus V and a striking visual difference in the micrographs. This is the desired and expected result, as the xerogels are functionalised to capture collagen I not V, and confirms two of the initial assumptions that are key to proving that the ELISA-type functionalisation and detection technology can be successfully applied to these xerogels.

First, the presence of clear and measurable signal after the full sandwich ELISA type detection process including multiple washing steps confirms that it is possible not only to capture proteins, but also to confirm their presence by means of primary and secondary detection antibodies. Furthermore, the lack of signal when the same anti-collagen I xerogel is exposed to a collagen V environment confirms the protein specificity of the capture and detection process. The very minimal intensity measured in the control case can be considered to be background (typically around 10 FSU to 15 FSU) values as opposed to positive results, based on the numerous previous fluorescence intensity studies carried out in previous Examples. The lack of signal in this case also confirms the positive nature of the detection and washing process; if instead the collagen I result has an artefact of excess secondary detection antibody aggregation and therefore the washing process not sufficient, the signal would be equally intense for the collagen V test. The fact that the signals vary significantly confirms that the collagen I scenario is a definite proof of specific protein capture, detection and retention through the washing steps leading to a genuine positive reading.

Example 22: Assessing the Extraction Time Frame Capacity

Results

The above described collagen I vs V test procedure indeed included an overnight substrate immersion in the collagen I and V solutions. Although this was deemed to be a necessary step in the first testing procedures to verify the validity of the protocol, it is clear that in a clinical setting, it is not feasible for such a device to be left in the nasal cavity for effectively 7 or 8 hours. It was therefore necessary to determine the extraction and detection time efficacy of the proposed system.

To satisfy the proposed clinical objective, the device should be able to extract and capture the relevant biomarkers within no more than an hour, and ideally in only a matter of minutes. 60 minutes has been set as the maximum time during which the device can be exposed to the physiological environment, reflected in the cytotoxicity assessments with the 1 hour MTT cell media exposure time. To this end, the protocol described above and of which the results are shown in FIG. 90, was repeated removing the anti-collagen I xerogels after 5, 20 and 60 minutes. After removal from media and washing for unbound excess removal, the substrates were subjected to the identical detection method previously proposed to assess the amount of protein bound after shorter extraction times.

Figure 91:
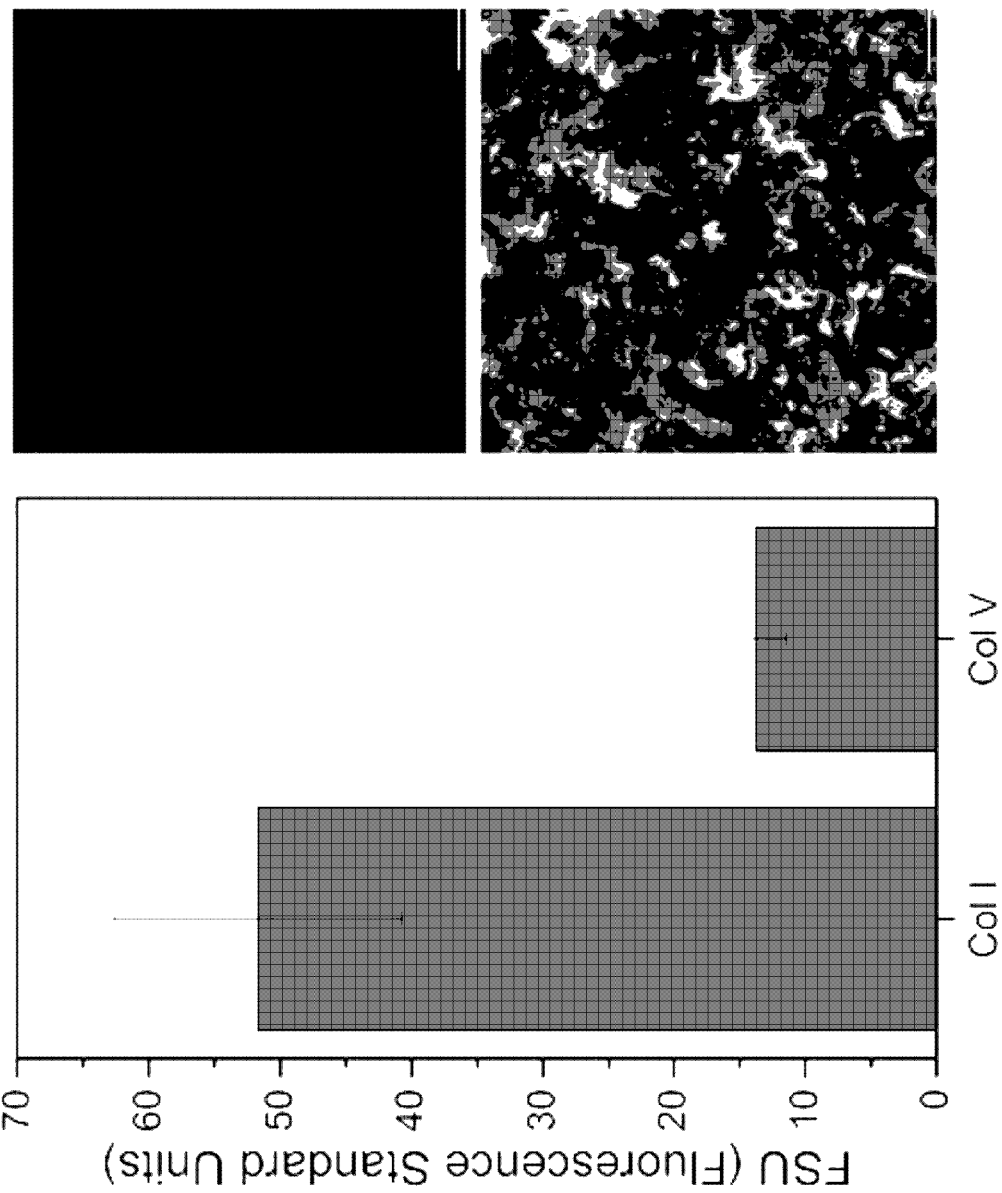
FIG. 91: a. Fluorescence intensity measurements of collagen I detection antibody functionalised xerogels and subsequent sandwich ELISA method detected collagen I and V and b. corresponding representative micrographs thereof (scale bar=100 μm).

The results of this limited exposure time investigation are shown in FIG. 91. As can be determined from both numerical and visual data, there is a clear increase in fluorescence signal with increasing immersion time, with 60-minute exposure time showing clear signal and an over fourfold increase in signal relative to control. The fluorescence signal in the micrograph also appears to reveal the full structure of the observed cross section, suggesting uniform protein adsorption across the sample and discounting any localised and therefore artefact-type result. Full hour exposure therefore appears to be sufficient to provide analytically relevant information by clear confirmation of the presence of the desired protein.

Having thus reduced the required exposure time from overnight to 1 hour, the intermediary time steps allow further investigation into just how time efficient the capture and subsequent detection can be. Although the representative micrograph taken after a 20 minute exposure and detection shows some clearly detectable signal, it reveals the xerogel structure slightly less than its overnight and hour counterparts, suggesting lesser adsorption. This is confirmed by the roughly 10 FSU lower measured intensity signal. Though lower, the signal obtained after 20 minutes is still sufficient to clearly distinguish between presence and absence of marker; indeed, if the metric of successful analysis is to reveal the presence of a given marker beyond reasonable doubt, the values and visuals after 20 minutes show that this is a sufficient amount of time to allow biomarker extraction.

Figure 90:
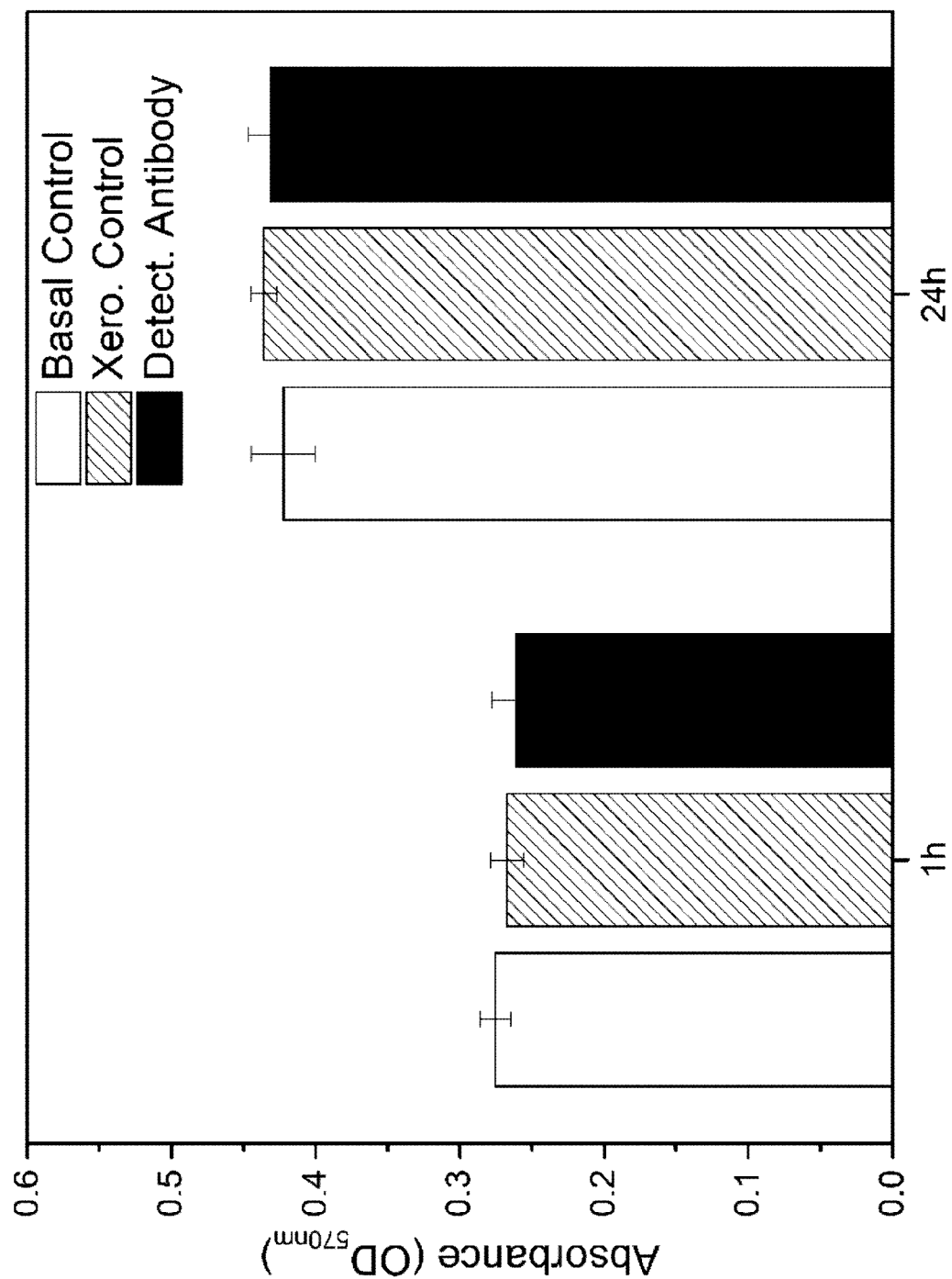
FIG. 90: MTT assay testing of basal media control, control and detection antibody functionalised xerogels.

A few additional trends can further be identified by comparing values and micrographs of FIG. 90 and FIG. 91. First, fluorescence intensity values shown in FIG. 91 exhibit an overall increasing trend with no clear sign of plateauing out, suggesting that a longer time would yield similarly significant increases in measured intensity. However, comparing the intensity values at 60 minutes extraction in FIG. 91 and the overnight exposure shown in FIG. 90 with values of 38 FSU and 51 FSU respectively, it can be considered that an hour exposure time is sufficient to obtain conclusive results. This is furthermore hinted at by the fact that baseline control intensity in FIG. 90 is of 12 FSU as opposed to 7.5 FSU in FIG. 91.

Secondly, observing and comparing micrographs also points towards a type of aggregation phenomenon with increased exposure or immersion time. Indeed, comparing micrographs in FIG. 90b. FIG. 91b, increasingly predominant regions of what appear to be saturated fluorescence signal can be observed. This most likely points towards an aggregation of the secondary fluorescence labelled detection antibodies, which would in turn suggest that a lower concentration therefore could be used to avoid the formation of these artefacts. Reducing the concentration would however not only go against supplier and protocol recommendation, but decrease the shorter immersion time sensitivity of the procedure.

Example 23: Towards a Diagnostically Relevant Protein Assay

Results

The results point towards a valid type-specific protein extraction and detection mechanism that can be achieved by immersing the proposed device into the relevant physiological media for only 20 minutes. However, these processes have been conducted using collagen type I as the diagnostic biomarker, which is of little clinical diagnostic relevance in the context of the device's actual application.

To address this, similar tests were conducted by functionalising the surface of the xerogel with anti-interferon α capture antibodies in lieu of collagen type I. As interferon and specifically interferon α play a key role in the cellular signaling pathway of the host derived immune response to infection [64, 65], they are directly relevant to the potential clinical implementation being addressed here. The ability of the proposed xerogel-based devices to successfully detect this protein would therefore constitute further evidence of their being devices with real diagnostic potential. GMBS treated xerogels were functionalised with mouse anti-human interferon α antibodies, and then immersed in separate 25 µg/mL solutions of interferon α and collagen I (the former used in this case as negative control) for 20 minutes, the duration previously confirmed to be diagnostically sufficient.

Figure 92:
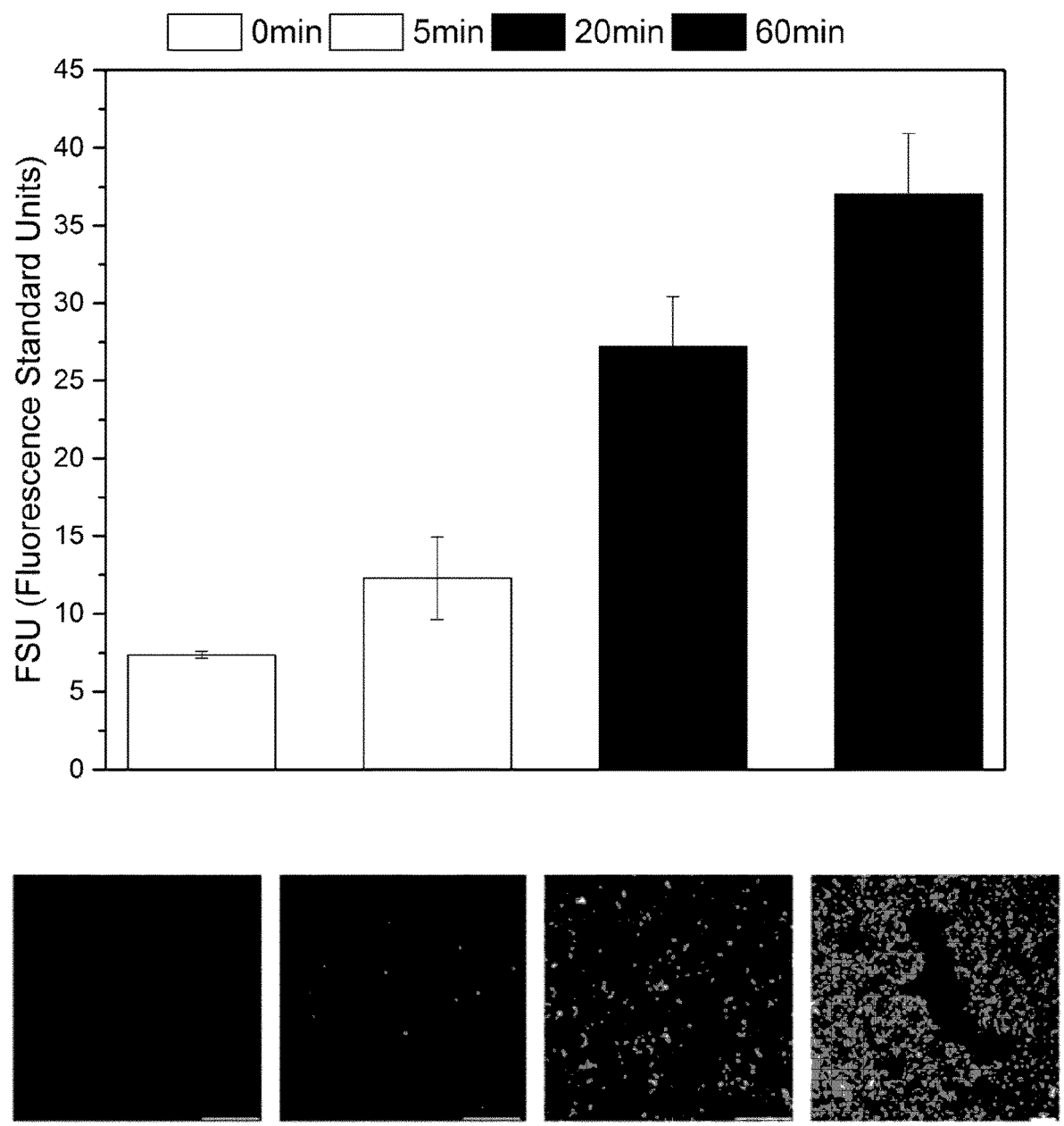
FIG. 92: a. Fluorescence intensity measurements of collagen I detection antibody functionalised xerogels and subsequent sandwich ELISA method detected collagen I after various antigen detection times and b. corresponding representative micrographs thereof (scale bar=100 μm).

The results presented in FIG. 92 are as very similar to those in FIG. 90. Indeed, a clear distinction can be observed between the fluorescence intensities associated with interferon α and collagen I, the former being once again a near fourfold increase relative to the latter (negative control). The intensity values of 37.5 FSU obtained after only 20 minutes of immersion are however much higher than those obtained after 20 minutes in the case of collagen type I shown in FIG. 91, the values obtained here actually being almost identical to those obtained for 60-minute immersion times in the case of collagen type I. This can once again be attributed to a range of factors, including the variability across such measurements in the baseline values the positive outcomes are compared to.

Figure 93:
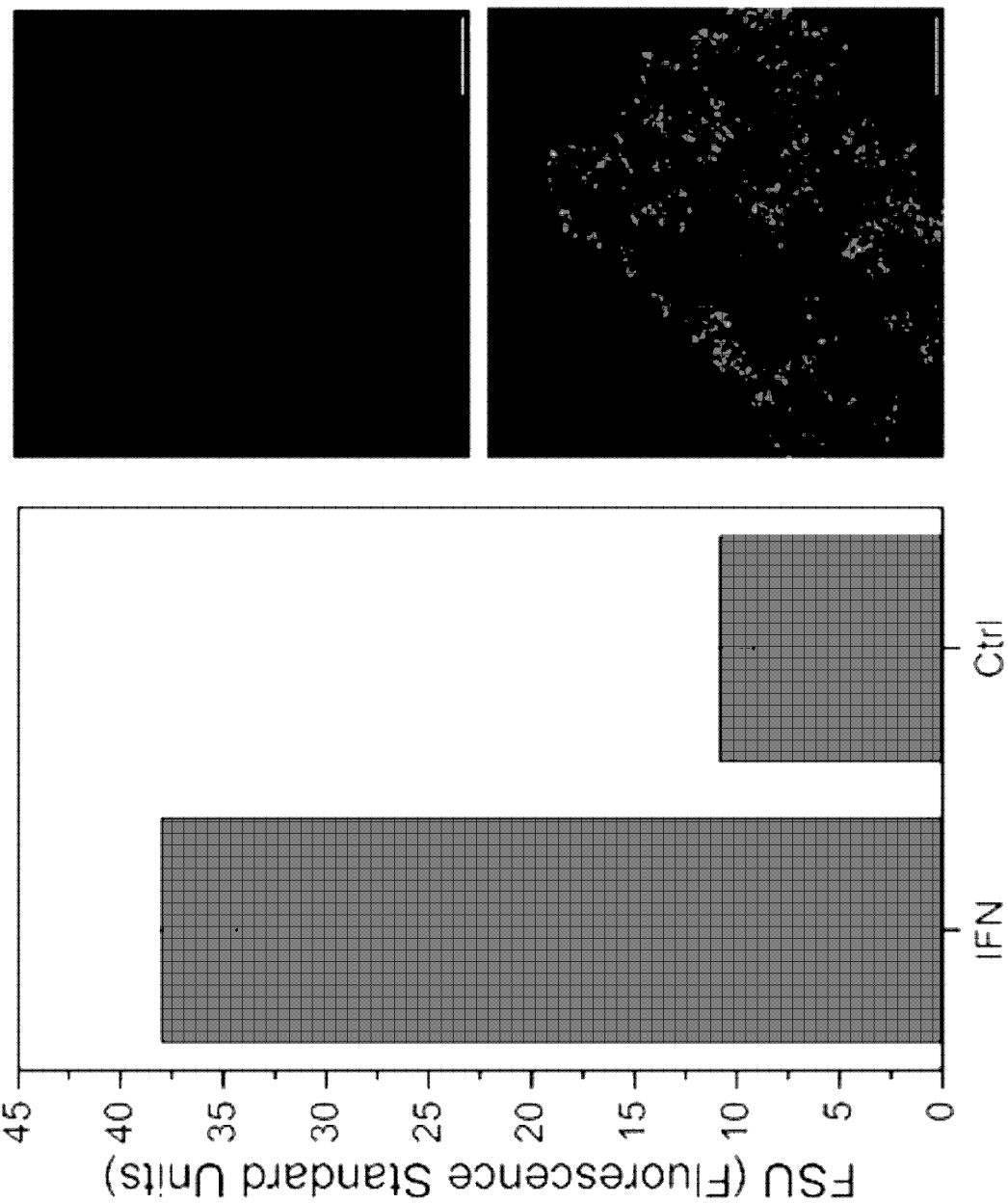
FIG. 93: a. Fluorescence intensity measurements of interferon α detection antibody functionalised xerogels and subsequent sandwich ELISA method detected interferon α and b. corresponding representative micrographs thereof (scale bar=100 μm).

Cross-experiments comparison should mostly be made on a semi-quantitative basis, referring to the relevant control for full qualitative analysis due to the nature of experimental set up and analytical processes. However, the slight variability in numerical results does not mitigate the clearly positive result herein presented. The fully visible structure shown in FIG. 69b. further confirms this, a visible structural having been previously been set as a positive benchmark for successful and non-artefact type results. The regions of lesser signal within the structure visible here are due to the innate non-uniform structure of the xerogels combined with the low depth of field of the confocal microscope set up used, rendering out of focus regions either blurry or dark when focusing on another plane. Cross section images such as those shown in FIG. 93, which as with various other fluorescence-based results point towards a successful experimental outcome.

FIG. 92 therefore confirms the successful nature of specific biomarker capture and detection processes applied, in this case to the infection diagnosis relevant interferon α biomarker.

Summary of Examples 19 to 23

The aim of these experiments was to establish whether the xerogels proposed and characterised in previous Examples could be used as protein-extracting devices equivalent to ELISA plates but used in-situ to extract relevant proteins. The above results show that it is possible to transfer from traditional glass or plastic plates to what is considered here to be an in-situ biomarker extraction device, designed with the considerations of patient comfort and ease of synthesis.

Both collagen type I and the more diagnostically relevant interferon α were extracted and detected using sandwich ELISA type protocol applied to the functionalised xerogel substrate. The control protocols used confirm the validity of the presented results.

REFERENCES

1. Sneha, A. K., S. M. Imtiaz, and V. Kunjukrishna, *Electrochemical Characterization of Self-Assembled Monolayers on Semiconducting Substrates for MEMS Applications*. Journal of Physics: Conference Series, 2006. 34(1): p. 322.
2. Qin, S., et al., *Synthesis of Block, Statistical, and Gradient Copolymers from Octadecyl (Meth)acrylates Using Atom Transfer Radical Polymerization*. Macromolecules, 2003. 36(24): p. 8969-8977.
3. Yoo, H., et al., *Polyoctadecyl methacrylate brushes via surface-initiated atom transfer radical polymerization*. Applied Organometallic Chemistry, 2013. 27(11): p. 378-682.
4. Powell, W. S., *Rapid extraction of oxygenated metabolites of arachidonic acid from biological samples using octadecylsilyl silica*. Prostaglandins, 1980. 20(5): p. 947-57.
5. Kataoka, H., H. L. Lord, and J. Pawliszyn, *Applications of solid-phase microextraction in food analysis*. J Chromatogr A, 2000. 880(1-2): p. 35-62.
6. Saner, C. K., et al., *Self-assembly of octadecyltrichlorosilane: Surface structures formed using different protocols of particle lithography*. Beilstein Journal of Nanotechnology, 2012. 3: p. 114-122.
Patiño Herrera, R., et al., *Hydrophobic coatings for prevention of dental enamel erosion*. Vol. 275. 2015.
8. Wong, J. X. H. and H.-Z. Yu, *Preparation of Transparent Superhydrophobic Glass Slides: Demonstration of Surface Chemistry Characteristics*. Journal of Chemical Education, 2013. 90(9): p. 1203-1206.
9. Bhatia, S. K., et al., *Use of thiol-terminal silanes and heterobifunctional crosslinkers for immobilization of antibodies on silica surfaces*. Anal Biochem, 1989. 178(2): p. 408-13.
10. Stott, C. A. and Y. Higashi, *Cholesterol sulfate in human physiology: what's it all about?* J Lipid Res, 2003. 44(7): p. 1268-78.
11. Arima, M. and T. Fukuda, *Prostaglandin D(2) and T(H)2 Inflammation in the Pathogenesis of Bronchial Asthma*. The Korean Journal of Internal Medicine, 2011. 26(1): p. 8-18.
12. Chung, J. J., et al., *Biodegradable inorganic-organic hybrids of methacrylate star polymers for bone regeneration*. Acta Biomaterialia, 2017. 54: p. 411-418.
13. Marutani, E., et al., *Surface-initiated atom transfer radical polymerization of methyl methacrylate on magnetite nanoparticles*. Polymer, 2004. 45(7): p. 2231-2235.
14. Matyjaszewski, K. and J. Xia, *Atom Transfer Radical Polymerization*. Chemical Reviews, 2001. 101(9): p. 2921-2990.
15. Abbasi, F., H. Mirzadeh, and A.-A. Katbab, *Modification of polysiloxane polymers for biomedical applications: a review*. Polymer International, 2001. 50(12): p. 1279-1287.
16. Hui, C. M., et al., *Surface-Initiated Polymerization as an Enabling Tool for Multifunctional (Nano)Engineered Hybrid Materials*. Chemistry of Materials, 2014. 26(1): p. 745-762.

17. Mandal, K., M. Balland, and L. Bureau, *Thermoresponsive Micropatterned Substrates for Single Cell Studies.* PLOS ONE, 2012. 7(5): p. e37548.
18. Ma, H., et al., *Monitoring kinetics of surface initiated atom transfer radical polymerization by quartz crystal microbalance with dissipation.* Biointerphases, 2006. 1(1): p. 35-39.
19. Wertz, C. F. and M. M. Santore, *Effect of Surface Hydrophobicity on Adsorption and Relaxation Kinetics of Albumin and Fibrinogen: Single-Species and Competitive Behavior.* Langmuir, 2001. 17(10): p. 3006-3016.
20. Pruski, P., et al., *Medical Swab Analysis Using Desorption Electrospray Ionization Mass Spectrometry: A Noninvasive Approach for Mucosal Diagnostics.* Analytical Chemistry, 2017. 89(3): p. 1540-1550.
21. Yaqoob, P., *Fatty acids as gatekeepers of immune cell regulation.* Trends in Immunology, 2003. 24(12): p. 639-645.
22. Cangiano, G., et al., *Lactate dehydrogenase concentration in nasal wash fluid indicates severity of rhinovirus-induced wheezy bronchitis in preschool children.* Pediatr Infect Dis J, 2014. 33(12): p. 1285-7.
23. Hayase, G., et al., *Facile Synthesis of Marshmallow-like Macroporous Gels Usable under Harsh Conditions for the Separation of Oil and Water.* Angewandte Chemie International Edition, 2013. 52(7): p. 1986-1989.
24. Hayase, G., K. Kanamori, and K. Nakanishi, *New flexible aerogels and xerogels derived from methyltrimethoxysilane/dimethyldimethoxysilane co-precursors.* Journal of Materials Chemistry, 2011. 21(43): p. 17077-17079.
25. Wei, Y., et al., *Autocatalytic synthesis of molecular-bridged silica aerogels with excellent absorption and super elasticity.* Vol. 5. 2015.
26. Kanamori, K., et al., *New Transparent Methylsilsesquioxane Aerogels and Xerogels with Improved Mechanical Properties.* Advanced Materials, 2007. 19(12): p. 1589-1593.
27. Zhang, X. and Y. Cai, *Octadecyltrichlorosilane (OTS)-coated ionic liquid drops: Micro-reactors for homogenous catalytic reactions at designated interfaces.* Beilstein Journal of Nanotechnology, 2012. 3: p. 33-39.
28. Du, Z., et al., *Synthesis of hybrid silica nanoparticles grafted with thermoresponsive poly(ethylene glycol) methyl ether methacrylate via AGET-ATRP.* RSC Advances, 2015. 5(22): p. 17194-17201.
29. Yoo, H., et al., *Polyoctadecyl methacrylate brushes via surface-initiated atom transfer radical polymerization.* Applied Organometallic Chemistry, 2013. 27(11): p. 378-682.
30. Bhattacharya, S., et al., *Studies on surface wettability of poly(dimethyl) siloxane (PDMS) and glass under oxygen-plasma treatment and correlation with bond strength.* Journal of Microelectromechanical Systems, 2005. 14(3): p. 590-597.
31. Laaniste, A., et al., *"Thiol-ene" photoclick chemistry as a rapid and localizable functionalization pathway for silica capillary monolithic columns.* Journal of Chromatography A, 2014. 1355: p. 296-300.
32. Durães, L., A. Maia, and A. Portugal, *Effect of additives on the properties of silica based aerogels synthesized from methyltrimethoxysilane (MTMS).* The Journal of Supercritical Fluids, 2015. 106: p. 85-92.
33. Harris, F. M., K. B. Best, and J. D. Bell, *Use of laurdan fluorescence intensity and polarization to distinguish between changes in membrane fluidity and phospholipid order.* Biochim Biophys Acta, 2002. 1565(1): p. 123-8.
34. Ciancaglini, P., et al., *Proteoliposomes in nanobiotechnology.* Biophysical Reviews, 2012. 4(1): p. 67-81.
35. Pulfer, M. and R. C. Murphy, *Electrospray mass spectrometry of phospholipids.* Mass Spectrom Rev, 2003. 22(5): p. 332-64.
36. Kasumov, T., et al., *QUANTIFICATION OF CERAMIDE SPECIES IN BIOLOGICAL SAMPLES BY LIQUID CHROMATOGRAPHY-ELECTROSPRAY TANDEM MASS SPECTROMETRY.* Analytical biochemistry, 2010. 401(1): p. 154-161.
37. Vogeser, M. and K. G. Parhofer, *Liquid chromatography tandem-mass spectrometry (LC-MS/MS)—technique and applications in endocrinology.* Exp Clin Endocrinol Diabetes, 2007. 115(9): p. 559-70.
38. Ivanova, P. T., et al., *Electrospray ionization mass spectrometry analysis of changes in phospholipids in RBL-2H3 mastocytoma cells during degranulation.* Proceedings of the National Academy of Sciences of the United States of America, 2001. 98(13): p. 7152-7157.
39. Yu, D., et al., *A controlled thiol-initiated surface polymerization strategy for the preparation of hydrophilic polymer stationary phases.* Chemical Communications, 2015. 51(79): p. 14778-14780.
40. Siegwart, D. J., J. K. Oh, and K. Matyjaszewski, *ATRP in the design of functional materials for biomedical applications.* Progress in Polymer Science, 2012. 37(1): p. 18-37.
41. Paris, R. and J. L. de la Fuente, *Bulk atom transfer radical polymerization of allyl methacrylate.* Journal of Polymer Science Part A: Polymer Chemistry, 2005. 43(11): p. 2395-2406.
42. Paris, R. and J. L. de la Fuente, *Diblock copolymers based on allyl methacrylate: Synthesis, characterization, and chemical modification.* Journal of Polymer Science Part A: Polymer Chemistry, 2007. 45(16): p. 3538-3549.
43. Zhang, Q., *Novel strategies in the synthesis of functional glycopolymers.* 2013, University of Warwick.
44. Berges, C., et al., *A cell line model for the differentiation of human dendritic cells.* Biochem Biophys Res Commun, 2005. 333(3): p. 896-907.
45. Matsumoto, A., M. Fujihashi, and H. Aota, *Copolymerization of Poly(allyl methacrylate) Crosslinked Polymer Microspheres with Allyl Benzoate.* Polymer Journal, 2001. 33: p. 636.
46. Greszta, D., D. Mardare, and K. Matyjaszewski, *"Living" radical polymerization. 1. Possibilities and limitations.* Macromolecules, 1994. 27(3): p. 638-644.
47. de la Fuente, J. L., et al., *Solvent Effects on the Synthesis of Poly(methyl methacrylate) by Atom-Transfer Radical Polymerization (ATRP).* Vol. 202. 2001. 2565-2571.
48. Kurtulus, I., et al., *A new proton sponge polymer synthesized by RAFT polymerization for intracellular delivery of biotherapeutics.* Polymer Chemistry, 2014. 5(5): p. 1593-1604.
49. Kawamura, K., et al., *Differentiation, maturation, and survival of dendritic cells by osteopontin regulation.* Clin Diagn Lab Immunol, 2005. 12(1): p. 206-12.
50. Pustylnikov, S., et al., *Targeting the C-type lectins-mediated host-pathogen interactions with dextran.* J Pharm Pharm Sci, 2014. 17(3): p. 371-92.
51. Wollenberg, A., et al., *Expression and Function of the Mannose Receptor CD206 on Epidermal Dendritic Cells in Inflammatory Skin Diseases.* Journal of Investigative Dermatology, 2002. 118(2): p. 327-334.
52. Nagai, T., *Difference between Immature Dendritic Cells (imDCs) and Mature Dendritic Cells (mDCs) Derived*

*from Human Monocytes.* The Journal of Immunology, 2017. 198(1 Supplement): p. 201.16.
53. Kop, W. J. and A. A. Weinstein, *C-Reactive Protein A2—Fink, George,* in *Encyclopedia of Stress* (Second Edition). 2007, Academic Press: New York. p. 653-658.
54. Tanaka, T., M. Narazaki, and T. Kishimoto, *IL-6 in Inflammation, Immunity, and Disease.* Cold Spring Harbor Perspectives in Biology, 2014. 6(10).
55. Llor, C., et al., *C-reactive protein testing in patients with acute rhinosinusitis leads to a reduction in antibiotic use.* Family Practice, 2012. 29(6): p. 653-658.
56. Aabenhus, R., et al., *Biomarkers as point-of-care tests to guide prescription of antibiotics in patients with acute respiratory infections in primary care.* Cochrane Database of Systematic Reviews, 2014(11).
57. Limper, M., et al., *The diagnostic role of Procalcitonin and other biomarkers in discriminating infectious from non-infectious fever.* Journal of Infection, 2010. 60(6): p. 409-416.
58. Oved, K., et al., *A Novel Host-Proteome Signature for Distinguishing between Acute Bacterial and Viral Infections.* PLOS ONE, 2015. 10(3): p. e0120012.
59. Kitamura, K., et al., *A fluorescence sandwich ELISA for detecting soluble and cell-associated human interleukin-2.* J Immunol Methods, 1989. 121(2): p. 281-8.
60. Fu, Y. R., et al., *Proteomic analysis of sputum in patients with active pulmonary tuberculosis.* Clinical Microbiology and Infection, 2012. 18(12): p. 1241-1247.
61. Bhatia, S. K., et al., *Use of thiol-terminal silanes and heterobifunctional crosslinkers for immobilization of antibodies on silica surfaces.* Anal Biochem, 1989. 178(2): p. 408-13.
62. Shriver-Lake, L. C., et al., *Antibody immobilization using heterobifunctional crosslinkers.* Biosensors and Bioelectronics, 1997. 12(11): p. 1101-1106.
63. Hayase, G., et al., *A Superamphiphobic Macroporous Silicone Monolith with Marshmallow-like Flexibility.* Angewandte Chemie International Edition, 2013. 52(41): p. 10788-10791.
64. Platanias, L C., *Mechanisms of type-I- and type-II-interferon-mediated signalling.* Nature Reviews Immunology, 2005. 5: p. 375.
65. Begitt, A., et al., *STAT1-cooperative DNA binding distinguishes type 1 from type 2 interferon signaling.* Nature Immunology, 2014. 15: p. 168.
66. Iguchi, Y., K. Yao, and M. Okamoto, *A characteristic protein in nasal discharge differentiating non-allergic chronic rhinosinusitis from allergic rhinitis.* Rhinology, 2002. 40(1): p. 13-7.

The invention claimed is:
1. A surface-functionalised xerogel comprising a functional group that selectively binds to a biological molecule from a subject,
wherein the surface-functionalised xerogel is monolithic and configured to have a size and shape suitable for insertion into a body orifice, a body cavity, or a bodily tube, and for contacting a mucous membrane therein, thereby sampling the biological molecule from the subject, and
wherein the shape of the surface-functionalised xerogel is substantially that of a cylinder, a rod, a disk, a sphere, a cone, or a frustocone.
2. The surface-functionalised xerogel according to claim 1, wherein the functional group selectively binds to a cell, protein, lipid or nucleic acid biomarker, or metabolite.
3. The surface-functionalised xerogel according to claim 1, wherein the surface-functionalised xerogel is a silica xerogel.
4. The surface-functionalised xerogel according to claim 1, wherein the functional group is selected from an antigen-binding protein, a nucleic acid, a lipid-binding moiety, a sugar or glycoprotein, or a block group-presenting co-polymer.
5. The surface-functionalised xerogel according to claim 4, wherein:
   a. the lipid-binding moiety comprises a C4-C20 alkyl silicate functionalised silica xerogel, optionally an octadecylsilyl (ODS) group; or
   b. the sugar is mannose; or
   c. the antigen-binding protein is an antibody or an antigen-binding fragment thereof.
6. The surface-functionalised xerogel according to claim 1, wherein the xerogel is a reaction product of tri-functional and di-functional siloxane precursors, wherein at least one of the tri-functional and/or di-functional siloxane precursors is a mercaptosilane; and wherein the surface-functionalised xerogel is:
   a. a C4-C20-alkyl-silicate-functionalised silica xerogel, optionally an octadecylsilyl (ODS)-surface-functionalised silica xerogel; or
   b. a mannose-surface-functionalised silica xerogel; or
   c. an antibody-, or antigen-binding antibody fragment-, surface-grafted silica xerogel, optionally wherein the antibody or antigen-binding fragment is attached to the xerogel by a linker.
7. A method for preparation of a surface-functionalised xerogel, the method comprising:
surface functionalising the xerogel with:
   i. N-octadecyl methacrylate p(ODMA) by thiol-ene surface-initiated polymerisation (TSIP);
   ii. Mannose methacrylate by thiol-ene surface-initiated polymerisation (TSIP); or
   iii. an antibody or an antigen-binding fragment thereof by reacting a thiol xerogel with a heterobifunctional crosslinking compound and an antibody or an antigen-binding fragment thereof; and
forming the surface-functionalised xerogel into a sampling device having a size and shape suitable for insertion into a body orifice, a body cavity, or a bodily tube, and for contacting a mucous membrane therein, thereby sampling a biological molecule from a subject,
wherein the surface-functionalised xerogel is monolithic, and
wherein the shape of the surface-functionalised xerogel is substantially that of a cylinder, a rod, a disk, a sphere, a cone, or a frustocone.
8. The method according to claim 7, wherein the xerogel is a silica xerogel prepared from tri-functional and di-functional siloxane precursors, wherein at least one of the tri-functional and/or di-functional siloxane precursors is a mercaptosilane, optionally wherein the tri-functional and di-functional siloxane precursors are:
   a. Dimethoxydimethylsilane and (3-Mercaptopropyl)trimethoxysilane, optionally combined in a 2:3 molar ratio; or
   b. (3-Mercaptopropyl)methyldimethoxysilane and Trimethoxymethylsilane, optionally combined in a 2:3 molar ratio; or
   c. Vinyltrimethoxysilane and (3-Mercaptopropyl)methyldimethoxysilane.
9. The method according to claim 7, wherein the xerogel is:

an octadecylsilyl (ODS)-surface-functionalised silica xerogel and is surface-functionalised in a presence of 0.05-0.2 g/ml ODMA;

a mannose-surface-functionalised silica xerogel and is surface-functionalised with mannose methacrylate; or an antibody-surface-grafted silica xerogel and the heterobifunctional crosslinking compound is reactive towards amino and sulfhydryl groups, optionally wherein the heterobifunctional crosslinking compound is N-maleimidoburyryl-oxysuccinimide ester (GMBS), m-maleimidobenzoyl-N-hydroxysuccinimide ester (MBS), N-ε-malemidocaproyl-oxysuccinimide ester (EMCS), succinimidyl 3-(2-pyridyldithio)propionate (SPDP), Succinimidyl 6-[3-(2-pyridyldithio)propionamido] hexanoate (LC-SPDP), succinimidyl 4-(p-maleimidophenyl)butyrate (SMPB), 4-(4-N-maleimidophenyl) butyric acid hydrazide (MPBH), or 3-(2-pyridyldithio) propionyl hydrazide (PDPH).

10. The surface-functionalised xerogel according to claim 1, characterized by one or more of an absorbance capacity of at least 0.5 g/g and optionally a wicking capacity of at least 0.5 g/g within 120 s, and a strain of 60-90% at 5 N, and a stress of 0.1-0.3 at 5 N.

11. A method of sampling a mucosal fluid from a mucous membrane of a subject, the method comprising contacting the mucous membrane with the xerogel according to claim 1.

12. The method according to claim 11, wherein the method comprises sampling cells from the mucosal fluid.

13. The method according to claim 12, wherein the cells are
 a. host cells, optionally immune cells, optionally dendritic cells; or
 b. host cells, optionally cancerous or pre-cancerous cells, optionally ovarian cancer cells; or
 c. pathogen cells, optionally bacterial cells.

14. The method according to claim 11, wherein the method comprises sampling a protein biomarker and/or a lipid biomarker from the mucosal fluid.

15. A sampling device for sampling a biological fluid, the sampling device comprising the xerogel according to claim 1, optionally wherein the sampling device is a point-of-care sampling device.

16. The method of claim 11, wherein:
 a. the xerogel is an antibody surface-functionalised silica xerogel;
 b. sampling the mucosal fluid comprises detecting a presence or absence of a protein biomarker in the mucosal fluid; and
 c. the method further comprises diagnosing the subject with a disease or disorder based on the presence or absence of the protein biomarker in the mucosal fluid.

17. The method according to claim 16, wherein the mucosal fluid is nasal fluid from a subject with an infection and wherein the protein biomarker is interferon α, and wherein a presence of interferon α is indicative of a bacterial infection and an absence of interferon α is indicative of a viral infection.

18. The method of claim 11, wherein:
 a. the xerogel is a mannose-surface-functionalised xerogel; and
 b. wherein sampling the mucosal fluid comprises detecting the presence or absence of dendritic cells in the mucosal fluid.

19. The sampling device of claim 15 which is contained in a kit for detecting biomarkers, wherein the kit optionally further comprises reagents for elution and/or analysis of the biomarkers.

20. The surface-functionalised xerogel according to claim 1, wherein the xerogel is a silica xerogel prepared from tri-functional and di-functional siloxane precursors, and wherein only one of the tri-functional and di-functional siloxane precursors is a mercaptosilane.

* * * * *